(12) United States Patent
East et al.

(10) Patent No.: US 8,232,322 B2
(45) Date of Patent: Jul. 31, 2012

(54) HIGH MOLECULAR WEIGHT POLYMERS, DEVICES AND METHOD FOR MAKING AND USING SAME

(75) Inventors: Anthony East, New Brunswick, NJ (US); Alan Letton, New Brunswick, NJ (US); Suseela Kanamathareddy, New Brunswick, NJ (US); Bryant J. Pudil, New Brunswick, NJ (US); Stephen Goodrich, New Brunswick, NJ (US); Michael B. Hicks, New Brunswick, NJ (US); Yun Choe, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 333 days.

(21) Appl. No.: 12/500,438

(22) Filed: Jul. 9, 2009

(65) Prior Publication Data

US 2010/0152410 A1 Jun. 17, 2010

Related U.S. Application Data

(62) Division of application No. 10/861,881, filed on Jun. 4, 2004, now Pat. No. 7,662,864.

(60) Provisional application No. 60/475,766, filed on Jun. 4, 2003.

(51) Int. Cl.
A61K 47/32 (2006.01)
A61K 31/43 (2006.01)

(52) U.S. Cl. ............ 514/772.5; 514/197; 514/201; 514/567

(58) Field of Classification Search .......... 514/197, 514/201, 567
See application file for complete search history.

(56) References Cited

U.S. PATENT DOCUMENTS

| | | | |
|---|---|---|---|
| 4,757,128 A | 7/1988 | Domb et al. | |
| 4,857,311 A | 8/1989 | Domb et al. | |
| 4,886,870 A | 12/1989 | D'Amore et al. | |
| 4,888,176 A | 12/1989 | Langer et al. | |
| 4,916,204 A | 4/1990 | Domb et al. | |
| 4,933,431 A | 6/1990 | Domb et al. | |
| 4,997,904 A | 3/1991 | Domb | |
| 4,999,417 A | 3/1991 | Domb | |
| 5,019,379 A | 5/1991 | Domb et al. | |
| 5,264,540 A | 11/1993 | Cooper et al. | |
| 5,902,599 A | 5/1999 | Anseth et al. | |
| 6,486,214 B1 * | 11/2002 | Uhrich ............... | 514/772.5 |
| 7,411,031 B2 | 8/2008 | Uhrich et al. | |
| 7,662,864 B2 | 2/2010 | Kanamathareddy et al. | |
| 2003/0086895 A1 | 5/2003 | Hanes et al. | |
| 2008/0234235 A1 | 9/2008 | Uhrich et al. | |

FOREIGN PATENT DOCUMENTS

| | | |
|---|---|---|
| EP | 0511292 B1 | 4/2000 |
| GB | 2226821 A | 7/1990 |
| WO | WO 89/01005 | 2/1989 |
| WO | WO 01/41753 | 6/2001 |
| WO | WO 03/046034 | 6/2003 |

OTHER PUBLICATIONS

Peter Pinther, Manfred Hartmann, Synthesis of Polyanyhdrides containing ester groups, May 21, 1990, Makromol. Chem. Rapid. Commun. 11,403-408, (1990).*
Domb, et al., "Biodegradable Polymers Derived from Amino Acids," *Polymer Preprints, Divsion of Polymer Chemistry, ACS*, 30(2), 189-190, (1989).
Domb, et al., "Excretion of a radiolabelled anticancer biodegradable polymeric implant from the rabbit brain," *Biomaterials*, 16, 1069-1072, (1995).
Domb, et al., "Poly(anhydrides). 2. One-Step Polymerization using Phosgene or Diphosgene as Coupling Agents", *Macromolecules*, 21, 1925-1929, (1988).
Erdmann, L., et al., "Degradable poly(anhydride ester) Implants: effects of localized salicylic acid release on bone", *Biomaterials*, 21, 2507-2512, (2000).
Kricheldorf, et al., "Polyanhydrides, XI. Poly(ester-anhydride)s Derived from 4-Hydroxybenzoic Acid, Vanillic Acid and Aliphatic Dicarboxylic Acids," *J.M.S.—Pure Appl. Chem.*, A35(2), 359-373, (1998).
Leong, et al., "Synthesis of Polyanhydrides: Melt-Polycondensation, Dehydrochlorination, and Dehydrative Coupling" *Macromolecules*, 20, 705-712 (1987).
Pinther P. et al., "Synthesis of polyanhydrides containing ester groups", *Makromol. Chem. Rapid Commun. 11*, 403-408, (1990).
Patent Cooperation Treaty, International Searching Authority, International Search Report for PCT/US2004/17916, 2 pages, Aug. 24, 2005.
Patent Cooperation Treaty, International Preliminary Report on Patentability for PCT/US2004/17916, 19 pages, Feb. 8, 2006.
Domb et al., "Biodegradable polymers derived from amino acids", *Biomaterials*, vol. 11, pp. 686-689, 1990.
Erdmann, et al., "Synthesis and degradation characteristics of salicylic acid-derived poly(anhydride-esters)", *Biomaterials*, 21, pp. 1941-1946, 2000.
Kumar et al., "Polyanhydrides: an overview", *Advanced Drug Delivery Reviews*, 54, pp. 889-910, 2002.

* cited by examiner

*Primary Examiner* — Michael G Hartley
*Assistant Examiner* — Jagadishwar Samala
(74) *Attorney, Agent, or Firm* — Viksnins Harris & Padys PLLP

(57) ABSTRACT

Anhydride polymers that release active or activatable agent(s) have pre-selected properties such as molecular weight, flexibility, hardness, adhesiveness, and other valuable properties. The polymers are suitable for use in compositions, formulations, coatings, devices, and the like that benefit from the controlled release of an agent(s) over a period of time. The polymers are prepared by a process involving various alternative and sequential steps that allow the design a priori of products with specific characteristics. The polymers are suitable as delivery systems, either by themselves, as compositions, formulations or devices.

18 Claims, 1 Drawing Sheet

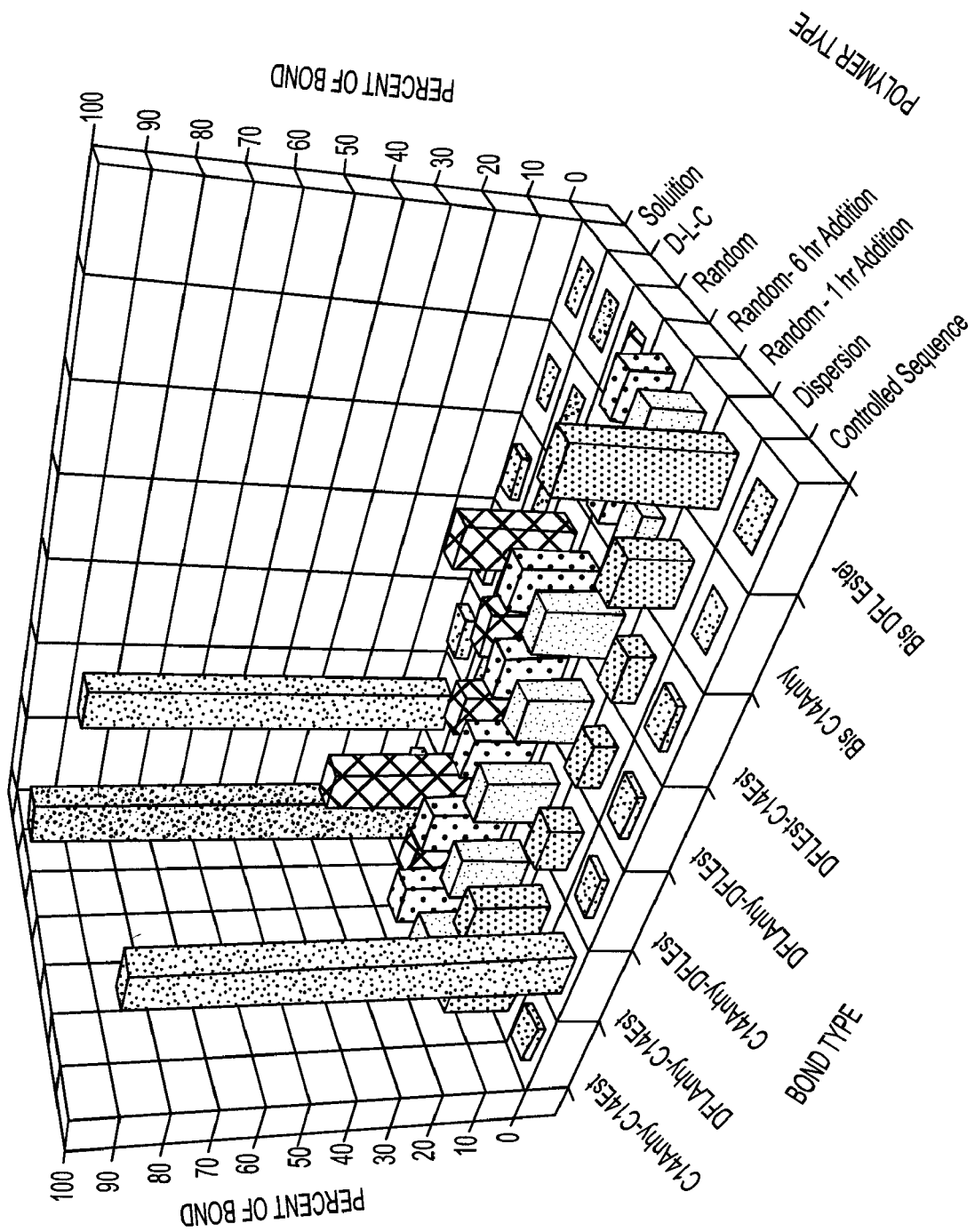

HIGH MOLECULAR WEIGHT POLYMERS, DEVICES AND METHOD FOR MAKING AND USING SAME

RELATED APPLICATIONS

This application is a divisional of and also claims priority to U.S. application Ser. No. 10/861,881, filed Jun. 4, 2004 and U.S. Provisional Application Ser. No. 60/475,766, filed Jun. 4, 2003, which are hereby incorporated by reference herein their entireties.

FIELD OF THE INVENTION

This invention relates to novel polymers that release active or activatable compounds having desirable properties, such as high molecular weight (MW), rigidity, stability, flexibility, adhesiveness, temperature range, etc. These polymers are useful for delivering compounds in situ, preventing and treating diseases, coating and protecting surfaces and articles, and for multiple other applications.

BACKGROUND

The safe and effective delivery of an active agent(s) to a specific location enables a site-specific delivery that generally is associated with lesser side effects than more widespread delivery. Site-specific delivery is particularly desirable for the treatment of localized health conditions such as cancer, cardiovascular disease, orthopedic conditions, dental conditions, wounds and auto-immune diseases such as arthritis or gastrointestinal (G.I.) conditions. Such site-specific delivery is also desirable for the protection of inanimate products including marine, construction, and articles that are exposed to water and biological contamination, among others. The use of polymers for drug delivery began in the 1960s as controlled-release oral formulations of an agent coated with a non-therapeutic polymer. Many such formulations, however, induce inflammation or host responses at the delivery site, or have low and/or unpredictable potency, breakdown products, non-zero-order release rates, burst effects (drug delivery spikes), or other untoward effects.

Devices such as stents, grafts, implants, and surgical and wound healing devices frequently induce, or are associated with, undesirable side effects that include pain, inflammation, swelling, infection, adjacent tissue hyperproliferation, capsule, and foreign body response, such as granuloma or fibroma formation surrounding an implant. Although more biocompatible polymer coatings and other surface technologies were developed in order to reduce these effects, the polymers employed are either not biodegradable, or are inherently highly inflammatory and unpredictable in nature. Non-biodegradable coatings are disadvantageous, in addition, because they suffer from fatigue over time and they delaminate in situ.

Polymers containing therapeutic and other agents incorporated into a polymer backbone have been described for use in formulations and devices for use in medical and other applications. Many polymers, however, have limitations associated with, for example, adhesion (or lack thereof), and temperature dependency that detract from their performance. Most of the problems stem from lack of control over polymer structure and growth during the synthetic process. Up to now, the polymeric backbone had been formed by standard reaction mechanisms, such as the formation of a phenolic di-ester and conversion to free aromatic diacids reacted to form a polymeric anhydride; known methods being represented by three main synthetic routes. In the first method, a mixed anhydride is prepared by reaction of a diacid with a low molecular weight aliphatic acid anhydride, e.g. acetic or propionic acid, and the mixed anhydride is heated under reduced pressure to form a polyanhydride in the molten state. Because of its low molecular weight, the acid anhydride may be discarded as a volatile by-product.

A second method involves reacting stochiometric amounts of an acid chloride of a diacid with a free diacid in the presence of an acid-acceptor, e.g. triethylamine, to generate a polyanhydride.

A third method relies on the polymerization-dehydration of a diacid with a dehydrating agent such as phosgene, diphosgene, triphosgene, or organophosphorus derivative, to obtain a pre-polyanhydride that is then polymerized.

Each of these methods, however, has disadvantages. The synthesis of polyanhydride-esters by melt condensation polymerization using a pre-polymer intermediate is generally conducted at high temperature, e.g. about 180 C, under vacuum. The increasing viscosity of the polymer melt as the reaction proceeds slows polymerization considerably and results in polymers of low molecular weight. Moreover, portions of the polymer melt undergo local decomposition due to the occurrence of localized high temperatures and incomplete mixing, and produce undesirable brownish polymers.

Certain applications require the use of resilient materials and tenacious films that require polymers of substantial molecular weight (MW), many times in excess of 100,000 Dalton. As is known in the art, the physical characteristics of a polymer depend on its molecular structure; discreet monomer units of regular structure tend to form crystalline or semi-crystalline materials, whereas polymers of irregular structure such as random copolymers tend to be amorphous. For other applications, polymers need to be solvent-cast into tough films or coatings, or molded under pressure into shaped articles, and then subjected to sterilization by ionizing radiation or electron beam bombardment, which seriously affect the polymer's molecular weight. It has heretofore been problematic to increase a polymer's molecular weight while retaining other desirable qualities. These polymers either fail to achieve a desired molecular weight, or form insoluble gels requiring extensive heating in the melt, or develop a high polydispersity index (MW/Mn), or both, due to the occurrence of side reactions. In the case of step-growth polymers, the polydispersity index (MW/Mn) often greatly exceeds a theoretical value of 2.0, possibly due to chain branching and/or interference from large ring macrocyclic oligomers.

Thus, there is a need for polymers, and for drug and other formulations and medical devices employing them, that exhibit a range of improved characteristics such as flexibility (or rigidity), adhesiveness, hardness, biocompatibility, processability temperature range, loading capacity, duration of delivery, and others, while at the same time limiting or avoiding one or more of the above described disadvantages. Many of these characteristics are achieved by producing high molecular weight polymers, and by careful control of the polymer structure and characteristics. In order to attain this goal, there is a need for novel synthetic processes that produces polymers of desired characteristics, in high yield, and with high purity.

SUMMARY OF THE INVENTION

This invention relates to the development of new processes for the preparation of high molecular weight polymers and there uses. A more complete appreciation of the invention and other intended advantages may be readily obtained by reference to the following detailed description of embodiments of the invention.

BRIEF DESCRIPTION OF THE FIGURES

FIG. 1. Bond type distribution.

DETAILED DESCRIPTION

I. Introduction

This invention relates to polymers, formulations, and medical devices employing them, all of which release, under appropriate conditions, one or more agents that are active upon delivery, or are activated in situ by hydrolysis or other processes. The polymers, compositions, and devices of the invention contain high loads of one or more agents, and can release active or activatable agents in high amounts, e.g. about 70 wt % to about 90 wt % agent(s). This makes them highly potent, and provides an excellent means for controlled or sustained delivery of an agent. These polymers and compositions may be used to form, or as coatings for, medical devices, or may be provided as a delivery formulation comprising nano- or micro-particles in the form of spheres or other desired shapes. The polymers, compositions, and devices may also be used as carriers for other agents to be released as the polymer degrades.

For historical reasons many of the polymers, their chemical structures, physical characteristics, and synthetic routes will be described in this patent with reference to certain anti-inflammatory drugs, e.g. salicylic acid and diflunisal, some of their characteristics being shown in Table 1a below. The overall concepts and description, however, are intended broadly to encompass all types of agents, formulations, and devices, and their applications.

TABLE 1a

Anti-Inflammatory Properties of Salicylic Acid and Diflunisal

| Property | Salicylic Acid | Diflunisal |
|---|---|---|
| Molecular Weight | 138 | 250 |
| Water Solubility | High | Very Low |
| Plasma half-life (hours) | 2.5 | 8 to 12 |
| Clinical Use | | |
| Single Oral Dose (mg) | 650 | 500 |
| Repeated Dosing | 650 mg (4 × Day) | 250 to 500 mg (2 × Day) |
| Plasma Levels* (μg/ml) | 150 to 300 | 50 to 190 |
| $LD_{50}$ (μg/kg) | 1,300 | 439 |
| Metabolism | | |
| No. Metabolites | ≧10 | 2 |
| Where Metabolized | Liver, Intestine Other Tissues | Liver, Intestine |

*Anti-Inflammatory Effectiveness

Exemplary polymers provided throughout this patent are tabulated in the following Table 1b.

TABLE 1b

Exemplary Polymers throughout the Patent

| Compound No. | Compound Name |
|---|---|
| 125PL | poly (ester-anhydride) made from monomer of (salicylic acid-C12-salicylic acid)$_n$ by a melt polymerization process. |
| 261PL | poly (ester-anhydride) made from monomer of (salicylic acid-C8-salicylic acid)$_n$ by a melt polymerization process. |
| 510PL | poly (ester-anhydride) made from monomer of (salicylic acid-C6-salicylic acid)$_n$ by a melt polymerization process. |
| 657PL | poly (ester-anhydride) made from monomer of (diflunisal-C14-diflunisal)$_n$ by a melt polymerization process. |
| 749PL | poly (ester-anhydride) made from monomer of (salicylic acid-C10-salicylic acid)$_n$ by a melt polymerization process. |

Note:
n is a positive integer showing the degree of polymerization.

II. Glossary

The following definitions are used throughout this patent, unless otherwise indicated.

The article "a" and "an" as used herein refers to one or to more than one, i.e. at least one, of the grammatical object of the article. By way of example, "an element" means one element or more than one element.

As used herein, an "agent" is a chemical compound that is suitable for incorporation into the polymer, formulation, or device of this patent, and includes "active" and "activatable" agents; an "active agent" refers to a substance that has a physiological effect when present in a living system; and an "activatable agent" refers to an agent or its precursor that may be activated either upon or after its release by any mechanism.

An agent may be a compound that has a use. For example, an agent may be a marker, a compound that has an effect for a certain application, be it for use to ascertain, diagnose, foster or impede biological life, or otherwise. An agent may be a compound suitable for use in construction, land and marine applications. It may be a drug or therapeutic compound or precursor of a compound used to treat a specific disease or medical condition. The active agent may be "biologically active," meaning that the active agent is active and/or exhibits some effect on a biological system, whether plant, animal, when applied to a living system or to the inanimate world.

The active agent may also be "therapeutically active," meaning that the active agent has therapeutic properties in a living system, such as aiding in the prevention or treatment of an undesired occurrence or condition in the living system.

A "physiological effect" may be, for example, any effect on the functioning of an organism, such as, e.g., alteration of normal function, alteration of abnormal function, and/or restoration to normal function. A physiological effect may include, but is not limited to, binding to a biomolecule, i.e. DNA, protein, carbohydrate, lipid, inhibition of enzyme activity, and sequestration of small molecule cofactors, i.e. metal ions, amino acids. Biologically active compounds that may be incorporated into the polymers of the invention either possess, or are chemically or biologically added, at least two functional groups capable of forming a breakable bond or linkage, e.g. an ester, thioester, amide, thioamide, carbonate, and the like, within the polymer. Such bonds or linkages, upon erosion, breakage, or hydrolysis of the polymer in situ, will release the agent(s). Examples of functional groups for the agent or compound comprise, e.g. hydroxy (—OH), mercapto (—SR), amine (—$NR_2$, or —$NR_3^+$) or carboxylic acid (—COOH), where R may be H or a ($C_1$-$C_{20}$) substituent that may be substituted with O, N, P, or halogen), among others.

The term ester linkage refers to —OC(=O)— or —C(=O)O—; the term thioester linkage refers to —SC(=O)—, —OC(=S)—, —C(=O)S—, or —C(=O)S—; the term amide linkage refers to —N(R$^2$)C(=O)— or —C(=O)N(R$^2$)—, the term urethane or carbamate linkage refers to —OC(=O)N(R)— or —N(R$^2$)C(=O)O—, wherein each R$^2$ is a suitable organic radical, such as, for example, hydrogen, (C$_1$-C$_{20}$)alkyl, (C$_3$-C$_{20}$)cycloalkyl, (C$_3$-C$_{20}$)cycloalkyl(C$_1$-C$_{20}$)alkyl, aryl, heteroaryl, aryl(C$_1$-C$_{20}$)alkyl, or heteroaryl(C$_1$-C$_{20}$)alkyl; and the term carbonate linkage refers to —OC(=O)O—.

"Heteroaryl" refers to a radical attached via a ring carbon or heteroatom, or via an appended chain of an aromatic ring containing 3 to 20 ring atoms consisting of carbon and heteroatoms comprising O, S, P, or N, which may be substituted by R, wherein R may be absent or H, O, halogen, (C$_1$-C$_{20}$) alkyl, (C$_3$-C$_{20}$)cycloalkyl, (C$_3$-C$_{20}$)aryl, including phenyl, benzyl, and bicyclic structures, all of which may be further substituted by a heteroatom, e.g. a (C$_3$-C$_{20}$)heterocyclic group, particularly a benzyl derivative or, one derived by fusing a propylene, trimethylene, or tetramethylene diradical thereto.

As used herein, "administering an active agent near the site" means applying the agent at, or proximal to, a given site to produce a desired or stated therapeutic effect in a localized manner, e.g. to reduce bone resorption, stop bleeding, or foster bone growth at the site.

"Alkyl", "alkoxyl", etc. may denote both straight and branched groups; a reference to an individual radical such as "propyl" may denote a straight chain radical; a branched chain isomer such as "isopropyl" being specifically referred to.

The term "amino acid" refers to residues of the natural amino acids, e.g. the D or L forms of alanine (Ala), arginine (Arg), asparagine (Asn), aspartic acid (Asp), cysteine (Cys), glutamic acid (Glu), glutamine (Gln), glycine (Gly), histamine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val), and non-natural amino acids, e.g. phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine, among many others. The term "amino acid" also comprises natural and non-natural amino acids bearing a conventional amino protecting group e.g. acetyl or benzyloxycarbonyl, as well as natural and non-natural amino acids protected at the carboxy terminus, e.g. as a (C$_1$-C$_6$) alkyl, phenyl or benzyl ester or amide; or as an α-methylbenzyl amide. Other suitable amino and carboxy protecting groups are known to those skilled in the art, and are included within the context of this invention. See, for example, Greene, T. W. and Wutz, P. G. M. "Protecting Groups In Organic Synthesis", Second Edition, New York, John Wiley & Sons, Inc., 1991, and references cited therein.

As used herein, an agent is "appended" to a polymer when the agent is bonded or complexed to the polymer as a side chain or side group, but is not part of the polymer backbone. The agent is bonded to the polymer preferably through a breakable linkage that will release it when applied or administered according to the methods of the invention. For example, an agent or compound may be linked to a polymer through a hydrolyzable linkage such as an anhydride or ester linkage. Others, however, are also suitable.

"Aryl" denotes any aromatic residue, including phenyl and ortho-fused bi- or tri-cyclic carbo- or hetero-cyclic residue having about 4 to 20 ring atoms in which at least one ring may be aromatic.

As used herein, an agent or functional group may be "associated" with the polymer by one of many forms, including by direct, linear integration (i.e. chemical bonding) into the polymer backbone, as a side chain or side residue chemically bonded to the polymer backbone not part of the backbone, electrostatic bonding to the polymer backbone, linkage to the polymer backbone through a linking group, pendent (i.e. an off-shoot of the backbone) neither oligomeric nor polymeric, attachment to the polymer backbone, or bonding to one or more endings of the backbone. The association used will depend on the functional characteristics (e.g., number and type of reactive groups) of the functional group.

A substance is said to be "bioabsorbable", but not necessarily biocompatible or biodegradable, when it may be absorbed by, whether integrated or not into, a living system in which it is placed.

A substance is said to be generally "compatible", e.g. "biocompatible", when it has the properties of being compatible with a system, e.g. a living system, and is not detrimental to the general existence and functioning of the system, e.g. neither toxic to, nor causes a detrimental reaction (e.g. immunological reaction) in a living system, so that it would make it undesirable to continue its use. A substance is said to be "degradable", e.g. "biodegradable", when it is broken down into components smaller than its original size when present in the target system, e.g. a living system.

A "diagnostic agent or compound" refers to a substance that may be employed to assess a certain status or presence by a known means.

A "tracer" or "marker" refers to an agent or compound that, although it may or may not have its own activity, may be located when placed in a pre-determined position, or it may be followed to ascertain where it lodges, therefore providing information on the path it followed and its current location.

"Therapeutically active compounds", or "detectable, diagnostically, veterinarily or therapeutically active compounds" include diagnostic and therapeutic agents that provide a diagnostic, preventative or therapeutic effect when administered to a subject, e.g. an animal such as a mammal including a human.

A "functional group" refers to a chemical residue or moiety that may be incorporated into a polymer, e.g., into an ester, thioester, or amide linkage of a polymer as discussed in detail below, such that it releases the agent or its precursor upon erosion or breakage of the polymer, e.g. hydrolysis, enzymatic breakage for example by esterases. These groups may independently be a hydroxy group (—OH), a mercapto group (—SH), an amine group (—NHR), a carboxylic acid (—COOH), a halo that comprises fluoro, chloro, bromo, or iodo, and others known in the art.

The term "peptide" refers to sequences of about 2, 3, or 5 to about 15, 20, or 35 and more amino acids as defined above, or peptidyl residues that may be linear or cyclic, such as those that may be prepared or result from the formation of disulfide bridges between two cysteine residues. Peptide derivatives may be prepared as disclosed in U.S. Pat. Nos. 4,612,302; 4,853,371; 4,684,620, or as described in the Examples provided below. Peptide sequences specifically provided in this patent are written with the amino terminus on the left and the carboxy terminus on the right.

As used herein, "physiological conditions" are the conditions in a physiological system or environment, such as a mammal, e.g. a human, and may be "normal physiological conditions" such as those encountered in a normal, healthy subject or patient, or "abnormal physiological conditions" such as those in an unhealthy, sick, or injured subject or patient. Physiological conditions may be found, for example, inside a mammal, or on the surface of a mammal, such as in skin or hair.

An agent is considered to be "physiologically irrelevant" when it does not perform a physiological or biological function, such as for example when incorporated into a polymer backbone. The fact that the agent is chemically coupled in the polymeric structure renders it unavailable to interact with a target.

An agent may be considered "physiologically inactive" when it is in a form in which it may not perform a biological function, even when it is freely available in the biological milieu.

An agent is considered "physiologically relevant" when in a chemical form in which it may perform its desired biological function, e.g. interacting with a biological molecule, or sequestering of a relevant substance.

Even though it is present in a physiologically relevant form, an agent may not be "active" in a physiological environment. The agent may be, for example, dispersed in, or sequestered inside empty spaces of the polymer, rendering it unavailable to the surrounding biological milieu. As a result, even though it is present in a biologically active form, the biological activity of that active agent is nill until released from the polymer. A physiologically relevant active agent is said to be "physiologically active" when it is available to the surrounding biological milieu and actively involved in its biological role.

As used herein, the term "healing" means the repair of a defect or non-normal condition or state, and it may be applied to a living or non-living entity. When applied to a living entity healing refers to the restoration of health or the process of a return to health. When applied to a non-living entity, "healing" refers to the return to a normal or acceptable state, or to the fixing of a condition so that the entity is operational.

The inventive polymers form biodegradable bonds within the backbone of the polymer that may be broken by regular hydrolysis, proteolysis, or other biological or biochemical processes when placed in contact with an aqueous environment, microorganisms, body tissues, fluids, and the like.

A substance is said to be "resorbable", e.g. "bioresorbable", when its material is a naturally occurring material, e.g. in a living system, and is capable of being absorbed by, and integrated into, a system, e.g. the living system, when placed into it or when created and subsequently placed in the system.

As used herein, the term "dispersed through the polymer matrix" means that an agent or compound is located within a matrix, for example a polymer by mixing, spreading, sprinkling, thoroughly mixing, physically admixing, or dispersing in the polymer matrix, among others, so that it may be released in a controlled manner over a period of time when placed in a system, e.g. within a living host.

As used herein, the term "dissociate" indicates that an agent, compound, or substance is separated or broken into smaller parts that may be chemically similar to the undissociated whole or they may be chemically dissimilar to the undissociated whole. Chemically dissimilar dissociation products may be heterogeneous or homogeneous with respect to either chemical properties or size, or both. Dissociation products may also be able to recombine to recreate the original undissociated whole, or they may remain permanently dissociated. Dissociation may occur spontaneously, as an inherent property of the undissociated whole, or as a result of a physical or chemical process, such as hydrolysis of the undissociated whole.

The term "formed into" includes a polymer, compound, composition, or formulation of the invention that may be physically placed into various shapes, geometries, structures and configurations including, but not limited to a film(s), coating(s), fiber, rod, coil, suture, closure, sealer, sphere, pin, corkscrew, hook, cone, pellet, tablet, tube (smooth or fluted), disc, membrane, formulations comprising microparticles, nanoparticles, and/or "biobullets" (i.e., bullet shaped), seed (i.e., bullet shaped or targeted seeds), sleeve, cuff, free standing film, sheath, wrap, tube, cuff, stitches, formed gel, etc.

A "sleeve" is a physical conformation of a compound, agent or article that is placed adjacent to and fits around or covers a second compound, agent or article, for example a medical or therapeutic device. A plastic coating surrounding a metal rod may be considered to be a sleeve for the rod. A sleeve may also be placed adjacent to a separate compound, agent or article without completely enclosing the latter. A sleeve may describe a compound, agent or article that is formed into, for example, a coating, a film, a sheath, a wrap, a tube, a cuff, or a formed gel partially or wholly surrounding a second compound, agent or article, such as a medical device or implant.

As used herein, a substance is said to be solid when it has three dimensions and has the properties of a solid; namely it is not in liquid or gaseous form. For example, a piece of paper, a metal rod, a steel needle are all considered to be solids in the context of this patent.

A substance is said to be "semi-solid" when it has some properties of a solid, and some of a liquid; for example it is easily deformable by physical or chemical action. For example, gel and clay are "semi-solids" in accordance with this definition.

As used herein formulated for "controlled release" refers to an agent formulated to be released over an extended period of time when administered according to this invention. For example, the agent may be formulated for release over a period of at least about 1, 2, 5, or 10 hour(s), about 1, 2, 5, 10, 20, 40, or 90 days, about 1, 2, 4, 6, 9, or 12 months, or 1 or more years. The agent is formulated for release over about 1-10 days. For the treatment of hard tissue, the agent is formulated for release over about 8, 15, or 30 to about 45, 60, or 90 days, and for the treatment of soft tissue over about 1, 2, or 3 to about 5, 10, or 30 days.

As used herein, the term "hard tissue" includes tissue that has become mineralized, such as, for example, bone, cartilage, or both.

The term "host" includes animals and plants, such as, e.g., a mammal, including a human. A host may also be a "human patient" or an "non-living environment" to which the polymer is applied.

For purposes of the present invention a "low molecular weight agent" includes any compound with, but not limited to, one carboxylic acid group and at least one amine, thiol, carboxyl, amide, alcohol or phenol group within its structure, wherein the compound has a specific activity, e.g. pharmaceutical activity, and up to about 1000 molecular weight.

By "device" it is meant a structure that is formed of, or covered by, a polymer of the invention. Devices may be used for different applications on inanimate and living systems.

A "medical device" or "medical implant" refers to a therapeutic device or a therapeutic implant, respectively, that is used specifically for a medically-related purpose. For example, a bone "screw", "cuff", or "pin" are both medical devices and medical implants. A device, whether therapeutic or otherwise may comprise more than one component. A therapeutic device that is either temporarily or permanently placed either partially or wholly inside a living system may also be referred to as a "therapeutic implant", and may be active when implanted, or activated after implantation. The administration or application of an agent "to" or "near a tissue" refers to the delivery of agent to a location proximal to, or in direct contact with, the tissue to produce the desired localized therapeutic effect. A "veterinary device" refers to a device that is adapted specifically for use in an animal, whether wild, domesticated, marine, zoological animals, and the like.

III. Structure of the Inventive Polymers

A. Introduction

The polymers of the invention are suitable for delivering an agent(s) or compound(s) to a pre-selected site, such as a biocompatible and biodegradable polymer that is capable of releasing at least one agent(s) upon degradation and/or hydrolysis of the polymer under appropriate conditions, e.g. physiological conditions, for monitoring, diagnostic, prophylactic and therapeutic applications. Suitable polymers include backbones comprising an agent(s) and are suitable as delivery systems. Such polymers may incorporate an agent(s) as a repeating unit of the backbone, which units are linked by labile bonds such as esters, thioesters, amides, thioamides, urethanes, carbamates, carbonates, ethers, azo links, and carbonates, among others.

When delivered into a host, such as a mammal, and more specifically a human, the polymer will break down over a period of time and release the agent(s). In one embodiment, a suitable polymer degrades over a period of time to produce relatively high, localized levels of an agent(s) to deliver an enhanced therapeutic effect while minimizing side effects associated with the systemic delivery of drugs. In one embodiment, a suitable polymer is biocompatible. In another embodiment, the polymer is biodegradable and demonstrates favorable solubility and processability, as well as degradation properties suitable for the desired use. In yet another embodiment, the active agent is released over a period of time as the polymer hydrolyzes under physiological conditions, providing for an extended-release formulation that provides a consistent and continuous source of the therapeutic substance for an extended period of time. Suitable polymers for use in the present invention include polyesters, such as poly(ester-esters) and poly(ester-carbonates), polyamides, polycarbonates, and polyanhydrides such as poly(anhydride-esters), and poly(azo-anhydrides), among others. Examples may found in U.S. Pat. Nos. 6,328,988; 6,365,146; 6,468,519; 6,486,214; 6,497,895; 6,602,915; 6,613,807; 4,916,204; and 4,868,265; U.S. Published Patent Applications 2002/0071822 A1; 2002/0106345 A1; 2003/0035787 A1; 2003/0059469 A1; 2003/0104614A1; 2003/0170202A1; U.S. Ser. Nos. 09/508,217; 10/368,288; 10/622,072; 10/646,336; 10/647,701; WO 99/12990; WO 01/28492; WO 01/41753; WO 01/58502; WO 02/09767; WO 02/09768; WO 02/09769; WO 03/005959; WO 03/046034; WO 03/065928; and WO 03/072020; and Erdmann, L., Uhrich, K. E., Biomaterials, 21: 1941-1946 (2000), the relevant portions of all of which being incorporated herein by reference. The polymer of the invention may be a polyanhydride, preferably having a backbone comprising one or more groups that will release a compound upon hydrolysis or enzymatic degradation of the polymer.

The polymers of this invention have valuable physical and chemical properties that are useful for a broad number of applications, such as the delivery of biologically active compounds, the preparation of formulations, tamponades, films, coatings, devices, implants, and coated devices. The polymers of the invention may be readily processed into pastes, films, coatings, nanoparticles, microparticles, gels, powders, sprays, creams, ointments, tablets, capsules, emulsions, solutions, suspensions, granules, fillers, covers, linings, grids, meshes, gramps, and fibers for use in the design of articles, e.g. devices and implants, of different geometric shapes using techniques known in the art, such as solvent casting, solution or suspension spraying, compression molding or extrusion. Applications of these products may be found in every aspect of modern life, from coatings for articles of use in the home, such as to protect bathroom, laundry room, and kitchen facilities and their polymeric, metal and ceramic surfaces, pictures, furniture, and other articles from mildew, dust deposition, microbial contamination, and the like, to marine, construction, medical, veterinary, agricultural, dental, surgical, orthopedic, laundry, household, and hair and cosmetic uses. Some applications will benefit from incorporating short half-life polymers that will disappear after a pre-determined initial stage. Examples of these are laundry products, cosmetics and hair products, and the like that only need be active until the next application. Coloring products, however, may be made for short or long lasting effects as is known in the art. The color of short acting polymers will wear out after a few washes whereas the longer half-life polymers will permanently alter the color of hair and other materials. Other applications are more suited for the use of polymers of longer half-lives that will preserve the activity of the incorporated agent for extended periods of time. Examples of the latter are household applications such as coating of surfaces with a prolonged half life polymer that will deliver a desired agent for periods of months or years, or for the duration of the life of the article if the polymer is incorporated into the article itself or mixed therein with other polymers or natural substances such as wood derivatives and the like.

B. General Formulas

The present invention provides a compound of formula H—Y—C(=Y)—$R^1$-A-$R^1$—C(=Y)—Y—H ("Formula 1a"), wherein each $R^1$ comprises, independently from one another, a residue(s) of a diagnostically, traceably, biologically or therapeutically active or activatable agent(s) or compound(s) that is(are) released upon polymer degradation; each Y comprises independently O, S, $NR^2$, where $R^2$ comprises H, alkyl, alkenyl, alkynyl, all of which may be substituted with O, N, S, P or halogen; each A, independently from one another, comprises ester, amide, thioester, azo, or thioamide, or their combination.

In another embodiment, the compound, and the polymer comprising unit(s) of this compound, comprise the chemical formula H—Y—C(=Y)—$R^1$-A-L-A-$R^1$—C(=Y)—Y—H ("Formula Ib"), wherein all variables are defined as above; and L comprises a linking group. In one embodiment, A comprises an amide, an ester, or both, and in another embodiment, A comprises a thioamide, a thioester, or combinations thereof. Typically, the $R^1$ may comprise monomers, dimmers, trimmers, tetramers, and higher metric units of the agent's residue. These individual residues may be bound directly to one another, or through a linking group(s). Suitable linking groups are those described in this patent and include all other suitable functional groups and residues known in the art.

The polymers of the present invention comprise an agent(s) or compound(s), and an optional linker group(s) bonded through a labile linkage such as an ester, thioester, amide, thioamide, azo, anhydride, carbonate, ether, thioether, or a combination thereof. Due to the presence of the ester, thioester, amide, and/or thioamide linkages, the polymers may be hydrolyzed, enzymatically, or otherwise degraded under physiological conditions to provide the biologically active compounds. Thus, the polymers of the present invention are particularly useful as for controlled release of agents, whether for biological or other types of applications, and as a means for localized delivery of agents to a selected site or target. The polymers of the invention may be used, for example, for the localized delivery of an agent to a targeted site within the human body, e.g. within or near a tumor, where the polymer provides a localized, controlled release of the agent. The polymers prepared using the processes of the invention may have an average molecular weight ($MW_{AVE}$) of about 1,500; 3,000; 10,000; 30,000; 50,000; 100,000; 250,000; 500,000; or 1,000,000 Dalton to about 20,000; 50,000; 100,000; 200,000; 350,000; 500,000; 750,000; 1,000,000; 1,200,000; 1,350,000; or 1,500,000 Dalton, and even higher, as determined by Gel Permeation Chromatography (GPC) relative to narrow molecular weight polystyrene standards as is known in the art. The present polymers exhibit a backbone linking one or more agents or compounds into polymeric delivery systems. The polymers are typically biocompatible and biodegradable, and preferably demonstrate excellent solubility and processability, as well as suitable degradation properties, such as erodability, due to the presence of bonds such as anhydride, ester, amide, urethane, carbamate, azo, and carbonate, among many others, that are breakable under specified conditions. Suitable polymer bonds for use in the present invention include, for example, polyesters, polyamides and polyanhydrides of the type described in WO 99/12990; U.S. patent application Ser. Nos. 09/917,231; 09/917,194; 09/508,217; 09/422,294; 09/732,516; 60/220,707; 60/261,337; 60/058,328; and 60/220,998.

The invention provides a compound of the formula

-(M)$_m$- (IIa)

B-[(M)$_m$]$_y$ (IIb)

Where M is a moiety suitable for polymerization and B is a moiety with multiple functional groups. M represents the number of repeating units, e.g., M may be about 2, 5, 10, 15, 20, 30, 50 to about 100 or any higher number as needed to reach a desired average molecular weight of about 1,500; 3,000; 5,000; 7,500; 10,000; 20,000; 50,000; or 100,000 Dalton to about 50,000, 75,000; 100,000; 250,000; 500,000; 1,000,000, and higher Dalton; and y is a positive integer between 2-8. B can be a moiety with multiple functional groups suitable to start polymerization such as, e.g., COOH, NH$_2$, SH, and others. Examples of compounds which could be used as B are, 1,3,5-benzene tricarboxylic acid, 1,2,3,4-butane tetracarboxylic acid, cis-aconitic acid, and trans-aconitic acid.

In one embodiment, M comprises one or more units of the chemical formulas

—R$^1$-A-R$^1$— (IIIa) and

—R$^1$-A-L-A-R$^1$— (IIIb)

wherein R$^1$ independently comprises one or more residues comprising an agent(s) that is released upon polymer degradation; A independently comprises a labile group such as amide, thioamide, ester, thioester, carbonate, azo, or thiocarbonate, among others; and L, which may or may not be present in the polymer backbone, independently from one another, comprises one or more units of a linking residue(s). Such a polymer is particularly useful for the administration of a combination of more than one agent. In one embodiment, R$^1$ comprises a monomer, dimer, trimer, tetramer, pentamer, and higher mers such as a decamer, dodecamer, hexadecamer, etc., of the same or different agent(s).

The polyanhydride made of formulas (IIIa) and/or (IIIb) or combinations thereof serves as the backbone of a delivery system that provides a controlled delivery of an agent(s) or compound(s) to any targeted site, e.g., of a host such as a human, animal, plant, or article of manufacture. In one embodiment, the polymer of formula (III) comprises a low molecular weight agent(s) with functional groups such as carboxylic acid, thioacid, amine, amide, thiol, thioamide, carbonate, azo, alcohol or phenol, among many that form labile bonds, including those comprising heteroatoms such as P, S, N, and the like. In another embodiment, the polymer comprises a unit(s) comprising formula (IIIa) and/or (IIIb), wherein each R$^1$, independently from one another, comprises and is capable of releasing an aromatic agent(s), such as an NSAID, or any other agent(s) to be delivered by the polymer, some of which are listed below. Examples of suitable salicylates include, but are not limited to, diflunisal, diflucan, thymotic acid, 4,4-sulfinyldinailine, 4-sulfanilamidosalicylic acid, sulfanilic acid, sulfanilylbenzylamine, sulfaloxic acid, succisulfone, salicylsulfuric acid, salsallate, salicylic alcohol, salicylic acid, orthocaine, mesalamine, gentisic acid, enfenamic acid, cresotic acid, aminosalicylic acid, aminophenylacetic acid, acetylsalicylic acid, and the like. The identification of a suitable R$^1$ and A to release an aromatic agent(s), e.g., a salicylate, may be readily determined by those of ordinary skill in the art without undue experimentation. In one embodiment, the active agent is salicylic acid or one of its derivatives that are well known in the art. In another embodiment suitable azo monomers are polymerized to provide polyazo compounds and then polyazo anhydrides. In a preferred embodiment the polymer may be a polyester or a polyamide, and it comprises units containing at least two free hydroxyl, phenols, amines, or combinations thereof available for co-polymerization with carboxylic acids or bis(acyl) chlorides. Another preferred polymer may comprise one or more units of formula

—R$^1$-A-L-A- (IV)

wherein all variables are as defined above. Another exemplary polymer of the invention is a co-polymer that comprises one or more units of formula

—R$^1$-A-L-A-R$^1$-A- (IX)

wherein all variables are as defined above. In one embodiment, the polymer comprises one or more units of formula.

—R$^2$-A-L-A-R$^3$-A-L-A- (V)

wherein R$^2$ and R$^3$, independently from one another, comprise a residue that will yield a compound(s) upon polymer hydrolysis or enzymatic degradation; and other variables are as defined above. Polymers where R$^2$ and R$^3$ comprise residues that will yield different compounds upon polymer degradation are particularly useful for the administration of combination therapy. Another preferred embodiment comprises a co-polymer of one or more units of formula

—R$^1$-A-L$^2$-A-R$^1$-A-L$^3$-A- (VI)

wherein L$^2$ and L$^3$, independently from one another, comprise a linking group; each A, independently from one another, comprises amide, thioamide, carbonate, azo, ether, thioester, or ester, among labile bonds; and each R is independently a group that will yield a active compound upon hydrolysis or enzymatic degradation of the polymer. In this embodiment L$^2$ and L$^3$ are linking groups that impart different physical properties to the polymer that makes them particularly useful for customizing the physical characteristics of the polymer for a specific application. In one embodiment, the active agent is salicylic acid, and the polymer comprises a poly(ester-ester).

In one embodiment, the polymer comprises one or more units of formula

-A-R$^1$—N=N—R$^1$-(A-L)$_n$- (VIIa)

and/or units of formula

-A-R$^1$—N=N—R$^1$-(A-L)$_n$- (VIIb)

wherein each R$^1$—N, independently from one another, comprises a group that will provide a biologically active compound upon polymer degradation; each A, independently from one another, comprises anhydride, amide, thioamide, thioester, carbonate, enter, or ester; L comprises a linking group as already described; n is 0 to 10. Suitable monomers are polymerized to provide the polyazo compounds. In one embodiment, the polyazo compound comprises at least one free amine group to form the azo group and at least one free carboxylic acid, alcohol or amine available for self-polymerization or co-polymerization with other carboxylic acids or bis(acyl) chlorides. In one embodiment, the polymer comprises more than one agent(s) incorporated into a poly(azo-anhydride) that serves as a polymeric drug delivery system for oral delivery of a cancer drug. The polymer may have two, three, or more different R groups, each of which will provide a different agent(s) upon polymer degradation, and each R group may have one or more repeats of the same or different agent(s), e.g. monomer, dimer, etc. In one preferred embodiment, the polymer comprises a non-steroidal anti-inflammatory agent (NSAID), such as, e.g., salicylic acid and/or diflunisal. Such polymers may comprising repeating units of chemical formula II, III, VII and/or X, or combinations thereof.

The polymers of the invention may be prepared by any suitable method known in the art. Examples are those described in WO 99/12990; U.S. Ser. Nos. 09/917,231; 09/917,194; 09/508,217; 09/422,294; 09/732,516; 60/220,707; 60/261,337; 60/058,328; and 60/220,998; and Conix, Macromol. Synth. 2: 95-99 (1966). When specific characteristics are desired, the polymers may be prepared using processes described herein.

In another embodiment the polymer comprises poly(ester-anhydride) bonds. One preferred polymer comprises units of the chemical formula

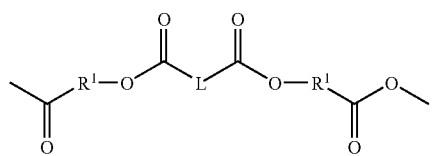

(II)

wherein all variables are as defined above.

In another embodiment the polymer comprises poly(ester-ester) bonds. One preferred polymer comprises units of the chemical formula

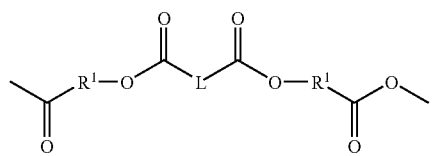

(X)

wherein all variables are as defined above.

In another embodiment the polymer comprises poly(ester-carbonate) bonds. One preferred polymer comprises units of the chemical formula

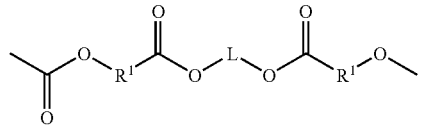

(XI)

wherein all variables are as defined above.

The polymer may have two, three, or more different $R^1$ groups, each of which may provide a different agent(s) upon polymer degradation. Such polymers are particularly useful for the application or administration of a combination of two or more agents to a host, such as an animal or plant, or an article of manufacture. In another embodiment the polymer comprises a homopolymer, and in another it comprises a co-polymer.

The polymer(s) described herein will release their agent(s) when placed at a pH of about 3, 4, 5, 6, 7 to about 8, 9, 10, 11, 12, 13, and higher over a period of time of about 1, 2, 3, 5, 10 20, 50, 75 days to about 2, 3, 5, 7, 9, 12, 24 months or longer. When the polymer is placed at a pH below its pKa it will degrade slowly, for example over a period of 6 months or longer. When $R^1$ comprises a drug residue(s), the polymer may function as a drug(s) delivery system that provides a controlled effective amount of the agent(s) as a function of polymer degradation at any pre-determined site to which it is applied, or delivered. Polyanhydride materials have been extensively described. See, for example, U.S. Pat. Nos. 4,757,128; 4,997,904; 4,888,176; 4,857,311; 5,264,540; and WO 99/12990; WO 02/09769; WO 02/09767. In general, anhydride polymers of higher average molecular weights such as, e.g., polymers described herein, possess unexpected and advantageous properties, such as greater mechanical strength and higher stability, that polymers of lower average molecular weights do not possess. Because of this higher molecular weight, these polyanhydrides may be laid as harder and thicker coatings. In one embodiment, the polymer of the invention may have an average molecular weight ($MW_{AVE}$) of at least about 200,000, and preferably above about 250,000 Dalton, and up to 1,000,000 Dalton and higher.

The polymer of the invention typically have a glass transition temperature ($T_g$) about −10, −5, 0, 10, 30, 50 to about 60, 70, 80, 100, 130, 160, 200 C, with a most preferred $T_g$ is in the vicinity of or below about 50 C.

The polymer may comprise any number of agents, whether biologically, diagnostically, prophylactically, therapeutically or otherwise active or inactive, or whether the agents have other activities that make them suitable for applications other than to microorganisms, plants, animas, humans, or articles of manufacture. In fact any type of agent that may be polymerized or appended, or mixed, blended, dispersed or otherwise incorporated into a polymeric formulation, and released from its structure is suitable for use in this application. Such agent(s) may be loaded in amounts of about 0, 5, 10, 15, 20% w/w to about 25, 30, 35, 40, 45, 50% w/w, although other amounts are also contemplated including up to 70 wt %, and 90 wt %, and even higher.

In one embodiment, the polymer comprises a non-steroidal anti-inflammatory agent (NSAID) such as salicylic acid and/or diflunisal, and units of chemical formula I, among others, or their combinations, where each $R^1$ may be a monomer, dimer, trimer, tetramer, or higher mer of an agent(s). In another embodiment the polymer is combined with one or more agents in any suitable manner, such as by physically admixing, blending, embedding, appending, or dispersing the additional agent(s) in the polymeric matrix. The agent(s) may be also incorporated into the backbone, chemically linked in the backbone directly or through a linker or spacer, directly or indirectly chemically linked to a chemical group attached to the backbone, or electrostatically or in any other manner attached to the polymer or its backbone. In one embodiment, the active agents may be attached to repeating units of the polymers of the present invention by covalent bonds linked to an aromatic (Ar) ring or an linear, branched, or cyclic aliphatic (R) organic residue, providing for sustained release of the agent(s). In another embodiment the agent(s) may merely reside in the unoccupied spaces present in the polymer. In another embodiment, the agent(s) form(s) a salt(s) with the polymer or its backbone. In still another embodiment the agent is located in the unoccupied spaces of a polymer and is present as a homogeneous functional group, or is incorporated into a salt(s), micelle(s), liposome(s), or heterogeneous aggregate(s). The polymer may comprise various segments comprising one or more similar or different residues of an agent(s) that will be released either directly or indirectly by polymer degradation. The polymer may also comprise a second or additional agent(s) that is physically admixed, embedded or dispersed in, or combined with the polymer as is known in the art.

In another embodiment, the compound(s), and the polymer comprising unit(s) of the compound(s), of chemical formula (Ia) or (Ib) shown above comprises a diagnostically, traceably, biologically or pharmaceutically active or activatable agent(s) or compound(s) of the chemical formula

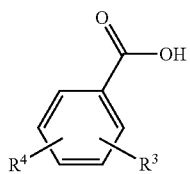

(II)

wherein, $R^3$, comprises hydroxy, amine, thiol, or an aliphatic or aromatic organic residue that may further comprise hydroxy, amine, or thiol; and $R^4$ comprises H, halo, $NHR^5$, a cycloaliphatic residue, or aryl, and may be further substituted with HO, halo or halo($C_1$-$C_4$)alkyl; wherein $R^5$ is H, ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$)alkyl, or heteroaryl($C_1$-$C_6$)alkyl or ($C_1$-$C_4$)alkyl carbonyl. Preferred $R^4$ groups include but are not limited to —$NH_2$, —NHAc, Cl, 2,4-difluorophenyl, chloromethyl, difluoromethyl, —$CF_3$ and the like. The diacids of chemical formulas (Ia) and (Ib), including those comprising monomers, dimers, trimers, tetramers, and higher numbers of units of the agent(s) or compound(s), may be incorporated into the polymer backbone of this invention, and may be employed also by appending, dispersing, blending, or admixing them, in the polymer. Biocompatible, hydrophobic polyanhydride matrices of this invention are suitable for use in many applications, including surgical, wound healing, hemostatic, orthopedic and dental applications, such as prosthesis and implants. The biodegradable polymer networks of the invention for use in these and other applications may be formed by polymerizing anhydride pre-polymers and employing the method(s) of this patent. Controlled or sustained release polyanhydrides prepared as described in this patent release biologically or pharmaceutically active agents, e.g. salicylate or difluorophenyl derivatives, or their precursors, e.g. pharmacophores, by in vivo biodegradation, as well as other agents that are incorporated either into the polymer backbone, or appended thereto, or added into a formulation of the polymer.

Some other suitable polymers are shown below:

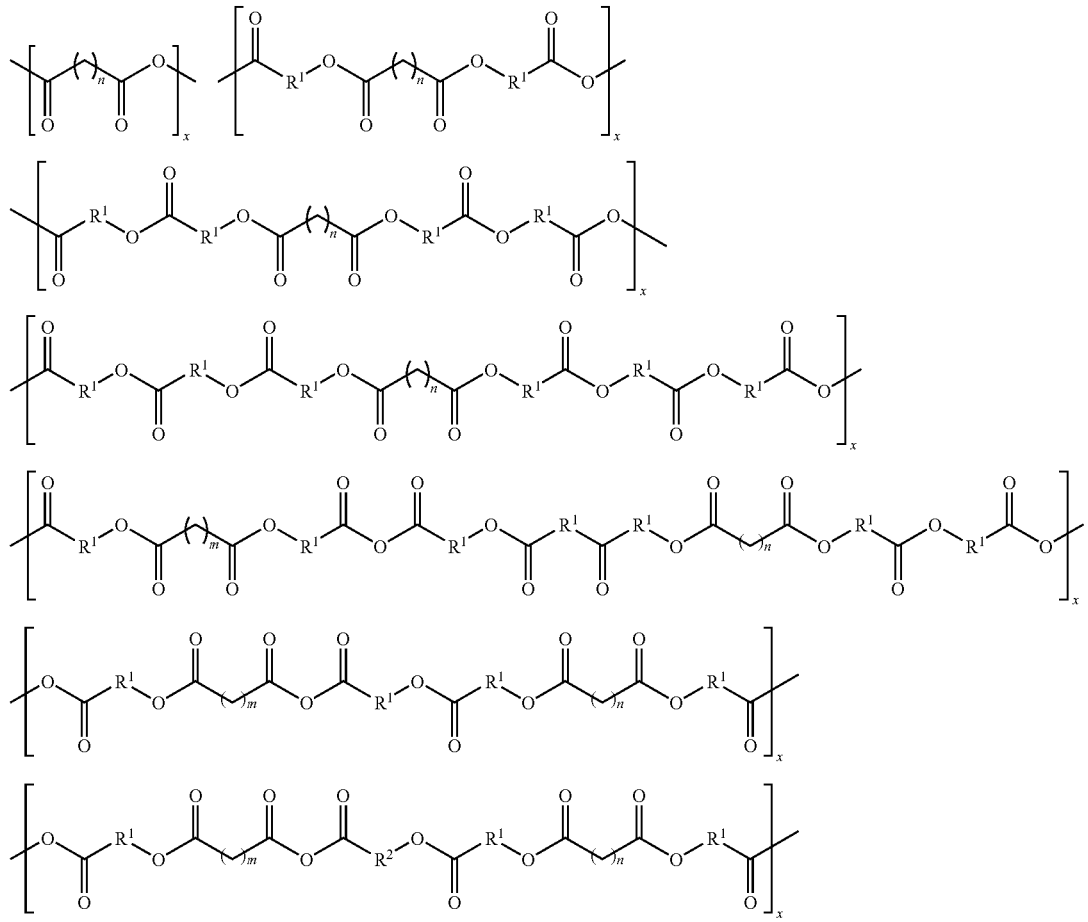

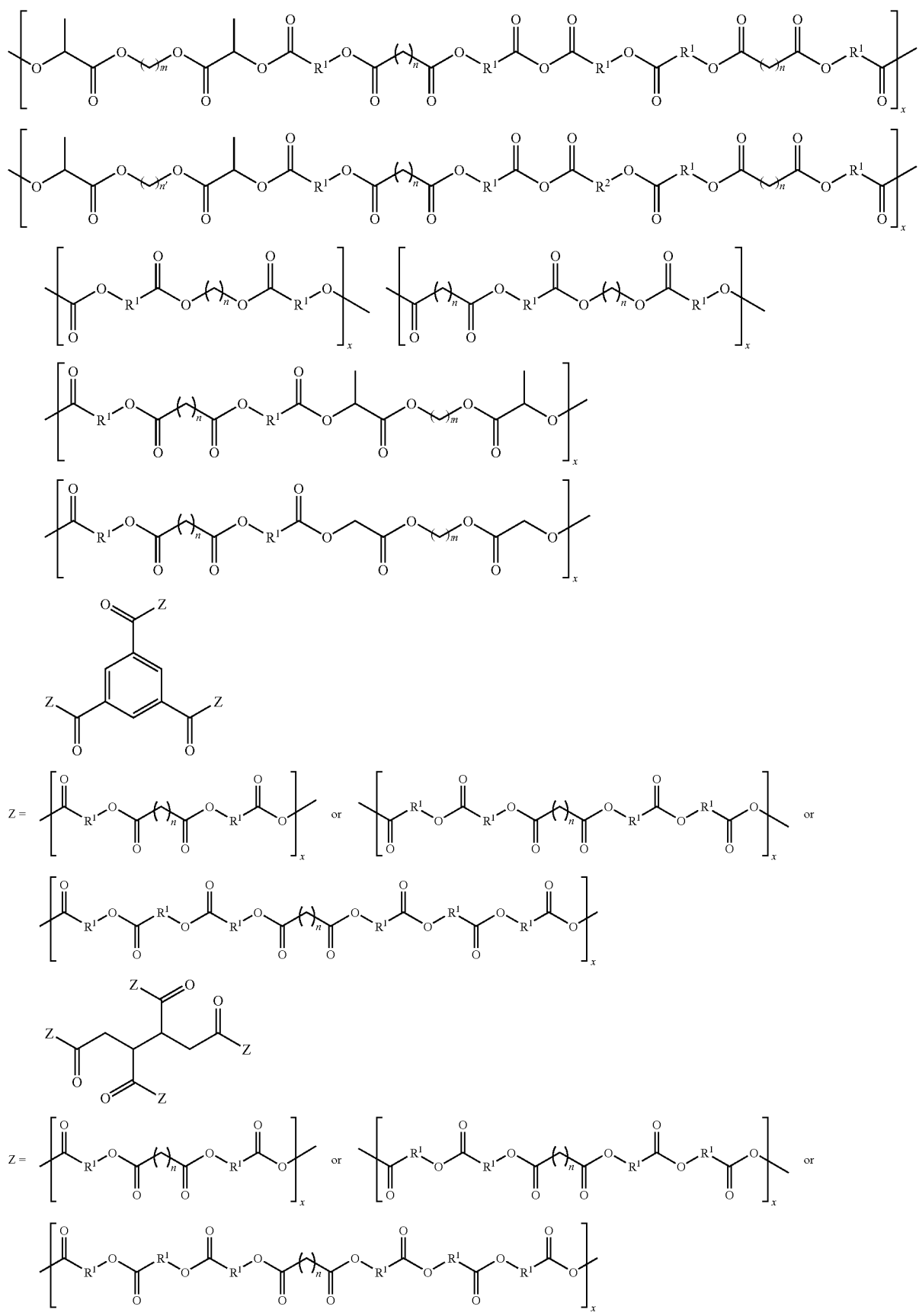

-continued
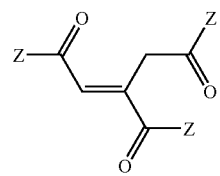
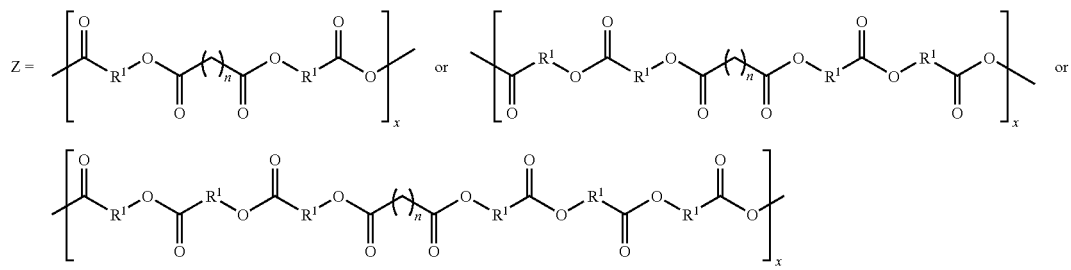
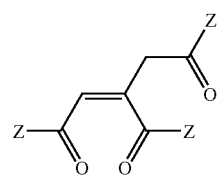
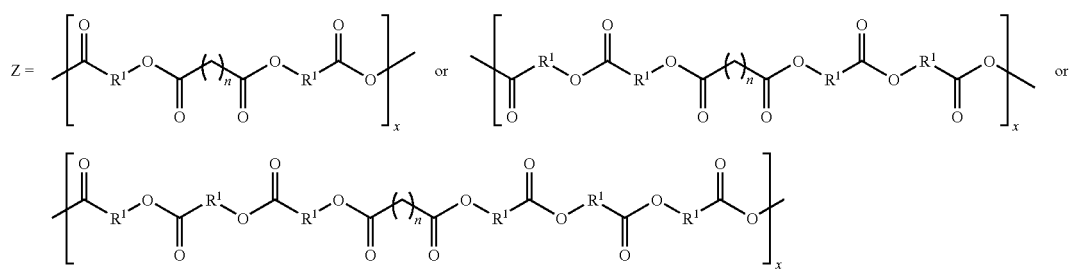
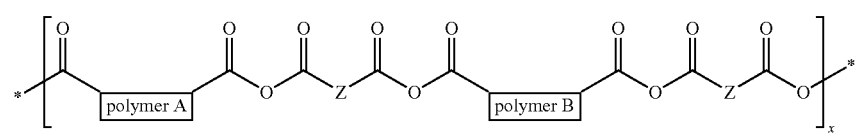
$Z = R^1\text{-}L\text{-}R^1$
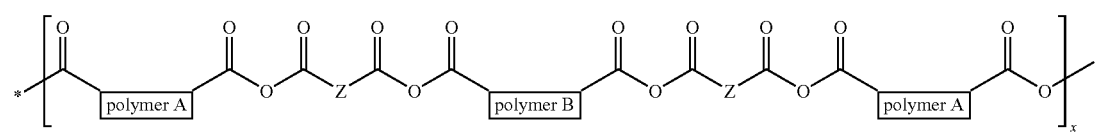
$Z = R^1\text{-}L\text{-}R^1$
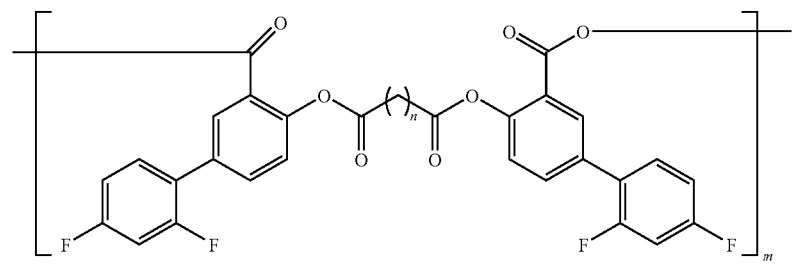

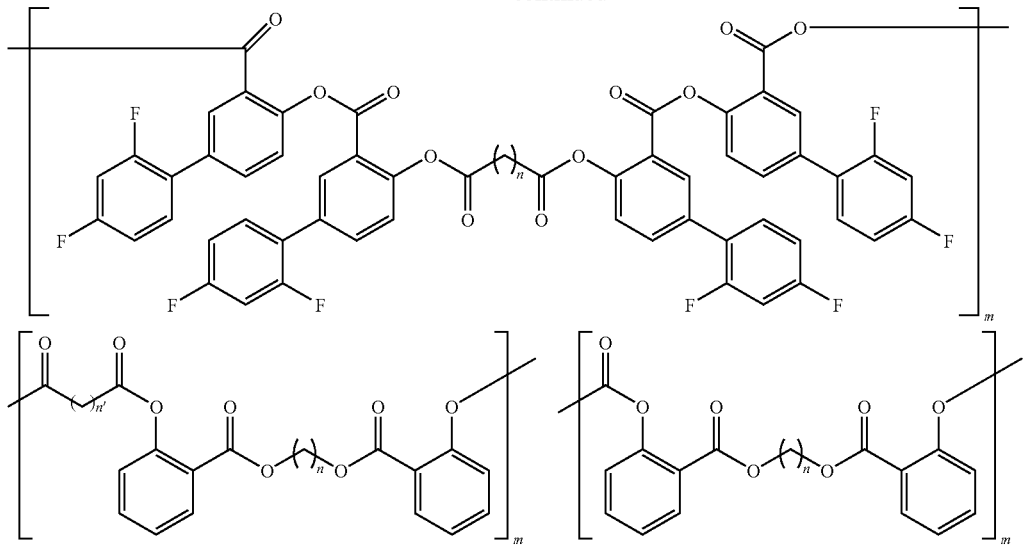

wherein R, $R^1$ and $R^2$ comprise, independently from one another, an agent(s) as defined above; and n and M are, independently from one another, 0 or a positive integer showing the degrees of polymerization.

C. Linking Groups

The mechanical and degradation properties, e.g. hydrolytic properties, of polymers comprising an agent(s) or compound(s) may be determined by incorporating and/or modifying a linking group into the polymer backbone. Among other properties, selecting molecular weight and chemical composition of a linking group will critically affect the polymer's glass transition temperature (Tg) and, accordingly, the mechanical properties of the polymer(s) and coatings they form at various temperatures. In general, the higher the molecular weight, the greater the toughness of the material in terms of elasticity and tear strength. The polymers of the invention may comprise backbones wherein an agent(s) or compound(s) and a linking group(s) are bonded together through breakable linkages, such as ester, thioester, amide, carbonate, and many others known in the art as well as combinations thereof. These linkages form biodegradable bonds that are hydrolyzed, broken by proteolysis, or broken by other biological of biochemical processes when placed in contact with the appropriate medium, e.g. body tissues or fluids, to release an active agent(s) or compound(s).

In some embodiments, the linking group(s) may be selected in coordination with the actual agent(s) to impart desirable physical, chemical, and biological properties, such as adhesion to smooth and porous surfaces, e.g. metallic, polymeric, asphaltic, ceramic, or glass surfaces. Such surfaces may be located in diverse environments, including marine surfaces, constructions sites including cement structures, plastic and other polymeric artifacts, alloys, stainless steel, and other metals, or on implantable dental, medical and veterinary devices to allow formation of a coating that may withstand handling, coating, implantation, and exposure to inclement weather, water contact, body tissues and/or fluids, and the like. Other desirable characteristics that are critically influenced by the linker type are mechanical strength, flexibility, and ability to withstand application of mechanical stress without failure, low sticking to a surface so that adhesion to delivery vehicles and neighboring surfaces may be minimized, e.g. when implanted in an animal or human. Also important is resistance to sterilization conditions by different methods, e.g. gamma irradiation, electron beam (E beam), treatment with ethylene oxide, or other chemical or physical treatments providing sterilization. Suitable linking groups typically comprise a divalent organic residue of molecular weight about 25, 40, 75, 100, 130 Dalton to about 100, 170, 250, 330, 400, 520 Dalton. In one embodiment, L comprises a divalent, branched or unbranched, saturated or unsaturated ($C_1$-$C_{25}$) hydrocarbon chain, where one or more carbon atoms may be further substituted by —O—, —$NR^2$—, an amino acid, a peptide, ($C_1$-$C_6$) alkoxy, ($C_3$-$C_6$) cycloalkyl, ($C_1$-$C_6$) alkanoyl, ($C_1$-$C_6$) alkanoyloxy, ($C_1$-$C_6$) alkoxycarbonyl, ($C_1$-$C_6$) alkylthio, azido, cyano, nitro, halo, hydroxy, oxo, carboxy, aryl, aryloxy, heteroaryl, or heteroaryloxy. In one embodiment, the polymer is employed to coat the surface of an article or device, e.g. a stent, such that it will allow for its expansion, contraction or torsion during the application and useful life of the article. In such case a linking group(s) may be a (C3-C35) dicarboxlyic acid hydrocarbon residue.

In one embodiment, the polymer of the invention may comprise a linking group(s) that may be present in the polymer backbone along with the agent(s) through bonds that release the agent(s) under certain environmental conditions. Examples of bonds are esters, thioesters, amides, thioamides, urethanes, carbamates, thiocarbamates, carbonates, thiocarbonates, and any others than fulfill a similar function. This includes combinations and mixtures thereof. The linking bonds may comprise other groups, and atoms, including P, C, O, S, halogens, metals, and other inorganic and organic atoms provided that they form labile bonds that may release under appropriate circumstances the agent(s) within the backbone, and the agent(s) mixed into the polymer. The linking group(s) may be selected as well to impart to the polymer desirable physical, chemical, and/or biological properties. Examples of these are adhesion to metallic, polymeric, ceramic or glassy surfaces on implantable medical and veterinary devices to allow formation of a coating that may withstand handling, implantation, and exposure to body tissues and/or fluids post-implantation; sufficient mechanical strength, flexibility, and ability to withstand without failure application of mechanical stress without failure; minimal stickiness on the surface of the resulting coating to minimize adhesion to vehicles used in the delivery or implantation of the medical or veterinary device in the body of a human or animal; and the ability to sterilize the coating and the associated medical or veterinary device by the application of gamma irradiation, electron beam (E beam), treatment with ethylene oxide, or other chemical or physical treatments providing sterilization. Suitable linking groups are widely known in the art, and need not be fully detailed here. Examples are described in U.S. Pat. Nos. 6,613,807; 6,328, 988; 6,365,146; 6,468,519; 6,486,214; 6,497,895; 6,602,915; 6,613,807; U.S. Published Patent Applns. 2002/0071822 A1; 2002/0106345 A1; 2003/0035787 A1; 2003/0059469 A1; 2003/0104614 A1; 2003/0170202 A1; U.S. Ser. Nos. 09/508, 217; 10/368,288; 10/622,072; 10/646,336; 10/647,701; and International Patent Applications WO 99/12990; WO 01/28492; WO 01/41753; WO 01/58502; WO 02/09767; WO 02/09768; WO 02/09769; WO 03/005959; WO 03/046034; WO 03/065928; and WO 03/072020. The nature of the linking group (L) in a polymer of the invention may be employed to provide the polymer of the invention with one or more desirable physical, chemical, and/or biological properties, such as mechanical and thermal properties; adhesiveness; wettability; hardness; drug generation, and release kinetics and solubility; and tissue compatibility and response for the selected therapeutic application. The linking group L is typically a divalent organic radical having a molecular weight (MW) about 25, or 40 daltons to about 200, or 400 daltons. The mechanical and degradative properties, e.g. hydrolytic properties, of the polymer of the invention may be controlled by incorporating and/or modifying a specific linking group (L) into the polymer backbone.

The mechanical and degradative properties, e.g. hydrolytic properties, of the polymer of the invention may be controlled by incorporating and/or modifying a specific linking group (L) into the polymer backbone. L may be any substituted and unsubstituted hydrocarbon unit, such as, for example, propane, butane, pentane, etc. A suitable number of carbon atoms includes any number of carbon atoms that will result in a functional polymer, e.g., about 2 to about 20 carbon atoms, about 2 to about 18 carbon atoms, about 4 to about 16 carbon atoms, about 4 to about 14 carbon atoms, about 6 to about 16 carbon atoms, about 8 to about 12 carbon atoms, or about 6 to about 10 carbon atoms. Further, the nature of the linking group L in a polymer of the invention is not critical provided the polymer of the invention possesses acceptable mechanical properties and release kinetics for the selected therapeutic application. The linking group L is typically a divalent organic radical having a molecular weight of from about 5, 10, 15, 20, 25, or 40 to about 100, 200, 300, or 400 Dalton, and a length of from about 5, 10, 30, or 40 to about 50, 75, or 100 Angstrom using standard bond lengths and angles. The linking group may be biologically inactive, or may itself possess biological or other activity.

One preferred polymer comprises L representing a residue of a linking group(s) that, independently from one another, comprises linear or branched (C3-C30) aliphatic, alicyclic or aromatic residue that may be further substituted; n, independently from one another, may be 0 to 28; and m represents the number of units and is correlated to the polymer molecular weight. Although any agent(s) may be polymerized in this manner, particularly suited are aliphatic, alicyclic, aromatic small and large organic molecules that have at least two functional groups, and optionally additional groups such as OH, SH, COOH, COOR, phosphate, amine, amide, thioester, thiamide, S, P, N, halogen, ether, aldehyde, ketone, and many others: such molecules being known as suitable for regulation of properties such as hydrophilicity, solubility, and the like. In one embodiment, the active agent is salicylic acid, and the linker is a dicarboxylic acid hydrocarbon chain with an even number of carbon atoms. The nature and presence of the linking group L in the polymer is not critical as long as it does not negatively impact the polymer's acceptable mechanical properties and release kinetics for the selected therapeutic application.

In one embodiment, the linking group L typically comprises a divalent organic residue of molecular weight about 25, 40, 60, 100, 130, or 150 Daltons to about 80, 110, 125, 140, 170, 250, 370, or 400 Daltons, and any combination thereof. In another embodiment the linking group(s) L typically comprises a length of about 5, 10, 15, 20, or 25 Angstrom to about 30, 35, 45, 50, 75, or 100 Angstrom using standard bond lengths and angles.

In one embodiment, the linking group may be biologically inactive, and in another it may possess biological activity. The linking group may also comprise other functional groups including hydroxy, mercapto, amine, halo, SH, —O—, —C=O, —N=, —P=, or carboxylic acid, as well as others that may be used to modify the properties of the polymer. These may be employed for example for polymer branching, cross-linking, appending other molecules, e.g. another compound(s), to the polymer, changing the polymer solubility, or affecting the biodistribution of the polymer, among others.

In one embodiment, the linking group may incorporate other biodegradable groups such as alpha-ester (lactate, glycolate), e-caprolactone, ortho-ester, or enzymatically biodegradable groups such as amino acids. In another embodiment, the linking group may be a water-soluble, non-biodegradable segment such as a polyethylene glycol (PEG), polyvinyl alcohol (PVA) or polyvinyl pyrrolidone (PVP). In yet another embodiment, the linking group may be a water-insoluble, non-biodegradable segment such as polypropylene glycol (PPG), polyetherurethane (PEU), or poly(n-alkyl ether). In still another embodiment, the linker may be an amorphous or semicrystalline biodegradable polymer, such as poly(d, l-lactide), poly(trimethylene carbonate), poly(dioxanone), poly-anhydridepoly(orthoester) poly(glycolide), poly(l-lactide) poly(e-caprolactone) and co-polymers of e-caprolactone, glycolide, trimethylene carbonate, dioxanone, d,l-lactide, l-lactide and d-lactide. In another embodiment, the linking group may have surfactant properties, such as a Pluronic block copolymer with polyethylene glycol and polypropylene glycol blocks, and in another it may have polar or charged moieties, including carboxylic acid groups from poly (acrylic acid) and poly(alginates), sulfonic acid groups from poly(2-acrylamido-2-methyl-propanesulfonicacid) (AMPS), hydroxy groups from poly(vinyl alcohol), polysaccharides and poly(alginates), and amino groups from poly(L-lysine), poly(2,2-dimethylaminoethyl methacrylate) and poly(amino acids).

In addition, the linking group may be a segment that undergoes thermoreversible gellation, such as Pluronic F127 and poly(N-isopropyl acrylamide). It may incorporate structurally-reinforcing segments, such as polyetherurethane, polyesterurethane, etc. In yet another embodiment, the linking group may be a divalent, branched or unbranched, saturated or unsaturated, hydrocarbon chain, having from 1 to 25 carbon atoms, wherein one or more, e.g. 1, 2, 3, or 4, of the carbon atoms is optionally replaced by (—O—), (—S—), (—P—), or (—NR—), and wherein the chain is optionally substituted with one or more, e.g. 1, 2, 3, or 4, substituents comprising (C1-C6) alkoxy, (C3-C6) cycloalkyl, (C1-C6) alkanoyl, (C1-C6) alkanoyloxy, (C1-C6) alkoxycarbonyl, (C1-C6) alkylthio, azido, cyano, nitro, halo, hydroxy, oxo, carboxy, aryl, aryloxy, heteroaryl, or heteroaryloxy, among others. The linking group may be a divalent (C2-C32) branched or unbranched, saturated or unsaturated hydrocarbon chain optionally further substituted with one or more, e.g. 1, 2, 3, or 4, substituents comprising (C1-C6) alkoxy, (C3-C6) cycloalkyl, (C1-C6) alkanoyl, (C1-C6) alkanoyloxy, (C1-C6) alkoxycarbonyl, (C1-C6) alkylthio, azido, cyano, nitro, halo, hydroxy, oxo, carboxy, aryl, aryloxy, heteroaryl, or heteroaryloxy, among many others.

The linking group may be also a biological molecule such as a carbohydrate, saccharide, polysaccharide, fatty acid, lipid, nucleic acid, peptide, amino acid, or combinations thereof.

The linking group may be a divalent, branched or unbranched, saturated or unsaturated (C3-C31) hydrocarbon chain, preferably of uneven number of carbons, with one or more optionally substituted by —O— or —NR—; or a divalent, branched or unbranched, saturated or unsaturated, hydrocarbon chain, having from about 3, 6, 9 to about 12, 15 carbon atoms, wherein one or more, e.g. 1, 2, 3, or 4, of the carbon atoms is optionally replaced by —O— or —NR— or —S—, and wherein the chain is optionally substituted on carbon with one or more, e.g. 1, 2, 3, or 4, substituents selected from the group consisting of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, azido, cyano, nitro, halo, hydroxy, oxo, carboxy, aryl, aryloxy, heteroaryl, and heteroaryloxy. The linking group may be a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—S—), (—P—), or (—NR—); or a divalent branched or unbranched, saturated or unsaturated, hydrocarbon chain, having from 3 to 15 carbon atoms; or a divalent, branched or unbranched, hydrocarbon chain, having from 3 to 15 carbon atoms; or a divalent, branched or unbranched, (C6-C10) hydrocarbon chain; or a divalent (C7-C9) hydrocarbon chain, or a divalent C8 hydrocarbon chain.

The linking group may be biologically inactive, or may itself possess biological or other activity, and may comprise other functional groups. Examples of functional groups that the linker may have are hydroxy, mercapto, amine, carboxylic acid, halogen, aliphatic and aromatic hydrocarbons with and without heteroatoms, and many others useful for modifying the properties of the polymer, e.g. for branching, cross linking, increasing hydrophilicity or hydrophobicity, solubility, degradation rate, hardness, flexibility, elasticity, ability to append another agent(s) to the polymer, or biodistribution of the polymer, among many others. In one embodiment, the linker may have two or more functional groups that, among others, may be hydroxy —OH, mercapto —SH or SR, amine —NH— or —NR—, carboxylic acid —COOH, and many others that form degradable bonds with the agent(s) to be polymerized, e.g. hydrolyzed, or cleaved by proteolytic, or other biological of biochemical processes when placed in contact with body tissues or fluids. L may be an amino acid, a peptide, a nucleic acid, a carbohydrate or polysaccharide, or any other type of chemical structure. L generally comprises a divalent, branched or unbranched, saturated or unsaturated, hydrocarbon chain, having about 3, 6, 8, 10, 12, or 14 to about 16, 18, 20, 22, or 25 carbon atoms, and at times more carbon atoms, wherein one or more, e.g. 1, 2, 3, or 4, carbon atoms is optionally replaced by (—O—) or (—NR—). L may be a divalent, branched or unbranched, saturated or unsaturated, hydrocarbon chain, having from 1 to 25 carbon atoms, wherein the chain is optionally substituted on carbon with one or more, e.g. 1, 2, 3, or 4, substituents comprising ($C_1$-$C_6$) alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, or other functional groups. In one embodiment, L comprises a dicarboxylic acid hydrocarbon chain with about 3, 4, 6, 8, or 10 to about 12, 14, 16, 18, 22, 24, or 26 carbon atoms, preferably an even number of carbon atoms that may be the same or different. This linker may be used with any suitable active agent, such as, e.g., salicylic acid, diflunisal and/or a derivative thereof.

In another embodiment the polymer may be employed to coat a rigid article, e.g. an implantable orthopedic device, including a hip, knee, shoulder, or elbow replacement, a fixation device(s) for other orthopedic applications, and many others. In such case, the linking group(s) may be a (C3-C35) dicarboxylic acid hydrocarbon residue(s) The linking group contributes to the control of a polymer's characteristics, mechanical properties and release kinetics for selected applications. The linking group(s) typically is(are) about 5, 10, 15, 25, 50, 80, or 120 Angstroms to about 75, 100, 140, 180, 230, or 300 Angstroms employing standard bond lengths and angles. The linking group may be biologically inactive, or may itself possess biological activity, and may further comprise O, N, P, halogen, etc. Suitable functional groups that may be attached to the linking group(s) is(are) hydroxy, keto, aldehyde, lactame, mercapto, amide, acryl, vinyl, amine, carboxyl, halogen, and many others that may be used to modify the properties of the polymer for example by branching, cross linking, for appending other molecules, e.g. other biologically active of activatable compound(s), to the polymer, for changing the solubility of the polymer, or for affecting the biodistribution of the polymer, etc.

Thus, different embodiments may be prepared changing the chemical structure of the linker that will evidence a direct or reverse correlation with the Tg of the specific type of polymers. This invention provides an improved process for the preparation of the present polymers which permits the synthetic design of polymers with pre-designed properties and, moreover, of properties never before attained with prior synthetic processes. For example, in one embodiment of the process of this invention the polymer may be prepared from an agent(s) or compound(s) of chemical formula $Z_1$—$R^1$—$Z_2$ and a linker precursor of formula $X_1$-L-$X_2$, wherein $Z_1$, $Z_2$, $X_1$, and $X_2$, independently from one another, comprise functional groups that are able to form degradable bonds in situ. Examples of these functional grouped are shown in Table 2 below.

Essentially across this range, the polymers of the invention e.g. poly-NSAIDs are highly flexible at room and body temperature. Soaking the polymers for an hour in PBS at about 37 C caused no observable change in flexibility as shown in Table 2 below.

TABLE 2

Functional Groups & Polymer Bonds

| Agent Functional Group ($Z_1$ or $Z_2$) | Linker Functional Group ($X_1$ or $X_2$) | Polymer Bond (A) |
|---|---|---|
| —COOH | —OH | Ester |
| —COOH | —NHR | Amide |
| —COOH | —SH | Thioester |
| —OH | —COOH | Ester |
| —SH | —COOH | Thioester |
| —NHR | —COOH | Amide |

$Z_1$—$R^1$—$Z_2$ + $X_1$-L-$X_2$ → —[C(=O)—$R^1$-A-L-A-$R^1$—C(=O)—O]$_n$— (IV) wherein n is a positive integer showing the degree of polymerization An agent(s) or compound(s) and a linker precursor may be polymerized, for example, by condensation, to provide a polymer of the invention such as, for example, that of chemical formula (IV), wherein each A, independently from one another, comprises a bond that is degradable in situ, e.g. in vivo when administered to a living organism. Examples of breakable bonds comprise an ester, thioester, thioamide, azo, carbonate, or amide. Depending on the reactive functional groups $Z^1$ and $Z^2$ present in the agent(s) or compound(s), a corresponding functional group $X^1$ or $X^2$ may be selected for the linking group or second functional group of the agent(s) or compound(s) to provide one or more of the breakable bonds described above in the formation of the polymeric backbone. The polymers the present invention may be prepared in at least two general manners or embodiments, which embodiments are expanded by the addition, and various permutations, of the optional steps that each of the illustrative methods shown in the Schemes Stated below. In one embodiment, the polymerization step occurs in a non-aqueous dispersion medium. Once a pre-polymer(s) or a diacid monomer(s) is synthesized as described above, and activated as a mixed anhydride, it may be heated above its melting point in the presence of a solvent for the pre-polymer(s), e.g. an inert, high boiling point pre-polymer solvent, to allow polymerization to occur while the thus produced polymer remains out of solution as it is generated. This process is capable of yielding polymers of high molecular weights, e.g. in excess of 40,000 Dalton. Vigorous mechanical mixing or stirring may be favorably employed with an optional addition of a minor amount of, or even without, a non-aqueous dispersing agent or surfactant that will foster the formation of a suitable emulsion of molten droplets of the polymerization phase.

D. Agents and Compounds

Any diagnostic agent(s) may be incorporated into the backbone of the polymers of the invention, or be dispersed into, or carried by them. Examples are phosphorescent agents, fluorescent agents, radioactive agents, enzymatic agents, among others.

Any therapeutic agent(s) is suitable for use in the polymer backbone, or dispersed into, or carried by the polymer. Examples of therapeutic agents include antibacterial, antiviral, antiproliferative, anticancer, anti-inflammatory, analgesic, anesthetic, antipyretic, antiseptic, and antimicrobial compounds. Examples of such compounds include salicylic acid, 4-aminosalicylic acid, 5-aminosalicylic acid, 4-(acetylamino)salicylic acid, 5-(acetylamino)salicylic acid, 5-chlorosalicylic acid, salicylsalicylic acid (salsalate), 4-thiosalicylic acid, 5-thiosalicylic acid, 5-(2,4-difluorophenyl)-salicylic acid (diflunisal), 4-trifluoromethylsalicylic, sulfasalazine, diclofenac, penicillamine, balsalazide, olsalazine, mefenamic acid, carbidopa, levodopa, etodolac, cefaclor, captopril, and the like. Any traceable agent(s) or compound(s) is suitable for use in this invention.

The synthetic process of this invention enables the preparation of different embodiments by modifying the chemical structure of a linker taking into consideration that such change will evidence a direct or reverse correlation with the $T_g$ of the specific polymers. The present process enables the preparation of polyanhydrides that release a broad scope of families of agents and drugs, such as those disclosed in U.S. Pat. No. 6,486,214. Compounds suitable for incorporation into the polymer of this invention preferably have relatively low molecular weights, e.g. up to 1,000 dalton. The compounds generally contain within their molecular structure at least one functional group, and preferably two functional groups, more preferably one of the functional groups comprises carboxylic acid. The functional groups of the compound(s) are preferably hydroxy (—OH), thiol (—SH), amine (—NHR), amide (—CNR), azo, carbonate (—COO—), carboxy (—COR), and similarly breakable groups. These functional groups from breakable, e.g. biodegradable, bonds within the polymer and are able to release the compound in its active form or as a precursor. The polymeric bonds may be broken by hydrolysis, such as proteolysis, or by other biological or biochemical processes when placed in contact with the target environment, e.g. body tissues or fluids.

The compounds may also comprise other functional groups, including hydroxy, phenol, ketone, aldehyde, double and triple bond C—C substituents, amide, mercapto, amine, halide, carboxylic acid, and many others known in the art, all of which may be used to modify the properties of the polymer, such as for branching, cross-linking, appending other molecules to the polymer, changing polymer characteristics such as solubility, consistency, adhesiveness, or rigidity, among others, or for affecting polymer distribution in a specific system, e.g. biodistribution. One skilled in the art will be able to readily select from the listed compounds those that possess, or may be modified by methods known in the art to possess, the necessary functional groups for polymerization in accordance with the method of the invention. Suitable therapeutic and diagnostic compounds may be found, for example, in the Physician's Desk Reference, 55 Ed., Medical Economics Company, Inc., Montvale, N.J. (2001); USPN Dictionary of USAN and International Drug Names, The United States Pharmacopeial Convention, Inc., Rockville, Md. (2000); The Merck Index, 12 Ed., Merck & Co., Inc., Whitehouse Station, N.J. (1996). Any suitable agent may be employed in the polymers of the invention. In one embodiment, the active agents that may be incorporated into the polymers of the invention possess at least two functional groups that may each be incorporated into an ester, thioester, urethane, carbamate, carbonate or amide linkage of a polymer, such that, upon hydrolysis or enzymatic degradation of the polymer, the active agent is obtained. The functional groups may independently be a hydroxy group (—OH), a mercapto group (—SH), an amine group (—NHR), or a carboxylic acid (—COOH). These functionalities form biodegradable bonds with the drug to be polymerized that are hydrolyzed, broken by proteolytic process, or broken by other biological of biochemical processes when placed in contact with body tissues or fluids. An active agent may also comprise other functional groups (including hydroxy groups, mercapto groups, amine groups, and carboxylic acids, as well as others) that may be used to modify the properties of the polymer, e.g. for branching, for cross linking, for appending other molecules, e.g. another active compound, to the polymer, for changing the solubility of the polymer, or for effecting the biodistribution of the polymer. One skilled in the art may readily select active agents that possess the necessary functional groups for incorporation into the polymers of the invention from these lists. The agent may comprise a biological, diagnostic, therapeutic, or other type of agent such as suitably functionalized analgesics, anesthetics, anti-acne agents, antibiotics, anti-cholinergics, anti-coagulants, anti-convulsants, anti-diabetic agents, anti-dyskinetics, antifibrotic agents, antifungal agents, anti-glaucoma agents, anti-infectives, anti-inflammatory compounds, antimicrobial compounds, anti-neoplastics, anti-Parkinson's agents, antiosteoporotics, antiseptics, antisporatics, anti-thrombotics, antiviral compounds, bacteriostatic compounds, bone resorption inhibitors, calcium regulators, cardioprotective agents, cardiovascular agents, central nervous system stimulants, cholinesterase inhibitors, contraceptives, deodorants, disinfectants, dopamine receptor agonists, erectile dysfunction agents, fertility agents, gastrointestinal agents, gout agents, hormones, hypnotics, immunomodulators, immunosuppressives, keratolytics, migraine agents, motion sickness agents, muscle relaxants, nucleoside analogs, obesity agents, opthalmic agents, bone healing, osteoporosis agents, parasympatholytics, parasympathomimetics, prostaglandins, psychotherapeutic agents, respiratory agents, sclerosing and anti-sclerosing agents, sedatives, skin and mucous membrane agents, smoking cessation agents, sympatholytics, ultraviolet screening agents, urinary tract agents, vaginal agents, contraceptives, hormones, sexual function aid agents, and vasodilators. See, Physicians' Desk Reference, 55 Ed., Medical Economics Company, Inc., Montvale, N.J., pages 201-202 (2001). Suitable active agents may be found, for example, in: Physician's Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J.

Other therapeutically active families of compounds that may be incorporated into the polymers of the invention include, but not limited to, analgesics, anesthetics, skin treating agents such as exfoliating agents, anti-acne agents, pore refining agents, skin sloughing agents, cleansers, pore closing agents, skin toning agents, skin revitalizing agents, anti-infectives including disinfectants, antiseptics, antibiotics, antifungal agents, anti-viral agents, anti-microbial agents, antisporatic agents, or bacteriostatic agents, among others, anticholinergics, anti-coagulants, anti-convulsants, anti-diabetic agents, anti-dyskinetics, anti-fibrotic agents, anti-inflammatory agents, anti-neoplastic agents, anti-glaucoma agents, anti-Parkinson's agents, anti-osteoporotic agents, anti-thrombotic agents, bone resorption inhibitors, bone growth inducing agents, calcium regulators, cardioprotective agents, cardiovascular agents, central nervous system (CNS) acting agents such as sedatives, hypnotics, anti-depressants, stimulants, anti-bipolar agents, anti-schizophrenic agents, psychotherapeutic agents in general, CNS receptor agonists and antagonists such as serotonin, dopamine, epinephrine, norepinephrine, gamma amino butyric acid (GABA), receptor agonists and antagonists, among others, sympathomimetic agents, sympatholytic agents, cholinergic and anti-cholinergic agents, cholinesterase inhibitors, parasympatholytic agents, parasympathomimetic agents, contraceptive agents, fertility inducing agents, deodorants, hormones, immunomodulating agents such as immunosuppressive and immunostimulating agents, keratolytic agents, hair follicle treating agents, muscle relaxants, anti-cancer agents such as antibodies and their fragments, radioactive materials, anti-angiogenic agents, carcinolytic agents, nucleoside analogs, antisense agents, anti-oxidant agents, metabolic and anti-metabolic agents, among others known in the art, anti-sense agents, nail treating agents, opthalmic and otical agents, vasodilators, prostaglandins, smoking cessation agents, ultraviolet screening agents, agents for the treatment of erectile dysfunction, migraine, motion sickness, osteoporosis, alzheimer's disease, sclerosis, obesity, anorexia, bulimia, and gastrointestinal (G.I.), skin, mucous membrane, aesophagal, respiratory, gout, mouth, nasal, throat, glandular, lymphatic, urinary tract, vaginal and colonic conditions and ailments, among many others. See, for example, Physicians' Desk Reference, 55 Ed., pp. 201-202 (2001). Examples of specific therapeutic, screening and diagnostic agents or compounds that may be incorporated into the polymers of the invention are bupivacaine; mepivacaine, atorvastatin; enalapril; ranitidine; ciprofloxacin; pravastatin; clarithromycin; cyclosporin; diflunisal; famotidine; leuprolide; acyclovir; paclitaxel; azithromycin; lamivudine; budesonide; albuterol; indinavir; metformin; alendronate; nizatidine; zidovudine; carboplatin; metoprolol; amoxicillin; diclofenac; lisinopril; ceftriaxone; captopril; salmeterol; xinafoate; imipenem; cilastatin; benazepril; cefaclor; ceftazidime; morphine; dopamine; bialamicol; fluvastatin; phenamidine; podophyllinic acid 2-ethylhydrazine; acriflavine; chloroazodin; arsphenamine; amicarbilide; aminoquinuride; quinapril; oxymorphone; buprenorphine; butorphanol; nalbuphine. streptozocin; doxorubicin; daunorubicin; plicamycin; idarubicin; mitomycin C; pentostatin; mitoxantrone; cytarabine; fludarabine phosphate; floxuridine; cladribine; 6-mercaptopurine; thioguanine; capecitabine; docetaxel; podophyllotoxin; etoposide; gemcitabine; camptothecin; topotecan; irinotecan; vinorelbine; vincristine; vinblastine; teniposide; tamoxifen; melphalan; methotrexate; 2-p-sulfanilyanilinoethanol; 4,4'-sulfinyldianiline; 4-sulfanilamidosalicylic acid; acediasulfone; acetosulfone; amikacin; amphotericin B; ampicillin; apalcillin; apicycline; apramycin; arbekacin; aspoxicillin; azidamfenicol; aztreonam; bacitracin; bambermycin(s); biapenem; brodimoprim; butirosin; capreomycin; carbenicillin; carbomycin; carumonam; cefadroxil; cefamandole; cefatrizine; cefbuperazone; cefclidin; cefdinir; cefditoren; cefepime; cefetamet; cefixime; cefmenoxime; cefminox; cefodizime; cefonicid; cefoperazone; ceforanide; cefotaxime; cefotetan; cefotiam; cefozopran; cefpimizole; cefpiramide; cefpirome; cefprozil; cefroxadine; cefteram; ceftibuten; cefuzonam; cephalexin; cephaloglycin; cephalosporin C; cephradine; chloramphenicol; chlortetracycline; clinafloxacin; clindamycin; clomocycline; colistin; cyclacillin; dapsone; demeclocycline; diathymosulfone; dibekacin; dihydrostreptomycin; dirithromycin; doxycycline; enoxacin; enviomycin; epicillin; erythromycin; flomoxef; fortimicin(s); gentamicin(s); glucosulfone solasulfone; gramicidin S; gramicidin(s); grepafloxacin; guamecycline; hetacillin; isepamicin; josamycin; kanamycin(s); leucomycin(s); lincomycin; lomefloxacin; lucensomycin; lymecycline; meclocycline; meropenem; methacycline; methsalamine; micronomicin; midecamycin(s); minocycline; moxalactam; mupirocin; nadifloxacin; natamycin; neomycin; netilmicin; norfloxacin; oleandomycin; oxytetracycline; p-sulfanilylbenzylamine; panipenem; paromomycin; pazufloxacin; penicillin N; pipacycline; pipemidic acid; polymyxin; primycin; quinacillin; ribostamycin; rifamide; rifampin; rifamycin SV; rifapentine; rifaximin; ristocetin; ritipenem; rokitamycin; rolitetracycline; rosaramycin; roxithromycin; salazosulfadimidine; salicylic acid, sancycline; sisomicin; sparfloxacin; spectinomycin; spiramycin; streptomycin; succisulfone; sulfachrysoidine; sulfaloxic acid; sulfamidochrysoidine; sulfanilic acid; sulfoxone; teicoplanin; temafloxacin; temocillin; tetroxoprim; thiamphenicol; thiazolsulfone; thiostrepton; ticarcillin; tigemonam; tobramycin; tosufloxacin; trimethoprim; trospectomycin; trovafloxacin; tuberactinomycin; vancomycin; azaserine; candicidin(s); chlorphenesin; dermostatin(s); filipin; fungichromin; mepartricin; nystatin; oligomycin(s); perimycin A; tubercidin; 6-azauridine; 6-diazo-5-oxo-L-norleucine; aclacinomycin(s); ancitabine; anthramycin; azacitadine; azaserine; bleomycin(s); carubicin; carzinophillin A; chlorozotocin; chromomycin(s); denopterin; doxifluridine; edatrexate; eflornithine; elliptinium; enocitabine; epirubicin; mannomustine; menogaril; mitobronitol; mitolactol; mopidamol; mycophenolic acid; nogalamycin; olivomycin(s); peplomycin; pirarubicin; piritrexim; prednimustine; procarbazine; pteropterin; puromycin; ranimustine; streptonigrin; thiamiprine; tamoxifen; Tomudex® (N-[[5-[[(1,4-Dihydro-2-methyl-4-oxo-6-quinazolinyl)methyl]methylamino]-2-thienyl]carbonyl]-L-glutamic acid), trimetrexate, tubercidin, ubenimex, vindesine, zorubicin; argatroban; coumetarol; dicoumarol; ethyl biscoumacetate; ethylidene dicoumarol; iloprost; lamifiban; taprostene; tioclomarol; tirofiban; amiprilose; bucillamine; gusperimus; mycophenolic acid; procodazole; romurtide; sirolimus (rapamycin); tacrolimus; butethamine; fenalcomine; hydroxytetracaine; naepaine; orthocaine; piridocaine; salicyl alcohol; 3-amino-4-hydroxybutyric acid; aceclofenac; alminoprofen; amfenac; bromfenac; bromosaligenin; bumadizon; carprofen; diclofenac; diflunisal; ditazol; enfenamic acid; etodolac; etofenamate; fendosal; fepradinol; flufenamic acid; gentisic acid; glucamethacin; glycol salicylate; meclofenamic acid; mefenamic acid; mesalamine; niflumic acid; olsalazine; oxaceprol; S-adenosylmethionine; salicylic acid; salsalate; sulfasalazine; and tolfenamic acid, among many other suitable.

Examples of suitable agents are 2-p-sulfanilyanilinoethanol; 3-amino-4-hydroxybutyric acid; 4,4'-sulfinyldianiline; 4-sulfanilamidosalicylic acid; 6-azauridine; 6-diazo-5-oxo-L-norleucine; 6-mercaptopurine; aceclofenac; acediasulfone; acetosulfone; aclacinomycin(s); acriflavine; acyclovir; albuterol; alendronate; alminoprofen; amfenac; amicarbilide; amikacin; aminoquinuride; amiprilose; amoxicillin; amphotericin B; ampicillin; ancitabine; anthramycin; apalcillin; apicycline; apramycin; arbekacin; argatroban; arsphenamine; aspoxicillin; atorvastatin; azacitadine; azaserine; azidamfenicol; azithromycin; aztreonam; bacitracin; bambermycin(s); benazepril; bialamicol; biapenem; bleomycin(s); brodimoprim; bromfenac; bromosaligenin; bucillamine; budesonide; bumadizon; buprenorphine; butethamine; butirosin; butorphanol; candicidin(s); capecitabine; capreomycin; captopril; carbenicillin; carbomycin; carboplatin; carprofen; carubicin; carumonam; carzinophillin A; cefaclor; cefadroxil; cefamandole; cefatrizine; cefbuperazone; cefclidin; cefdinir; cefditoren; cefepime; cefetamet; cefixime; cefmenoxime; cefminox; cefodizime; cefonicid; cefoperazone; ceforanide; cefotaxime; cefotetan; cefotiam; cefozopran; cefpimizole; cefpiramide; cefpirome; cefprozil; cefroxadine; ceftazidime; cefteram; ceftibuten; ceftriaxone; cefuzonam; cephalexin; cephaloglycin; cephalosporin C; cephradine; chloramphenicol; chloroazodin; chloroazodin; chlorozotocin; chlorphenesin; chlortetracycline; chromomycin(s); cilastatin; ciprofloxacin; cladribine; clarithromycin; clinafloxacin; clindamycin; clomocycline; colistin; coumetarol; cyclacillin; cyclosporin; cytarabine; dapsone; daunorubicin; demeclocycline; denopterin; dermostatin(s); diathymosulfone; dibekacin; diclofenac; dicoumarol; diflunisal; dihydrostreptomycin; dirithromycin; ditazol; docetaxel; dopamine; doxifluridine; doxorubicin; doxycycline; edatrexate; eflornithine; elliptinium; enalapril; enfenamic acid; enocitabine; enoxacin; enviomycin; epicillin; epirubicin; erythromycin; ethyl biscoumacetate; ethylidene; etodolac; etofenamate; etoposide; famotidine; fenalcomine; fendosal; fepradinol; filipin; flomoxef; floxuridine; fludarabine phosphate; flufenamic acid; fluvastatin; fortimicin(s); fungichromin; gemcitabine; gentamicin(s); gentisic acid; glucamethacin; glucosulfone; glycol salicylate; gramicidin S; gramicidin(s); grepafloxacin; guamecycline; gusperimus; hetacillin; hydroxytetracaine; idarubicin; iloprost; imipenem; indinavir; isepamicin; josamycin; kanamycin(s); lamifiban; lamivudine; leucomycin(s); leuprolide; lincomycin; lisinopril; lisinpril; lomefloxacin; lucensomycin; lymecycline; mannomustine; meclocycline; meclofenamic acid; mefenamic acid; melphalan; menogaril; mepartricin; meropenem; mesalamine; metformin; methacycline; methotrexate; methsalamine; metoprolol; micronomicin; midecamycin(s); minocycline; mitobronitol; mitolactol; mitomycin C; mitoxantrone; mopidamol; morphine; moxalactam; mupirocin; mycophenolic acid; nadifloxacin; nae- paine; nalbuphine; natamycin; neomycin; netilmicin; niflumic acid; nizatidine; nogalamycin; norfloxacin; nystatin; oleandomycin; oligomycin(s); olivomycin(s); olsalazine; orthocaine; oxaceprol; oxymorphone; oxytetracycline; paclitaxel; panipenem; paromomycin; pazufloxacin; penicillin N; pentostatin; peplomycin; perimycin A; phenamidine; pipacycline; pipemidic acid; pirarubicin; piridocaine; piritrexim; plicamycin; podophyllinic acid 2-ethylhydrazine; polymyxin; pravastatin; prednimustine; primycin; procarbazine; procodazole; p-sulfanilylbenzylamine; pteropterin; puromycin; quinacillin; quinapril; ranimustine; ranitidine; ribostamycin; rifamide; rifampin; rifamycin SV; rifapentine; rifaximin; ristocetin; ritipenem; rokitamycin; rolitetracycline; romurtide; rosaramycin; roxithromycin; S-adenosylmethionine; salazosulfadimidine; salicyl alcohol; salicylic acid; salmeterol; salsalate; sancycline; sirolimus (rapamycin); sisomicin; solasulfone; sparfloxacin; spectinomycin; spiramycin; streptomycin; streptonigrin; streptozocin; succisulfone; sulfachrysoidine; sulfaloxic acid; sulfamidochrysoidine; sulfanilic acid; sulfasalazine; sulfoxone; tacrolimus; taprostene; teicoplanin; temafloxacin; temocillin; teniposide; tetracycline; tetroxoprim; thiamiprine; thiamphenicol; thiazolsulfone; thioguanine; thiostrepton; ticarcillin; tigemonam; tioclomarol; tirofiban; tobramycin; tolfenamic acid; Tomudex7 (N-[[5-[[(1,4-Dihydro-2-methyl-4-oxo-6-quinazolinyl) methyl]methylamino]-2-thienyl]carbonyl]-L-glutamic acid), topotecan; tosufloxacin; trimethoprim; trimetrexate; trospectomycin; trovafloxacin; tuberactinomycin; tubercidin; ubenimex; vancomycin; vinblastine; vincristine; vindesine; vinorelbine; xinafoate; zidovudine; zorubicin; and any enantiomers, derivatives, bases, salts or mixtures thereof.

In one embodiment, the active agent comprises a non-steroidal anti-inflammatory drug(s) (NSAID(s)) such as those described in U.S. Ser. No. 09/732,516, filed 7 Dec. 2000; 3-amino-4-hydroxybutyric acid, aceclofenac, alminoprofen, amfenac, bromfenac, bromosaligenin, bumadizon, carprofen, diclofenac, diflunisal, ditazol, enfenamic acid, etodolac, etofenamate, fendosal, fepradinol, flufenamic acid, gentisic acid, glucamethacin, glycol salicylate, meclofenamic acid, mefenamic acid, mesalamine, niflumic acid, olsalazine, oxaceprol, S-adenosylmethionine, salicylic acid, salsalate, sulfasalazine, tolfenamic acid and the like. In another embodiment, the active agent is an antibacterial, for example, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin and the like.

In still another embodiment, the active agent comprises an anti-fungal agent such as amphotericin B, azaserine, candicidin(s), chlorphenesin, dermostatin(s), filipin, fungichromin, lucensomycin, mepartricin, natamycin, nystatin, oligomycin(s), perimycin A, tubercidin, and the like. In another embodiment the active agent comprises an anti-cancer, e.g., carcinomas, sarcomas, leukemias and cancers derived from cells of the nervous system), including antineoplastic, for example, 6-azauridine, 6-diazo-5-oxo-L-norleucine, 6-mercaptopurine, aclacinomycin(s), ancitabine, anthramycin, azacitadine, azaserine, bleomycin(s), capecitabine, carubicin, carzinophillin A, chlorozotocin, chromomycin(s), cladribine, cytarabine, daunorubicin, denopterin, docetaxel, doxifluridine, doxorubicin, edatrexate, eflornithine, elliptinium, enocitabine, epirubicin, etoposide, floxuridine, fludarabine, gemcitabine, idarubicin, mannomustine, melphalan, menogaril, methotrexate, mitobronitol, mitolactol, mitomycin C, mitoxantrone, mopidamol, mycophenolic acid, nogalamycin, olivomycin(s), paclitaxel, pentostatin, peplomycin, pirarubicin, piritrexim, plicamycin, podophyllinic acid 2-ethylhydrazine, prednimustine, procarbazine, pteropterin, puromycin, ranimustine, streptonigrin, streptozocin, teniposide, thiamiprine, thioguanine, Tomudex☐ (N-[[5-[[(1,4-Dihydro-2-methyl-4-oxo-6-quinazolinyl)methyl]methylamino]-2-thienyl]carbonyl]-L-glutamic acid), topotecan, trimetrexate, tubercidin, ubenimex, vinblastine, vindesine, vinorelbine, zorubicin and the like. In yet another embodiment, the active agent comprises an anti-thrombotic, for example, argatroban, coumetarol, dicoumarol, ethyl biscoumacetate, ethylidene dicoumarol, iloprost, lamifiban, taprostene, tioclomarol, tirofiban and the like. The agent may also comprise an immunosuppressive, for example, 6-mercaptopurine, amiprilose, bucillamine, gusperimus, mycophenolic acid, procodazole, romurtide, sirolimus (rapamycin), tacrolimus, ubenimex and the like; a general or local anesthetic such as butethamine, fenalcomine, hydroxytetracaine, naepaine, orthocaine, piridocaine, salicyl alcohol and the like, and many others whose list is too extensive to incorporate into the text of this patent.

In still another embodiment the active agent is a low molecular weight drug suitable for linkage into degradable copolymers via a polyanhydride. Such low molecular weight drugs typically have a relatively low molecular weights of approximately 1,000 daltons or less, and may comprise one or more of a carboxylic acid (—COOH), amine (—NH—, —NR—), thiol (—SH, —SR—), alcohol (—OH), phenol (—Ph—OH), ester (—COO—), carbonate (OCOO—), or others that are suitable as well. Suitable examples of low molecular weight drugs with the required functional groups within their structure may be found in almost all classes of drugs including, but not limited to, analgesics, anesthetics, antiacne agents, antibiotics, synthetic antibacterial agents, anticholinergics, anticoagulants, antidyskinetics, antifibrotics, antifungal agents, antiglaucoma agents, anti-inflammatory agents, antineoplastics, antiosteoporotics, antipagetics, anti-Parkinson's agents, antisporatics, antipyretics, antiseptics/disinfectants, antithrombotics, bone resorption inhibitors, calcium regulators, keratolytics, sclerosing agents and ultraviolet screening agents. Particularly important classes of agents are analgesics, anesthetics, antiacne agents, antibiotics, anticancer agents, anticholinergics, anticoagulants, anticonvulsants, antidiabetic agents, antidyskinetics, antifibrotic agents, antifungal agents, antiglaucoma agents, anti-infectives, anti-inflammatory compounds, antimicrobial compounds, antineoplastics, anti-Parkinson's agents, antiosteoporotics, antiseptics, antisporatics, antithrombotics, antiviral compounds, bacteriostatic compounds, bone resorption inhibitors, calcium regulators, cardioprotective agents, cardiovascular agents, central nervous system stimulants, cholinesterase inhibitors, contraceptives, deodorants, disinfectants, dopamine receptor agonists, agents for the treatment of erectile dysfunction, fertility agents, agents for the treatment of gastrointestinal ailments, agents for the treatment of gout, hormones, hypnotics, immunomodulators, immunosuppressives, keratolytics, agents for the treatment of migraine, agents for the treatment of motion sickness, muscle relaxants, nucleoside analogs, agents for the treatment of obesity, opthalmic agents, osteoporosis agents, parasympatholytics, parasympathomimetics, prostaglandins, psychotherapeutic agents, agents for the treatment of respiratory ailments, agents for the treatment of sclerosis, sedatives, agents for the treatment of skin and mucous membrane ailments, smoking cessation agents, sympatholytics, ultraviolet screening agents, agents for the treatment of urinary ailments, agents for the treatment of vaginal ailments, and vasodilators.

One highly preferred embodiment includes, but is not limited to, agents and compounds such as analgesics, anesthetics, anti-acne agents, antibiotics, synthetic antibacterial agents, anti-cholinergic agents, anti-coagulants, anti-dyskinetics, anti-fibrotics, anti-fungal agents, anti-glaucoma agents, anti-inflammatory agents, anti-neoplastic agents, anti-osteoporotic agents, antipagetic agents, anti-Parkinson's disease agents, anti-sporatics, anti-pyretics, antiseptics/disinfectants, anti-thrombotic agents, bone growth stimulating agents, hemostatic agents, bone resorption inhibitors, calcium, sodium and potassium ion regulating agents, keratolytics, anti-sclerosing agents and detectable and signal p producing agents for screening and diagnostic purposes such as ultraviolet (U.V.), fluorescent, phosphorescent, radioactive, enzymatic, antibodies, and other known screening agents, among many others. One highly preferred embodiment of the polymer of this invention includes NSAIDs such as 4-aminosalicylic acid, 5-aminosalicylic acid, 4-(acetylamino) salicylic acid, 5-(acetylamino) salicylic acid, sallsallate, 5-chlorosalicylic acid, 5-(2,4-difluorophenyl) salicylic acid (diflunisal), by themselves or in combination with one another, or in combination with other types of agents such as anti-fibrotic agents, antiseptic agents, antimicrobial agents, hemostatic agents, analgesic agents, antipyretic agents, or anti-coagulating agents, among many others. Yet another preferred polymer includes agents or compounds such as CNS acting agents of the type described above, which may be in the form of a monomer, or in combination with one another, or in combination with non-centrally acting agents such as muscle relaxants, local anesthetics, and the like, all of which would be known to an artisan. Still another highly preferred embodiment includes agents by themselves or in combination with other agents, as an artisan would know to select. Moreover, any combination of agents, whether or not specifically described in this patent are included within the four corners of this invention.

Preferred agents included in the manufacture of the polymer of the invention for applications other than in the pharmaceutical, biological and veterinary fields, include anti-infectives such as disinfectants, antiseptics, antibiotics, antifungal agents, anti-viral agents, anti-microbial agents, antisporatic agents, or bacteriostatic agents, among others, hydrophobicity increasing agents, insulating agents, acustic promoting and shielding agents, adhesives, sealants or coatings, among others, suitable for use in the polymers of this invention. The present polymers may be combined in the form of a co-polymer with segments of tacky polymers, among many others known in the art. The polymers of the invention may also be admixed with adhesives, coatings and/or coatings used in different industries, including the paint, cement, nautical, boating, vehicle, construction materials, electrical, electronics, furniture, household article manufacturing, industries, among many others.

In another embodiment, each $R^1$, independently from one another, comprises at least one residue(s) of the chemical formula

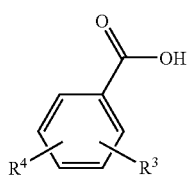

(II)

wherein $R^3$ comprises amine, thiol, carbonate, amide, halo, or hydroxy; $R^4$ comprises hydrogen, halo, $NHR^2$, or aryl, which may be substituted with hydroxy, halo or halo($C_1$-$C_4$)alkyl; and $R^2$ comprises hydrogen, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$)alkyl, heteroaryl($C_1$-$C_6$)alkyl, or ($C_1$-$C_4$)alkylcarbonyl, all of which may be further substituted. In another embodiment $R^1$ comprises an aryl comprising residue that will yield the agent(s) in an active or activatable form upon hydrolysis of the polymer. In another embodiment each agent comprises, independently from one another, an anti-inflammatory, analgesic, anesthetic, or anti-pyretic compound comprising carboxylic acid and at least one amine, thiol, amide, carbonate, or hydroxy. All specific and preferred values for residues, substituents, linking groups, and ranges in this patent are provided for illustration only, and should serve as mere guidance to an invention that is not limited by the specific information listed. More specifically, lower alkyl may be straight or branched ($C_1$-$C_6$)alkyl such as methyl, ethyl, propyl, isopropyl, butyl, iso-butyl, sec-butyl, pentyl, 3-pentyl, or hexyl, among others; ($C_3$-$C_6$)cycloalkyl such as cyclopropyl, cyclobutyl, cyclopentyl, or cyclohexyl; ($C_3$-$C_6$)cycloalkyl($C_1$-$C_6$)alkyl may be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl, among others; ($C_1$-$C_6$)alkoxy such as methoxy, ethoxy, propoxy, isopropoxy, butoxy, iso-butoxy, sec-butoxy, pentoxy, 3-pentoxy, or hexyloxy, among others; ($C_1$-$C_6$)alkanoyl such as acetyl, propanoyl or butanoyl, among others; ($C_1$-$C_6$)alkoxycarbonyl such as methoxycarbonyl, ethoxycarbonyl, propoxycarbonyl, isopropoxycarbonyl, butoxycarbonyl, pentoxycarbonyl, or hexyloxycarbonyl, among others; ($C_1$-$C_6$)alkylthio such as methylthio, ethylthio, propylthio, isopropylthio, butylthio, isobutylthio, pentylthio, or hexylthio, among others; ($C_2$-$C_6$)alkanoyloxy such as acetoxy, propanoyloxy, butanoyloxy, isobutanoyloxy, pentanoyloxy, or hexanoyloxy, among others; aryl such as phenyl, indenyl, or naphthyl, among others; and heteroaryl may be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide), among others.

One preferred linking group comprises a divalent, branched or unbranched, saturated or unsaturated ($C_1$-$C_{20}$) hydrocarbon, which is optionally substituted with, e.g. 1, 2, 3, 4, or more, substituents comprising ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy. Other specific substituents comprise —(CHR$^5$)$_4$—, where each $R^5$ comprises hydrogen, —C(=O)—(CH$_2$)$_{10}$CH$_3$, or —O—P(=O)—O(CH$_2$)$_{10}$CH$_3$, among others. Other preferred linking groups comprise an amino acid(s), peptide(s), protein(s), divalent, branched or unbranched, saturated or unsaturated ($C_1$-$C_{10}$) hydrocarbon residue(s), wherein one or more carbon comprise(s) or is(are) substituted by —O—, or —NR—. Still other preferred linking groups comprise divalent, branched or unbranched, saturated or unsaturated ($C_3$-$C_{20}$) hydrocarbon residue(s), wherein one or more, e.g. 1, 2, 3, 4, or more, carbon atoms is(are) optionally replaced by —O—, or —NR—, and may be further substituted by ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and/or heteroaryloxy, among others. Still other preferred linking groups comprise divalent, branched or unbranched, saturated or unsaturated ($C_3$-$C_{20}$) hydrocarbon, wherein one or more, e.g. 1, 2, 3, 4, or more, atoms is(are) substituted by —O—, —C(=O)O—, —C(=S)O—, —C(=O)S—, —C(=O)NR$^7$—, —C(=S)NR$^7$—, or —NR$^7$—, wherein $R^7$ comprises hydrogen, or ($C_1$-$C_6$) aliphatic residue.

Another group of polymers comprise a linking agent(s) that comprise(s) a divalent, branched or unbranched, saturated or unsaturated ($C_3$-$C_{20}$)hydrocarbon, more preferably a ($C_4$-$C_{15}$)hydrocarbon, and even more preferably n-butyl, n-hexyl, n-octyl, n-decyl, n-dodecyl or n-tetradecyl. Yet another group of polymers includes an agent(s) or compound(s) where $R^3$, independently from one another, comprise(s) HO($C_1$-$C_6$)alkylene; HS($C_1$-$C_6$)alkylene, $R^6$HN($C_1$-$C_6$)alkylene, —OH, —SH, —NH$_2$, —HNR$^6$, wherein $R^6$ comprises alkyl, alkenyl, alkynyl, alkoxy, carboxy, cycloaliphatic residue, aryl, among others, which may be further substituted with halogen, O, N, S, or P; $R^4$, independently from one another, comprises halo, $NHR^5$, cycloaliphatic residue, or aryl, which may be substituted with hydroxy, halo or halo($C_1$-$C_4$)alkyl, wherein $R^5$ comprises hydrogen or ($C_1$-$C_4$) alkyl carbonyl, —NH2, —NHAc, —Cl, 2,4-difluorophenyl, chloromethyl, difluoromethyl, —CF3, with —Cl, and 2,4-difluoro-phenyl being highly preferred. Another preferred group of polymers comprises a residue where $R^5$ comprises H or ($C_1$-$C_6$)alkyl, more preferably methyl, ethyl or propyl. Another highly group of polymers comprises a residue where $R^6$, independently from one another, comprises H, ($C_1$-$C_6$)alkyl, ($C_3$-$C_6$)cycloalkyl, ($C_3$-$C_6$)cycloalkyl($C_1$-$C_6$)alkyl, aryl or aryl($C_1$-$C_6$)alkyl; $R^7$, independently from one another, comprises H, methyl, ethyl or propyl; and $R^8$, independently from one another, comprises —C(=O)CH$_3$. A group of compounds and polymers is that where Y comprises O. Another group of polymers releases an active or activatable agent(s) or compound(s) comprising a biologically active hydroxy-carboxylic acid(s), or that may be converted to such agent(s) upon release by the polymer in situ. The hydroxy-carboxylic agent(s) may be aliphatic or aromatic agents. Preferred among these are agents such as a —($C_1$-$C_{20}$) aliphatic carboxylic acid(s) comprising 1 to 40 hydroxyl residues, including alpha-hydroxy carboxylic and beta-hydroxy carboxylic acids, where preferred are —$(CH_2)_8$—, —$(CH_2)_{14}$—. Another preferred group of agents are hydroxy-aryl carboxylic acids, such as ortho-hydroxy aryl carboxylic acids, particularly those having anti-inflammatory activities. In another embodiment, the polymer of the invention is such where each agent included in $R^1$, independently from one another, comprises residues of different agents or compounds. This embodiment is particularly suitable for the administration of a combination of, or complementary agents, such as in the case of adjunct therapy administered to a subject e.g. in medical, veterinary and agricultural applications, among others. Such polymers are also useful for applications other than screening, diagnosis and therapy where, for example, an additive such as an anti-infective is combined with a coating agent in the polymer backbone to seal an inanimate surface. These applications are particularly suited for the paint, coating, and many other industries, and may applied to surfaces and porous bodies in maritime, engineering, construction, building, oil, mining, and other industries, among many others.

Examples of suitable agents are 2-p-sulfanilyanilinoethanol; 3-amino-4-hydroxybutyric acid; 4,4'-sulfinyldianiline; 4-sulfanilamidosalicylic acid; 6-azauridine; 6-diazo-5-oxo-L-norleucine; 6-mercaptopurine; aceclofenac; acediasulfone; acetosulfone; aclacinomycin(s); acriflavine; acyclovir; albuterol; alendronate; alminoprofen; amfenac; amicarbilide; amikacin; aminoquinuride; amiprilose; amoxicillin; amphotericin B; ampicillin; ancitabine; anthramycin; apalcillin; apicycline; apramycin; arbekacin; argatroban; arsphenamine; aspoxicillin; atorvastatin; azacitadine; azaserine; azidamfenicol; azithromycin; aztreonam; bacitracin; bambermycin(s); benazepril; bialamicol; biapenem; bleomycin(s); brodimoprin; bromfenac; bromosaligenin; bucillamine; budesonide; bumadizon; buprenorphine; butethamine; butirosin; butorphanol; candicidin(s); capecitabine; capreomycin; captopril; carbenicillin; carbomycin; carboplatin; carprofen; carubicin; carumonam; carzinophillin A; cefaclor; cefadroxil; cefamandole; cefatrizine; cefbuperazone; cefclidin; cefdinir; cefditoren; cefepime; cefetamet; cefixime; cefmenoxime; cefminox; cefodizime; cefonicid; cefoperazone; ceforanide; cefotaxime; cefotetan; cefotiam; cefozopran; cefpimizole; cefpiramide; cefpirome; cefprozil; cefroxadine; ceftazidime; cefteram; ceftibuten; ceftriaxone; cefuzonam; cephalexin; cephaloglycin; cephalosporin C; cephradine; chloramphenicol; chloroazodin; chloroazodin; chlorozotocin; chlorphenesin; chlortetracycline; chromomycin(s); cilastatin; ciprofloxacin; cladribine; clarithromycin; clinafloxacin; clindamycin; clomocycline; colistin; coumetarol; cyclacillin; cyclosporin; cytarabine; dapsone; daunorubicin; demeclocycline; denopterin; dermostatin(s); diathymosulfone; dibekacin; diclofenac; dicoumarol; diflunisal; dihydrostreptomycin; dirithromycin; ditazol; docetaxel; dopamine; doxifluridine; doxorubicin; doxycycline; edatrexate; eflornithine; elliptinium; enalapril; enfenamic acid; enocitabine; enoxacin; enviomycin; epicillin; epirubicin; erythromycin; ethyl biscoumacetate; ethylidene; etodolac; etofenamate; etoposide; famotidine; fenalcomine; fendosal; fepradinol; filipin; flomoxef; floxuridine; fludarabine phosphate; flufenamic acid; fluvastatin; fortimicin(s); fungichromin; gemcitabine; gentamicin(s); gentisic acid; glucamethacin; glucosulfone; glycol salicylate; gramicidin S; gramicidin(s); grepafloxacin; guamecycline; gusperimus; hetacillin; hydroxytetracaine; idarubicin; iloprost; imipenem; indinavir; isepamicin; josamycin; kanamycin(s); lamifiban; lamivudine; leucomycin(s); leuprolide; lincomycin; lisinopril; lisinpril; lomefloxacin; lucensomycin; lymecycline; mannomustine; meclocycline; meclofenamic acid; mefenamic acid; melphalan; menogaril; mepartricin; meropenem; mesalamine; metformin; methacycline; methotrexate; methsalamine; metoprolol; micronomicin; midecamycin(s); minocycline; mitobronitol; mitolactol; mitomycin C; mitoxantrone; mopidamol; morphine; moxalactam; mupirocin; mycophenolic acid; nadifloxacin; naepaine; nalbuphine; natamycin; neomycin; netilmicin; niflumic acid; nizatidine; nogalamycin; norfloxacin; nystatin; oleandomycin; oligomycin(s); olivomycin(s); olsalazine; orthocaine; oxaceprol; oxymorphone; oxytetracycline; paclitaxel; panipenem; paromomycin; pazufloxacin; penicillin N; pentostatin; peplomycin; perimycin A; phenamidine; pipacycline; pipemidic acid; pirarubicin; piridocaine; piritrexim; plicamycin; podophyllinic acid 2-ethylhydrazine; polymyxin; pravastatin; prednimustine; primycin; procarbazine; procodazole; p-sulfanilylbenzylamine; pteropterin; puromycin; quinacillin; quinapril; ranimustine; ranitidine; ribostamycin; rifamide; rifampin; rifamycin SV; rifapentine; rifaximin; ristocetin; ritipenem; rokitamycin; rolitetracycline; romurtide; rosaramycin; roxithromycin; S-adenosylmethionine; salazosulfadimidine; salicyl alcohol; salicylic acid; salmeterol; salsalate; sancycline; sirolimus (rapamycin); sisomicin; solasulfone; sparfloxacin; spectinomycin; spiramycin; streptomycin; streptonigrin; streptozocin; succisulfone; sulfachrysoidine; sulfaloxic acid; sulfamidochrysoidine; sulfanilic acid; sulfasalazine; sulfoxone; tacrolimus; taprostene; teicoplanin; temafloxacin; temocillin; teniposide; tetracycline; tetroxoprim; thiamiprine; thiamphenicol; thiazolsulfone; thioguanine; thiostrepton; ticarcillin; tigemonam; tioclomarol; tirofiban; tobramycin; tolfenamic acid; Tomudex (N-[[5-[[(1,4-Dihydro-2-methyl-4-oxo-6-quinazolinyl) methyl]methylamino]-2-thienyl]carbonyl]-L-glutamic acid), topotecan; tosufloxacin; trimethoprim; trimetrexate; trospectomycin; trovafloxacin; tuberactinomycin; tubercidin; ubenimex; vancomycin; vinblastine; vincristine; vindesine; vinorelbine; xinafoate; zidovudine; zorubicin; and any enantiomers, derivatives, bases, salts or mixtures thereof.

In one embodiment the agent(s) comprise(s) a non-steroidal anti-inflammatory drug(s) (NSAID(s)) such as those described in U.S. Ser. No. 09/732,516, filed 7 Dec. 2000; 3-amino-4-hydroxybutyric acid, aceclofenac, alminoprofen, amfenac, bromfenac, bromosaligenin, bumadizon, carprofen, diclofenac, diflunisal, ditazol, enfenamic acid, etodolac, etofenamate, fendosal, fepradinol, flufenamic acid, gentisic acid, glucamethacin, glycol salicylate, meclofenamic acid, mefenamic acid, mesalamine, niflumic acid, olsalazine, oxaceprol, S-adenosylmethionine, salicylic acid, salsalate, sulfasalazine, tolfenamic acid and the like. In another embodiment, the active agent is antibacterial, for example, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprin, butirosin, capreomycin, carbenicillin, carbomycin, p carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin, and the like.

In still another embodiment, the active agent comprises an anti-fungal agent such as amphotericin B, azaserine, candicidin(s), chlorphenesin, dermostatin(s), filipin, fungichromin, lucensomycin, mepartricin, natamycin, nystatin, oligomycin(s), perimycin A, tubercidin, and the like. In another embodiment the active agent comprises an anti-cancer, e.g., carcinomas, sarcomas, leukemias and cancers derived from cells of the nervous system), including antineoplastic, for example, 6-azauridine, 6-diazo-5-oxo-L-norleucine, 6-mercaptopurine, aclacinomycin(s), ancitabine, anthramycin, azacitadine, azaserine, bleomycin(s), capecitabine, carubicin, carzinophillin A, chlorozotocin, chromomycin(s), cladribine, cytarabine, daunorubicin, denopterin, docetaxel, doxifluridine, doxorubicin, edatrexate, eflornithine, elliptinium, enocitabine, epirubicin, etoposide, floxuridine, fludarabine, gemcitabine, idarubicin, mannomustine, melphalan, menogaril, methotrexate, mitobronitol, mitolactol, mitomycin C, mitoxantrone, mopidamol, mycophenolic acid, nogalamycin, olivomycin(s), paclitaxel, pentostatin, peplomycin, pirarubicin, piritrexim, plicamycin, podophyllinic acid 2-ethylhydrazine, prednimustine, procarbazine, pteropterin, puromycin, ranimustine, streptonigrin, streptozocin, teniposide, thiamiprine, thioguanine, Tomudex☐ (N-[[5-[[(1,4-Dihydro-2-methyl-4-oxo-6-quinazolinyl)methyl] methylamino]-2-thienyl]carbonyl]-L-glutamic acid), topotecan, trimetrexate, tubercidin, ubenimex, vinblastine, vindesine, vinorelbine, zorubicin and the like. In yet another embodiment, the active agent comprises an anti-thrombotic, for example, argatroban, coumetarol, dicoumarol, ethyl biscoumacetate, ethylidene dicoumarol, iloprost, lamifiban, taprostene, tioclomarol, tirofiban and the like. The agent may also comprise an immunosuppressive, for example, 6-mercaptopurine, amiprilose, bucillamine, gusperimus, mycophenolic acid, procodazole, romurtide, sirolimus (rapamycin), tacrolimus, ubenimex and the like; a general or local anesthetic such as butethamine, fenalcomine, hydroxytetracaine, naepaine, orthocaine, piridocaine, salicyl alcohol and the like, and many others whose list is too extensive to incorporate into the text of this patent.

In still another embodiment the agent(s) is(are) a low molecular weight drug suitable for linkage into degradable copolymers via a polyanhydride. Such low molecular weight drugs typically have a relatively low molecular weights up to about 1,000 Dalton, and may comprise one or more of a carboxylic acid (—COOH), amine (—NH—, —NR—), thiol (—SH, —SR—), alcohol (—OH), phenol (-Ph-OH), ester (—COO—), carbonate (OCOO—), or others that are suitable as well. Suitable examples of low molecular weight drugs with the required functional groups within their structure may be found in almost all classes of drugs including, but not limited to, analgesics, anesthetics, antiacne agents, antibiotics, synthetic antibacterial agents, anticholinergics, anticoagulants, antidyskinetics, antifibrotics, antifungal agents, antiglaucoma agents, anti-inflammatory agents, antineoplastics, antiosteoporotics, antipagetics, anti-Parkinson's agents, antisporatics, antipyretics, antiseptics/disinfectants, antithrombotics, bone resorption inhibitors, calcium regulators, keratolytics, sclerosing agents and ultraviolet screening agents. Particularly important classes of agents are analgesics, anesthetics, antiacne agents, antibiotics, anticancer agents, anticholinergics, anticoagulants, anticonvulsants, antidiabetic agents, antidyskinetics, antifibrotic agents, antifungal agents, antiglaucoma agents, anti-infectives, anti-inflammatory compounds, antimicrobial compounds, antineoplastics, anti-Parkinson's agents, antiosteoporotics, antiseptics, antisporatics, antithrombotics, antiviral compounds, bacteriostatic compounds, bone resorption inhibitors, calcium regulators, cardioprotective agents, cardiovascular agents, central nervous system stimulants, cholinesterase inhibitors, contraceptives, deodorants, disinfectants, dopamine receptor agonists, agents for the treatment of erectile dysfunction, fertility agents, agents for the treatment of gastrointestinal ailments, agents for the treatment of gout, hormones, hypnotics, immunomodulators, immunosuppressives, keratolytics, agents for the treatment of migraine, agents for the treatment of motion sickness, muscle relaxants, nucleoside analogs, agents for the treatment of obesity, opthalmic agents, osteoporosis agents, parasympatholytics, parasympathomimetics, prostaglandins, psychotherapeutic agents, agents for the treatment of respiratory ailments, agents for the treatment of sclerosis, sedatives, agents for the treatment of skin and mucous membrane ailments, smoking cessation agents, sympatholytics, ultraviolet screening agents, agents for the treatment of urinary ailments, agents for the treatment of vaginal ailments, and vasodilators.

IV. Polymer Preparation

A. Introduction

The following Table 3 provides a schematic description of the features of the different embodiments of the process of the invention.

TABLE 3

| Features of Embodiments of Invention Preparative Process |||
| --- | --- | --- |
| Process Embodiment | | Result of Structure or Process |
| Solution Polymerization | | Ability to produce wide range of polymeric forms e.g. elastomers, semi-crystalline polymers, controlled cross-linked polymers, etc. |
| Properties | Medical Device | Structures |
| Exact control over structure and molecular weights. Exact control of end groups of polymer Control enables creation of ethylene oxide and radiation resistant polyanhydrides - new properties. Release behavior is unaffected by sterilization Shelf life and solvent stability is extended significantly with new chemistry Exact control over release profile (duration, rate & induction period) Vary structure's solubility to control incorporation of agents (match solubility parameters of polymer with agent) Exact Structure control, molecular weight control, ability to create unique bond sequences. | Applies to all medical devices. | See below thermoplastic elastomer, multiblock polymers, semi-crystalline polymers, thermoset polymers, various molecular weights |
| Process Embodiment | How Obtained | Result of Structure or Process |
| Block Copolymer of controlled sequence & length | The solution polymerization route proposed allows one to create blocks of any molecular weight and structure desirable. These blocks are then end-linked as described in the examples to create a single polymer with multiple blocks where each block can be a different drug based sequence or different sequences of the same therapeutic agent but with different release characteristics. | Multiple therapeutics from one polymer. Multiple release profiles from one polymer Crystallizable segments in the same polymer Phase separated segments in one polymer. Reactive segments in one polymer (blocks that can be cross-linked for example with blocks that cannot. |
| Unique Properties | Medical Device | Structures |
| Can create thermoplastic elastomers (based on crystalline segments or associated segments - see examples below). Can create unique block sequences. Multiple properties within one polymer. Thermal temperature differences between the blocks (Tg1 – Tg2, Tm – Tg) Differences in any physical property (release rate, compatibility, solubility, solubility for a specific agent, refractive index, etc.) Differences in any chemical property. | All medical devices. Devices would include flexible biodegradable items (sutures, mesh, coatings onto elastic surfaces, etc.). applications that require multiple therapeutics from one device/coating/microsphere or nanosphere | Blocks of different chemical compositions; for example different therapeutics, Blocks of different physical properties; for example different Tg's, different solubilities, different dielectric constant, different rate of degradation, different wettability, etc. |

TABLE 3-continued

Features of Embodiments of Invention Preparative Process

| Process Embodiment | How Obtained | Result of What Structure or Process | |
|---|---|---|---|
| Altering linker chain length | Change the linker length used to create the polymer. Mixtures of various linker lengths in one polymer randomly can produce similar effects as well. | Change in linker length Change in linker bond type Change in linker type. | |
| Properties | Medical Device | | |
| Direct control of physical properties (Tg, % crystallinity, modulus, adhesion for example) Carbon length of linker and flexibility of linker (can be quantified as persistence length). | All | | |

| Process Embodiment | How Obtained | Result of What Structure or Process | |
|---|---|---|---|
| Non-Aqueous Dispersion Process | Dispersion provides uniform temperatures and temperature control No surfactant avoids poisoning. Particular mix of solvents creates a ratio of viscosities and surface tension that stabilizes the dispersion during polymerization. | Dispersion process as described | |
| | Medical Device | | |
| | All | | |

| Process Embodiment | How Obtained | Result of What Structure or Process | Prepare by Previous Method |
|---|---|---|---|
| End capping & End linking | Solution chemistry method described above. | Solution Chemistry | No |
| Properties | Medical Device | Structure | |
| see solution polymerization, TPE and Block Polymers; end groups, end group chemistry | All | Blocks, muti-agent polymers, very high molecular weights. | |

| Process Embodiment | How Obtained | Result of What Structure or Process | |
|---|---|---|---|
| Branching at Well-defined Branch Points | For example, random branches can be placed by using muti-acids as part of the normal solution synthesis. Star-like branches can be created by polymerizing from an initial branch point and growing the chain my solution polymerization. Branching at various lengths (molecular weights) can be created by forming polymers of know Mw's, creating the appropriate end groups, and then end linking to create the final polymer. | The solution chemistry and end-linking methods enable this practice. | |
| Properties | Medical Device | Structure | |
| Control elasticity Control of melt elasticity and melt elongation Control of Fatigue Resistance Control of toughness Control of adhesion Ability to create branches that are chemically different than the | Applies to all devices Applies to processes for coating or making devices. To increase the melt elasticity for making blow-molded devices, branching has to be incorporate. This allows for the production of biodegradable bottle-like | Branched. | |

TABLE 3-continued

Features of Embodiments of Invention Preparative Process

| | | |
|---|---|---|
| main chain<br>Ability to create branches that have different physical and chemical properties than the main chain.<br>Surfactant-like molecules that may serve as blend (or phase) compatibilizers and stabilizers<br>The ability to have targeting structures (branches) on a polymer chain.<br>Chain & branch composition<br>Molecular weight<br>Molecular weight between branches<br>Distribution of the two pervious items<br>Physical & chemical properties of branches and chain<br>End group or branch point chemistry (anhydride vs. carbonate for example.) | structures.<br>To modify coating application (higher viscosity without changes in molecular weight), branching is used to alter solution viscosity. | |

| Process Embodiment | How Obtained | Result of What Structure or Process |
|---|---|---|
| Thermoplastic Elastomer | Polymers based on two incompatible units are created so that they phase separate when processed. Incompatibility means difference in solubility as defined by the Van Krevlin (for example) solubility parameter, or differences based on crystallizability. One component is selected with a glass transition temperature or crystalline melt temperature above the targeted use temperature. The second component is selected to have a Tg below the targeted use temperature. On processing, these materials phase separate and form anchored phases that create a rubber-like material that can be re-processed by heating about the Tg or Tm of the higher temperature polymer.<br>As a compatibilizer, the solubility of a particular block is selected to be similar to one of the phases of a blend that needs to be compatibilized (homogeneous polymers that are not compatible with each other). Similar approach is taken to match the additional block(s) with the additional phase(s). The compatibilizer (usually in the range of 5% w/w or less) is blended with the two homopolymers to create a compatibilized system. | Result of the block structure enabled by the solution chemistry method and end-linking chemistry. |

| Properties | Medical Device | Structure |
|---|---|---|
| Elastomeric behavior over a wide temperature range.<br>Multi therapeutic (at least two in the preferred embodiment)<br>Multi-release profile (at least two in preferred embodiment)<br>Control phase or domain morphology by varying the degree of compatibility.<br>Can server as a mechanical reinforcing agent when incorporated into homopolymers or homopolymer blends. | All devices with specific opportunity to coat devices that require elastomeric flexibility (artificial hart valves, bone pin sheaths, ocular devises, dermal applications, bandages, wound closure devices, coatings on organs, coatings on dimensionally changing medical devices, etc.) | As described. |

TABLE 3-continued

Features of Embodiments of Invention Preparative Process

Glass transition, Tg
Melt Temp., Tm
Relative Solubility (solubility, parameter)

| Process Embodiment | How Obtained | Result of What Structure or Process |
|---|---|---|
| MW Molecular Weight Distribution Tg,1-Tg,2 Temperature range for phase separated amorphous TPE Tm-Tg2, temperature range for crystalline separated TPE. In both cases, Tg,2 is the lower temperature and Tm & Tg,1 are the higher temperatures. | | |

The polymers of this invention, such as the polySA and polyDF being described for exemplary purpose only, may be produced by a number of methods. In each case, the polymers are produced by chemically connecting repeating monomers ("-mers"). Each repeating unit contains two drug molecules connected via ester bonds to one linker molecule; the drug molecules are connected via anhydride bonds. In the standard "melt condensation" approach used to prepare the polymers of this invention, e.g. polyAspirin, the monomers were dissolved in a solvent and stirred for several hours at relatively high temperatures. The inventors produced polymers such as polySA and polyDF polymers by this method, with molecular weights ranging from about 30,000 to about 90,000 and polydispersities, a measure of polymer homogeneity, of about 1.5 to about 3.0. Other methods permit the preparation of polymers in higher yields, as well as of higher MWs and greater uniformity than prior methods permitted.

By definition, all biodegradable polymers are designed to degrade and release its agent(s) over a period of time. Unlike other poly(anhydride-ester) polymers reported in the literature, the present polymers are highly soluble in common industrial solvents, and are relatively stable (as measured by loss of molecular weight) both in bulk and in solution. The desirable "bulk stability", or molecular weight stability of the polymers at room temperature is generally about 1 week, 1 month, 6 months to about 8 months, 1 year, 2 years, although longer periods of stability may be attained as well. As with most other drugs the stability of the polymers of this invention is enhanced by storage under dry conditions and at low temperatures e.g. −20° C. However, even under unprotected ambient conditions, polymers such as polyNSAIDs are stable for weeks, and storage-related changes in molecular weight do not significantly affect polymer performance for drug delivery.

B. Non-Aqueous Dispersion Process

This embodiment provides a process for polyanhydride polymerization to attain a high molecular weight, e.g. in excess of 40,000 Dalton, polymer with negligible or no gel formation. This is a novel process for the preparation of a polyanhydride starting from a mixed anhydride of a dicarboxylic acid, also called here a pre-polymer, by non-aqueous dispersion polymerization. The method comprises heating a pre-polymer above its melting point in the presence of a solvent for the pre-polymer, e.g. an inert high boiling point solvent, that will not be a solvent for the polymer, under conditions effective for removing a mixed anhydride evolved upon polymerization. The mild conditions of this novel process permit the extension of a polyanhydride to a higher molecular weight than attainable by existing processes that form gelatinous or insoluble polymer fractions that slow the polymerization reaction and impede the extension of the polymer.

The inventors discovered that the melt-polymerization of polyanhydrides from selected diacids formed as mixed anhydrides with lower molecular weight acids e.g. acetic or propionic acids permits the extension of the polymer backbone to molecular weights exceeding 40,000 Dalton without formation of a gel. This is achieved by carrying out the reaction as a non-aqueous dispersion of molten droplets suspended in a stable high boiling heat-transfer fluid that is generally chemically unreactive with respect to the polymer. In practicing this method, the formation of a stable non-aqueous dispersion (NAD) may be carried out by any known method, such as by vigorous mechanical mixing or stirring, for example with a variety of agitator designs or proprietary mixing devices, or by incorporating a minor amount of a dispersing agent or surfactant, e.g. a non-aqueous agent or surfactant, to encourage the formation of a stable emulsion of molten droplets of the polymerization phase as a dispersion in the continuous phase of the inert fluid. In one embodiment, the dispersing agent should not react chemically with the polyanhydride, its chemical nature being free from any functional groups that would react with the anhydride moieties in the polymer.

In another embodiment, the reaction is carried out in the absence of any surfactant. The particle size of the suspended droplets is preferably about 0.5, 1.0, 2.5, or 5.0 to about 7.5, 10, 25, 35, or 50 micron in diameter, and any combination thereof, although values for the droplet diameter outside of this range are also contemplated. A small particle size encourages rapid removal of volatile materials, for instance under vacuum, and provides uniform, constant heating to the system. Local overheating phenomena, or localized "hot spots" that are prone to occur in the monolithic melt procedures of the prior art led to undesirable side-reactions that may result, for example, in gel-formation and the like. Moreover, the viscous heating effects produced by stirring a high melt viscosity molten polymer employed by the prior art also caused local overheating.

In the present method, the dispersion is almost always fluid, and this avoids all the undesirable effects mentioned above. The heat transfer fluid itself (the pre-polymer solvent) is preferably not volatile, and a poor solvent or a non-solvent for the molten polymer. The pre-polymer solvent, in addition, should have a sufficiently high boiling point so that it will not distill extensively from the system under high vacuum during the course of polymerization. Examples of heat transfer liquids or pre-polymer solvents comprise, although not being limited to, mineral oils, vegetable oils, silicone oils, napthalenes, biphenyls, decalines, and substituted benzenes, among others. The inventors have found that hydrocarbon oils such as "white mineral oils" are eminently suitable.

Although generally conducted at ambient pressure, the polymerization reaction in accordance with this invention may be conducted at a pressure as low as about 0.002 mmHg with little loss of oil by distillation, and clearly at any pressure therebetween. The polymerization may also be conducted at higher pressures, up to about 0.0002 mmHg, and even higher. As the reaction progresses the reaction's volatile materials may be removed from the system, e.g. condensed separately in a trap cooled to −78° C. with a solid carbon dioxide/isopropanol mixture. Other methods for removal of volatile substances known in the art may also be employed. The polymerization is preferably conducted at a temperature of about 100, 120, 140, or 160° C. to about 160, 180, or 200° C., with a preferred temperature for certain polyanhydride esters being about 160 C±20° C. When polymerization is completed the reaction mixture may be allowed to cool with agitation, under e.g. constant and vigorous agitation, until the molten drops solidify and form a suspension of solid spherical particles in the matrix fluid. Upon cooling the particles may be separated from the reaction medium, e.g. by filtration, and washed with a substance that dissolves the mineral oil but not the particles. Although other substances may be employed, light petroleum fractions with an about 40° C. to about 60° C. boiling point were found particularly suitable for this purpose. The particles may be subjected to continuous extraction in a suitable apparatus, such as a Soxhlet apparatus, if desired. The temperature of the solvent during the extraction step should preferably not exceed the glass transition temperature (Tg) of the polymer to avoid causing sintering of the polymer particles. To this end, the use of a modified Soxhlet apparatus is preferred such that the extraction is performed with cooling of the solvent.

C. Solution Polymerization Process

This embodiment comprises a process for synthesizing polymers in solution by controlling the polymer structure and molecular weight (MW) to attain polymers of enhanced properties such as mechanical properties, stability, and hydrolytic stability, among others. The invention entails the selection of monomer structure and amount, feed ratio, and activation strategy to obtain polymers of molecular weight greater, and of enhanced performance, than previously attained by the prior art. This embodiment enables the choice and amount of monomer, solvent, and use of activation chemistry in a selection that impacts the performance characteristics of the resulting polymer. The present process teaches the selection of these parameters for the preparation of different types of polymers of selected characteristics such as polyesters, polycarbonates, polyanhydrides, and polyamides, among others. This patent teaches how to produce a polymer possessing desired performance properties by choosing specific monomers, solvents, reaction conditions, and optional steps as described below. This process enables the selection of a plurality of monomers, and reaction conditions to produce a polymer possessing a random array of conjoined monomer units imparting to the product desirable properties.

One embodiment of this process employs an acylating or dehydrating agent, e.g. phosgene or phosgene analogue, equivalent or substitute e.g. triphosgene, preferably in stoichiometric combination with an aliphatic or aromatic diacid salt(s) in the presence of a solvent for the diacid salt(s) e.g. volatile organic solvent, comprising halogenated hydrocarbons e.g. chlorinated hydrocarbons, ethers, esters, amides, and sulfoxides having boiling points less than 200° C., among others. Preferred solvents include halogenated solvents e.g. chlorinated solvents with boiling points less than about 100° C., an example being dichloromethane. In a preferred embodiment, the aliphatic or aromatic diacid salt(s) may be monomeric, oligomeric or polymeric in nature. In another preferred embodiment, the monomeric, oligomeric, or polymeric diacid chloride may be replaced by phosgene and the corresponding diacid. In another embodiment, various diacid ammonium and alkali metal salts may be utilized as well.

Still another embodiment of the solution polymerization process for preparation of the polymers of this invention comprises employing the synthetic routes described below with or without different optional steps. Various permutations of the different steps shown in the overall schemes illustrated below provide the flexibility of designing polymers of desired characteristics such as molecular weight, flexibility, hardness, adhesiveness, and the like by modulating different parameters associated with their manufacture, such as linker length, substituents, combining stretches of different

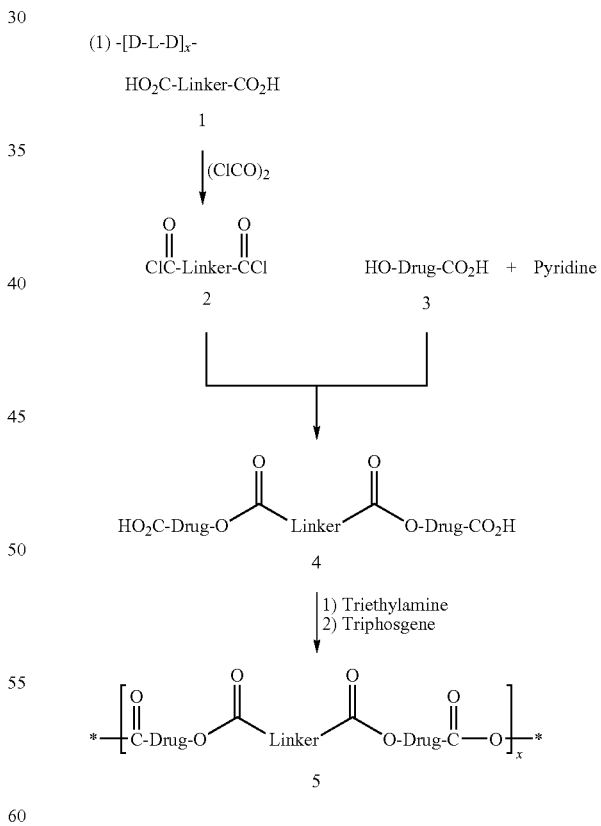

polymers of different physical and chemical properties, end-capping, combining aromatic with aliphatic moieties in the linkers and co-polymer segments, and the like, as described below. Schemes 1(1) and 1(2) provided below show two embodiments of the process of this invention involving solution polymerization.

Scheme 1(1)

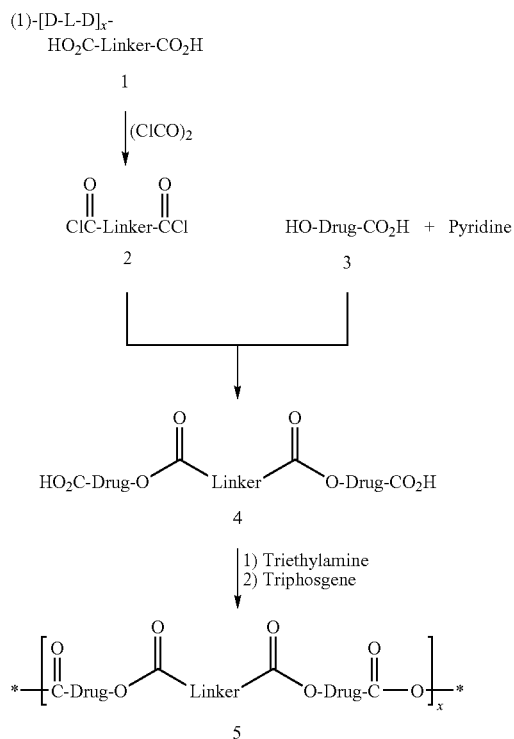

In the embodiment shown in Scheme 1(1) above, the hydroxyl group of each of two molecules of an agent(s) or compound(s) of interest is(are) reacted with a bi-functional linker(s) that has been activated by acylation to obtain the corresponding acid chloride(s) (2) in the presence of a solvent and allowed to form a diacid intermediate (4) comprising two end agent units, in the example 2 drug molecules, with one linker between them. The diacid intermediate (4) is then placed in the presence of an amine, e.g. a tertiary amine, such as triethyl amine, pyridine and/or di-isopropylethylamine to obtain a quaternary ammonium salt, which in the presence of an effective amount of triphosgene or similar agent dissolved in a solvent, e.g. an anhydrous solvent such as dichloromethane or chloroform, that is preferably added slowly to the quaternary ammonium salt of the diacid mixture to form a desired polyanhydride (5). In this embodiment, the molecular weight may be determined by the amount of triphosgene as well as the period of time the reaction is allowed to proceed. The growth of the molecular weight may be monitored as the polymer is extended, for example by GPC as is known in the art. The reaction may be conducted across a wide range of temperatures, e.g. about $-20, -15, -10, -5, 0,$ or $5°$ C. to about $5, 7, 10, 15,$ or $20$, ambient temperature, provided that the temperature does not facilitate the occurrence of side reactions that might impede the linear growth of the polymer, e.g. $<25°$ C. If practiced in the manner described, this process produces a polymer comprising alternating units of the agent(s) or compound(s) and the linking group(s).

Scheme 1(2)

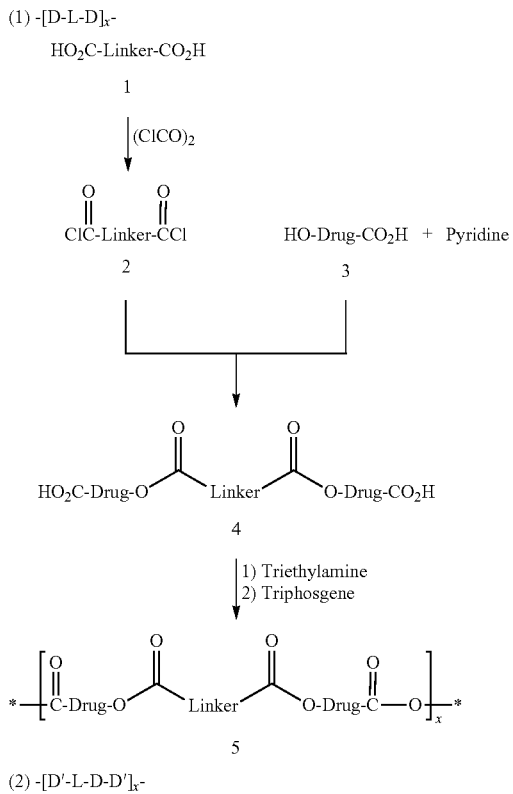

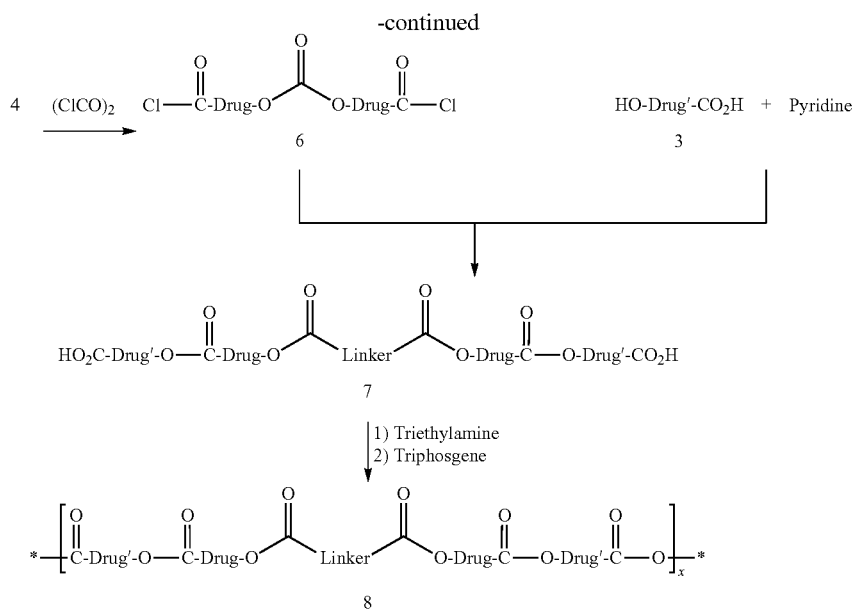

In another embodiment shown in Scheme 1(2) above the diacid intermediate (4) may be activated by acylation to attain a diacid halide (6) comprising two molecules of agent(s) and one linker, which is then reacted with the hydroxyl of two molecules of agent(s) or compound(s) to form a diacid comprising four agent(s) units, and so on. This diacid may then be subjected to the remaining steps of the process described above to form its triethylammonium salt, and then placing the salt in the presence of triphosgene to form a polymer in accordance with this invention comprising alternating units of one linker and four drug moieties. In the same manner the process may be adapted to design polymers of varying numbers of agent(s) units bonded to one another and then linked through one linker, or by employing the same or other linkers and other agents to vary the chemical sequence of the resulting polymer. Yet another embodiment of the process of the invention is shown in Scheme 2 below.

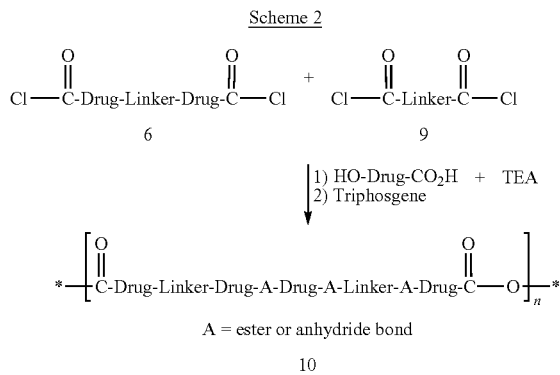

This embodiment of the process of the invention comprises generating a pre-polymer with a relatively low molecular weight, e.g. about <20,000, by reacting two different diacids that may be activated as acid chlorides (6) and (9) with, e.g. a triethyl ammonium salt of an agent(s) or compound(s) in an anhydrous solvent. The thus formed pre-polymer may be isolated and linked together by addition of, for example triphosgene, to the quaternary ammonium salt of the pre-polymer to achieve a higher molecular weight, e.g. about <50,000, by end-linkage. Depending on the composition and the order of addition of the different components, the arrangement around the agent(s) or compound(s) units may be modified by using this procedure to attain sequences such as -L-D-L-, -L-D-D-L-, -L-D-D-D-L-, or -L-D-D-D-D-L-, wherein D comprises an agent(s), and L comprises a linking group(s), among many others. The thus produced bonds between linker and agent(s) or compound(s), agent(s)-agent(s), or linker(s)-linker(s) may comprise ester or anhydride depending on the combination of process. It will be appreciated by those skilled in the art that the compounds of the invention may comprise a chiral center(s) and, therefore, may exist in and be isolated in optically active and racemic forms. Some compounds may exhibit polymorphism. The present polymers comprise any racemic, optically-active, polymorphic, or stereoisomeric form, and their mixtures, including those of an agent(s) or compound(s) possessing the useful properties described herein. Based on the description of the process of the invention, an artisan will know how to prepare optically active forms, for example by resolution of the racemic form by recrystallization techniques, by synthesis from optically-active starting materials, by chiral synthesis, and by chromatographic separation using a chiral stationary phase, among others, and how to determine cADPR agonist or antagonist activity of the polymers and agents or compounds using standard tests that are either described here or are well known in the pertinent art.

Intermediates useful for preparing compounds of formula (I) are also provided as further embodiments of the invention. In cases where compounds are sufficiently basic or acidic to form acid or base salts, use of the compounds as salts may be appropriate. Examples of acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate, among others. Suitable inorganic salts may also be formed, including hydrochloride, sulfate, nitrate, bicarbonate, and carbonate salts, among many others. Acceptable salts may be obtained using standard procedures well known in the art such as by reacting a sufficiently basic compound such as an amine with a suitable acid affording a physiologically acceptable anion. Alkali metal (for example, sodium, potassium or lithium) or alkaline earth metal (for example, calcium) salts of carboxylic acids may also be made. The ability of a compound of the invention to be polymerized may be determined using polymer formation techniques that are well known to the art. The activity of the polymers may be determined using assays that are well known to the art or described herein.

D. Solution Process-Structure & Molecular Weight Control

This embodiment of the solution polymerization process of the invention comprises novel polymer workup steps, and produces polymers that exhibit marked improvements over prior art polymers in overall performance as it applies to various structural and performance polymer properties. The process of the present invention produces polymers that greatly improves on the desirable characteristics of prior art polymers, particularly in attaining higher molecular weights e.g. up to about 100,000; 200,000; 350,000; 500,000; 750,000; 1,000,000 Dalton, and higher. The process of the invention results in polymers that exhibit specific unexpected properties that are described below.

1) Enhanced structural control is employed to achieve targeted polymer assembly characteristics by polymerization of pre-designed co-monomers and/or linking chemistries. The present polymers attain configurations representing a broad spectrum ranging from purely alternating, to random, to tapered block, to multiblock polymeric structures. An illustrative, non-limiting example includes hybrid ester-anhydride polymers based on salicylic acid derivatives. These compounds contain relatively labile phenolate esters that are readily amenable to concerted trans-esterification and anhydride exchange. This feature is controlled by the method of the invention to attain a targeted, controlled structure during the solution polymerization process.

2) Enhanced yield and purity are achieved through inhibition or suppression of deleterious oxidative, cross-linking, and other side-reactions by employing mild polymerization temperatures, e.g. ambient and lower solution-polymerization temperatures that are milder by comparison with the prior art melt-condensation temperatures typically well in excess of 100° C.

3) Enhanced capability to control polymer molecular weight, and in particular a demonstrated capability to achieve high polymer molecular weights, both in one-pot, and in post-end-linking syntheses. These molecular weights are higher that were ever reported by the prior art using melt-condensation, and solution polymerization.

4) Greatly enhanced storage stability (shelf life) and "pot-life" stability, particularly in terms of hydrolytic stability in organic solvents and in the solid state, achievable with a wide range of alternating, randomized and block polymer structures. This is generally imparted during an acidic work-up and isolation of the polymer following the solution-polymerization step.

5) Ability to control the performance properties of a polymer e.g. degradation rate and mechanical strength, for instance by selection of appropriate co-monomer and linking chemistry configurations. This may be implemented by the following means.

a. Inhibition of, or decreased, pitting that is mostly due to crystallization of a less randomized polymeric structure (a more regular crystalline structure) as it degrades. Bulk and surface integrity and mechanical strength may be maintained by preventing unwanted crystallization. This facilitates sustained polymer surface erosion, inhibits transition to bulk erosion, and enhances long-term adhesion to surfaces and predictable/controllable active compound generation rates from polymer films and other forms and shapes, even when wet.

b. Prevention of formation of long block structures of phenolate-ester-linked diflunisal units that typically arise during melt polycondensation and are very slow to degrade. This prolongs the time to achieve complete elution of diflunisal.

c. Prevention of formation of long block units that arise during melt-polycondensation and increase instability in organic solvents, and in the solid state due to enhanced hydrolytic lability of non-aromatic anhydride linkages.

6) Ability to obtain high polymer molecular weights of up to about 600,000 Dalton, and even higher, by solution polymerization. These molecular weights are substantially higher than those attained by melt-polycondensation by the prior art. Such high molecular weights enhance the mechanical strength, flexibility, and toughness, among other properties, of the polymer.

The unexpected ability to control a polymer's structure, performance and stability provided by the process of the invention relative to the prior art melt-polycondensation processes arises largely from the interplay of various factors, two of which being described below.

1) The use of a solution medium in the polymerization process of this invention eliminates the occurrence of "melt incompatibility" that is prevalent in melt-polycondensation methods of the prior art. The net effect is seen most readily when co-monomer units highly incompatible in the melt, such as fluorinated aromatic-fatty aliphatic co-monomer units, e.g. diflunisal-C14 diacids; are polymerized by these two distinct methods. In the melt-polymerization process of the prior art, this melt incompatibility may drive the ultimate formation of segregated, tapered block co-monomer arrangements. In melt polycondensation, melt segregation may also contribute to the formation of insoluble domains, or chemically- or physically-cross-linked gels. This significantly lowers the yield of useful polymer, and requires the extraction of soluble polymer portions upon completion of the synthesis. In the specific case of the mentioned C14 diflunisal polymer, for example, the occurrence of block sequences of bis-C14 anhydride may compromise the polymer's hydrolytic stability in organic solution and in the solid state whereas block sequences of phenolate-ester-linked diflunisal units degrade very slowly and, thereby extend the time for complete polymer degradation and diflunisal release.

2) The solution process of the invention utilizes highly-reactive linking chemistries in combination with low temperatures that facilitate the design and attainment of desired end-structures and disfavors unwanted side reactions that are prevalent under the high temperatures required by melt-polycondensation. The nature of the polymer end-groups, e.g. aromatic and aliphatic carboxylic acids, produced by solution polymerization in combination with an acidic aqueous workup procedure facilitates the conversion of anionic salts to carboxylic acids, and produces a marked improvement in both storage and "pot-life" hydrolytic stability. In the specific case of polymer-drugs such as the C14-diflunisal ester-anhydride polymer the end group factor adds to the improved control of the polymer structure the formation of lesser sequences of bis-C14 anhydrides, all of which contribute to improving hydrolytic stability in organic solvents and in the solid state.

E. Process Employing End-Capping/End-Linking

This is another embodiment of the solution polymerization process that was suitably designed to attain high molecular weight polymers, e.g. polyanhydrides and hybrid poly(ester-anhydrides), by addition of controlled end-group structures through solution end-linking chemistry. In one embodiment, end-linking or end-capping involves the use of an acylating or dehydrating agent e.g. phosgene, preferably in stoichiometric combination, with an aliphatic or aromatic diacid ammonium salt(s), preferably alkylammonium or alkali metal salt(s), in the presence of a solvent e.g. an organic solvent. For polymeric extension by coupling or polymer end-capping preferred diacid salts comprise oligomeric or polymeric aliphatic or aromatic diacid salts. An oligomeric or polymeric diacid halide, e.g. diacid chloride, may be substituted for phosgene, and the corresponding diacids and/or diacid ammonium and alkali metal salts utilized. The choice of end-linking chemistry for polymer extension to increase the polymer's molecular weight vs. reactive propagation of co-monomer functional groups impacts the type of structural arrangement produced, in terms of both linking bonds and co-monomer arrangement, the resulting configurations ranging from purely alternating to random to tapered block to multi-block structures. The following are non-limiting examples intended to illustrate the numerous conceivable synthetic permutations encompassed by this process.

1) Polymerization of two different diacid alkylammonium salts with phosgene produces a randomized co-monomer.

2) Polymerization of two different diacids, one present as an acid halide, e.g. chloride, and the other present as an alkylammonium salt, yields a strictly alternating co-monomer.

3) Polymerization of two different diacids forming part of an acid halide, and alkylammonium salt produces a randomized co-monomer.

4) Utilization of a co-monomer with a phenol group, e.g., salicylate drugs, in the form of an alkylammonium salt imparts an enhanced capability for concerted transesterification and anhydride exchange during the synthesis of ester-anhydride polymers based on them. The frequency may be modulated by starving the pot of free phenol groups to varying degrees. This method achieves a wide range of polymer structures incorporating varying degrees of randomization and/or blocking of both co-monomer units and linking structures.

In one embodiment, the choice of chemistry for polymer end-capping differs primarily from chain extension in that the end-cap comprises a mono-functional rather than di-functional entity. Non-limiting examples of possible compounds for end-linking include acetyl chloride with an alkylammonium carboxylate-terminated polymer to produce a mixed acetic anhydride end-group. Conversely, alkylammonium acetate with a carboxylic acid chloride-terminated polymer may be employed to produce a mixed acetic anhydride end-group. Fatty acid halides, e.g. chlorides, or fatty alkylammonium or metal salts, such as palmitoyl halides, e.g. chloride, may be similarly employed to produce fatty acid end-groups. Clearly, other structural end-groups may be used if suitably pre-functionalized to allow end-capping with the polymer of interest. The chemical reactions or steps of the process involved in end-linking may be implemented in-situ as the last step of a polymer synthesis.

In another embodiment this effect may be attained by end-capping a pre-synthesized polymer. In this embodiment where a pre-synthesized polymer is employed, it is preferable to use cross-linked acid-acceptor beads instead of tri-ethylamine or other tertiary amine to make an alkylammonium carboxylate salt. This preferred modification greatly facilitates the manipulation of the polymer subsequent to end-capping. A choice of linking chemistry may be implemented by selection of the propagating co-monomer functional groups. This selection will impact the type of structural arrangement produced, e.g. linking bonds and co-monomer arrangement, resulting in structure configurations ranging from purely alternating to random to tapered-block to multi-block structures. Non-limiting examples intended to illustrate the numerous conceivable synthetic permutations are described below.

This process conducts the polymerization with all acylating agents at temperatures e.g. ambient to about 0° C., and even lower temperatures. Such temperature range will generally suffice for the facile acylating propagation reactions, and polymerization may typically be achieved in times ranging from as little as about ½ hour to about 6 hours. In one embodiment low polymerization temperatures are more amenable to temperature sensitive co-monomer units than the prior art melt polycondensation process that requires long intervals of sustained high temperatures e.g. in excess of 100° C., typically in excess of 140° C., for more than 12 to 24 hours.

In yet another embodiment. when phosgene or phosgene-generating substitutes like triphosgene are employed it is preferred to utilize a temperature below phosgene's boiling point (8° C.) to prevent its loss during the reaction. This embodiment extends the range of molecular weight and end-capping capabilities achievable with the above described solution method for synthesis of polyanhydrides and poly (ester-anhydrides), among other polymers. The advantages of the above described process extend to this embodiment as well. Although end-capping has been used in the art, the use of polymer extension by end-linking, e.g. with phosgene in particular, is novel and unobvious.

F. Process with Controlled Sequence Domains

This embodiment of the process of the invention may employ either melt-condensation or solution-polymerization to produce new polymers comprising two or more different monomeric units covalently joined in defined molar ratios. This embodiment results in a polymer of predictable domains that is constructed by careful selection of the nature and quantity of the input monomer feeds, and by an appropriate choice of reaction conditions. Each of the polymer domains results from the structural characteristics of the individual monomers and imparts to the overall polymer useful chemical and physical properties such as hardness, adhesion, hydrophobicity, permeability, crystallinity, flexibility, hydrolytic stability, intrinsic thermogravimetric profile, among many other properties that may be also enhanced and are contemplated in this invention. These properties may be altered in a predictable pattern by controlling the input molar % of monomer to obtain polymers of unexpectedly superior chemical and other characteristics, and a freely tunable rate of degradation and, thereby, agent(s) or compound(s) released in situ. The process of this invention provides a means of designing a desired polymer by correlation of the nature and mole ratio of constituent monomers with specific polymer performance characteristics. The present inventors realized that individual polymer characteristics may be qualitative or quantitative measured as is their contribution to the overall co-polymer characteristics. This permits them to select a defined ratio of two or more constituent monomers or alter the mole ratio of reactant monomers to design specific co-polymers of predictable polymer performance parameters.

The following is an example provided for illustrative purposes only, and it relates to the formation of a co-polymer comprising A and B monomer units, where monomer A is Diflunisal-Diflunisal-C14 Linker-Diflunisal-Diflunisal (DFL-DFL-C14-DFL-DFL), and monomer B is diflunisal-C14 Linker-Diflunisal (DFL-C14-DFL). An increase in the content of monomer A from 0% to 50 mol % in a mixture of monomers A and B, with monomer B going from 100% to 50%, resulted in polyanhydrides with regularly increasing hydrolytic stability and Glass Transition Temperatures (Tgs). Prior to the present invention it had not been recognized that the performance characteristics of a resultant polymer may be controlled by modifications of the structure and mole fraction of the participating monomers. Given the relationship between individual monomer mole fraction and particular polymer parameters, the process of this invention provides an unexpected advantage of allowing the design of polymers of pre-determined performance characteristics by proper choice of mole % monomer ratio(s). In the above example it was observed that a step-wise increase in the mole fraction of monomer A in a solution-based process led to polymers with increasingly different performance parameters, e.g. Tg, flexibility, and hydrolytic stability, among others. Thus, the inventors found unexpectedly that they could manufacture a polymer that possesses a desired Tg and hydrolytic stability profile by choosing the appropriate mole % fraction of one monomer over the other, e.g. monomer A over monomer B. The polymers of the present invention possess refined performance characteristics, and may be employed, for example, as coatings, films, laminates, adhesives, formed implantable structures, e.g. drug-containing nano- and micro-spheres, medical devices, orthopedic and dental implants, and pharmaceutical formulations, among others.

G. Branching Process at Well-Defined Branch Points

This embodiment of the process of this invention incorporates well-defined branch points into polymeric materials to permit the modification by branching of their performance characteristics. The process relies on the structure, synthesis, and deployment of branching agents as a preferred embodiment of either melt dispersion or solution phase polymerization processes of the invention. Suitable branching agents may comprise tri-, tetra-, penta-, hexa-, or higher-order functional groups. The functional group for a branching agent may be selected to impart the polymer properties such as increased elasticity, increased melt elasticity, change in toughness and fatigue resistance, among many others. The performance of each specific branched polymer will be determined by factors such as the amount of each branched segment and the molecular weight of the segments between branching points. In one embodiment a branching agent(s) may be incorporated into the process at the beginning of polymerization to produce star-like polymeric structures. In another embodiment the branching agent(s) may be incorporated late in the polymerization process to yield highly networked structures.

Another embodiment of this process provides for combinations of these two extreme modes by varying the ratio and time of incorporation into the polymerization step of the process. The molecular weight of the polymeric segments present between branch points may range from one unit to any number of repeating units.

In one embodiment of the process molecular weights above those necessary for chain entanglement are produced and are preferred. Any percentage of branching agents is effective with a demonstrated and preferred embodiment of about 1%, 2%, 3%, 5%, or 10%, and higher, but less than the amount necessary to cause significant gelation during polymerization. The prior art required branching to be incorporated as a random adjunct to polymerization in polyanhydrides.

In still another embodiment of the process of the invention the specific chemistries employed by this process enables a significant control of the polymer structure where the molecular weight of segments between branching points, branch point distribution, and branch point type may be selected to yield controlled structures of pre-determined erosion kinetics. In yet another embodiment this process permits control of mechanical properties such as fatigue resistance, elasticity, and others, that had heretofore not been engineered to the extent provided by this invention.

H. Process of Preparation of Thermoplastic Elastomers

A further embodiment of the invention provides a process for the synthesis of a biodegradable polymer with increased elasticity at its application temperature. The thus designed polymer may be formed by heat-based synthesis, and cast using known coating technologies. The ability to increase the elasticity of a polymer provides advantages in terms of, for example, better flexibility, malleability, resilience, and flow behavior, among many others. The present inventors discovered that their specific solution chemistry process would help create the block structures needed to synthesize these materials. Applications where flexibility is necessary, e.g. in medical and other devices, require a polymer of rubber-like behavior for enhanced or maintained performance. Examples of this type of applications are all types of stents, coatings on tubing and other flexible surfaces, coating of Nitinol and other similar nickel-based alloy devices, opthalmological applications requiring flexible erodable polymers to assist in non-inflammatory support or substance delivery, and many others.

In one embodiment the solution polymerization process of this invention permits the design of materials that will lead to phase separation. Block co-polymers may be created from a repeating structure based on a linker and incorporating an agent(s) of one solubility, as determined by any acceptable solubility calculation, and a linker and incorporating an agent(s) of different solubility. This will generally result in phase separation of the two blocks observed as two distinct glass transition temperatures, as measured by any acceptable technique. The co-polymer blocks may be selected such that the glass transition temperature (Tg) of the two phases bracket the application temperature of interest. That is, the Tg of one phase is lower while the Tg for the other phase is higher than the target temperature.

Various polymers, such as polyester, polycarbonate, polyamide, polyurethane, polyanhydride, may be prepared in this manner by proper choice of condensation conditions. As the block phases separate they form an extended network that results in increased elasticity. The new polymer is more rubber-like at the designed application temperature. Yet, when the polymer is heated above the glass transition temperature of the higher Tg block, it may be processed into a variety of shapes by standard polymer processing techniques. This embodiment of the process may be carried out by means of a solution based coupling process known to those skilled in the art. A non-limiting example comprises coupling of two pre-polymers having different $T_g$s in a volatile solvent for the pre-polymer employing a condensing agent(s) such as phosgene, diphosgene, triphosgene, oxalyl chloride, thionyl chloride, alkanedioic dichlorides, phosphochloridates, and carbodiimides, among many others known in the art. Suitable volatile solvents include, but are not limited to, chlorinated hydrocarbons, chlorinated hydrocarbons, ethers, esters, amides, and sulfoxides having boiling points less than about 200° C., among others known in the art. A group of preferred solvents includes chlorinated solvents with boiling points less than about 100° C. In another embodiment the thermoplastic elastomeric block co-polymer may be synthesized by other polymerization techniques such as a melt process.

I. General Processes for the Synthesis of Inventive Polymers

The following Schemes are illustrative of the synthetic process for the preparation of various inventive compounds described in the examples. The numbers assigned to each of the monomers and polymers will be referred to later on in the actual description of the compound's synthesis or its use for the preparation of another compound. Scheme 3 below shows the preparation of a diacid monomer employing two di-ortho hydroxy-carboxylic acid residues bound by a $(CH_2)_n$ linking group. By means of example, the starting material represents a dicarboxylic acid 11 that has a linking group of either 12 (Compound 11a), or 14 (Compound 11b) carbon atoms. Similarly, the intermediate compound 15 represents a diacid halide of an ortho hydroxy carboxylic acid, where the substituent R and the number of carbons in the linking group may be H/6 (Compound 15a), H/8 (Compound 15b), o,p-difluorophenyl/10 (Compound 15c), o,p-difluorophenyl/12 (Compound 15d), o,p-difluorophenyl/14 (Compound 15e), o,p-difluorophenyl/6 (Compound 15f), or o,p-difluorophenyl/8 (Compound 15g). The resulting monomer (Compound 16) is a diacid of an aromatic ester dimer bridged by an aliphatic linking group, where the substituent R and the number of carbons in the linking group may be H/6 (Compound 16a), or o,p-difluorophenyl/12 (Compound 15d).

Scheme 3

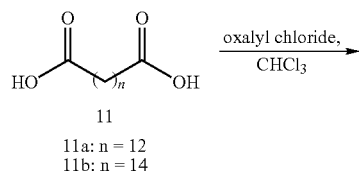

11
11a: n = 12
11b: n = 14

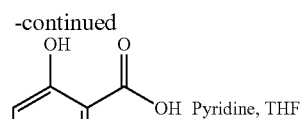

13a: R = H (SA)
13b: n = o,p-difluorophenyl (DF)

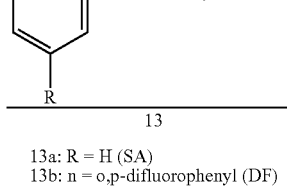

14
14a: n = 6, R = H
14b: n = 8, R = H
14c: n = 10, R = o,p-difluorophenyl
14d: n = 12, R = o,p-difluorophenyl
14e: n = 14, R = o,p-difluorophenyl 15
15a: n = 6, R = H
15b: n = 8, R = H
15c: n = 10, R = o,p-difluorophenyl
15d: n = 12, R = o,p-difluorophenyl
15e: n = 14, R = o,p-difluorophenyl
15f: n = 6, R = o,p-difluorophenyl
15g: n = 8, R = o,p-difluorophenyl 16
16a: n = 6, R = H
16b: n = 12, R = o,p-difluorophenyl Scheme 4 bellow shows the synthesis of a linking group starting from a salt of an hydroxy carboxylic acid (Compound 17) where the cation is sodium (Compound 17a), or tetra n-butiryl-amino (Compound 17b), and a dihalide of the desired linking group (Compound 18) where the halide and number of carbons are Br/6 (Compound 18a), I/10 (Compound 18b), or Br/8 (Compound 18c) to obtain a di-hydroxy di-anhydride of the linking group (Compound 19) where the number of carbons is 6 (Compound 19a), 10 (Compound 19b), or 8 (Compound 19c). The second reaction shown in Scheme 4 represents the synthesis of a specific product (Compound 21) of this group where the substituent R and the number of carbons in the linking group are H/8 (Compound 21a) that results from reacting an aliphatic hydroxy carboxylic acid (Compound 20) with a di-halide of the linking group (Compound 18c) in a solvent at about 60° C.

Scheme 4

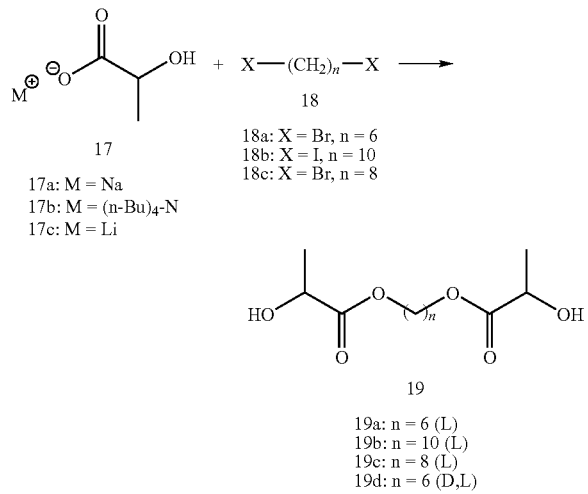

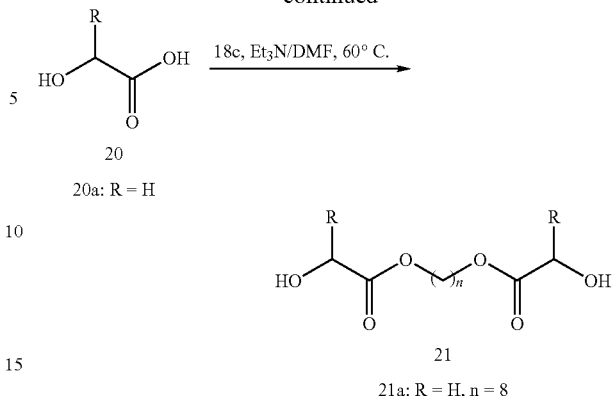

Scheme 5 below shows the polymerization by non-aqueous dispersion method where polymers with anhydride bonds between diacid monomer units bonded by an aliphatic linking group (Compound 14), that is formed via a di-anhydride (Compound 22) where R and the number of carbons in the linking group are H/6 (Compound 22a), or o,p-difluorophenyl/12 (Compound 22b). The resulting polymer (Compound 23) has repeating units of the diacid linked through an anhydride bond where R and the number of carbons in the linking group are H/6 (Compound 23a), or o,p-difluorophenyl/12 (Compound 23b).

Scheme 5

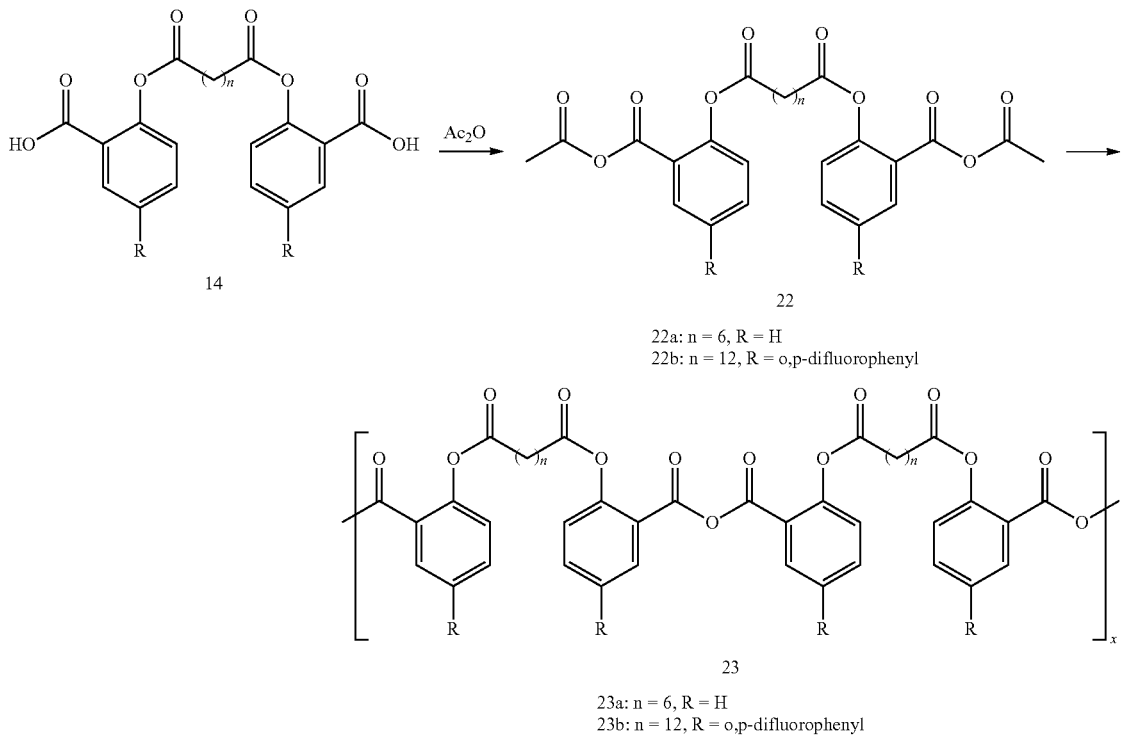

Scheme 6 below shows the polymerization of a di-carboxylic acid (Compound 11) to form an anhydride polymer 24 by solution polymerization that results in a high molecular weight polymer, (Compound 24a), when the number of carbons in the linking group is 8.

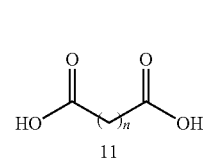

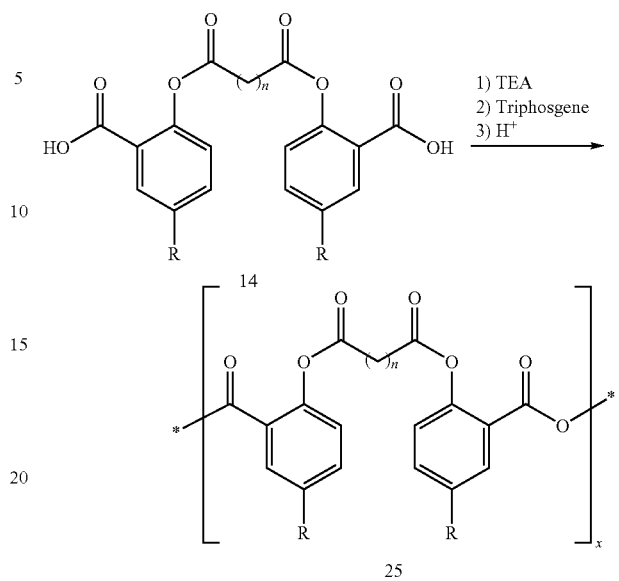

Scheme 7 below shows the polymerization of an aromatic diacid (Compound 14) to form an anhydride polymer (Compound 25) by solution polymerization where R and the number of carbons in the linking group are o,p-difluorophenyl/12 (Compound 25a), H/6 (Compound 25b), or H/8 (Compound 25c).

Scheme 8 below shows the syntheses of three mixed random polymers (Compound 26) in different compositions where the units are a di-aromatic diacid (Compound 14) and a tetra-aromatic diacid (Compound 16), both bridged by aliphatic linkers via esters.

Scheme 8

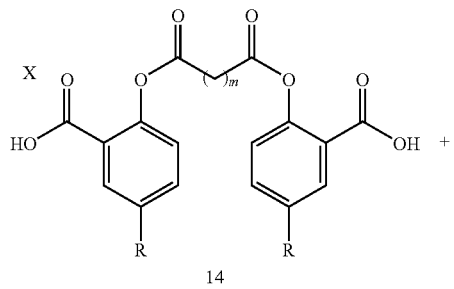

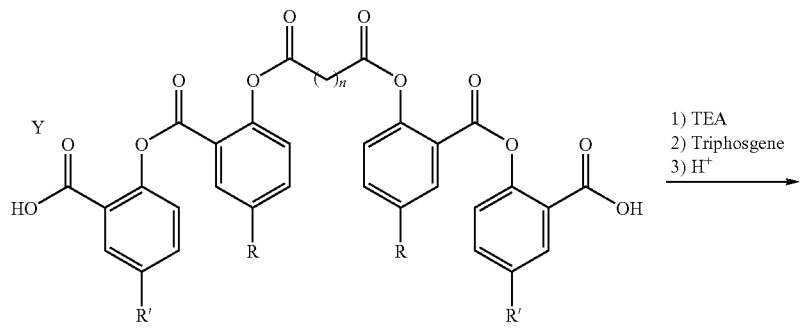

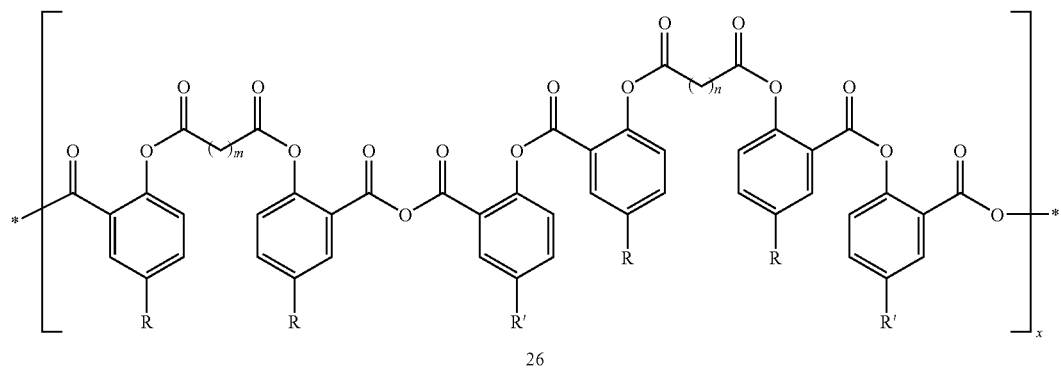

26a: m = 8, n = 8, X = 3, Y = 1, R = R' = H
26b: m = 14, n = 14, X = 3, Y = 1, R = R' = o,p-dufluorophenyl
26c: m = 16, n = 14, X = 85, Y = 15, R = R' = o,p-difluorophenyl Scheme 9 below shows the syntheses of a mixed random polymers (Compound 27) in different compositions where the units are di-aromatic diacid chloride (Compound 15), linker diacid chloride (Compound 12), and triethyl ammonium salt of aromatic hydroxyacid (Compound 13, and other active agents) by solution polymerization.

Scheme 9

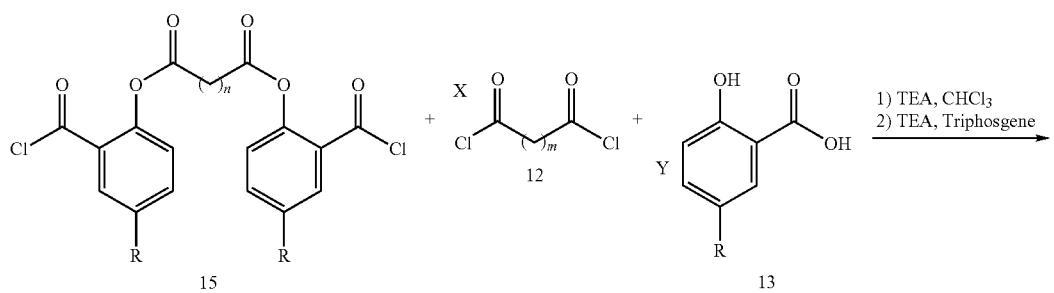

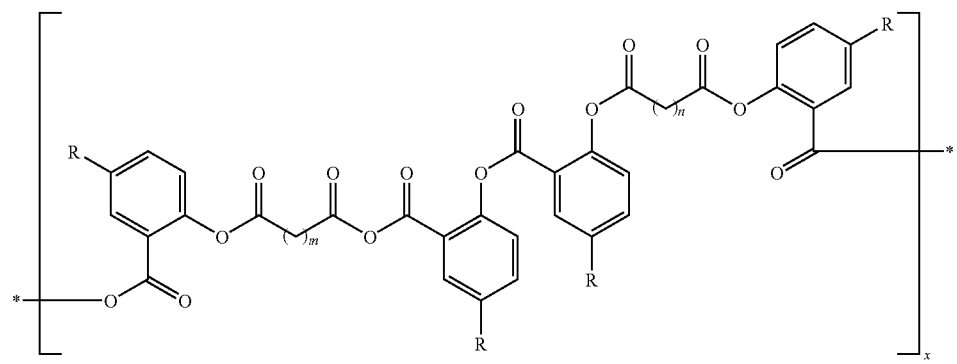

27a: n = 14, m = 14, X = 1, Y = 2, R = o,p-difluorophenyl
27b: n = 8, m 8, X = 1 , Y = 2, R = H
27c: n = 14, X = 0, Y = 1, R = o,p-difluorophenyl

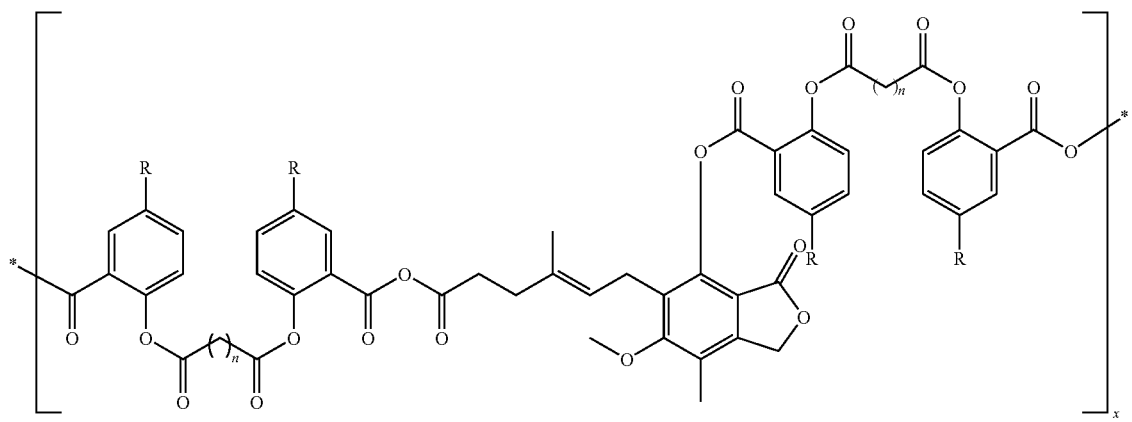
27d
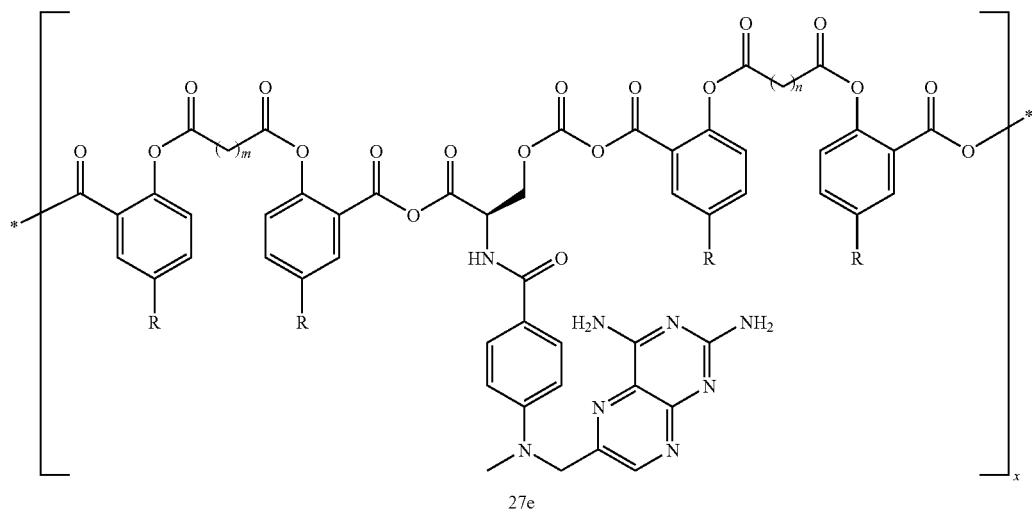
27e
Scheme 10 below shows the syntheses of a mixed random polymers (Compound 28) with α-hydroxyester linker where the units are di-aromatic diacid chloride (Compound 15), α-hydroxyester linker (Compound 12), and tri ethyl ammonium salt of aromatic o-hydroxyacid (Compound 13) by solution polymerization.
Scheme 10
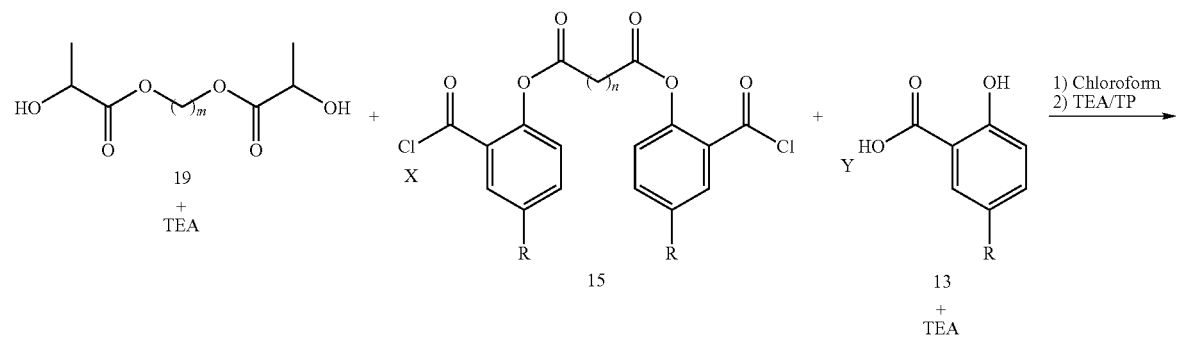

-continued

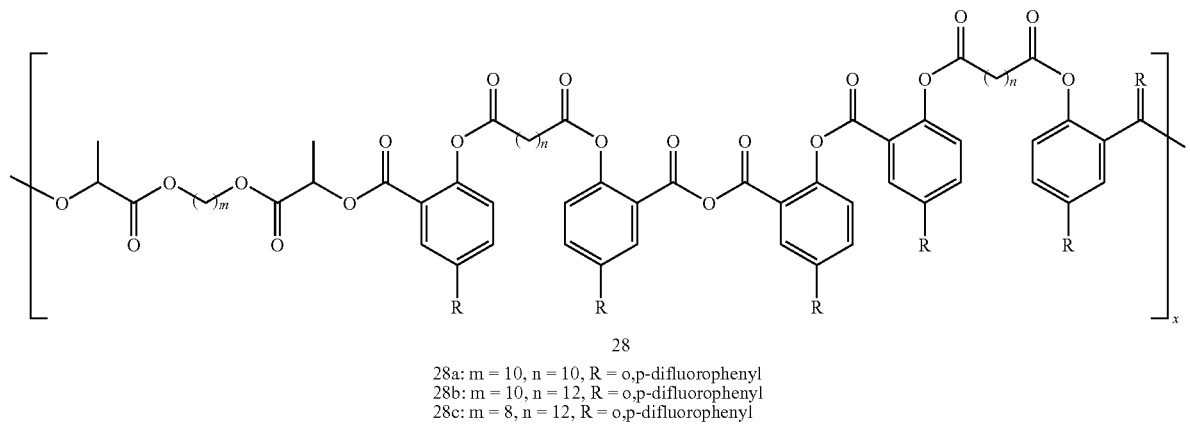

28

28a: m = 10, n = 10, R = o,p-difluorophenyl
28b: m = 10, n = 12, R = o,p-difluorophenyl
28c: m = 8, n = 12, R = o,p-difluorophenyl Scheme 11 below shows the syntheses of polymer (ester-carbonate) where di-aromatic diol (Compound 29a) was polymerized by solution method using triphosgene.

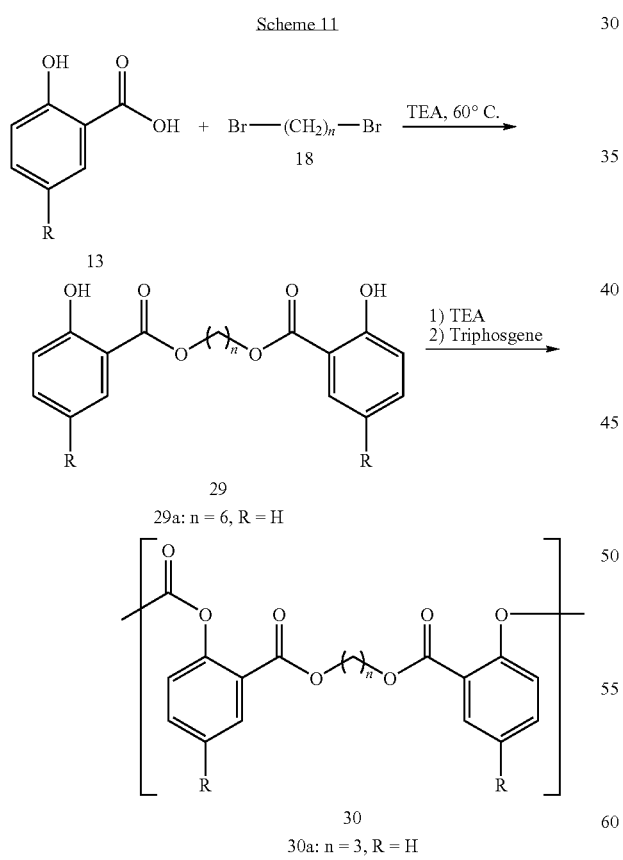

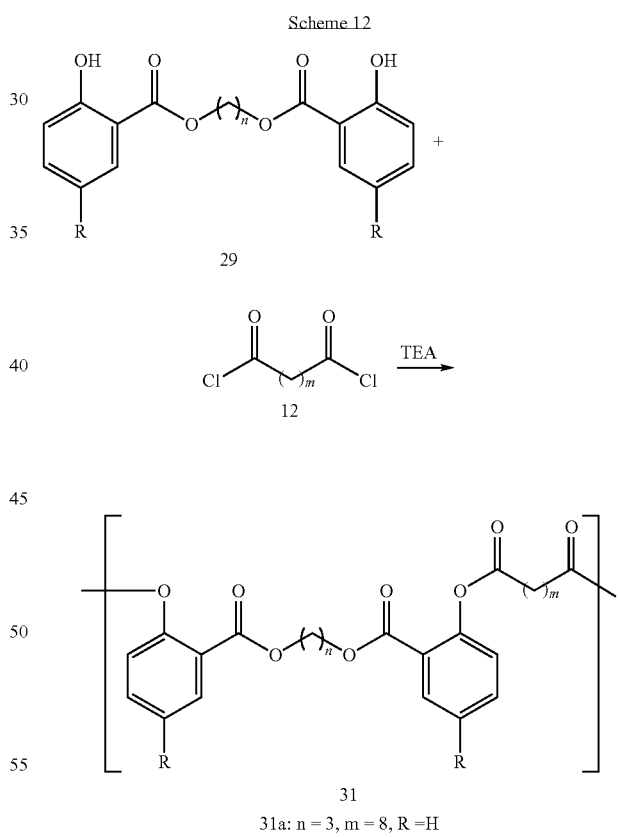

Scheme 12 below shows the syntheses of polymer (ester-ester) where di-aromatic diol (Compound 29) and linker diacid chloride (Compound 12) were polymerized by solution method using triphosgene.

Scheme 13 below shows the syntheses of polymer (ester-ester-ester) with α-hydroxy ester linkers, where di-aromatic di-acid chloride (Compound 15) and α-hydroxy ester linker diol chloride (Compound 19 or Compound 21) were polymerized by solution method using triphosgene.

Scheme 13

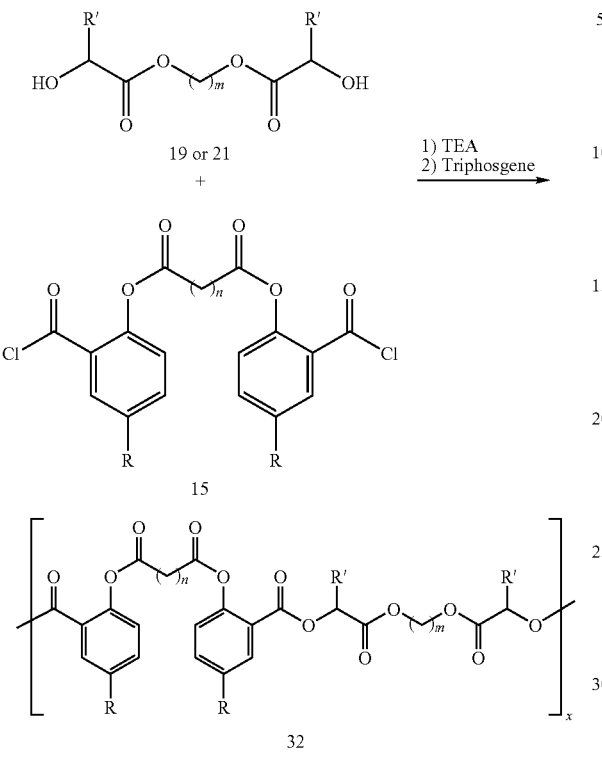

32a: m = 8, n = 6, R = o,p-difluorophenyl, R' = H
32b: m = 6, n = 8, R = o,p-difluorophenyl, R' = CH₃

Scheme 14 below shows the syntheses of the branched polymer with a defined branch point and controlled degree of polymerization by solution method from 1,3,5-benzene tricarboxylic acid (Compound 33) and di-aromatic linker di-acid (Compound 14).

Scheme 14

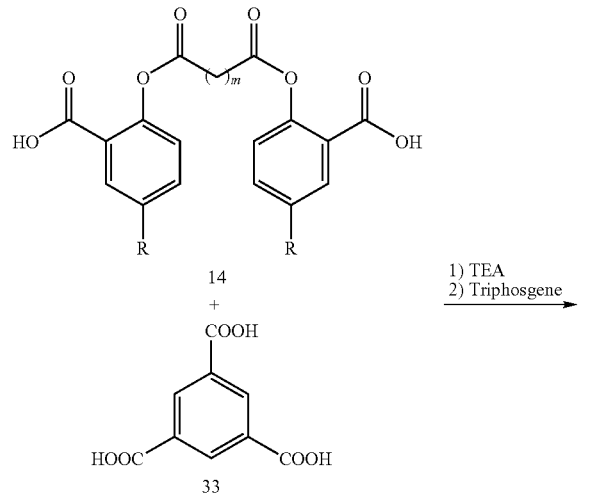

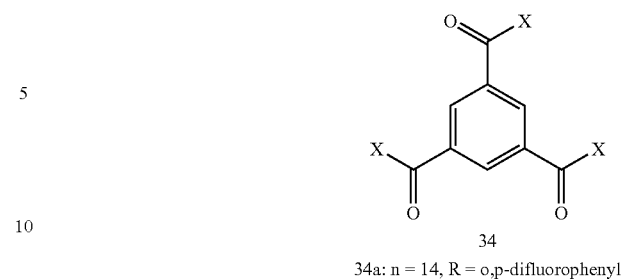

34a: n = 14, R = o,p-difluorophenyl

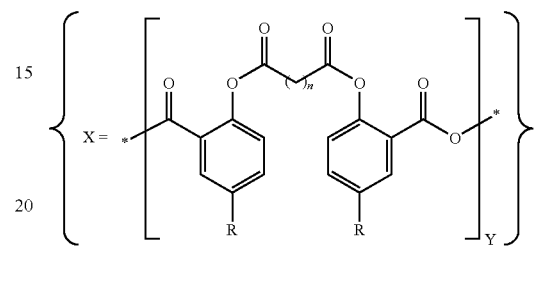

Scheme 15 below shows the syntheses of the branched polymer with a defined branch point and controlled degree of polymerization by solution method from 1,2,3,4-butane tetracarboxylic acid (Compound 35) and di-aromatic linker di-acid (Compound 14).

Scheme 15

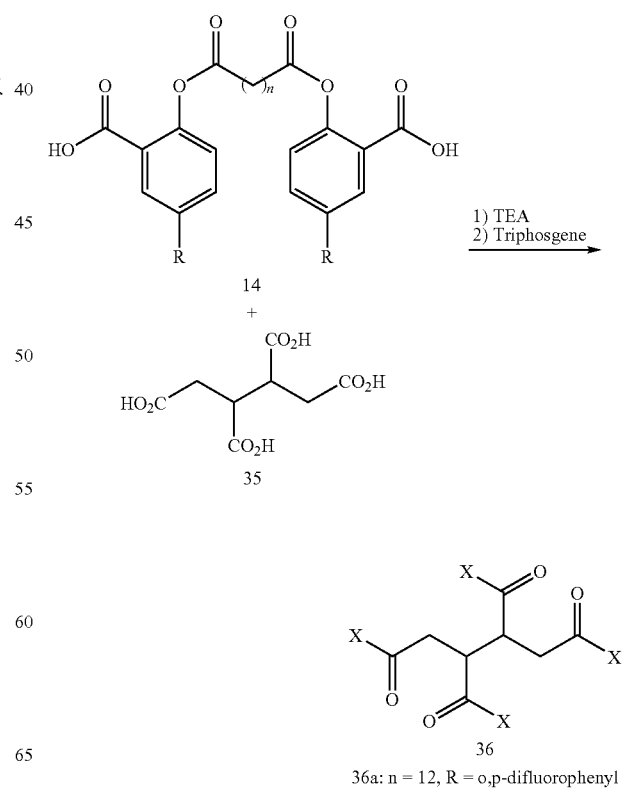

36a: n = 12, R = o,p-difluorophenyl

-continued

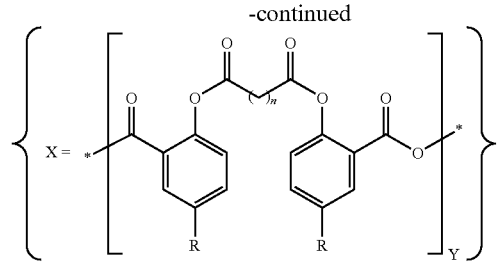

Scheme 16 below shows the syntheses of the branched polymer with a defined branch point and controlled degree of polymerization by solution method from trans-aconitic acid (Compound 37) and di-aromatic linker di-acid (Compound 14).

Scheme 16

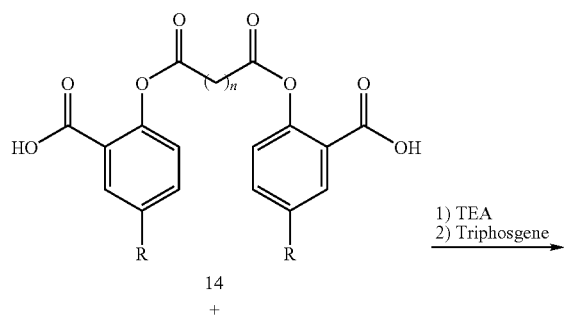

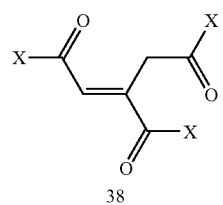

38a: n = 12, R = o,p-difluorophenyl

-continued

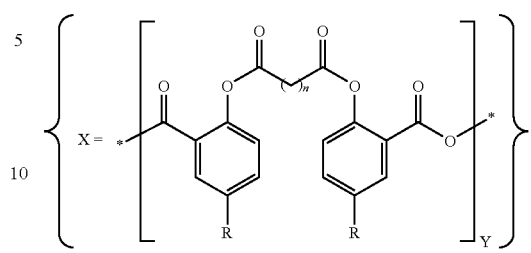

Scheme 17 below shows the synthesis of random block copolymer using polymer A (Compound 26b) and polymer B (Compound 25c) by solution polymerization method.

Scheme 17

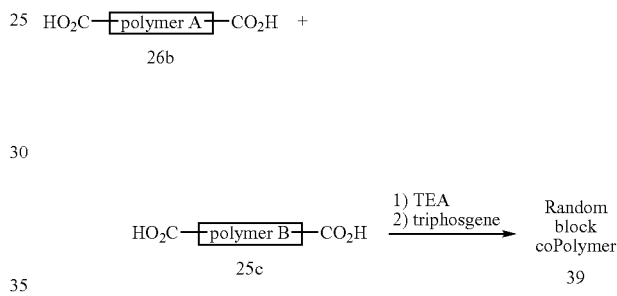

Scheme 18 below shows the synthesis of alternate block thermoplastic elastomeric polymer (Compound 40) using a high $T_g$ block, polymer A (Compound 26b) and low $T_g$ block, polymer B (Compound 25c) by solution polymerization method.

Scheme 18

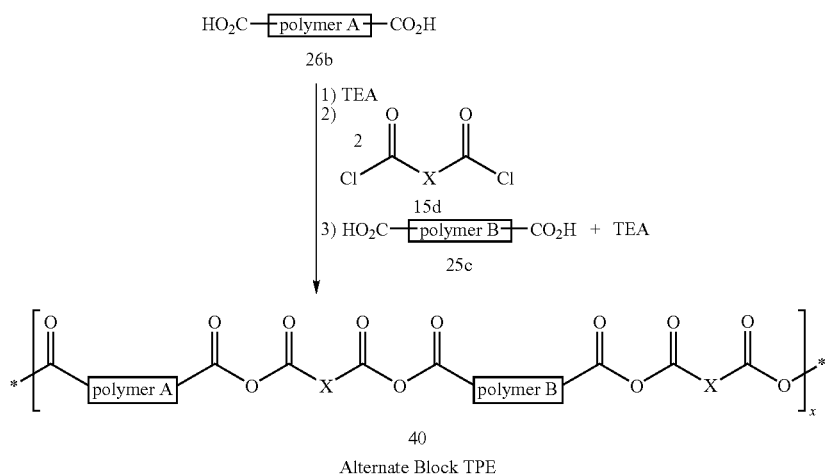

40
Alternate Block TPE

Scheme 19 below shows the synthesis of tri-block thermoplastic elastomeric polymer (Compound 42) using a high $T_g$ block, polymer A (Compound 26b) and low $T_g$ block, polymer B (Compound 25c) by solution polymerization method where the inside block was activated with di-aromatic di-acid chloride to achieve the definite connecting point for the blocks.

variable, however, at 37° C. Gamma radiation had no effect on the molecular weight, flexibility, or adhesiveness of the polymers of the invention, such as polySA and poly DF, and only minor effects on their hardness.

K. Layering Coatings of Polymers

The polymers of the invention may be layered onto devices with other polymers of the invention, or other polymers in

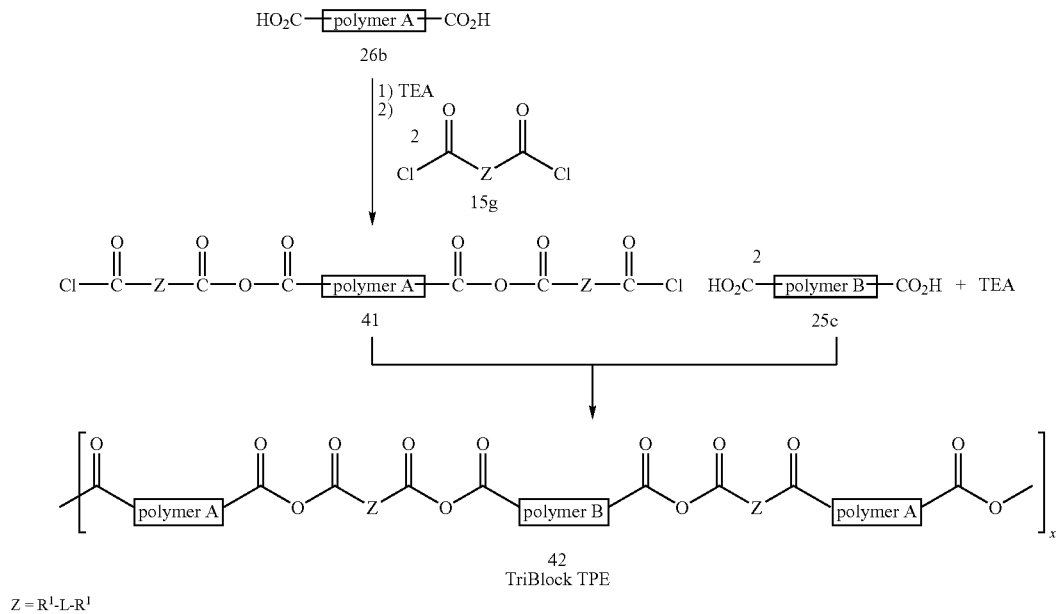

J. Sterilization

All implantable and percutaneous medical devices should be sterilized before utilization, e.g., before or after packaging. Commonly employed sterilization methods are gamma ray irradiation, electron beam ("E-beam"), and ethylene oxide treatment. Gamma ray irradiation penetrates objects deeply, and is used for sterilizing foodstuffs and many medical device products. This method, however, requires relatively prolonged exposure times. E-beam sterilization requires shorter exposure times but has poor object penetration making the procedure useful mainly for surfaces. Ethylene oxide sterilization is more complex and more aggressive on organic materials than the other two methods, and is being replaced by them wherever possible because it is an environmental hazardous agent. The relatively high temperatures and humidity conditions required by many ethylene oxide sterilization protocols make it not to be highly compatible with many poly(anhydride-ester)polymers. The sterilization methods of choice for the polymers of this invention, therefore, comprise gamma radiation or E-beam sterilization. Experimental results show that E-beam (3.5 mRad) and gamma radiation (25-35 Kgys) sterilization have no effect on the pattern of diflunisal release from polydiflunisal (polyDF) coated stainless steel samples incubated in serum at 37° C. Notwithstanding its lack of effect on polymer degradation, gamma ray and e-beam irradiation sterilization do produce some changes in the molecular weight and mechanical properties of polymers. The tensile modulus of melt-polymerized polySalicylic Acid (polySA), for example, was seen to decrease at room temperature by about a third after gamma sterilization (25-35 Kgys). There was no change in either general, to form coatings with desirable properties. The therapeutic polymers may be structured and/or layered as a coating with one or more additional coatings that may or may not be biodegradable (i.e., degradable by hydrolysis or enzymatic/proteolytic activity when placed in contact or exposed to body tissues or fluids). The additional coatings may contain the same polymerized active compound, a different polymerized active compound, no polymerized active compound, or one or more admixed drugs or agents. This structuring may be in the form of a layer of a coating on the exposed surface of the coating of the therapeutic polymer such that this coating lies between the polymerized active compound, and the body tissues and/or fluids following implantation. Alternatively, a second polymer or smaller molecular-weight species may be physically blended with the therapeutic polymer, and a series of layered coatings of therapeutic polymer compositions that have different chemical compositions and/or physical, e.g. mechanical, properties.

In some embodiments of the invention, layering permits refinement of the rate or duration of generation, release, or elution of active agents over time, including the possibility of having one or more outer coatings with higher or lower permeability to modulate the breakdown of one or more inner coatings and thereby result in a more constant release of active agent over particular periods of time. In embodiments in which one or more outer coatings are biodegradable, the breakdown and resulting increase in permeability of these outer coatings may compensate for a rate of generation (by breakdown of the polymer) or release of an active agent that varies with time by increasing the rate of permeation of the active agent from the inner coating through the outer coatings.

Such embodiments may be used to create a rate of delivery of drug from the coatings on the device that vary less temporally (i.e., are more closely more zero-order) and that may be adjusted based on the preferred shape and, therefore, surface area of the device and changes in surface area that occur as the coatings erode. Multiple layers of polymers generating, eluting, or releasing inert and active products upon breakdown may be designed for specific applications, including those applications in which one class or member of a class of agents is to be generated, eluted, or released from the coating before a second class or a second member of the first class of agents is generated, eluted, or released from the coating. Possible structuring of layers of coatings, in which one or more of these layers contains a polymerized agent(s) or compound(s), e.g. drug, for implantable medical and veterinary devices are contemplated within this invention. Examples of these are a single layered coating, a multiple layered coating in which the layers may have different compositions and physical properties, including thickness, molecular weight, and others, and in which the top layer(s) comprise(s) or do(does) not comprise (s) the polymerized agent(s) or compound(s) and the bottom layer(s) comprise(s) or do(does) not comprise(s) a polymerized agent(s) or compound(s), a bilayered or multilayered coating in which the top and bottom layers comprise(s) a polymer of the invention of different composition(s). An example of such a layered coating releases an anti-inflammatory agent, e.g. an NSAID(s) substantially before an anti-proliferative agent is generated, eluted, or released from the coating. Such types of layered coatings enable tuning of the rate of generation, elution, or release of drugs from the coating over time, such that a near constant, gradually increasing, gradually decreasing, or a combination thereof amount of drug most appropriate for treatment of tissues in the vicinity of the device may be delivered to these tissues. In one embodiment of the invention, an inert polymer coating(s) may applied as a top coat(s) on one or more polymer coatings, even those that have drugs or other agents admixed therein. A top coating(s) may be applied to increase the hardness and/or lubricity of an outer coating(s) to facilitate use and insertion of a device. A top coating may be applied also to vary, e.g. increase or decrease, the rate of hydration or enzyme penetration to vary, e.g. increase or decrease, the rate of backbone or admixed drug release, or the release of other agent(s) from underlying coating(s). A top coating(s) may be applied as well to increase the shelf life of the final product by limiting water and/or oxygen contact with the underlying therapeutic polymer coating. In one preferred embodiment the top coatings comprises a biodegradable polymer. The polymers of this invention achieve degrees of hardness suitable for a variety of applications. Typically, the polymer of the invention may attain a hardness of about 24, 26, 28, 35, 45, 55 to about, 60, 70, 80, 95, 101, based on a Shore hardness range. Different applications Polymers of the invention have different degrees of hardness that are suitable for different applications, such as for use in the devices of the invention.

L. Admixing Component Materials

The formation of a composite of two or more materials results in a new material that may have physical properties and performance characteristics substantially different from any of the individual component materials comprising the new material. In the case of polymers, these altered physical properties may include an increase or decrease in glass transition temperature, tensile or shear moduli, effective viscosity, yield strength and elongation, elongation at failure, tackiness or adhesiveness, hardness, color, rate of thermal or biological breakdown, surface texture, or wettability by water or other fluid. For example, the mechanical properties of bone, a composite of inorganic calcium phosphates and organic collagen molecules, are distinct from the mechanical properties of either calcium phosphates or collagen alone. In one embodiment, a polymer of the invention is admixed with an anti-proliferative agent, such sirolimus, everolimus or paclitaxel, or other material or agent, such as specific RNA and DNA sequences and their chemical mimics or derivatives, calcium phosphate, hydroxyapatite, an antibiotic, an immunosuppressive agent, or another agent. These added compounds may alter the mechanical properties of the polymer (e.g., by modifying the degradation rate, the tensile modulus, the yield strength, and/or the elongation at which failure of the material occurs). Coatings made from the therapeutic polymer will also exhibit the altered mechanical properties. The extent to which the admixture of one or more drugs or other therapeutic agents changes the physical properties and performance characteristics of the coating will depend on the amount or concentration of each of the drugs or agents, with a trend that increasing the amount or concentration of a drug or agent is expected to increase, if at any changes occurs at all, one or more of these properties or characteristics. In practice, coatings with about 0.1, 1, 3, 5, 10 wt % or more to about 15, 20, 30, 35, 40, 45 wt % admixed drug or agent may be achieved by blending the admixed compound into the polymer prior to coating or by first applying the polymer as a coating and then absorbing the compound to be admixed into the coating by exposing the coating to a solution with the compound. In an exemplary embodiment, a coating of a polymer with an admixed drug, applied on an expandable stent, comprises a dicarboxylic acid with more than six carbon atoms in the linear alkyl chain, or a co-polymer or physical blend of polymers or co-polymers that approximate the physical properties and performance characteristics of the polymer with a linker with more than six carbon atoms in the linear alkyl chain, such that these polymers approximate the physical properties and performance characteristics of a polymer with a linker of suberic acid (C8). In another exemplary embodiment, a coating of a polymer with an admixed drug, applied on an orthopedic implant, comprises a dicarboxylic acid with more than four carbon atoms in the linear alkyl chain, or a co-polymer or physical blend of polymers or co-polymers that approximate the physical properties and performance characteristics of the polymer with a linker with more than four carbon atoms in the linear alkyl chain, such these polymers approximate the physical properties and performance characteristics of a polymer with a linker of succinic (C4) or adipic (6C) acid. In some embodiments, compositions comprising polymers may have optimum physical and chemical properties derived by blending compounds into the polymer that decrease or increase the rate of penetration of water and/or enzymes into the polymer matrix and, thereby, decrease or increase the rate of breakdown of the polymer, thereby modulating the duration of generation of drug from the components of the polymer backbone and/or the release of admixed drug or agent. In addition, qualities such as shelf life, e.g. stability in the presence of elevated temperatures, humidities, or electromagnetic radiation, rates of depolymerization, e.g. by hydrolysis or proteolytic activity, or oxidation, and rates of hydration may be varied by adding antioxidants or lipophilic molecules to reduce oxidation or hydration of the polymer blend, respectively. In some cases, the qualities of the admixed drug or agent may influence the physical or chemical properties, including shelf life, tolerance to sterilization methods, or degradation rate of the final product. For example, the admixed drug or agent may extend the shelf life, increase the types and/or dosages of sterilant that may be applied without changing other properties of the material, or decrease or increase the degradation rate of the final product.

V. General Overview of the Uses of the Inventive Polymers

The present invention also relates to methods of using compositions comprising at least one agent(s) linked to the polymer backbone in any application wherein delivery of the active agent or agents is desired. A route of delivery may be selected in accordance with the drug being administered and the condition being treated. In one embodiment, the polymers decompose harmlessly while delivering a selected low molecular weight drug at the site of implantation within a known time period. Another embodiment provides a method for site-specific or systemic drug delivery by implanting in the body of a patient in need thereof an implantable drug delivery device containing a therapeutically effective amount of a biologically or pharmaceutically active compound in combination with the polymer. In one embodiment, the polymers of the invention may be particularly useful for the controlled delivery of an agent(s), or as a medium for the localized delivery of an agent(s) to a selected site. For example, the polymers of the invention may be used for the localized delivery of a therapeutic agent to a selected site within the body of a human patient, i.e. within or near a tumor, where the polymer degradation provides a localized, controlled release of the therapeutic agent(s). In another embodiment a method for delivering an active agent to a patient comprises providing a medical device having at least one surface, comprising a first polymer on all or a portion of the surface, wherein the polymer is capable of breaking down, e.g. including but not limited to hydrolyzing, in the physiologic milieu to form a first active agent(s), and administering the device to the patient so that the first agent(s) is(are) delivered to the patient. The device may comprise additional polymers and/or additional active agents such as a second agent, third agent, and so on, where the additional active agents are, e.g. incorporated, blended, attached, appended or dispersed within the polymer as described herein, or otherwise annexed to or associated with the polymer such that the additional agent(s) dissociate from the polymer upon hydrolysis and are delivered to the patient. The device may comprise active agents that combine in vivo to form a new active agent or agents that is delivered to the patient. The active agent(s) may be delivered to any suitable site(s) in a patient, such as the circulatory system e.g. a vein or artery, a tissue, an organ e.g. lung, liver, spleen, kidneys, brain, eye, heart, muscle, and the like, a bone, cartilage, connective tissue, epithelium, endothelium, nerves, a tumor, or other site suitable for delivery of an active agent(s). Suitable sites will typically be sites that are or will be in need of treatment with an active agent or agents, such as, e.g., an injured site or a site that may become injured, for example, due to a disease, a medical condition, or during or after a medical procedure, e.g. a balloon angioplasty and/or implantation of a medical device. In one embodiment, a method for delivering an active agent to an interior surface of a vein or artery is provided. The method comprises providing a medical device having at least one surface, comprising a first polymer on all or a portion of the surface, wherein the polymer is capable of breaking down e.g. hydrolyzing, in the physiologic milieu to form a first active agent, and positioning the medical device at or near the interior surface of the vein or artery such that the first active agent dissociates upon hydrolysis and is delivered to the interior surface of the vein or artery. The device may comprise additional polymers and/or additional active agents, e.g. an additional active agent(s), where the additional active agents may be incorporated, attached, appended or dispersed within the polymer, as described herein, or otherwise annexed to or associated with the polymer such that the additional active agents dissociate from the polymer upon hydrolysis and are delivered to the interior surface of the vein or artery. The device may comprise active agents that combine in vivo to form a new active agent or agents that are delivered to the interior surface of the vein or artery. In one embodiment, the method prevents, reduces, and/or inhibits the development of restenosis in the blood vessel. Restenosis may be defined as, for example, the narrowing of the vessel to about 80%, about 70%, about 60%, about 50%, about 40%, about 30%, about 20%, about 10% or less, of the diameter of the vessel after removal of any blockages from the vessel and the placement of the device into the vessel. The compositions, devices and methods of the present invention are useful for treating a wide array of diseases and conditions, including, for example, those set forth below and/or otherwise described herein. In cardiology, such compositions, devices and methods may be used, for example, to develop coatings for stents, sutures and pacemakers, or other devices used in cardiology as otherwise referenced herein. In ophthalmology, such compositions, devices and methods may be used, e.g., to develop a lens replacement for cataracts with a translucent polymer; for a direct injection of microspheres into the eye to provide a depot of anti-inflammatory therapy; or for the treatment of glaucoma. In otolaryngology, such compositions, devices and methods may be used, e.g., to develop antibiotics for otic administration, e.g. amoxicillin microspheres or nanospheres; for reconstructive surgery, e.g. bone restructuring; as a treatment for tuberomandibular joint (TMJ) pain by direct injection; as a treatment of chronic sinusitis by injection of microspheres; or for compositions delivered via inhalers, e.g. dry powders or admixed with non-CFC propellants. In bone and orthopedic applications, such compositions, devices and methods may be used, e.g., to develop orthopedic injections of inventive compositions; for bone implants; for the prevention of bone erosion; for wound healing by inhibiting osteoclasts and preventing spurious bone growth; as bone putty; for spinal cage bone pins e.g. mixture of inventive polymers with hydroxyapatite fillers and other fillers; as a coating for orthopedic implants to decrease pain, inflammation, bone erosion and infections; as combinations of poly-NSAIDs=plus poly-antibiotics to treat osteomyelitis or other bone infections by direct injection into the marrow; for the treatment of bone cancer with antiproliferatives; for the treatment of trauma; as prosthetic devices and coatings therefore; or other devices used in bone and orthopedic applications as otherwise referenced herein.

In neurology, such compositions, devices and methods may be used, for instance to develop microspheres injections for injection into the cerebral spinal fluid. In oncology, such compositions, devices and methods may be used for treating cancers, such as liver, ovarian, prostate, breast, or colon, cancer, among many others; for delivery to any surgical site where cancer is removed and there exists a concern that not all cancer cells were removed; or to develop compositions of poly-antiproliferatives sprinkled into the peritoneum, which slowly erode and circulate through the lymphatic system where the primary metastases congregate. In dentistry, such compositions, devices and methods may be used to develop alveolar bridges, tooth implants, patches for treating long-term pain, microspheres to treat or prevent dry socket, chips and wafers, chewing gum, dental floss and microspheres coatings on toothbrushes; and for the prevention of bone erosion. In gastroenterology, such compositions, devices and methods may be used for oral administration of inventive polymers with antacids to treat ulcers, heartburn and other acid-related diseases; for the treatment of irritable bowel syndrome with inventive compositions having a particular particle size; or for use of the compositions, e.g. a poly-NSAID, to prevent or treat inflammation at a colostomy sinus. In obstetrics and gynecology, such compositions, devices and methods may be used for the prevention of toxic shock syndrome by using the inventive compositions in fibers of tampons; for the treatment of yeast infections; for the treatment of chlamydia infections; as suppositories; as a cervical ring to treat or prevent cramps or premenstrual syndrome, among others; and as surgical meshes and coatings to treat hernias and the like. Surgical applications of the compositions, devices and methods include coatings for bladder catheters and others; coatings for indwelling catheters; as coatings for biosensors, particularly the leads, to prevent scarring and granulomas and to avoid signal interference and increase battery life; as compositions as surgical adhesives; as microspheres sprinkled into any surgical field to prevent adhesions; and for subdural barriers or films to prevent swelling and inflammation. The compositions, devices and methods may also be used in wound healing applications, including as sutures, surgical meshes, bandages, and other mechanical wound closure products, coatings, and the like. The compositions may be also be in the form of microparticles e.g. microspheres, microplatelets or other microstructures, as a powder or pellets to be applied locally e.g. sprinkling, to the affected area, and many others. In dermatology, such compositions, devices and methods may be used for instance to develop sunscreens and the like; insect repellants of admixed or polymerized compounds such as DEET, Merck IR 3535, citronella, and other safe ones; bandages; as microspheres in patches to deliver systemically active drugs; for the treatment of psoriasis e.g. poly-methotrexate optionally combined with a poly-NSAID(s) and/or other agents; for the treatment of seborrhea, dandruff, and other skin and hair conditions. The polymers of the invention may also be incorporated into oral formulations and into products such as skin moisturizers, deodorant, cleansers, pads, plasters, lotions, creams, gels, ointments, solutions, shampoos, tanning products and lipsticks for topical application.

VI. Polymer Formulations

A. Introduction

The polymers of the invention may be formulated as pharmaceutical compositions and administered to a mammalian host, such as a human patient in a variety of forms adapted to the chosen route of administration, i.e., orally, rectally, or parenterally, by intravenous, intramuscular, intraperitoneal, intraspinal, intracranial, topical, ocular, pulmonary or subcutaneous routes. For some routes of administration, the polymer may conveniently be formulated as micronized particles. Thus, the present compounds may be systemically administered orally, in combination with a pharmaceutically acceptable vehicle such as an inert diluent or an assimilatable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of agent or polymer in the compositions and preparations may, of course, be varied and may conveniently be about 0.1, 1, 25, 10, 30, 45 to about 50, 60, 75, 80 wt %, and any ranges defined by their combination, and of a given unit dosage form. The amount of polymer in such therapeutically useful compositions is such that an effective dosage level will be obtained. The tablets, troches, pills, capsules, and the like may also comprise binders such as gum tragacanth, acacia, corn starch, gelatin or others; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially nontoxic in the amounts employed. In addition, the active compound may be incorporated into sustained-release preparations and devices.

The polymer may also be administered subcutaneously, intramuscularly, intravenously, intraspinally, intracranially, intrauterally, rectally, intraperitoneally, and into and around any applicable body cavity, wound and surgical site by infusion or injection. Solutions of the polymer may be prepared with a suitable solvent such as an alcohol, optionally mixed with a nontoxic surfactant. Dispersions may also be prepared in glycerol, liquid polyethylene glycols, triacetin, and mixtures thereof and in oils. Under ordinary conditions of storage and use, these preparations contain a preservative to prevent the growth of microorganisms. The pharmaceutical dosage forms suitable for injection or infusion may include sterile solutions or dispersions or sterile powders comprising the polymer containing the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage.

The liquid carrier or vehicle may be a solvent or liquid dispersion medium comprising, for example, ethanol, a polyol (for example, glycerol, propylene glycol, liquid polyethylene glycols, and the like), vegetable oils, nontoxic glyceryl esters, and suitable mixtures thereof. The proper fluidity may be maintained, for example, by the formation of liposomes, by the maintenance of the required particle size in the case of dispersions or by the use of surfactants. The prevention of the action of microorganisms may be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Prolonged absorption of the injectable compositions may be brought about by the use in the compositions of agents delaying absorption, for example, aluminum monostearate and gelatin. Sterile injectable solutions are prepared by incorporating the polymer in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present polymers may be applied in pure form. However, it will generally be desirable to administer them as compositions or formulations, in combination with a dermatologically acceptable carrier, which may be a solid or a liquid. Examples of useful dermatological compositions which may be used to deliver the polymers of the invention to the skin are known to the art. See, for example U.S. Pat. Nos. 4,608,392; 4,992,478; 4,559,157; 4,820,508.

Useful solid carriers include finely divided solids such as talc, clay, microcrystalline cellulose, silica, alumina and the like. Useful liquid carriers include alcohols or glycols or alcohol/glycol blends, in which the present compounds may be dissolved or dispersed at effective levels, optionally with the aid of non-toxic surfactants. Adjuvants such as fragrances and additional antimicrobial agents may be added to optimize the properties for a given use. The resultant liquid compositions may be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials may also be employed with liquid carriers to form spreadable pastes, gels, ointments, soaps, and the like, for application directly to the skin of the user. The polymer may be formulated so that it will be released over an extended period of time when administered in accordance with the invention, e.g. over at least about 2, 5, 7, 10, 20, 40, 60, 80, 100, 120, 140, 160, or 180 to about 200, 220, 240, 260, 280, 300, 320, 340, or 360 days, and even over longer periods of time. For example, when applied for treatment of hard tissue the polymer may be formulated for release over a period of about 30 to about 90 days; for treatment of soft tissue about 1, 2, 5, or 10 to about 12, 15, 20, or 30 days, or over about 1 to 2 years. A polymer of this invention may have for example properties compatible with dosage of drug delivered, pharmacokinetics, rate of generation, elution or release, duration of release, elution or generation of the drug, agent solubility and binding characteristics to other agents and substances in the environment, another agent interaction, e.g. drug interaction. The polymer may have properties compatible with the physical, chemical, and/or biological requirements for matching the environment for which it is intended, e.g. coating with the surface and bulk of a medical or veterinary device, such as the coating's adherence to the surface of the implanted medical device during processing/coating as well as during implantation, coating stability on the device, coating reproducibility and reliability, non-planar coating ability, porous, and textured geometries, the void filling ability for providing agent reservoirs, and the ability of the coating to withstand mechanical e.g. tensile, compressive, torsional, and shear, and frictional forces generated during coating processing/application, implantation and subsequent use.

One example is the behavior of a coating during subsequent tissue response of an implanted medical or veterinary device. The polymers of the present invention may also be incorporated into systemic and topical formulations and among these, preferred are formulations that are suitable for inhalation, oral, rectal, vaginal, nasal, ophthalmic, otical, intracavitary, intraorgan, topical (including buccal, sublingual, dermal and intraocular), parenteral (including subcutaneous, intradermal, intramuscular, intravenous and intraarticular), intracavitary, CNS penetrating, and transdermal administration, among others. The compositions may conveniently be presented in single or multiple unit dosage forms as well as in bulk, and may be prepared by any methods well known in the art of pharmacy.

The composition of the invention may also be provided in the form of a kit containing instructions for its use, whether already formulated or with instructions for its formulation and administration regime. The kit may also contain other agents, such as those which were described in this patent, and for example when for parenteral administration, also a carrier in a separate container, cartridge, pack or pouch, which may be sterile. The present composition may also be provided in a sterile contained for addition of a liquid carrier prior to administration. See, e.g. U.S. Pat. No. 4,956,355; UK Patent 2,240,472; EPA 429,187; PCT 91/04030; Mortensen, S. A., et al., Int. J. Tiss. Reac. XII(3): 155-162 (1990); Greenberg, S., et al., J. Clin. Pharm. 30: 596-608 (1990); Folkers, K., et al., Proc. Nat'l. Acad. Sci. 87: 8931-8934 (1990), the relevant preparatory and compounding portions of all of which being incorporated herein by reference.

Formulations suitable for topical, oral, colonic, inhalable, and parenteral administration are preferred. All methods include the step of bringing the polymer carrying an agent(s) or compound(s) into association with a carrier and one or more accessory ingredients. In general, the formulations are prepared by uniformly and intimately bringing the polymer into contact or association with any agents that will be dispersed therein, and optionally with a liquid carrier, a solid carrier, or both, and then, if necessary, shaping the product into desired formulations described elsewhere in this patent.

Compositions suitable for oral administration may be presented in discrete units, such as capsules, cachets, lozenges, or tablets, each containing a predetermined amount of the active compound; as a powder or granules; as a solution, or suspension in an aqueous or non-aqueous liquid; or as an oil-in-water or water-in-oil emulsion. Such compositions may be prepared by any suitable method of pharmacy that includes the step of bringing into association the polymer with any agent to be carried by the polymer, and an optional suitable carrier.

In general, the compositions of the invention are prepared by uniformly and intimately admixing the active compound with a liquid or finely divided solid carrier, or both, and then, if necessary, shaping the resulting mixture. For example, a tablet may be prepared by compressing or molding a power or granules containing the active compound, optionally with one or more accessory ingredients. Compressed tablets may be prepared by compressing, in a suitable machine, the compound in a free-lowing form, such as a powder or granules optionally mixed with a binder, lubricant, inert diluent, and/or surface active/dispensing agent(s), among other formulation ingredients known in the art. Tablets may be made by molding in a suitable machine, the powdered polymer moistened with an inert liquid binder.

Compositions for oral administration may optionally include enteric coatings known in the art to prevent degradation of the compositions in the stomach and provide release of the drug in the small intestine. Compositions suitable for buccal (sub-lingual) administration include lozenges comprising the active compound in a flavored base, usually sucrose and acacia or tragacanth; and pastilles comprising the compound in an inert base such as gelation and glycerin or sucrose and acacia. Compositions suitable for parenteral administration comprise sterile aqueous and non-aqueous injection solutions of the polymer, and are preferably isotonic with the blood of the intended recipient, and may contain in addition to other agents antioxidants, buffers, bacteriostats and solutes which render the compositions isotonic with the blood of the intended recipient.

Aqueous and non-aqueous sterile suspensions may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Compositions suitable for topical application to the skin preferably take the form of an ointment, cream, lotion, paste, gel, spray, aerosol, or oil, and the carriers that may be used include vaseline, lanoline, polyethylene glycols, alcohols, transdermal enhancers, and many others known in the art, as well as combinations of two or more of them. Compositions suitable for transdermal administration may be presented as discrete patches adapted to remain in intimate contact with the epidermis of the recipient for a prolonged period of time, and may be delivered by iontophoresis and typically take the form of an optionally buffered aqueous solution of the active compound. See, e.g. Pharmaceutical Research 3: 318 (1986), the brelevant portion of which is incorporated herein by reference.

The agent is loaded in the polymer of this invention within broad amounts of the composition. For example, the agent(s) may be contained in the composition in amounts of about 0.001%, about 1%, about 2%, about 5% to about 5%, about 10%, about 20%, about 40%, about 90%, about 98%, about 99%, or about 99.999% of the composition. These amounts may be adjusted when and if additional agents with overlapping activities are included as discussed above. Dosage will vary depending on the agent(s), age, weight, and condition of the subject, and the treatment may be initiated with small dosages less than optimal doses of the polymer of the invention, and increased until a desired or even an optimal effect under the circumstances, is reached. In general, the dosage comprises about 1, 5, 10, or 20 mg polymer/kg body weight to about 100, 200, 500 or 1000 mg polymer/kg body weight. Higher or lower doses, however, are also contemplated depending on the actual loading of the agent(s) in the polymer and are, therefor, within the confines of this patent. In general, the content of the agent in the amount of polymer delivered is preferably such that when administered it will provide a concentration at the desired site that will afford effective results without causing unduly harmful or deleterious side effects, and may be administered either as a single unit dose, or if desired in convenient subunits administered at suitable times throughout the day. The additional agent(s) are administered in amounts that are known in the art to be effective for the intended application. In cases where the additional agent in the composition has overlapping activities with the principal agent, i.e. an additional NSAID and its salts, the dose of one, the other or both agents may be adjusted to attain a desirable effect without exceeding a dose range which avoids untoward side effects. Thus, when other analgesic and anti-inflammatory agents are added to the composition, they may be added in amounts known in the art for their intended application or in doses somewhat lower that when administered by themselves.

In general, the present composition is provided as various systemic and topical formulations, which include, but are not limited to, oral, intrabuccal, intrapulmonary, rectal, intrauterine, intradermal, topical, dermal, parenteral, intratumor, intracranial, buccal, colonic, sublingual, nasal, injectable such as intramuscular, subcutaneous, intraglandular, intraorgan, intralymphatic, intraarticular, intravascular, intravenous, or intrathecal, inhalable, transdermal, intraarticular, intracavitary, implantable, transdermal, iontophoretic, intraocular, ophthalmic, vaginal, otical, implantable, slow release and enteric coating formulations. The actual preparation and compounding of these different formulations is known in the art and need not be detailed here. The poler of the invention may be administered once or several times per day, per week, per month, or per year, depending on its half life. The polymers disclosed herein may be administered to the inhalation system, e.g. to the lungs or nasally by any suitable means, but are preferably administered by generation of an aerosol comprised of respirable particles that the subject inhales. Respirable particles may be liquid or solid, and are of respirable size; that is particles of a size sufficiently small to pass through the mouth and larynx upon inhalation and into the bronchi and alveoli of the lungs. In general, particles ranging from about 0.5, 1, 2, or 5 micron to about 5, 7, 10, or 20 micron in size are respirable, whereas those larger than respirable size tend to deposit in the throat and be swallowed. Thus, the quantity of non-respirable particles in the aerosol is preferably minimized. For nasal administration, a particle size in the range of about 10, 15, 20, 30, or 50 µm to about 20, 75, 100, 200, 350, or 500 µm is preferred to ensure retention in the nasal cavity. Liquid pharmaceutical compositions of polymer for producing an aerosol may be prepared by combining the polymer alone or in admixture or dispersion with other polymers or agents with a stable vehicle, such as sterile pyrogen free water, or other known carriers.

Solid particulate compositions containing dry respirable particles of micronized active compound may be prepared by grinding dry polymer(s) with/without dispersed agents with a mortar and pestle, and then passing the micronized composition through a 400 mesh screen to break up or separate out large agglomerates. A solid particulate composition comprised of the polymer may optionally comprise a dispersant that facilitates aerosol formation. A suitable dispersant is lactose, which may be blended with the active compound in any suitable ratio, e.g. a 1 to 1 ratio by weight. Other dispersants, however, are also suitable and their identities and formulation characteristics may be learned from their use in the art. Aerosols of liquid particles comprising the polymer of the invention may be produced by any suitable means, such as with a Nebulizer. See, e.g. U.S. Pat. No. 4,501,729.

Nebulizers are commercially available devices that transform solutions or suspensions of the active ingredient into a therapeutic aerosol mist either by means of acceleration of a compressed gas, typically air or oxygen, through a narrow venturi orifice, or by ultrasonic agitation. Suitable compositions for use in a nebulizer consist of the polymer in a liquid carrier, the polymer comprising about 0.01, 1, 5, 10 w/w % to about 20, 30, 40 w/w % of the formulation, and some times even higher amounts. The carrier is typically water, or a dilute aqueous alcoholic solution, preferably made isotonic with body fluids by the addition of, for example sodium chloride. Optional additives include preservatives if the compositions is not prepared sterile, for example, methyl hydroxybenzoate, antioxidants, flavoring agents, volatile oils, buffering agents and surfactants. Likewise, aerosols of solid particles comprising the polymer with/without other polymers and/or agents may be produced with any sold particulate aerosol generator. Suitable aerosol generators for administering solid particulate medicaments to a subject produce respirable particles, and generate a volume of aerosol containing a predetermined metered dose of a medicament at a rate suitable for human administration.

Examples of such, aerosol generators include metered dose inhalers and insufflators. The dispersed agent(s) may be administered concurrently with the polymer(s), and may be an agent suitable for preventing and treating sleeplessness, mood disorders, anxiety, irritability, wasting, bulimia, anorexia nervosa, cancer, viral and microbial infections, heart conditions, ischemia, menopause, pain, inflammation, wounds and burns, muscle tension, low bone calcification, inflammatory diseases such as auto-immune diseases, COPD, and inflammatory bowel disease, and many more, and to treat and prevent steroid intake secondary effects and to improve body weight and increase muscle mass, preferably in the same composition, as described above.

The phrase "concurrently administering" as used herein refers to the polymer(s) and the dispersed or appended agent(s) being administered either (a) simultaneously in time, and preferably by formulating the two together in a common pharmaceutical carrier, or (b) at different times during the course of a common treatment schedule. In the latter case, the two may be administered at times effective to complement their half lives and, thereby offset a reduction in peak level of one with an increasing level of the other and, thereby, counter balance any decrease in activity of one with an increase in activity of the other as a result of their alternate administration schedule. Thus, the polymer may or may not be administered for a time sufficient to bring endogenous levels of an active agent(s) back to prior levels in the subject. If the present composition of formulations are administered for a time sufficient to replenish endogenous levels of an agent(s) (if lowered with respect to prior levels in the same subject), then the active agent(s) or its(their) precursor(s) present in the polymer, or their dispersions or mixtures with other polymers and/or agents are administered in amounts effective to increase levels to a desired level. Thereafter, the doses of the two or more polymers and agents may be reduced so as to maintain desired levels, whether the dispersed, appended or admixed polymer(s) or agent(s) has(have) overlapping activity(ies) with the active agent(s) or compound(s) released by the polymer or, if of different activity, the dose of the admixed, appended or dispersed polymer(s) and/or agent(s) may be reduced along with that of the active compound released by the polymer(s) in cases of reduced risk of relapse. If the polymer(s) is(are) administered for a time sufficient to replenish endogenous levels, and this is attained, the continuation of treatment will depend on whether levels are maintain in the absence of treatment or not. Moreover, whether the admixed, appended or dispersed agent(s)' dose is reduced or not will depend on whether or not it is necessary to continue its administration or the subject remains stable in its absence. If the practitioner perceives a need to offset a future relapse, be it as a decrease in agent(s) levels or even its depletion and/or a need or benefit from a continued administration of the dispersed, appended or admixed polymer(s) and/or agent(s), the treatment may be continued under close monitoring.

The admixed, appended or dispersed polymers and agents, examples of which are listed above, may be administered per se or in the form of their biologically, physiologically, pharmacologically, pharmaceutically or veterinarily acceptable salts. When used in medicine, the salts of these agents should be pharmacologically and pharmaceutically acceptable, but non-pharmaceutically acceptable salts may be used to prepare the free active compound or pharmaceutically acceptable salts thereof and are appropriately included within the scope of this invention. Such pharmacologically and pharmaceutically acceptable salts include, but are not limited to, those prepared from the hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulphonic and benzenesulphonic acids, among others. Pharmaceutically acceptable salts also may be prepared as alkaline metal or alkaline earth salts, such as sodium, potassium or calcium salts of the carboxylic acid group. The present pharmaceutical formulations, whether for veterinary or human use, may comprise, in addition to the polymer(s) and one or more appended, admixed or dispersed polymers and/or agents, one or more pharmaceutically acceptable carriers, and other markers, diagnostic, prophylactic and/or therapeutic ingredients suitable for specific applications. The carrier(s) should be biologically, physiologically, pharmacologically, pharmaceutically or veterinarily acceptable in the sense of being compatible with the other ingredients of the formulation and not unduly deleterious to the recipient thereof.

Formulations of the present invention suitable for oral administration may be presented in discrete units such as powders, granules, dragees, capsules, cachets, tablets or lozenges, each containing a pre-determined amount of the polymer that will release a desired dose of the active agent(s) in the form of a powder or granules; or a suspension in an aqueous liquor or non-aqueous liquid such as a syrup, elixir, emulsion or draught. Tablets may be made by compression or molding of the polymer(s), optionally with one or more agents and accessory ingredients. Compressed tablets may be prepared by compressing in a suitable machine, with the active compound being in a free-flowing form such as a powder or granules that may be mixed with a binder, disintegrant, lubricant, inert diluent, surface active agent or dispersing agent, among other ingredients. Molded tablets comprised of a mixture of the powdered active compound with a suitable carrier may be made by a suitable molding machine. Syrups may be made by adding the polymer to a concentrated aqueous solution of a sugar, for example sucrose, and then adding any desired admixed, or dispersed polymers and agents and accessory ingredient(s) such as flavorings, preservatives, crystallization retardation agent(s), and solubility increasing agents such as a polyhydric alcohol, glycerol or sorbitol, among others. Formulations suitable for parenteral administration may be prepared as a sterile aqueous formulation of the polymer(s) and agent(s), preferably isotonic with the blood of the recipient. Nasal spray formulations may be prepared as purified aqueous solutions of the active compound with preservative agents and isotonic agents, although others are also suitable. Such formulations are preferably adjusted to a pH and isotonic state compatible with the nasal mucous membranes.

Formulations for colonic, rectal or vaginal administration may be solid or liquid form, typically being presented as a suppository with a suitable carrier such as cocoa butter, or hydrogenated fats or hydrogenated fatty carboxylic acids, or a solution, suspension or emulsion in a liquid carrier suitable for colonic, vaginal or rectal administration.

Ophthalmic formulations may be prepared by methods similar to those for nasal sprays, except that the pH and isotonic factors are preferably adjusted to match that of the eye. Otical formulations are generally prepared in viscous carriers, such as oils and the like, as is known in the art, so that they may be easily administered into the ear without spilling.

Topical formulations comprise the polymer(s) of this invention in amounts effective to release the agent(s) or compound(s) dissolved or suspended in one or more media such as mineral oil, petroleum, polyhydroxy alcohols or other bases used for topical pharmaceutical formulations, and are provided in the form of products for the skin and hair such as skin moisturizers, deodorant, cleansers, pads, plasters, lotions, creams, gels, ointments, solutions, shampoos, conditioners, hair straighteners, hair revitalizing treatments, sun-blocking and tanning products, make-up and lipsticks for topical application.

Coating or filler formulations for applications other than those mentioned above are suitably prepared by methods known in the art, by mixing the polymer(s) of the invention and other desired ingredients in a manner suitable for the intended purpose. For example, if intended for coating marine or construction surfaces, or for filling porous articles, the polymer(s) of the invention may be applied by itself or with formulation ingredients as a primer or undercoating, with or without prior sanding and cleaning of the target surfaces, or it may be incorporated into a varnish, paint, or other type or coating normally employed on such surfaces. Other polymers and agents may be appended to, mixed with, or dispersed within the polymer(s) as desired. The addition of other admixed or dispersed polymers, agents and accessory ingredients may be desirable. In addition to the aforementioned ingredients, the formulations of this invention may further include one or more accessory ingredient(s) such as diluents, buffers, flavoring agents, binders, disintegrant, surface active agents, thickeners, lubricants, preservatives (including antioxidants), colorants, perfumes, sun-blockers, sun-tanning agents, preservatives, and the like. Other ingredients may also be utilized as is known in the art.

Useful doses of the polymers may be determined using techniques known in the art, such as, e.g., by comparing their in vitro activity with the in vivo activity of the therapeutic agent in animal models. Methods for the extrapolation of effective doses in mice, and other animals, to humans are known to the art; for example, see U.S. Pat. No. 4,938,949. Additionally, useful doses may be determined by measuring the rate of hydrolysis or enzymatic degradation for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician, and is easily determinable by one of ordinary skill in the art. The quantity of polymeric drug to be administered to a host that is effective for the selected use may be readily determined by those of ordinary skill in the art without undue experimentation. The quantity essentially corresponds stoichiometrically to the amount of drug which is known to produce an effective treatment for the selected use. The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The total amount of an agent(s) released will vary depending on the particular agent(s) and treatment protocol involved, as is easily determined by one ordinarily skilled in the art. The amount of active agent released will typically be from about 0.1 µg to about 10 g, preferably from about 1 µg to about 100 mg, more preferably from about 10 µg to about 10 mg, more preferably from about 50 µg to about 1 mg. Preferably, the polymers are formulated to provide local release of an effective amount of an active agent or agent over a period of at least about 2, about 5, about 10, about 20, or about 40 days. The compositions may also preferably be formulated to provide local release of an effective amount of the agent over a period of up to about 3 months, about 6 months, about 1 year, or about 2 years. The agent(s) may be released from the polymer at any rate suitable for appropriate delivery of the active agent to the patient. In one embodiment, the active agent is released at a rate from about 0.01 µg per day to about 100 mg per day, from about 1 µg per day to about 10 mg per day, or from about 10 µg per day to about 1 mg per day. It will be appreciated that the greater the potency of the coating, the better with regard to minimizing the space required for the administered product, the potential cost of the product, the ease of manufacturing the product, and the potential impact on other desired properties of the medical implant. The polymers of the present invention may be characterized by techniques known in the art. Degradation and drug release profiles of the polymer drug delivery systems of the present invention may also be determined routinely. The range of therapeutically effective dosages, that is, the dosage levels necessary to achieve the desired result, of a microparticle of the invention will be influenced by the route of administration, the therapeutic objectives, and the condition of the patient. As such, a polymer of the invention may be administered as a single daily dose, several times daily, every other day, weekly, etc. depending on the dosage requirements. Individual determinations will need to be made to identify the optimal dosage required.

As is known in the art a polymer dosage may be determined by comparing their in vitro activity, and in vivo activity of an agent(s), compound(s) or polymer(s) in an animal model. Methods for the extrapolation of effective dosages in mice, and higher animals, to humans are known to the art as well. See, for example, U.S. Pat. No. 4,938,949. Useful dosages may be determined also by measuring the rate of hydrolysis or enzymatic degradation for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician. The desired dose may conveniently be presented as a single daily dose, or as divided doses administered at appropriate intervals, for example, as multiple daily sub-doses. Each sub-dose itself may be further divided, e.g., into a number of discrete loosely spaced administrations. The polymers of the invention are also useful for the application, administration and release of a combination of agents typically by 1) dispersing a second agent(s) or compound(s) within a polymeric matrix of the invention comprising a first agent(s) or compound(s); both the first and second agents will be released upon polymer degradation; 2) appending a second therapeutic agent to a polymer of the invention, i.e. not incorporated into the polymer backbone, through hydrolyzable bonds; 3) incorporating into the polymer backbone more than a single agent, e.g. a polymer comprising different agent units; and/or 4) administering more than a single polymer, each comprising a different therapeutic agent(s) either as a blend, a mixture or as separate entities administered together or within a short period of time.

The invention thus provides a composition comprising a polymer of the invention incorporating a first agent(s) in its backbone, and a second agent(s) that is blended or admixed with, or dispersed within the polymer matrix. The invention also provides a pharmaceutical composition comprising a polymer of the invention of a first agent(s) in its backbone, and a second agent(s) appended to the polymer e.g. through hydrolyzable bonds that will release the second agent(s) under appropriate conditions. The polymers of the invention may also be employed, applied, or administered in combination with other agents that are effective to prevent, contain, or treat a given condition, such as is the case in combination therapy, and applications in the field of coating, paints, and many others. The present invention thus provides a method for delivering an agent(s) or compound(s) to a targeted site by applying, delivering, administering and the like an effective amount of the polymer(s) of the invention by itself(themselves, or in combination with other agent(s). In the veterinary and medical fields, the method will take the form of the prevention, containment, or treatment of a disease or condition comprising application, delivery, or administering of an effective amount of a polymer(s) of the invention by itself (themselves) along another prophylactic, containment, therapeutic and/or traceable agent(s). The polymer may be administered or applied as a composition comprising a pharmaceutically acceptable carrier or diluent, and optionally another agent(s).

B. Co-Polymers and Blends of Polymers

The therapeutic polymers and compositions thereof used in some applications, such as for coating implantable medical and veterinary devices, including stents and orthopedic implants, may require greater elasticity or flexibility while retaining sufficient hardness and adhesiveness to remain intact on the device as the device is handled or otherwise manipulated by the clinician or surgeon or within the body of the patient, such as, e.g., when the device interacts, e.g. mechanically and chemically, with the surrounding tissue or fluid or luminal wall, or, in the case of a stent, with the intraluminal wall of a vessel in which the vessel and stent experience pulsatile motion due to the pulsatile nature of blood flow and the contraction of the vessel wall by the associated smooth muscle. To provide desired physical properties, including mechanical strength, modulus, and elongation without failure, it is possible to create coating comprised of a co-polymer of two or more monomers used to create the two or more polymers that have physical properties and other performance characteristics bracketing those properties and characteristics desired. In one embodiment, copolymers of similarly sized or "sequential" linkers, i.e. adipic acid (C6) and suberic acid (C8) are made in order to "fine tune" the physical properties of the polymer to a state between the two available linkers. However, "non-sequential" co-polymers are also contemplated, for example a co-polymer containing adipic acid (C6) and sebacic acid (C10) linkers. Additionally, co-polymers comprising three or more linker group moieties are also contemplated. In one embodiment, the co-polymer is formed of monomers of salicylic acid and adipic acid, and salicylic acid and suberic acid, at about 50% or more mole percent of the co-polymer is the monomer salicylic acid and adipic acid respectively. However, proportions of any of the agent monomers may be employed in the polymers of the invention, such as about 5, 10, 20, 30, 40, or 50 to about 60, 70, 80, 90, 95, or 99 wt %. Alternatively or in combination with one or more of the co-polymers described above, it is possible to create a physical blend of two or more polymers or co-polymers in which the individual polymers or co-polymers blended each have a set of physical properties and performance characteristics that meet or exceed requirements for a coating for the specified implantable medical or veterinary device and its application but may have one or more physical properties and performance characteristics that are insufficient for that device and its application, such that the combination of properties and characteristics provided by the blend meet or exceed the required properties and characteristics needed for the device and its application.

These blends may be of polymers that are miscible or immiscible in each other. For example, it is possible to make a co-polymer or blend of polymers or co-polymers in which one monomer in the co-polymer or one polymer or co-polymer in the blend has a hardness that exceeds the requirements for the coating for the device and its application but a flexibility insufficient and another monomer in the co-polymer or another polymer or co-polymer in the blend that has a flexibility sufficient but a hardness insufficient for the device and its application. The physical properties and performance characteristics of the copolymer may be fine tuned further by selecting the percentage of each monomer in the copolymer or the percentage of each polymer or co-polymer in the blend towards the combination of monomers or polymers or co-polymers that produce a coating that has physical properties and performance characteristics closer to the desired set. In an exemplary embodiment, a polymer comprising salicylic acid or a derivative of salicylic acid, such as diflunisal, and linkers of dicarboxylic acids in which the pair of carboxylic acids within the diacid are separated by a linear alkyl chain, is coated on a stent or other device experiencing expansion, contraction, or torsion in application or use. A coating comprising a polymer in which the alkyl chain comprises six atoms of carbon (known as adipic acid) may crack or craze upon change in dimensions, e.g. expansion for a stent, whereas a coating comprising a polymer in which the alkyl chain comprises eight atoms of carbon (known as suberic acid) may be excessively tacky or otherwise adhere to the materials used in handling and implantation, e.g. the balloon used for expansion of the stent. For such applications, in the absence of an admixed drug or other additive that alters the physical properties and performance characteristics in a predictable and repeatable manner, a suitable coating may comprise, for example, a polymer of salicylic acid and suberic acid or a copolymer of monomers of salicylic acid and dicarboxylic acid or a physical blend of polymers or co-polymers of salicylic acid and dicarboxylic acid that approximate the tradeoffs in physical properties and performance characteristics, including hardness, tackiness, and flexibility, of polymers created with a linker of suberic acid. In another exemplary embodiment, a polymer comprising salicylic acid or a derivative of salicylic acid, such as diflunisal, and linkers of dicarboxylic acids with linear alkyl chains, and is coated on an orthopedic implant for use as a hip, knee, shoulder, elbow replacement, a fixation device, or another orthopedic application. In the absence of an admixed drug or other additive that alters the physical properties and performance characteristics in a predictable and repeatable manner, a suitable coating may comprise, e.g., a polymer of salicylic acid and a dicarboxylic acid linker with four, six, eight or ten carbon atoms in the linear alkyl chain (known as succinic and adipic acids, respectively) or a copolymer of monomers of salicylic acid and dicarboxylic acid or a physical blend of polymers or co-polymers of salicylic acid and dicarboxylic acid that approximate the tradeoffs in physical properties and performance characteristics, including hardness, tackiness, and flexibility, of polymers created with a linker of succinic or adipic acids.

C. Combination Therapies

The polymers of the invention are also useful for administering a combination of therapeutic agents to an animal. Such a combination therapy may be carried out in the following ways: 1) a second therapeutic agent may be dispersed within the polymer matrix of a polymer of the invention, and may be released upon degradation of the polymer; 2) a second therapeutic agent may be appended to a polymer of the invention (i.e. not in the backbone of the polymer) with bonds that hydrolyze to release the second therapeutic agent under physiological conditions; 3) the polymer of the invention may incorporate two therapeutic agents into the polymer backbone; or 4) two polymers of the invention, each with a different therapeutic agent may be administered together (or within a short period of time). Of course, more than one therapeutic agent may be used in each of the above cases. Thus, the invention also provides a medical device comprising a polymer that hydrolyzes to form a first active agent and a second active agent that is dispersed within the polymer matrix of a polymer of the invention. The invention also provides a medical device comprising a polymer that hydrolyzes to form a first active agent having a second active agent appended to the polymer (e.g. with bonds that will hydrolyze to release the second therapeutic agent under physiological conditions).

The polymers of the invention may also be administered in combination with other active agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier. Suitable drug combinations for incorporation into the polymers or the compositions of the invention include for example, a first active agent that is classified as a non-steroidal anti-inflammatory drug (NSAID), such as, e.g., salicylic acid or diflunisal, combined with a second active agent classified as an anti-cancer and/or anti-neoplastic agent, e.g. paclitaxel or methotrexate, or as an immunosuppressive, e.g. rapamycin. Preferred drug combinations for incorporation into the polymers or the compositions of the invention include amoxicillin/clavulanic acid; and imipenem cilastatin, among others.

D. Injectable Polymers SR for Immune Disease Treatment

Immune diseases such as rheumatoid arthritis (RA), lupus, and the like, are debilitating diseases affecting millions. Although RA will be discussed as an example of a group of immune diseases, it is intended to cover immune and particularly all auto-immune diseases in this description. By far the most troubling symptoms of RA are severe pain and swelling of the joints of the wrists, hands, ankles and feet, which occur when the body's immune system mistakenly attacks the synovium (the cells lining the joints), causing intense inflammation. The therapeutic mainstay of RA is oral NSAIDs, including non-selective COX inhibitors like aspirin and diflunisal, as well as the newer COX 2-specific NSAIDs, rofecoxib and celecoxib. As disease severity progresses, disease-modifying anti-rheumatic drugs (DMARDs) such as methotrexate, azothioprine, gold salts and immunosuppressive agents are used, despite their serious side effects. More recently, injectable biological response modifiers that block the action of tumor necrosis factor (etanercept and infliximab) have shown great promise, despite their high cost and associated risk of tuberculosis and cancer. Another injectable protein (anakinra) blocks the effects of IL-1, an inflammatory protein over-expressed in RA patients. Notwithstanding the effectiveness of these newer treatments, RA remains a chronic disease, the severity of which fluctuates over time. When pain and swelling flare, a standard treatment is to inject steroids directly into the affected joint, sometimes in combination with a local anesthetic. Such intra-articular injections provide rapid and long-lasting relief of pain and swelling, but only a few steroid injections may be administered safely at any one time, and repeated injections into the same joint may destroy cartilage. These drawbacks have spurred the development of "steroid-sparing" treatments for flared joints. A PLGA microsphere-based intra-articular product is being currently tested to provide slow-release of betamethasone, with the goal of minimizing tissue damage whereas intra-articular hyaluronic acid products are used mostly for osteoarthritis In one embodiment, the present invention is an injectable polymer, e.g. a polyNSAID product, comprising microparticles designed to provide sustained relief of swollen and painful joints after intra-articular injection and other uses. On example is a micro formulation of polyDF. In cases where polyDF alone may be insufficient, other drugs, including analgesics such as morphine, may be added during preparation of the microparticle formulation, or as a coating or core of the formulation. Long considered to produce analgesia by the activation of receptors located only within the central nervous system, new evidence demonstrates that narcotic analgesics have a potent local analgesic effect when injected into chronically-inflamed tissue. Clinical studies demonstrated profound pain relief from 1 mg morphine injected into chronically-inflamed (but not acutely-inflamed) gum tissue, and pain relief similar to that of 4 mg dexamethasone by the intra-articular injection of 3 mg morphine in RA patients.

The addition of strong analgesics, such as narcotic analgesics, e.g. morphine, to the polymer of the invention presents little or no abuse potential because only low concentrations of morphine are required, generally less than about 5 to 10 wt % as is known in the art, and morphine release from polyDF will be retarded generally by an about 15- to about 18-hr induction period before the onset of polymer biodegradation. For more extended effects, e.g. analgesia, antibiotic and antiseptic action, and the like, drugs such as narcotic analgesics, antibiotics, and other drugs, may also be incorporated into the backbone of the polymer.

E. Nanoparticle and Microparticle Formulations

All of the foregoing pharmaceutical applications may employ nano- and/or micro-particular formulations. Nanospheres and microspheres have been made form polydiflunisal having a mean diameter of about 10 to about 100 nm and about 10 to about 100 µm, with an average of 45-50 nm, and 45-50 µm, respectively, the latter being slightly smaller than the size commonly used for drug delivery. A process for preparing microencapsulated polymers of this invention, e.g. of chemical formula I, or for preparing intermediates useful for preparing compounds of formula I are provided in Table 4 below, and also as further embodiments of the invention.

TABLE 4

Microencapsulation Process

| Advantages | Microencapsulated Agent |
|---|---|
| U.S. Pat. No. 5,407,609 | Proteins |
| Fast Encapsulation Time (msec.) | Peptides |
| Minimal Exposure to Polymer Solvent | Small Molecules |
| High Encapsulation Efficiency | Water-Soluble Drugs |
| Good Yield | Hydrophobic Drugs |
| Yields Small Microparticles | Drugs Encapsulated in |
| (<100µ; <10µ) | Lactide/Glycolide Polymers |

Processes for making nanoparticle formulations are also known in the art, and need not be fully described in this patent. The surface eroding property of polymers such as polydiflunisal makes for solid, non-porous particles, e.g. nano- and micro-spheres, useful for sustained drug delivery, and their release duration may be controlled by varying particle diameter, e.g. larger microparticles biodegrade more slowly than smaller ones. Nano- and microparticles for pharmaceutical formulations may be designed to deliver an agent(s) or compound(s) incorporated into the polymer backbone and optionally an agent(s) blended, appended to, or dispersed in the polymer. When rats were administered a single subcutaneous injection of 250 mg polydiflunisal microspheres containing about 192 mg diflunisal formulated in a standard aqueous vehicle a peak plasma diflunisal of 35 µg/ml was achieved within two days, and thereafter the drug level declined slowly over about two weeks whereas a single oral dose of diflunisal produced a drug level that declined rapidly. Microparticle formulations of about 1, 2, 5, 7.5, 10, 25, 50 to about 10, 15, 30, 50, 75, 100, 250 µm are suitable for use in a pharmaceutical, veterinary or other type of formulations. Similarly, nanoparticle formulations may be administered for various applications, having a particle size about 1, 2, 5, 10 to about 15, 20, 30, 50, 100, 250, 500 nm, or various ranges between any two of these values. These polymers may also be employed as carriers for other agent(s) as has been demonstrated with polymers of the invention carrying paclitaxel and sirolimus. The anti-inflammatory properties of polyNSAIDs as delivery vehicles for an admixed pharmaceutical agent(s) and biological agent(s) is expected to significantly diminish the foreign body response associated with polymers commonly used for injectable depot products, such as PLGA. While the injection of a drug or biological agent carried by a polymer of the invention, e.g. a polyNSAID, may be expected to generate significant drug, e.g. NSAID, concentrations in tissues near the injection site, their systemic levels in most cases will remain less than about 0.1μ, which are far below therapeutic levels. The microparticles of the invention may be formed into various shapes and geometries e.g. spheres, and regular or irregular spheroid shapes. They may also be incorporated into various formulations or compositions, e.g. gelatin capsule, liquid formulation, spray dry formulations, formulations for use with dry powder or aerosol inhalers, compressed tablet, topical gels, topical ointments, topical powder. As would be understood by one of skill in the art, the desired size of a microparticle of the invention will depend on the desired application and mode of delivery. Modes of administration or delivery of a microparticle and nanoparticle formulations of the invention include those set forth herein, including orally, by inhalation, by injection, and topically. The present invention contemplates the administration of microparticle and nanoparticle formulations that upon degradation or bioerosion may be delivered as is, or yield a smaller particle and/or active agent for the effective treatment of a targeted organ or tissue. The present invention also contemplates administration of one or more of the same or different microparticle or nanoparticle formulations of the invention having either all the same size or a mixture of two or more different sizes. By varying the size of the microparticle, the rate of bioerosion and/or the rate of generation of active drug and/or the location of active drug generation may be controlled. As a result, timed e.g. delayed and/or sustained generation of active drug may be achieved. For example, treatment of the inflamed wall of the colon, e.g. the treatment of inflammatory bowel disease, infections, and the like, may be achieved by oral administration of a microparticle of the invention containing as the active agent an anti-inflammatory drug. Such a microparticle of about 1, to about 10 μm in size may be administered such that upon reaching the ileum region of the small intestine, the microparticle is about 0.1-1.0 μm in size, and about 0.01 to about 0.1 μm in size upon reaching the colon. See, for example Lamprecht et al., Abstracts/Journal of Controlled Release 72: 235-237 (2001). Once in the intestine, the microparticle may be physically entrapped by the villi and/or microvilli of the intestinal wall and/or by the mucous lining of the intestinal wall, thereby retarding expulsion, and prolonging gastrointestinal residence time and enabling timed sustained generation of the active agent in the proximity of the intestinal wall upon bioerosion of the polymer. The microparticles of the invention may be of about 0.1, 1, 10, 20, 50 to about 60, 70, 80, 90-100 μm, preferably about 0.1 to about 10 μm, and any ranges therewithin. The microparticle of the invention may be administered orally such that blood levels of the microparticle enable perfusion of the active agent into the surrounding tissue upon bioerosion. In yet another example, oral administration of a microparticles of the invention of about 0.6 μm, preferably about 0.3 μm, more preferably about 0.1 μm, or any sizes therebetween, may be used to deliver an active drug through the intestine and eventually to the liver via the lymph system. See, for example Jani et al., Pharm. Pharmacol. 42: 821-826 (1990); Desai et al., Pharmaceutical Research 13 (12): 1838-1845 (1996). Microparticles of the invention of about 1 to about 50 μm may be applied topically or ocularly. Preferably, the microparticle is about 5 to about 20 μm. For subcutaneous or intramuscular injection, about 1-70 μm microparticle of the invention may be used. In one preferred embodiment, about 10 to about 70 μm microparticle of the invention is used for subcutaneous or intramuscular injection. In another preferred embodiment, an about ≦10 μm microparticle of the invention is used to create a product that feels smooth when applied to human skin. In another preferred embodiment, about 1 to about 3 μm microparticles of the invention are used for skin penetration. However, many other ranges of microparticle sizes may be used as well, as exemplified by Smart Particle™ and others (PowderJect Pharmaceuticals, U.K.); U.S. Pat. Nos. 6,328,714, 6,053,889 and 6,013,050), in tissue e.g. skin, mucosa penetration applications that appear to rely more on shape and strength of the microparticle rather than size. The microparticles of the invention may also be used in an inhaled delivery, e.g. direct inhalation at a certain velocity, or by aerosol spray, to the lungs, including deep lungs, or pulmonary region. For example, a microparticle of the invention of about 0.5 to about 10 μm, preferably about 1-5 μm, more preferably about 1-3 μm, even more preferably about 1-2 μm may be formulated into an aerosol. For direct inhalation, about 0.5-6 μm, more preferably about 1-3 μm, microparticle may be used. See, for example AERx® System (Aradigm Corporation, Hayward, Calif.) as well as those described in U.S. Pat. Nos. 6,263,872, 6,131,570, 6,012,450, 5,957,124, 5,934,272, 5,910,301, 5,735,263, 5,694,919, 5,522,385, 5,509,404, and 5,507,277, and MicroDose DPI Inhaler (MicroDose Technologies Inc., Monmouth Junction, N.J.) as well as those described in U.S. Pat. Nos. 6,152,130, 6,142,146, 6,026,809, and 5,960,609. Microparticles of the invention of about ≦10 μm may be used for intraarticular injections in the treatment of, for example, arthritis. A microparticle of the invention of about 0.1 to about 100 μm, preferably about 0.1 to about 10 μm, more preferably about 0.1-1 μm, may be admixed with a suppository, e.g. glycerin suppository. Nanoparticle formulations of this invention have diameters (average or range of size) about 2, 5, 10, 20, 50, 100 nm to about 150, 250, 350, 500, 700, 850 nm may be applied to therapeutic and prophylactic applications, such as healing of wounds and the like.

A polymer, compound and/or composition of the invention may also be formed into pellets, "biobullets", i.e. bullet shaped, or seeds, e.g. bullet-shaped seeds, for inclusion in an implantable and/or injectable bioerodable, hollow carrier e.g. barrel, bullet, capsule, syringe or needle that are known in the art. Both animal and human applications are contemplated. Hollow needle-type carriers are also contemplated for use in the invention. In one embodiment, a hollow carrier may have a diameter ranging from about 0.5 to about 10 mm, although other gauges are also suitable. Pellets, "biobullets", and/or seeds of the invention may be placed inside the hollow cavity or chamber of a bioerodable needle-type carrier. According to the invention, one or more of the same or different pellet(s), "biobullet(s)" or seed(s) of the invention may be placed inside a hollow carrier or delivery device. The pellet, "biobullet" or seed may be any size that will enable placement inside the hollow carrier. The oral, injectable, implantable and topical formulations of the invention are suitable for uses in subcutaneous, intramuscular, intradermal, and many other types of injections, site-specific injection by themselves or at site of other implant placement e.g. by other medical devices, in conjunction with other implanted materials such as bone cement and other adhesives, xenographs, collagen and other fillers, resorbable biomaterials, biodegradable and non-degradable biomaterials, in conjunction with excipients for oral and tablet formulation, in creams, ointments and topical formulations and solutions, suspensions and emulsions intended for application on external and internal surfaces of the body. Particularly preferred particle diameters include nanoparticle and microparticle ranges of about $10^{-9}$, $10^{-8}$, $10^{-7}$ to about $10^{-6}$, $10^{-5}$ m, among others. Useful formulations of the present polymers comprise particles similar to those described for other uses as well as for topical applications, e.g. creams, ointments, suspension, and the like, including encapsulation of particles (coated particles) and particles coated with the polymers of this invention. The pellets, "biobullets", and seeds of the invention, all of which are forms known in the art, release upon bioerosion one or more agents. These products may be stored in hollow carriers that may itself comprise a polymer, compound and/or composition of the invention such that, when the hollow carrier is eroded it releases the pellets, "biobullets" and/or seeds of the invention. In one preferred embodiment, the pellets, "biobullets", and seeds comprise or are made from a polymer of the invention containing salicylic acid admixed with follicle stimulating hormone (FSH) and/or leuteinizing hormone (LH) which are then placed in the hollow cavity or chamber of a bioerodable hollow carrier or as part of a depot formulation, e.g. Lupron Depot®, for a timed release delivery of the hormones up to about 96 hours in order to stimulate ovulation. According to the invention, a pellet, "biobullet" or seed of the invention and/or one or more hollow carriers containing a pellet, "biobullet," or seed of the invention may be placed in a delivery device, e.g. injector, gas-driven applicator. In one embodiment, the delivery device may be further equipped with an axially slideable sleeve e.g. plunger, protrusions to prevent movement of the delivery device upon application e.g. chamfered protrusions, and handgrips. Examples of suitable carriers and/or delivery devices include, but are not limited to, those described in U.S. Pat. Nos. 6,001,385, 5,989,214, 5,549,560; WO 96/13300, WO 96/09070, WO 93/23110, and EPA 068053, each of which is herein incorporated by reference in its entirety. U.S. Pat. No. 5,989,214 and WO 96/13300, for example, describe an apparatus for injecting the body of humans or animals with a pharmaceutical preparation, wherein the preparation is arranged in a rigid carrier, wherein the apparatus includes: a chamber into which the carrier may be transported; and a channel connecting onto the chamber for transporting the carrier into the body including fixation means for fixing the end of the channel relative to the skin of the body for injecting in order to prevent a movement of the channel in the direction perpendicularly of the axis of the barrel and where according to one embodiment the fixation means are formed by chamfered protrusions formed on the part adapted for contact with the skin of the body and extending substantially in the direction of the axis of the channel. U.S. Pat. No. 5,549,560, WO 93/23110, and EPA 068053 describe a device for injecting humans and animals with a pharmaceutical preparation, wherein the preparation is held in a rigid carrier and the carrier is carried through the skin into the body by means of gas pressure, and wherein during carrying of a rigid carrier into the body by means of gas pressure the device with which the carrier is carried into the body is held against the body. U.S. Pat. No. 5,549,560, WO 93/23110, and EPA 068053 also describe a device for injecting animals or humans with a pharmaceutical preparation, wherein a chamber is present in which a carrier containing the pharmaceutical preparation may be placed, a barrel connecting onto this chamber and means for carrying the carrier by means of gas pressure through the barrel into the body for injecting, wherein means are present for blocking the use of the device when it is not pressed against a body. U.S. Pat. No. 6,001,385 and WO 96/09070, for example, describe "bullets" that are at least partly manufactured from substantially fully destructurized starch, particularly implants, suitable as vehicles for introducing active agents into the human or animal body in a transdermal manner.

F. Polymer Microparticles and Nanoparticles for Pharmaceutical Products

Microspheres have been made from a diflunisal polymer (polyDF) having a mean diameter of, for example about 45 µm, slightly smaller than the size commonly used for drug delivery. Polymers having surface eroding properties, e.g. polyDF are extremely suitable for making solid, non-porous microparticles, e.g. microspheres and nanospheres, useful for sustained drug delivery, particularly suitable for injectable formulations of particle size smaller than red blood cells (RBCs). The duration release for any agent(s) or compound(s) may be controlled by varying the particle diameter, e.g. larger particles biodegrade more slowly than smaller ones. Microparticles for pharmaceutical products may be designed to deliver a drug(s) incorporated into the polymer backbone as well as an agent(s) admixed or dispersed into the polymer. When rats were subcutaneous injected 250 mg polydiflunisal (polyDF) microspheres containing about 192 mg diflunisal formulated in a standard aqueous vehicle (FIG. 20) a peak plasma diflunisal of about 35 µg/ml was achieved within 2 days, thereafter the drug level declined slowly for about 2 weeks. In contrast a single oral dose of diflunisal produced a level of the drug that declined rapidly. Similarly, nanoparticle formulations may be administered for various applications, having a particle size about 0.5, 1, 2, 5, 10, 20, 35, 50, 75 to about 15, 20, 30, 50, 100, 250, 500 nm, or various ranges between any two of these values. One very preferred embodiment comprises a nanoparticular formulation comprising a particle size range smaller than red blood cells in a form suitable for intra venous (I.V.) injection. These polymers may also be employed as carriers for other drugs, as has been demonstrated with paclitaxel and sirolimus. The anti-inflammatory property of PolyNSAIDs as a delivery vehicle for admixed drugs and biologicals is expected to significantly diminish the foreign body response associated with polymers commonly used for injectable depot products, such as PLGA. The injection of an agent(s) or compound(s) or a biological agent(s) carried in a polymer of this invention, e.g. a polyN-SAID, will generate a significant agent(s) concentration, e.g. NSAID(s) concentrations, in tissues near the injection site. The systemic level of the agent(s), however, in most cases will remain less than about 0.1µ; that is far below therapeutic levels.

G. Polymer Microparticle and Nanoparticle Formulations for Injectable Biological Products In the pharmaceutical arena, the major marketed products in this area, LUPRON DEPOT® (leuprolide for prostate cancer and endometriosis), NUTROPIN DEPOT® (human growth hormone), TRELSTAR DEPOT® (triptorelin for prostate cancer), and SANDOSTATIN LAR® (octreotide for acromegaly), account for a market that is increasing very rapidly. Key drivers for growth are branded drug and biological products requiring product line extension, and new drug and biological products requiring delivery systems that improve patient compliance. Several leading products are summarized in Table 5 below.

TABLE 5

| | Injectable Drug and Biological Depot Products | | |
|---|---|---|---|
| Chiron | DEPOCYTE ® | Cytarabine | Depofoam ™ liposome |
| SkyePharma | DepoMorphine ™ | Morphine | Depofoam ™ liposome* |
| TAP Pharma | LUPRON DEPOT ® | Leuprolide | Medisorb ™ (PLGA) |
| Genentech | NUTROPIN DEPOT ® | HGH | Medisorb ™ (PLGA) |
| Pharmacia | TRELSTAR DEPOT ® | Triptorelin | Medisorb ™ (PLGA) |
| Novartis | SANDOSTATIN LAR ® | Octreotide | PLGA |
| J & J | Risperdal Consta ™ | Resperidone | Medisorb ™ (PLGA)* |

*Currently in Development

Many new products contain proteins formulated with aqueous suspensions of PGLA microspheres. While generally considered to have acceptable biodegradation kinetics, safety and biocompatibility, PLGA elicits localized inflammation and foreign body response, which may be severe depending on the tissues involved. This is evidenced by clinical studies involving 138 pediatric patients who received subcutaneous injections of NUTROPIN DEPOT®, a recombinant human growth hormone formulated with PLGA microspheres. Almost every patient reported two or three "injection site reactions" per injection, most of which represent hallmark foreign-body reactions, as shown in Table 6 below whereas patients receiving aqueous formulations of NUTROPIN reported infrequent foreign-body reactions.

TABLE 6

Reported Injection Site Reaction with NUTROPIN Products

| | INCIDENCE |
|---|---|
| NUTROPIN DEPOT ® | |
| Granuloma (nodules) | 61% |
| erythema (redness) | 53% |
| pain after injection | 47% |
| pain during injection | 43% |
| bruising | 20% |
| itching | 13% |
| swelling/puffiness | 8% |
| NUTROPIN AQ ® | |
| injection site discomfort | "reported" |
| NUTROPIN ® | |
| injection site plan | "reported infrequently" |

The polymers of the invention, such as e.g., polyNSAID microparticles, provide safe injectable depot formulations for proteins, monoclonal antibodies, polysaccharide, and nucleic acid prophylactic and therapeutic products with improved tolerability, enhanced bioavailability, and lower production costs compared to PLGA-based products.

VII. Devices

A. Introduction

Medical implant and device applications include the use of the polymers of this invention to form shaped articles such as grafts and stents, e.g., vascular and tissue regeneration grafts and stents; plates, e.g., bone plates and teeth; cuffs; pins; sutures; stitches; implantable sensors and drug delivery devices, and other articles that erode or decompose to release a desired agent(s) and non-toxic, non-inflammatory components within a period of time. The present polymers may be used also to form coatings and layers for similar articles that are made of other materials, including vascular grafts and stents, bone plates, sutures, implantable sensors, implantable drug delivery devices, stents for tissue regeneration, and other articles, which may require the release of an active compound. In one embodiment, the polymers described herein may be used to form, coat or otherwise treat medical devices. The medical device of the invention may be an implantable device. The polymers of the invention may be employed for forming or coating shaped articles such as stents and grafts, e.g., vascular grafts and stents; plates, e.g., bone, dental, and orthodontic plates; sutures; wound closing staples; stitches; surgical meshes; dental and bone implants; implantable sensors; cuffs; pins; sutures; implantable drug delivery and sensory or diagnostic devices; stents for tissue regeneration; and other articles suitable for implantation into a patient. Suitable medical devices include, for example, stents, e.g., coronary vascular stents and peripheral vascular stents; free standing films of about 0.08, 0.1, 0.2, 0.4 or 0.6 mm to about 0.5, 0.75, 0.9, 1, 1.5, or 2 mm, and in some cases even thicker, suitable for surgical coverings to prevent surgical adhesion and other uses; solutions, suspensions, emulsions, powders, gels, sprays, coats, creams, gels, in situ solidifying formulations, and semi-liquid and liquid formulations for "painting" surgically treated areas; urethral stents; binary stents; stents used for supporting the lumen of other anatomical tubes; and stents used for other medical treatments; catheters, e.g., surgical catheters and urinary catheters; grafts; and orthopedic implants including, e.g., hip, knee and shoulder implants, internal and external fixation devices and spinal cages and dental tooth implants; dry sockets; biosensor implants, e.g., for preventing fibrosis, ophthalmic implants and replacements; prolene mesh or thread; eye drops, e.g., non crystalline formulation; marine coatings; cervical rings, e.g., for contraception or sexual enhancement; other women's health applications; anti-infective coating on health aids such as bandages of the sort shown in U.S. Pat. No. 5,814,031; dental applications, e.g., fibrous and coated floss; cosmetic surgery fillers, e.g., botox, collagen, hyaluronic acid, etc.; fiber; strand form for sutures; dermabrasion treatments; wrinkle reduction; acne, e.g., with retinoic acid; breast implants; adhesions; capsular contracture; for employing products such as pivucane (e.g. APP Pharma), injectable formulations (e.g. Injectile Technologies), all of the relevant information relating to these products from publicly available sources being incorporated herein by reference.

In one embodiment, the present devices comprise a polymer(s) that will break down to release an agent(s), either active or that may be activated in situ, for example, at physiological conditions. In one embodiment, the medical device comprises a polymer comprising at least one active agent(s) or a pro-agent(s) that is (are) incorporated into the polymer backbone. In another embodiment, the polymer further comprises at least one agent(s) that is not incorporated into the polymer backbone. The agent(s) present in the backbone, appended to it, or otherwise admixed may be the same or different. The medical devices of the invention can compromise at least one polymer(s) on all or a part of their surface, and may be used, for example, to deliver the agent to a pre-determined site for effecting a specified action, such as to reduce or eliminate an adverse condition associated with the use of the device.

In one embodiment, the medical device is entirely formed of a polymer(s) that break down in situ, e.g. by hydrolysis or enzymatic activity of an agent(s). The medical devices may be formed in their entirety of the polymer, or comprise layers thereof, or be coated by a polymer(s), or many other possible configurations that will permit, for example, the release of an agent or different agents at different rates or times. One or more polymers may be arranged in accordance with this invention in alternating layers or coatings either in the formation of the device or formulation, or by subsequent coating of a device or formulation. The present device may be in the form of a stent, mesh, suture, pin, cuff, catheter, contraceptive device, reconstructive dental structure and tooth, orthopedic structure, drug delivery device, sensor, stitches, meshes, wound closure, implant, and the like. These devices may be formed of one or more polymers, and in addition may comprise an agent(s) mixed therein.

In another embodiment, these devices may be made of another material, such as metal, and the like, and may have one or more of their surfaces or a portion thereof covered with the polymer(s). The stent and other devices may comprise a polymer(s) comprising at least one agent(s), and the same agent(s) may also be mixed into the polymer matrix. The device, such as, e.g., a stent, may also comprise several layers of polymer(s) in accordance with the invention, which may comprise one or more agents within the backbone, and mixed in the polymer matrix. The devices of the invention may be employed for delivering an agent(s) to a specific site, such as is the case with the stent where the delivery may be to an interior surface of a vein or an artery.

The polymers, medical devices, pharmaceutical compositions and methods of treatment provided herein may be designed to reflect advantages such as, e.g., the ability to deliver a high potency or concentration of drug by weight if desired; a near "zero-order" drug release over short or long periods if desired; ease of fabrication into coatings, fibers, microspheres, pellets, etc.; little or no evidence of a "burst effect" or initial spike of drug; predictable breakdown products; multiple routes of administration; and localized delivery for improved efficacy and reduced side-effects. Furthermore, the polymers, medical devices, pharmaceutical compositions and methods of treatment provided herein may be designed such that they do not induce an inflammatory response when administered to or implanted within a host. In one embodiment, the present invention comprises the control of the onset and progression of adverse physiological conditions at a targeted site by means of a medical device or method of treatment in accordance with this invention. A directed application of pharmaceutical treatment circumvents the need for a general or systemic, i.e. "whole-body", or oral administration of the necessary therapeutic agent(s). Accordingly, such directed application of therapeutics provides faster, more targeted relief of the adverse conditions while minimizing side effects of the administration of the therapeutics.

Medical devices employed, for example, as implants, typically elicit foreign body responses characterized by thrombosis, inflammation, and infection, among others. Polymers of this invention, such as polyNSAIDs and others having anti-inflammatory and antiseptic properties, are extremely well suited for these applications. Other types of polymers described herein are well suited to impart properties such as biological, pharmaceutical, therapeutic or diagnostic properties.

The polymers of this patent have a broad range of fracture toughness, as measured in ksi (or 1000 psi), or times the square root of an inch. Generally, the fracture toughness values for the polymers of the invention fall in the range of about 0.2, 0.4, 0.5 ksi to about 0.6, 0.8, 0.9, 1.0, 1.2 ksi. Higher and lower ksi values, are also attainable. The polymers of the invention are suitable for releasing the contained agent(s) for a broad period of time, including, but not limited to, 1-2 hours, 12 hours, 24 hours, 2 days, 8 days, 2 weeks, 4 weeks, 3 months, 6 months to about 8 months, 12 months, 15 months, 18 months, 2 years, and even longer periods of time in specific applications that are specifically tailored for such a purpose.

In another embodiment, a medical device may be coated with a co-polymer comprising two or more monomers, each of them independently comprising a different linker group(s) and a different agent(s) or compound(s). In another embodiment, the medical device may be coated with a therapeutic polymer composition comprising at least two independent polymers that may be mixed after polymerization. In yet another embodiment a device, e.g. an implantable stent, is formed of or coated with one or more polymers in accordance with the invention. The device or stent may be made of any suitable material, including, e.g., many materials well known in the art, including electropolished 316L stainless steel, other metallic alloys, and/or polymeric materials. In one embodiment, the polymer coating exhibits 1) adequate wettability and adhesiveness to the surface of the stent to be coated, 2) adequate flexibility when crimped onto a balloon catheter, maneuvered into position, and then expanded in position in the body, 3) adequate hardness to avoid premature removal of the coating or its portions, pitting, or damage to the coating during implantation and thereafter such as may occur from handling, flow of body fluids such as blood, or organ, or recipient's body movement, and/or 4) appropriate rates of degradation that enable maintenance of the agent(s) or compound(s) levels for predictable lengths of time without causing local or systemic toxicity. Such a device may be used as a coronary, renal, or biliary stent, among other applications, and it may comprise a coating(s) of a thickness of about 100 nm, 1 µm to about 30 µm, 100 µm, and values therebetween and outside of this range as needed. Typically, devices, e.g., stents, for use in other medical or veterinary applications, coatings or sets of coatings preferably have a thickness less than about 100 µm.

One preferred rate of drug delivery may be achieved by using multiple layers of polymer. In some cases different concentrations of the same admixed drug may be used in each layer or different copolymers having different rates of drug generation and/or polymers with different breakdown rates for release of admixed drugs or agents may be used in each layer, thereby achieving a predictable and repeatable timing of delivery of one or more bioactive agents. Such layering effects may be enhanced by a combination of layers of inert polymer and/or layers with inert polymer with admixed drug or agents and/or layers with therapeutic polymers and admixed drugs or agents and/or layers with only therapeutic polymers. In an exemplary embodiment, an outer coating that would provide an initially high dose of anti-inflammatory agent that is followed by the release or generation of an anti-proliferative agent from underlying layers. In one embodiment, a medical device is coated with more than one layer of polymer, where at least one layer is the therapeutic polymer of the invention. The polymers include but are not limited to "inert" polymers that do not breakdown or breakdown into non-therapeutic agents. One or more coatings or layers of an inert or therapeutic polymers may be used to advantage with the therapeutic polymers of the invention to regulate the release of active agents released from or generated by therapeutic polymer underlying the coating or layer of polymer. In more preferred embodiments, the active agent(s) is predictably and repeated released over time. For example, the active agent may be released from the set of coatings at a steadily increasing or decreasing rate, or at a nearly constant rate over time. In other more preferred embodiments, the outer layer(s) of polymer slow or prevent the penetration of water and/or enzymes to the inner layer(s) of therapeutic polymer. These embodiments are useful to lengthen the shelf-life of the medical device, and/or to regulate the release or generation of the active agent in underlying layers. In most preferred embodiments, the layer(s) of therapeutic polymer on the medical device are further coated with a layer of polymer which is polylactic acid, a polymerized form of amino acids, a polymerized form of fatty acid metabolites, and derivatives and/or combinations of any of these. Both types of polymers have been made with several different linker molecules that modulate their physical properties and NSAID generation profiles. Table 7 and Table 8 below provide various examples.

TABLE 7

Coating Hardness of Salicylic Acid Polymer on Stainless Steel

| | Polymer | | | | |
|---|---|---|---|---|---|
| Conditions | 510PL | 261PL | 749PL | 125PL | 510PL + 14% Paclitaxel |
| | | | Hardness* | | |
| Ambient | F | B | 3B | 4B | F |
| 65 min 37° C. Saline, pH 7.4 | F | B | 9B | <9B | F |

*Hardness measured in the ASTM test for pencil hardness.
Rating 2H, –H, –F, –HB, –B, –2B, –3B, –4B, –5B, –6B, –7B, –8B, –9B
Harder <----------------------------------------------> Softer

TABLE 8

Straight-Chain Dicarboxylic Acid Linkers

| Linker | Chemical Formula | Comments |
|---|---|---|
| Succinic Acid | $HO_2C(CH_2)_2CO_2H$ | Rat Oral $LD_{50}$ = 8,530 mg/kg |
| Adipic Acid | $HO_2C(CH_2)_4CO_2H$ | Rat Oral $LD_{50}$ = 5,050 mg/kg |
| Suberic Acid | $HO_2C(CH_2)_6CO_2H$ | |
| Sebacic Acid | $HO_2C(CH_2)_8CO_2H$ | Rat Oral $LD_{50}$ = 14,470 mg/kg |
| Dodecanoic Acid | $HO_2C(CH_2)_{10}CO_2H$ | Marketed as dietary supplement |
| Tetradecanoic Acid | $HO_2C(CH_2)_{12}CO_2H$ | In Foods (e.g., butter) |
| Hexanedecanoic Acid | $HO_2C(CH_2)_{14}CO_2H$ | — |

All of these molecules are produced enzymatically by fatty acid synthase and are routinely present in the body (and in foods) in varying amounts. Available data indicate that they are highly non-toxic after oral administration. In fact, one form is currently being marketed in the U.S. as a dietary supplement. While many effects of these molecules administered directly to tissues are not fully known, they are likely to be innocuous. As noted above one of these molecules, sebacic acid, was approved by the FDA as a linker in a wafer for insertion into brain tissue (GLIADEL®, Guilford Pharmaceuticals).

In another preferred embodiment, the medical device comprises an orthopedic implant such as a hip, knee, and shoulder implant, and internal and external fixation devices and spinal implants. These orthopedic devices may be made of many kinds of materials well known in the art such as electropolished 316L stainless steel, other metallic alloys, inorganic ceramics such as calcium phosphate and/or hydroxyapatite, human and animal cadaveric bone, naturally-occurring and synthetic bone analogs, degradable and non-degradable polymers such as glycolic acid, lactic acid and/or caprolactone polymers and their co-polymers with other agents and/or their blends. The orthopedic implants may be coated with a polymer of the invention that preferably exhibits the characteristics listed above for implantable devices such as stents. In one embodiment, a polymer coating or film comprises an about 1 μm to about 1 mm thickness. Some entirely porous implants may benefit from a longer lasting effect that is enabled by a coating that fills the device's interstices with a thin coating on areas proximal to a target bone or tissue. In some cases it may be preferable to employ a nano- and/or micro-sphere formulation of a diameter typically less than about 10 μm for in situ administration or application, or for application to the surface of a device before placement. A sterile liquid may be used to coat the device to foster adherence of the nano- or micro-spheres for minutes to weeks to enable uncoated devices to act as coated devices do.

(i) Polymer Adhesion to Metal and Non-Metal Surfaces

The metallic components of many implantable orthopedic devices can be made of various alloys, such as nickel-titanium and cobalt-chromium. The adhesion load displacement profile of polymers in accordance to this invention, e.g., polyDF, on these metals at ambient temperature, were measured by testing polymers that were melt-coated directly onto clean, dry 1.25 metal butt-joints.

On one type of satin-finish titanium alloy, polyDF exhibited a load failure of 2,030 PSI. Testing of the polymer on a cobalt-chromium alloy was interrupted at 1,630 PSI when the metal grip pins used to hold the meal test cylinder broke. These results demonstrate that polyDF adheres to these metals as tightly as commonly used epoxies and glues. ASTM test methods were used to demonstrate the strong adhesion of polymers of the invention such as polySA and polyDF to electro-polished 316L stainless steel, i.e., the metal used for coronary vascular stents. This property is in sharp contrast to other polymers, many of which adhere to metals only after special treatment of the metal surfaces.

In general, the polymers of the invention exhibit excellent adhesion to non-metallic surfaces, including polymers such as biopolymers, polyanhydrides and other biocompatible and non-biocompatible polymers, nickel alloys, PMMA based materials, and the like. The polymers of this patent may be employed in conjunction and for covering and adhering to any material suitable for use in the applications mentioned here. The polymers of this invention achieve a broad range of cohesive failure values as measured by a 1.1" Butt Weld test. Generally, cohesive values of about 100, 200, 300, 400, 600, 700, 1000 to about 1500, 2000, 2500, 3000 psi are easily attained. The lower value represents minimal adhesion whereas the higher value represents cohesive failure of the polymer. Much broader range values are consistently achieved on surfaces such as titanium alloys, stainless steel, cobalt alloys, and chromium alloys.

(ii) Polymer Biodegradation

The degradation of polymers of the invention, such as polySA and polyDF, was tested with polymers coated onto samples of electro-polished 316L stainless steel. The polymers were dissolved in anhydrous chloroform and spread into thin films onto dry metal surfaces that had been cleaned with acetone, after which the solvent was removed overnight in a 40° C. vacuum oven. A 5 μm layer of polySA incubated in pH 7.4 PBS at 37° C. generated salicylic acid for about one week as shown in Table 9a below.

TABLE 9a

Erosion of PolySA (261PL) and PolyDF (657PL): Generation of NSAID into 37° C. pH 7.4 PBS from '5 um-thick Coatings on 316 SS Plates

| | Cumulative drug release 0 | |
|---|---|---|
| Time (Days) | Salicylic Acid - 261PL | Diflunisal - 657PL |
| 0 | — | 0.0 |
| 1 | 0.0 | 0.0 |
| 2 | 16.0 | 0.8 |
| 3 | 40.0 | 3.2 |
| 5 | 69.4 | 11.7 |
| 8 | 73.3 | 25.4 |
| 11 | 77.9 | 39.2 |
| 14 | 78.7 | 47.9 |
| 17 | | 54.7 |
| 20 | | 58.5 |
| 25 | | 71.4 |
| 32 | | 71.9 |
| 62 | | 97.8 |
| 74 | | 103.1 |

While not apparent from the Table, it should be noted that polySA did not begin to degrade until 8-10 hours after exposure to buffer or serum. This "induction period" is characteristic of poly(anhydride-ester) polymers; in general, the higher the molecular weight, the longer the induction time. In contrast, a similar 5 μm layer of polyDF generated diflunisal for a period of time of over 2 months. The results are shown in Table 9b below.

TABLE 9b

Effect of MW on Erosion: Generation of Diflunisal from 657PL into 37° C. Serum from Coatings on 316L SS Plates

| | Cumulative Diflunisal Generated (μg/cm$^2$) | |
|---|---|---|
| Time (days) | 33K - 9 μm thick coating | 100K - 22 μm thick coating |
| 0.17 | 0.00 | 0.00 |
| 0.33 | 3.90 | 0.00 |
| 1 | 41.73 | 7.14 |
| 3 | 471.55 | 101.55 |
| 5 | 751.92 | 267.76 |
| 7 | 753.74 | 346.20 |
| 13 | 959.21 | 658.26 |
| 19 | 814.59 | 756.35 |
| 25 | 731.07 | 796.82 |
| 34 | 835.77 | 945.26 |

Kinetic analysis of the results shown in Table 9b above evidence that the generation of salicylic acid from polySA proceeded in a sharply bi-phasic, non-linear rate, while the generation of diflunisal from polyDF was mono-phasic and linear. This high molecular-weight polymer has an induction time of 15-18 hours. These different kinetic profiles may be partly explained by the different degradation mechanisms of polySA versus polyDF. So-called "bulk eroding" polymers degrade throughout their structure, like a limp of sugar in water. Because essentially the whole polymer mass is available for degradation, the greater the amount of a bulk eroding polymer, the more breakdown product generated over time. This is exactly the case with polySA; when solid disks of this polymer were incubated in 37° C. PBS, the thicker disks generated more salicylic acid, as shown in Table 9c below.

TABLE 9c

Elution of 261PL, melt polymer on wafer of 6.7 mm diameter with different thickness of coating, in PBS at 37° C.

| Elapsed Time | Cumulative SA Generated (μg/cm$^2$) | | |
|---|---|---|---|
| (days) | 0.1 mm coating | 0.2 mm coating | 0.8 mm coating |
| 0 | 0.00 | 0.00 | 0.00 |
| 1 | 644.83 | 0.00 | 1563.63 |
| 4 | 2644.67 | 3415.78 | 14349.41 |
| 7 | 3338.06 | 5989.35 | 18160.02 |
| 11 | 3721.91 | 8698.98 | 20373.20 |
| 15 | 3646.73 | 9222.90 | 20968.46 |
| 20 | 3655.84 | 9041.59 | 19183.40 |
| 22 | 3632.68 | 8892.61 | 19024.90 |

"Surface-eroding" polymers, on the other hand, degrade only from their surface, like a bar of soap. Since only the polymer surface is available for degradation, the generation or breakdown products over time generally does not vary with polymer mass. This is the case with polyDF; when disks of this polymer were incubated in 37° C. PBS, the same amount of diflunisal was generated regardless of disk thickness. The surface eroding property of polyDF makes it ideal for use as coatings in settings where a constant, controlled rate of drug delivery is desired. This property of polyDF enabled an evaluation of the effect of polymer molecular weight on the generation of diflunisal. Two preparations of polyDF (molecular weights 33K and 100K) produced by the melt-condensation method were solvent coated onto electro-polished stainless steel samples and incubated in 37° C. serum, which contains esterase enzymes that might be expected to contribute to polymer degradation in the body. As shown in Table 9c, the 33,000 Dalton polymer degraded much more rapidly than the 100,000 Dalton polymer, which, in PBS, generated diflunisal for about two months.

The molecular profile of the products of polymer degradation that may be generated over a period of time is another important characteristic of biodegradable polymers. Polymers that biodegrade consistently into a small number of breakdown products generally have good biocompatibility, and will encounter fewer regulatory hurdles.

In the case of polySA, the HPLC chromatograms showed only breakdown products that contained salicylic acid with the linker itself not being observed. After two days, the main breakdown product in serum was salicylic acid, which exhibited a 2-minute elution time. Also observed were minor amounts of the monomer and several oligomers. By day three, the elution profile indicated increasing amounts of salicylic acid, with smaller amounts of monomer and oligomers. After seven days, only salicylic acid and one other compound were apparent, and by day 13, only salicylic acid was observed. The pattern of soluble breakdown products generated during the degradation of polyDF in 37° C. serum was less complex, consisting of diflunisal itself with a 7-minute elution time, with no other breakdown products observed in serum up to two days, and at every point thereafter.

B. Biodegradation of Polymers Containing Admixed Drugs

For many medical device applications it may be desirable to use polymers in accordance with this invention, e.g. polyN-SAIDs, in combination with other drugs added to the polymers to produce additional therapeutic effects. Such "solid solution" preparations may be created by simply mixing a polymer dissolved in a solvent with a solution of another drug dissolved in the same solvent, or by any other method known in the art. Evaporation of the solvent results in a homogeneous solid solution of drug in polymer. The usefulness of the invention's polymers in medical devices, such as drug-eluting coronary stents and others, led the inventors to prepare and evaluate solid solutions of, for example polyDF containing 20 wt % paclitaxel or sirolimus, i.e., 1 mg of polymer/drug admixture contained 0.8 mg polymer and 0.2 mg drug. Table 11 below shows the concurrent release of paclitaxel from a polyDF/paclitaxel admixture coated onto electropolished stainless steel samples and incubated in 37° C. serum. Paclitaxel was released at the same rate at which the polymer biodegraded to generate diflunisal (the relatively small percentage of paclitaxel released reflects the inability of serum to hold this very poorly water-soluble drug). The incorporation of paclitaxel into the polymer did not affect the generation of diflunisal, which proceeded at the same rate as from polyDF without paclitaxel. Similar results were obtained with a polyDF/sirolimus admixture.

C. Effect of Sterilization by Various Methods

All implantable and percutaneous medical devices must be sterilized before or after packaging. Sterilization methods commonly employed are gamma irradiation, electron beam ("E-beam"), and ethylene oxide. Sterilization by gamma radiation penetrates objects deeply, and is used for food and many medical device products, but the method requires relatively prolonged exposure times. E-beam sterilization allows shorter exposure times, but the electrons penetrate objects poorly, making the procedure useful mainly for surfaces. Ethylene oxide sterilization is more complex and more aggressive on organic materials than the other methods and is being replaced where possible due to environmental hazards. The relatively high temperatures and humidity employed in many ethylene oxide sterilization protocols is not very compatible with poly(anhydride-ester) polymers. Accordingly, gamma radiation and E-beam sterilization methods are preferred for use with such compositions. The sterilization with E-beam (3.5 mRad) and gamma radiation (25-35 Kgys) had no effect on the pattern of diflunisal generated from polyDF coated stainless steel samples incubated in 37° C. serum. Notwithstanding the lack of effect on polymer degradation, sterilization does produce some changes in molecular weight and mechanical properties. For example, the tensile modulus of melt-polymerized polySA at room temperature decreased by about a third after gamma sterilization (25-35 Kgys), but there was no change at 37° C. Gamma radiation had no effect on the molecular weight, flexibility, or adhesiveness of the polymers of the invention, such as polySA and poly DF, and only minor effects on hardness.

D. Polymer Coatings for Stents and Grafts

The example provided by the remarkable effectiveness of drug-coated stents in reducing the incidence of coronary arterial restenosis represents at the same time a breakthrough in the treatment of vascular disease, and provides a model for other applications of the present invention. Most leading stents under development are based on the sustained delivery of anti-proliferative and/or immunosuppressive drugs like paclitaxel and sirolimus. These drugs were selected because of their ability to reduce the over-growth of smooth muscle cells that occurs after insertion of stents into the arterial wall.

Stents are inserted, and then over-expanded into the arterial wall so that they will remain lodged in place. This produces a "wound" that rapidly leads to fibrin clot formation that walls off the damaged area, a process called thrombus deposition. At the same time, inflammation induces immune system cells to migrate into the area in order to engulf and destroy damaged cells in a classic response to a foreign body. This causes smooth muscle cells to overproliferate in the damaged area, which leads to abnormal tissue remodeling, also called restenosis. While the use of anti-proliferative drugs is a rational strategy to reduce restenosis, the overproliferation of arterial smooth muscle cells is thought to be a direct consequence of inflammation. The sustained delivery of drugs as disclosed herein, e.g. anti-inflammatory and other drugs, into the damaged area does itself prevent or substantially reduce the development of restenosis.

TABLE 10

Salicylic (261PL) & Diflunisal (657PL) Polymers Polymer

|  | 261PL | 657PL | |
|---|---|---|---|
| Hardness | | | |
| Ambient | B | F | 3H |
| 5 mn PBS 37° C. | B | 2B | B |
| 1 hr PBS 37° C. | — | 8B | 4B |
| Flexibility | | | |
| Ambient | <3 mm | <3 mm | |
| 5 min PBS 37° C. | <3 mm | <3 mm | |
| 1 hr PBS 37° C. | — | <3 mm | |
| Adhesion | | | |
| Ambient | 5B | 5B | 5B |

Table 10 above shows the properties of the stents that were coated with a 55 μm thick salicylic acid polymer coating (1 mg polySA), were subjected to E-beam sterilization, expanded via a balloon catheter, and soaked in serum 37° C. for 2 hours. Similar results were obtained with a diflunisal polymer (polyDF). Polymer-coated stents, such as these polyNSAID-coated stents, were implanted into the iliac arteries of rabbits employing uncoated stents as controls. The characteristics of the coatings employed are shown in Table 11 below.

TABLE 11

Coating Hardness, Flexibility & Adhesion of Diflunisal (261PL) Polymer Alone & Admixed with Paclitaxel

| | Diflunisal Polymer (657PL) | |
|---|---|---|
| | Polymer Alone | Polymer + % PAC |
| Hardness | | |
| Ambient | F | F |
| 5 Min in PBS, 37° C. | 2B | F |
| 1 Hr in PBS, 37° C.+ | 8B | 6B |
| Flexibility | | |
| Ambient | <3 mm | <3 mm |
| 5 Min in PBS, 37° C. | <3 mm | <3 mm |
| 1 Hr in PBS, 37° C. | <3 mm | <3 mm |
| Adhesion | | |
| Ambient Temp. | 5B | 5B |

Histological arterial sections collected seven days post-implantation of Salicylic Acid polymer-(polySA-) coated stents revealed no evidence of thrombosis or inflammation when compared to controls. In vitro poly-SA bulk eroded within about one week.

As in the case of polysalicylic acid, rabbit iliac arterial sections collected seven days after implantation of polydiflunisal-(polyDF-) coated stents revealed no thrombosis or inflammation as demonstrated in Table 12a.

TABLE 12a

Paclitaxel Release from Polymer Alone & Admixed with Paclitaxel

| Time Elapsed (Days) | Cumulative Drug Released (%) | | |
|---|---|---|---|
| | 0% PAC in Coating | 20% PAC in Coating | |
| | DF* | DF* | PAC+ |
| 0 | 0.00 | 0.00 | 0.00 |
| 3 | 40.22 | 17.28 | 0.72 |
| 5 | 45.00 | 48.72 | 2.48 |
| 7 | 49.41 | 58.35 | 3.87 |
| 10 | 61.88 | 58.76 | 4.09 |
| 12 | 79.51 | 78.94 | 4.31 |
| 14 | 68.88 | 68.87 | 5.42 |
| 20 | 76.13 | 74.82 | 6.24 |
| 26 | 69.04 | 67.11 | 5.69 |

*Diflunisal Release from DF Polymer into 37° C. Serum from 5 μm-thick Coatings on 316 SS Plates.
+Paclitaxel Release from Admixture with DF Polymer into 37° C. Serum from 5 μm-thick Coatings on 316 SS Plates.

TABLE 12b

Cumulative Diflunisal Released by Untreated & Sterilized Polymer

| Time Elapsed (days) | Cumulative Diflunisal* Released from 657PL Polymer (%) | | |
|---|---|---|---|
| | Not Irradiated | Gamma Irradiated | E-Beam Irradiated |
| 1 | 0.39 | 0.57 | 1.12 |
| 2 | — | 4.02 | 4.81 |
| 3 | 5.47 | — | — |
| 5 | 14.47 | — | — |
| 7 | 18.50 | 28.25 | 27.87 |
| 9 | — | 30.05 | 28.02 |
| 13 | 34.87 | 34.74 | 32.84 |
| 17 | — | 29.23 | 36.58 |
| 19 | 39.85 | — | — |
| 20 | — | 44.06 | 41.84 |
| 25 | 42.00 | — | — |
| 26 | — | 50.38 | 44.07 |
| 34 | 49.89 | — | — |

*Released by 5 μm Diflunisal Polymer Coated on 316LSS Plates & Placed in Serum at 37 C.

In contrast to the results obtained with polySA, these arterial sections clearly reveal the presence of the polyDF coating. In vitro tests evidenced that the latter will last at least one month. The effect of polySA-coated stents also were evaluated at 28 days post implantation, and were found to be indistinguishable from uncoated controls, most likely due to prior polymer depletion. Arterial sections from polyDF-coated stents revealed that the polymer was still present after 28 days, but evidenced only very mild inflammation (figure not shown). In a follow-up study, pig coronary arteries were implanted with stents coated with 1 mg polyDF alone, with polyDF containing 200 μg paclitaxel and with polyDF containing 200 μg sirolimus. After 28 days, the arteries receiving stents coated with polyDF alone showed considerably less fibrin deposition, hemorrhage, and inflammation than those treated with polyDF plus sirolimus or paclitaxel. These results are applicable also to polyNSAID coatings for self-expanding nitinol stents and grafts for non-coronary applications, e.g., endovascular applications, and are in marked contrast to the non-degradable, inflammation-generating polymers currently used for drug-coated stents. Results from 28-day and 90-day pig studies demonstrate that polyNSAIDs are biocompatible, biodegradable, anti-inflammatory materials effective for coronary stents, and to deliver drugs of interest.

Comparative studies were conducted on the characteristics of salicylic acid and diflunisal polymers before and after sterilization by various methods commonly employed in the art. A comparison of the results obtained is provided in Table 12c and Table 12d below.

TABLE 12c

Changes Produced by γ-Irradiation of Salicylic Acid (261PL) & Diflunisal (657PL) Polymer

| Property | 261PL | 657PL |
|---|---|---|
| Molecular Weight (Non Irradiated) | about 20,000 | about 100,000 |
| Molecular Weight (Irradiated) | about 20,000 (N.C.) | about 50,000 |
| Hardness | −2 Units | −3 Units |
| Flexibility | N.C. | — |
| Adhesion | N.C. | — |

N.C. No Change.

TABLE 12d

Changes Produced by E-Beam-Irradiation* of Salicylic Acid (261PL) & Diflunisal (657PL) Polymer

| Property | Polymer | | |
|---|---|---|---|
| | 261PL | 261PL | 657PL |
| | 261PL | 657PL | |
| Molecular Weight (Non Irradiated) | about 20,000 | about 33,000 | about 80,000 |
| Molecular Weight (Irradiated) | −26% | +5% | −30% |
| Hardness | −1 Unit | +2 Units | N.C. |
| Flexibility | N.C. | — | N.C. |
| Adhesion | −1 Unit | — | — |

*3-4.5 MRad E-Beam Radiation.
N.C. No Change.

Some characteristics of polyNSAIDs and prior art polymer coatings currently used on drug-eluting stents are provided in Table 13 below.

TABLE 13

PolyNSAIDs vs. Current Polymer Stent Coatings

| Property | PolyNSAID Coatings | Current Polymer Coatings |
|---|---|---|
| Biodegradable | Yes | No |
| Pharmacological Activity | Yes | No |
| Inflammation | Little/None | Significant |
| Additional Agent | OK | NOT OK |
| Application to metal | Easy | Complex |

The ability of the polymers of this invention, e.g. polyNSAIDs and others, to adhere strongly to metal, e.g. stainless steel, without need for glues or other surface treatments provides an important advantage over other available stents, and eliminates the need for treating the metal surface prior to affixing a drug-eluting polymer, and/or for an additional layer with another polymer coating to prolong drug release and prevent a "burst effect".

E. Polymer Coatings for Implanted Orthopedic Joint-Replacement/Aid Devices

Joint-replacement implants and bone aid devices are widely used to restore quality of life for million of patients with irreparably damaged shoulders, knees, and hips as well as for repairing broken and splintered bones. These devices are generally made of titanium/nickel or cobalt/chromium alloys, with metal stems that are inserted into the hollow portion of the arm or leg bones. Some of these stems have smooth surfaces that require the use of bone cement to ensure strong connection, while others have highly engineered, honeycomb-textured surfaces that become partially filled with bone and marrow cells during insertion, thereby seeding the stem for in growth of new bone and reducing the need for cement. Orthopedic surgeons are eager to incorporate agents into these surfaces that may accelerate bond growth. A number of recombinant bone morphogenic proteins (BMPs) and other "osteogenic" proteins are in development for this purpose, notwithstanding their high manufacturing costs and product development challenges.

The dynamics of bone formation, resorption, and repair are complex, and appear to vary for different types of bone. Dental studies showed that the inhibition of prostaglandin production by NSAIDs decreases bone resorption in the trabecular bone of the palate and alveolar bone of the jaw, causing a net increase in bond mass and density. This phenomenon was demonstrated in the mouse for "PolyAspirin" implants). In addition, polySA prevented bone erosion in a rat femur transaction model. Other animal studies suggest that the repair of long-bone fractures may be inhibited by long-term exposure to high levels of NSAIDs.

Different forms of the present polymers may be prepared that are suitable for these and other applications in the orthopedics and dental fields, among others. Polymers of this invention, such as polyNSAIDs and others, may be employed as coatings to reduce pain and inflammation associated with device implantation and adjustment of dental and orthopedic aids, to reduce the incidence of infection, which is a major problem associated with joint replacement devices, and to prevent and treat other conditions by delivering appropriate agents to the site. While infection at the implant/bone interface reportedly occurs in less than 1% of cases, the limited blood supply to the region makes these infections particularly hard to treat with systemic antibiotics. The antiseptic properties of a polymer of the invention, such as a polyNSAID, a polyantibiotic, a combination or mixture thereof, in a coating prevents or greatly reduces infection without the potential for bacterial resistance. Together with the properties of polymers such as polyNSAIDs summarized in Table 4, this characteristic makes PolyNSAIDs attractive for use on orthopedic, dental, ocular, and many other implanted medical devices.

Medical devices useful with coverings of the present invention include, but are not limited to, a fixation device, catheters, drain tubes, intravenous tubes, tampon applicators, ventilator tubes, endoscopes, syringes, arthroscopes, IUDs and other drug-based contraceptive implants and patches of all sorts for drug delivery, e.g. hormones, nicotine, and other patches, needles, condoms, barrier devices, monitoring and diagnostic devices such as a speculum, dental appliances, and surgical appliances. The polymers, compounds and/or compositions of the invention may be formed into a medical implant such as a medical, dental, orthopedic and surgical implant, or applied or coated onto such implant. In addition to the implants described above, other examples are implants for vascular, cardiovascular, coronary, peripheral vascular, orthopedic, dental, oro-maxillary, gastrointestinal, urogenital, ophthalmic, gynecological, pulmonary, surgical, physiological, metabolic, neurological, diagnostic and therapeutic uses, may be formed from or applied or coated with the above identified polymers, compounds and/or compositions. Such implants include, but are not limited to, stents, catheters, balloons, guidewires, grafts, sutures, meshes, joint prostheses, breast prostheses, fracture management devices, drug dosing devices, pacemakers, mechanical pumps, dental implants (e.g., dental, oro-maxillary, and alveolar), defibrillators, and filters.

Suitable medical implants also include, but are not limited to the ones described here. 1) Boston Scientific (Boston Scientific Corporation, Natick, Mass.) products Polaris™, NIR® Elite OTW Stent System, NIR® Elite Monorail™ Stent System, Magic WALLSTENT® Stent System, Radius® Self Expanding Stent, NIR® Biliary Stent System, NIROYAL™ Biliary Stent System, WALLGRAFT® Endoprosthesis, WALLSTENT® Endoprosthesis, RX Plastic Biliary Stents, UroMax Ultra™ High Pressure Balloon Catheter, Passport™ Balloon on a Wire Catheter, Excelsior™ 1018™ Microcatheter, Spinnaker® Elite™ Flow-Directed Microcatheter, Guider Softip™ XF Guide Catheters, Sentry™ Balloon Catheters, Flexima™ APD™ Drainage Catheters with Twist Loc™ Hub, Vaxcel™ Chronic Dialysis Catheter, PASV® PICC Peripherally Inserted Central Catheters, Chilli® Cooled Ablation Catheters, and Constellation® Catheters. 2) Cordis (Cordis, a Johnson & Johnson Company, Piscataway N.J.) products: BX Velocity™ Coronary Stents, Ninja FX™ Balloon Catheters, Raptor™ Balloon Catheters, NC Raptor™ Balloon Catheters, Predator™ Balloon Catheters, Titan Mega™ Balloon Catheters, Checkmate™ Brachytherapy Catheters, Infiniti™ Diagnostic Catheters, Cinemayre™ Diagnostic Catheters, SuperTorque Plus™ Diagnostic Catheters, and High Flow™ Diagnostic Catheters. 3) Medtronics (Medtronics, Inc., Minneapolis, Minn.) products: Aneurx Stentgraft, S7 Coronary Stents, S670 Coronary Stents, S660 Coronary Stents, BeStent 2 Coronary Stents, D1 Balloon Catheters, and D2 Balloon Catheters. 4) Avantec Vascular (Avantec Vascular, San Jose, Calif.) products: Duraflex™ Coronary Stent System, and Apollo™ Coronary Dilatation Catheter. 5) B. Braun (B. Braun Medical Ltd., Sheffield, England) products: Coroflex™ Coronary Stent, Cystofix™ Urogenital Catheters, and Urecath™ Urogenital Catheters. 6) Cook (Cook Group Inc., Bloomington, Ind.) products: V-Flex Plus™ Coronary Stent, and CR II® Coronary Stent. 7) Guidant (Guidant Corporation, Indianapolis, Ind.) products: Multilink Penta™ Coronary Stents, Multilink Pixel™ Coronary Stents, Multilink Ultra™ Coronary Stents, Multilink Tetra™ Coronary Stents, Multilink Tristar™ Coronary Stents, Ancure™ Stentgraft, Dynalink™ Biliary Stents, Rx Herculink™ Biliary Stents, Omnilink™ Biliary Stents, Megalink™ Biliary Stents, Rx Crosssail™ Balloon Dilatation Catheters, Rx Pauersail™ Balloon Dilatation Catheters, OTW Opensail™ Balloon Dilatation Catheters, OTW Highsail™ Balloon Dilatation Catheters, Rx Esprit™ Balloon Dilatation Catheters, Rx Viatrac™ Peripheral Catheters, and OTW Viatrac™ Peripheral Catheters. 8) Ethicon (Ethicon, a Johnson & Johnson Company, Piscataway, N.J.) products: Vicryl™ (resorbable braided coated), Pronova™, and Panacryl™. 9) USS/DG Sutures (U.S. Surgical, a division of Tyco Healthcare Group LP, Norwalk, Conn.) products: Decon II™ (coated, braided synthetic, absorbable), PolySorb™ (coated, braided synthetic, absorbable), Dexon S™ (Uncoated, braided synthetic, absorbable), Gut sutures (absorbable), Biosyn™ (synthetic monofilament, absorbable), Maxon™ (synthetic monofilament, absorbable), Surgilon™ (braided nylon, non-absorbable), Ti-Cron™ (coated, braided polyester, non-absorbable), Surgidac™ (coated, braided polyester, non-absorbable), SofSilk™ (coated, braided silk, non-absorbable), Dermalon™ (nylon monofilament, non-absorbable), Monosof™ (nylon monofilament, non-absorbable), Novafil™ (polybutester monofilament, non-absorbable), Vascufil™ (coated polybutester monofilament, non-absorbable), Surgilene™ (polypropylene monofilament, non-absorbable), Surgipro™ (polypropylene monofilament, non-absorbable), Flexon™ (stainless steel monofilament, non-absorbable), SURGALLOY™ needle, and SURGALLOY™ OptiVis™ needle. 10) Surgical Dynamics (Surgical Dynamics, Inc., North Haven, Conn.,) products: S*D*Sorb™ (suture anchor, Anchor Sew™ (suture anchor), S*D*Sorb E-Z Tac™ (bio-resorbable implant w/o sutures), S*D*Sorb Meniscal Stapler™ (delivers bio-absorbable repair implant), Ray Threaded Fusion Cage™ (spine), Aline™ (cervical plating system), SecureStrand™ (spinal reconstruction cable), and Spiral Radius 90D™ (spinal rod system). 11) Zimmer (Zimmer, Warsaw, Ind.) products: VerSys™ cemented stem hip system, VerSys Heritage™ Hip cemented stem hip system, VerSyS™ LD/Fx cemented stem hip system, CPT™ Hip cemented stem hip system, VerSys™ Cemented Revision/Calcar cemented stem hip system, Mayo™ Hip porous stem hip system, VerSys™ Beaded MidCoat porous stem hip system, VerSys™ Beaded FullCoat Plus porous stem hip system, VerSys™ Fiber Metal MidCoat porous stem hip system, and VerSys™ Fiber Metal Taper porous stem hip system, VerSys™ LD/Fx press-fit hip system, VerSys™ Cemented Revision/Calcar revision stem hip system, ZMR™ hip revision stem hip system, Trilogy™ Cup acetabular cup hip system, ZCA™ cup acetabular cup hip system, Longevity™ polyethylene hip system, Calcicoat™ coating hip system, NexGen™ Implant knee system, NexGen™ Instruments knee system, NexGen™ Revision Instruments knee system, IM™ Instruments knee system, MICRO-MILL™ 5-in-1 Instruments knee system, Multi-Reference™ 4-in-1 knee system, V-STAT™ Instruments knee system, Coonrad/Morrey™ elbow, Bigliani/Flatow™ shoulder, Cable Ready™ Cable Grip System, Collagraft™ Bone Graft Matrix, Herbert™ Bone Screw, M/DN™ Intramedullary Fixation, Mini Magna-Fx™ Screw Fixation, Magna-FX™ Screw Fixation, Periarticular™ Plating System, Versa-Fx™ Femoral Fixation system, Versa-Fix II™ Femoral Fixation System, and Trabecular™ Metal. 12) Alza technologies (ALZA Corporation, Mountain View, Calif.) products: DUROS® Implant, OROS™ osmotic, D-TRANS™ transdermal, STEALTH™ liposomal, E-TRANS™ electrotransport, Macroflux™, and ALZAMER depot. 13) described in Stuart, M., "Technology Strategies, Stent and Deliver," *Start-Up, Windhover's Review of Emerging Medical Ventures*, pp. 34-38, June 2000); van der Giessen, Willem J., et al. "Marked Inflammatory Sequelae to Implantation of Biodegradable and Nonbiodegradable Polymers in Porcine Coronary Arteries," *Circulation*, Vol. 94, No. 7, pp. 1690-1697 (Oct. 1, 1996); Gunn, J. et al., "Stent coatings and local drug delivery," European Heart Journal 20: 1693-1700 (1999); EP Applications 01301671, 00127666, 99302918, 95308988, 95306529, 95302858, 94115691, 99933575, 94922724, 97933150, 95308988, 91309923, 91906591, and 112119841; WO 00/187372, WO 00/170295, WO 00/145862, WO 00/143743, WO 00/044357, WO 00/009672, WO 99/03517, WO 99/00071, WO 98/58680, WO 98/34669, WO 98/23244, and WO 97/49434; U.S. Ser. Nos. 061,568, 346,263, 346,975, 325,198, 797,743, 815,104, 538,301, 430,028, 306,785, and 429,459; and U.S. Pat. Nos. 6,325,825, 6,325,790, 6,322,534, 6,315,708, 6,293,959, 6,289,568, 6,273,913, 6,270,525, 6,270,521, 6,267,783, 6,267,777, 6,264,687, 6,258,116, 6,254,612, 6,245,100, 6,241,746, 6,238,409, 6,214,036, 6,210,407, 6,210,406, 6,210,362, 6,203,507, 6,198,974, 6,190,403, 6,190,393, 6,171,277, 6,171,275, 6,165,164, 6,162,243, 6,140,127, 6,134,463, 6,126,650, 6,123,699, 6,120,476, 6,120,457, 6,102,891, 6,096,012, 6,090,104, 6,068,644, 6,066,125, 6,064,905, 6,063,111, 6,063,080, 6,039,721, 6,039,699, 6,036,670, 6,033,393, 6,033,380, 6,027,473, 6,019,778, 6,017,363, 6,001,078, 5,997,570, 5,980,553, 5,971,955, 5,968,070, 5,964,757, 5,948,489, 5,948,191, 5,944,735, 5,944,691, 5,938,682, 5,938,603, 5,928,186, 5,925,301, 5,916,158, 5,911,732, 5,908,403, 5,902,282, 5,897,536, 5,897,529, 5,897,497, 5,895,406, 5,893,885, 5,891,108, 5,891,082, 5,882,347, 5,882,335, 5,879,282, RE36,104, 5,863,285, 5,853,393, 5,853,389, 5,851,464, 5,846,246, 5,846,199, 5,843,356, 5,843,076, 5,836,952, 5,836,875, 5,833,659, 5,830,189, 5,827,278, 5,824,173, 5,823,996, 5,820,613, 5,820,594, 5,811,814, 5,810,874, 5,810,785, 5,807,391, 5,807,350, 5,807,331, 5,803,083, 5,800,399, 5,797,948, 5,797,868, 5,795,322, 5,792,415, 5,792,300, 5,785,678, 5,783,227, 5,782,817, 5,782,239, 5,779,731, 5,779,730, 5,776,140, 5,772,590, 5,769,829, 5,759,179, 5,759,172, 5,746,764, 5,741,326, 5,741,324, 5,738,667, 5,736,094, 5,736,085, 5,735,831, 5,733,400, 5,733,299, 5,728,104, 5,728,079, 5,728,068, 5,720,775, 5,716,572, 5,713,876, 5,713,851, 5,713,849, 5,711,909, 5,709,653, 5,702,410, 5,700,242, 5,693,021, 5,690,645, 5,688,249, 5,683,368, 5,681,343, 5,674,198, 5,674,197, 5,669,880, 5,662,622, 5,658,263, 5,658,262, 5,653,736, 5,645,562, 5,643,279, 5,634,902, 5,632,763, 5,632,760, 5,628,313, 5,626,604, 5,626,136, 5,624,450, 5,620,649, 5,613,979, 5,613,948, 5,611,812, 5,607,422, 5,607,406, 5,601,539, 5,599,319, 5,599,310, 5,598,844, 5,593,412, 5,591,142, 5,588,961, 5,571,073, 5,569,220, 5,569,202, 5,569,199, 5,562,632, 5,562,631, 5,549,580, 5,549,119, 5,542,938, 5,538,510, 5,538,505, 5,533,969, 5,531,690, 5,520,655, 5,514,236, 5,514,108, 5,507,731, 5,507,726, 5,505,700, 5,501,341, 5,497,785, 5,497,601, 5,490,838, 5,489,270, 5,487,729, 5,480,392, 6,325,800, 6,312,404, 6,264,624, 6,238,402, 6,174,328, 6,165,127, 6,152,910, 6,146,389, 6,136,006, 6,120,454, 6,110,192, 6,096,009, 6,083,222, 6,071,308, 6,048,356, 6,042,577, 6,033,381, 6,032,061, 6,013,055, 6,010,480, 6,007,522, 5,968,092, 5,967,984, 5,957,941, 5,957,863, 5,954,740, 5,954,693, 5,938,645, 5,931,812, 5,928,247, 5,928,208, 5,921,971, 5,921,952, 5,919,164, 5,919,145, 5,868,719, 5,865,800, 5,860,974, 5,857,998, 5,843,089, 5,842,994, 5,836,951, 5,833,688, 5,827,313, 5,827,229, 5,800,391, 5,792,105, 5,766,237, 5,766,201, 5,759,175, 5,755,722, 5,755,685, 5,746,745, 5,715,832, 5,715,825, 5,704,913, 5,702,418, 5,697,906, 5,693,086, 5,693,014, 5,685,847, 5,683,448, 5,681,274, 5,665,115, 5,656,030, 5,637,086, 5,607,394, 5,599,324, 5,599,298, 5,597,377, 5,578,018, 5,562,619, 5,545,135, 5,544,660, 5,514,112, 5,512,051, 5,501,668, 5,489,271, 6,319,287, 6,287,278, 6,221,064, 6,113,613, 5,984,903, 5,910,132, 5,800,515, 5,797,878, 5,769,786, 5,630,802, 5,492,532, 5,322,518, 5,279,563, 5,213,115, 5,156,597, 5,135,525, 5,007,902, 4,994,036, 4,981,475, 4,951,686, 4,929,243, 4,917,668, 4,871,356, 6,322,582, 6,319,445, 6,309,202, 6,293,961, 6,254,616, 6,206,677, 6,205,748, 6,178,622, 6,156,056, 6,128,816, 6,120,527, 6,105,339, 6,081,981, 6,076,659, 6,058,821, 6,045,573, 6,035,916, 6,035,751, 6,029,805, 6,024,757, 6,022,360, 6,019,768, 6,015,042, 6,001,121, 5,987,855, 5,975,876, 5,970,686, 5,956,927, 5,951,587, RE36,289, 5,924,561, 5,906,273, 5,894,921, 5,891,166, 5,887,706, 5,871,502, 5,871,490, 5,855,156, 5,853,423, 5,843,574, 5,843,087, 5,833,055, 5,814,069, 5,813,303, 5,792,181, 5,788,063, 5,788,062, 5,776,150, 5,749,898, 5,732,816, 5,728,135, 5,709,067, 5,704,469, 5,695,138, 5,692,602, 5,683,416, 5,681,351, 5,675,961, 5,669,935, 5,667,155, 5,655,652, 5,628,395, 5,623,810, 5,601,185, 5,571,469, 5,555,976, 5,545,180, 5,529,175, 5,500,991, 5,495,420, 5,491,955, 5,491,954, 5,487,216, 5,487,212, 5,486,197, 5,485,668, 5,477,609, 5,473,810, 5,409,499, 5,364,410, 5,358,624, 5,344,005, 5,341,922, 5,306,280, 5,284,240, 5,271,495, 5,254,126, 5,242,458, 5,236,083, 5,234,449, 5,230,424, 5,226,535, 5,224,948, 5,213,210, 5,199,561, 5,188,636, 5,179,818, 5,178,629, 5,171,251, 5,165,217, 5,160,339, 5,147,383, 5,102,420, 5,100,433, 5,099,994, 5,089,013, 5,089,012, 5,080,667, 5,056,658, 5,052,551, 5,007,922, 4,994,074, 4,967,902, 4,961,498, 4,896,767, 4,572,363, 4,555,016, 4,549,649, 4,533,041, 4,491,218, 4,483,437, 4,424,898, 4,412,614, D260,955, 4,253,563, 4,249,656, 4,127,133, D245,069, 3,972,418, 3,963,031, 3,951,261, 3,949,756, 3,943,933, 3,942,532, 3,939,969, 6,270,518, 6,213,940, 6,203,564, 6,191,236, 6,138,440, 6,135,385, 6,074,409, 6,053,086, 6,016,905, 6,015,427, 6,011,121, 5,988,367, 5,961,538, 5,954,748, 5,948,001, 5,948,000, 5,944,739, 5,944,724, 5,939,191, 5,925,065, 5,910,148, 5,906,624, 5,904,704, 5,904,692, 5,903,966, 5,891,247, 5,891,167, 5,889,075, 5,865,836, 5,860,517, 5,851,219, 5,814,051, 5,810,852, 5,800,447, 5,782,864, 5,755,729, 5,746,311, 5,741,278, 5,725,557, 5,722,991, 5,709,694, 5,709,692, 5,707,391, 5,701,664, 5,695,879, 5,683,418, 5,669,490, 5,667,528, 5,662,682, 5,662,663, 5,649,962, 5,645,553, 5,643,628, 5,639,506, 5,615,766, 5,608,962, 5,584,860, 5,584,857, 5,573,542, 5,569,302, 5,568,746, 5,566,822, 5,566,821, 5,562,685, 5,560,477, 5,554,171, 5,549,907, 5,540,717, 5,531,763, 5,527,323, 5,520,702, 5,520,084, 5,514,159, 5,507,798, 5,507,777, 5,503,266, 5,494,620, 5,480,411, 5,480,403, 5,462,558, 5,462,543, 5,460,263, 5,456,697, 5,456,696, 5,442,896, 5,435,438, 5,425,746, 5,425,445, 5,423,859, 5,417,036, 5,411,523, 5,405,358, 5,403,345, 5,403,331, 5,394,971, 5,391,176, 5,386,908, 5,383,905, 5,383,902, 5,383,387, 5,376,101, D353,672, 5,368,599, D353,002, 5,359,831, 5,358,511, 5,354,298, 5,353,922, 5,350,373, 5,349,044, 5,335,783, 5,335,775, 5,330,442, 5,325,975, 5,318,577, 5,318,575, 5,314,433, 5,312,437, 5,310,348, 5,306,290, 5,306,289, 5,306,288, 5,294,389, 5,282,832, 5,282,533, 5,280,674, 5,279,783, 5,275,618, 5,269,807, 5,261,886, 5,261,210, 5,259,846, 5,259,845, 5,249,672, 5,246,104, 5,226,912, 5,225,485, 5,217,772, 5,217,486, 5,217,485, 5,207,679, D334,860, 5,197,597, 5,192,303, D333,401, D333,400, 5,181,923, 5,178,277, 5,174,087, 5,168,619, 5,163,946, 5,156,615, 5,154,283, 5,139,514, 5,133,738, 5,133,723, 5,131,534, 5,131,131, 5,129,511, 5,123,911, 5,121,836, 5,116,358, 5,102,418, 5,099,676, 5,092,455, 5,089,011, 5,089,010, 5,087,263, 5,084,063, 5,084,058, 5,078,730, 5,067,959, 5,059,213, 5,059,212, 5,051,107, 5,046,513, 5,046,350, 5,037,429, 5,024,322, 5,019,093, 5,002,550, 4,984,941, 4,968,315, 4,946,468, 4,932,963, 4,899,743, and 4,898,156; among many others available in the public domain, the relevant portions of all of the above listed being hereby incorporated by reference in their entireties.

Polymeric drug delivery systems comprising the polymers of the invention may be readily processed into pastes or solvent cast to yield films, coatings, nanoparticles e.g. nanospheres, microparticles e.g. microspheres and fibers with different geometric shapes for design of various medical devices, and may also be processed by compression molding and extrusion. In one embodiment, a polymer or polymers may be coated onto or applied onto a medical device, such as, e.g., by forming the polymer or polymers into a covering. In another embodiment, the polymer or polymers may be formed into a medical device, such as, e.g., an implant. In one embodiment of the present invention, a polymer comprising a functional group or active agent may used to form a covering, such as, e.g., a coating or a sheath, that partially or completely covers and/or surrounds a medical device. Such a covering may cover a portion of the medical device or it may completely cover a medical device. The covering may be divided into separate portions or several smaller coverings may be present on the medical device. In another embodiment of the invention, a polymer may surround the medical device, or a portion thereof, and may have the form of a coating, a layer, a film, and combinations thereof. The polymer may be in the form of a solid or a semi-solid, such as a gel, sheath, a wrap, a tube or a cuff covering all or a portion of the medical device. The polymer may be rigid, semi-rigid, or non-rigid. The coating of polymer may comprise about 100 nm, 1 µm to about 1 mm, 1 cm thick, although some porous implants may benefit from longer lasting effects enabled by a coating that completely fills the interstices of the device with, in some cases, a thin coating on those surfaces proximal to bone or other tissue upon placement in the body. In one embodiment, the polymer coating is comprised of microparticles, such as microspheres that may typically but not necessarily be less than 10 microns in diameter. These microparticles may be applied to the surface of a medical device before placement in the body. A sterile liquid may be used to coat the device to adhere such microspheres for minutes to weeks to enable uncoated medical devices to benefit from the same or similar therapeutic benefits as coated devices.

A polymer, compound and/or composition of the invention may be applied or coated onto a medical implant by any means known in the art including, but not limited to, solvent methods such as, for example, dipping and spray-drying, and non-solvent methods such as chemical vapor deposition, extrusion coating, covalently grafting or dipping in molten polymer, compound and/or composition of the invention. The method of preparation may vary depending on the polymer, compound and composition and/or the medical implant. The medical implant may be formed from or coated with one or more layers of the same or different polymer, compound and/or composition of the invention. In another example, a polymer, compound and/or composition of the invention may be coated onto a medical implant in the shape of a membrane or tube for use in the treatment of injury or damage to the peripheral nervous system or a block of solid or foamed composition containing pathways drilled or otherwise formed to encouraged nerve growth or bone growth. In the above instances, bioerosion of the disc, membrane, tube or block would yield or generate an active agent included within the polymer or composition. The polymer may be formed into a device by any means known in the art including, but not limited to, molding e.g. compression or blow molding, and extrusion. The medical device may be formed from one or more of the same or different polymer, compound and/or composition of the invention.

A polymer, compound and/or composition of the invention may be formed, that is, physically configured, into various shapes, geometries, structures and configurations including, but not limited to, a film, fiber, rod, coil, corkscrew, hook, cone, pellet, tablet, tube e.g. smooth or fluted, disc, membrane, microparticle, nanoparticle, "biobullet" i.e. bullet shaped, seed i.e. bullet shaped or targeted seeds, as well as those described in the above identified products, patents and articles, including in some cases forming medical implants that have the same, similar or completely different functional characteristics compared to those functional characteristics of the medical devices described in the above identified products, patents and articles. The above-mentioned shapes, geometries, structures and configurations may contain additional features that will further enhance the desired application or use. For example, a polymer, compound and/or composition of the invention in the form of a rod, coil, or cone may have barbs that spring out upon insertion from a needle or cannula or when warmed to body temperature to reduce movement and/or expulsion.

The shape, geometry, structure or configuration of a device, such as a medical implant, will vary depending upon the use of the device. For example, for treatment of a spinal cord injury or concussion to the brain, a polymer, compound and/or composition of the invention may be formed into a medical implant in the shape of a disc for placement under the dura or dura mater, or a solution, suspension, emulsion, cream, gel, ointment, or other adhesive formulation form for covering the spine, dura or other surgically exposed areas, film, sprayed or coated formulation. In another example, a polymer, compound and/or composition of the invention may be formed into a medical implant in the shape of a membrane or tube for use in the treatment of injury or damage to the peripheral nervous system or a block of solid or foamed composition containing pathways drilled or otherwise formed to encourage nerve growth or bone growth. In another example, in the treatment of cancer, a polymer, compound and/or composition of the invention may be formed into a medical implant in the shape of a pellet, microparticle e.g. microsphere, nanoparticle e.g. nanosphere, rod, membrane, pin, cuff, disc, bullet, hook, rod or cone, with or without barbs, for insertion in a bone, joint, tumor excision site or other structures, or for insertion within the same and other structures. In the above instances, bioerosion of the medical implant would yield or generate an active agent.

The invention also contemplates that the shape, geometry, structure or configuration of a medical implant of the invention may change depending on the mode of delivery or administration and may enhance the therapeutic effect of the medical implant. For example, a medical device of the invention may be in the form of a linear rod when inserted in needles and stored but may become coil-like or form a multiplicity of coils or corkscrew shapes as the medical implant is pushed out of the needle by a trochar. As a result of the change of the shape, geometry, structure or configuration of the medical implant, expulsion from the tumor or tumor excision site by hydraulic pressures or body movements may be prevented and as much mass of active ingredient may be delivered to a small region with as small a diameter needle as possible.

The polymers of the present invention may take the form of a shape memory polymer, which is a stimulus responsive material that may change its shape in response to outside stimuli. Usually this is a temperature-related effect. It depends on the morphology of the material in combination with various processing parameters. Thus, many materials of widely different polymeric chemistry may behave as shape memory. See, e.g. Lendlein and Kelch, on Shape Memory Polymers, Encyclopedia of Polymer Science and Technology, Ed III, Publ. J Wiley & Sons, New York (2003). The material may be programmed initially by deforming the sample, usually at an elevated transition temperature, and then cooled in a distorted form so that it remains in this temporary state. It will remain there a long time but on reheating to above the programming transition temperature it will revert to its natural undeformed state.

Shape memory materials are all elastomers. They have a molecular structure consisting of network linked at certain net points either by physical or chemical cross-linking processes. The elastomer contains two types of polymer blocks whose phases are immiscible and have differing $T^m$ or $T^g$ values. Shape memory effects are usually recognized by tensile tests in a hot chamber over a range of transitions and seeing how the dimensions alter. The upper limit is the melting point of the highest Tm block. A cyclical regimen will show how well the polymer recovers its original shape. Examples of shape memory polymers are polyester-urethanes with hard and soft segments. A typical hard switching one is made from butane-1,4-diol and MDI with low Tg but crystalline polycaprolactone blocks. The $T^m$ of the hard 4G-MDI block is the upper temperature limit. Another segmented polyether-urethane is the one from polyTHF and butane diol with MDI. Here, the molecular weight of the soft poly (THF) segment is important—if it is too high the recovery may suffer.

Biodegradable shape memory polymers are possible based upon polycaprolactone diols capped with methacrylate groups and copolymerized with a low $T^g$ amorphous vinyl component such as polybutyl acrylate. Other compositions may include block copolyester-ethers with hard segments such as polylactide, glycolide and soft segments such as polyTHF diol or caprolactone-diol. Polyanhydride linkers could be incorporated and, if a phosgene route were used to make the polyanhydride, it could also generate carbamoyl chlorides and urethane links at the same time form suitable amine precursors. The polymers of this invention achieve a broad range of tensile modulus anywhere between about 500, 1000, 5000, 10000, 50000, 100000, or 300000 psi to about 500000, 600000, 850000, 1000000, 1200000, or 1500000 psi, among others, as well as any combination of ranges therebetween.

The mode of delivery, application, or administration of a device or implant of the invention may vary depending upon the use and may include those known in the art as well as those set forth herein. The thickness of the polymer, compound and/or composition as either the medical implant itself or as applied or coated onto a medical implant will vary depending upon one or more factors such as the physical and/or chemical characteristics of the polymer, compound and/or composition, the medical implant and/or the application or use. For example, a coronary artery stent may be formed from or applied or coated with a polymer, compound and/or composition of the invention to a thickness of about $\leq$30-50 µm while a vascular stent may be applied or coated with a polymer, compound and/or composition of the invention to a thickness of about $\leq$100 µm and a drug delivery device may be applied or coated with a polymer, compound and/or composition of the invention to a thickness of about $\leq$5 mm. In another example, round films/membranes for buccal (sublingual) administration, e.g. placement in lining of cheek, under the tongue, will have diameters of up to about 10 mm (1 cm) and a thickness of about 0.5-2.0 mm.

In the present invention, a covering may be affixed to a medical device in several ways. In one embodiment, the covering may be placed on the outside of the medical device, and through the natural properties of the polymer (i.e., stickiness or adhesiveness), adhere to the device. In one embodiment, the covering may fit snugly, form-fitting, or loosely around the medical device, such that no adhesive is required to affix the covering to the medical device. In another embodiment, a covering of the invention may be affixed to the medical device by means of a biocompatible adhesive, the characteristics of which would be understood by one skilled in the art. In another embodiment of the invention, a covering may be affixed to a medical device by means of a device external to both the covering and the medical device. For example, the covering may be affixed to the medical device by means of an external clamp, retaining pin, or other such device commonly known in the art. External retaining devices used to affix a covering to a medical device may also be used to retain the shape of the covering. External retaining devices may retain the covering adjacent to the medical device by existing on the outside of the covering, on the inside of the covering (i.e., in between the covering and the medical device), or as a combination both outside and inside of the covering. In yet another embodiment, the covering may be affixed to the medical device by means of a fastener. Non-limiting examples of materials that may be used to make an external fixing device for a covering of the present invention include surgical steel, nylon, polyethylene, and combinations thereof.

As a non-limiting example of the present invention, a medical device may be covered by a first covering in the form of a polymeric sheath, which is in turn covered by an external retaining device in the form of a semi-rigid or rigid sleeve. Such an external retaining device may be made of metal, plastic, a polymeric substance, or a combination thereof. Such an external retaining device may also be formed of, covered by, or impregnated with a polymer according to the present invention as described herein, or may be covered by or impregnated with an active agent that may be the same as or different than an active agent present in the first therapeutic device according to the present invention. An external retaining device may also contain a polymer that contains a functional group as described above. In another embodiment of the invention, an external retaining device that is formed from a polymer according to the present invention may contain at least one functional group and/or active agent in any of the forms as described above for a first covering.

In one embodiment, a cuff or sleeve comprising a polymer that generates an active agent, such as, e.g., an anti-inflammatory, an anti-infective, an antiseptic agent, or an anti-proliferative agent, is provided. Such a cuff may be made of the polymer entirely or made of an inert substance that is coated with the polymer. The cuff may adjoin or penetrate tissue layers to ensure delivery to the most likely sites of infection. The simplest version of the embodiment would be to coat the surfaces of a suitable device with the polymer and thereby enable a slow release of active agent along its length within the moist and enzyme rich milieu of body tissue. In preferred embodiment, the medical device is coated with a polymer composition comprising a active agent including, but not limited to, an anti-inflammatory agent, an anti-infective agent, an antiseptic, and an anti-proliferative agent or drug.

Polymers and compositions thereof with specific physical properties may be developed by one of skill in the art using the guidance given herein. In some preferred embodiments, a vascular device maybe further coated with a polymer that has lubricating qualities.

A polymer, compound and/or composition of the invention may be combined or admixed with other ingredients prior to or while being formed into or coated onto a medical device or into a particular coating for a medical device. Examples of suitable additives include, but are not limited to, stabilizers, mechanical stabilizers, plasticizers, hardeners, emulsifiers, other polymers including other biocompatible and biodegradable polymers, e.g. biocompatible and biodegradable polyanhydrides as set forth in U.S. Ser. No. 09/917,231 and PCT US/01/23740, biocompatible and biodegradable polyazo compounds as set forth in U.S. Ser. No. 09/917,595 and PCT US/01/23748, biocompatible and biodegradable polyesters, polythioesters, and polyamides as set forth in U.S. Ser. No. 09/917,194 and PCT US/01/23747, the relevant portions of which are incorporated herein by reference in their entireties, radioopaque and/or radioisotopic materials, e.g., boron, iodine, etc., suppositories, and other diagnostic or therapeutic agents or drugs.

An added ingredient may enhance stability of the polymer, compound and/or composition itself, the medical implant itself and/or may enhance the diagnostic or therapeutic effect and/or may enhance or enable diagnostic activity. For example, if the added ingredient is a diagnostic or therapeutic agent or drug, bioerosion would not only release the agent(s) but also the diagnostic or therapeutic agent(s). In another example, by adding a radioopaque material, visualization of both the targeted area e.g. tumor site, tumor, and the medical implant e.g. catheter would be enabled during and/or after, e.g. angioplasty, dental applications, joint injections, etc., insertion of the medical implant. In another example, the radioopaque material may also be used to control and/or enhance bioerosion of the medical implant and thereby control and/or enhance generation of the active agent by the generation of heat resulting from neutron capture.

An added ingredient may also enhance the overall mechanical stability of the medical implant, e.g. carbon fibers. The type of additive used would vary and depend upon the desired property and application. In one embodiment, a medical device is coated with a therapeutic co-polymer of two or more monomers or more monomers that each independently have different linker groups. In other preferred embodiments, the medical device is coated with a therapeutic polymer composition that is comprised of at least two therapeutic polymers that are mixed after polymerization.

The first and second active agents may be the same or different, and in one embodiment, the first and second agents may both be incorporated into the polymer backbone or attached directly to it, for example, through a linker or spacer, or by direct or indirect chemical linkage to a chemical group attached to the polymer backbone; or the second active agent may be dispersed within the polymer matrix or appended to the polymer, while the first active agent is incorporated into the backbone of the polymer or attached directly to the backbone, for example, through a linker or spacer, or by direct or indirect chemical linkage to a chemical group attached to the polymer backbone; or the first and second active agent may be dispersed, within the polymer matrix of the polymer or appended to the polymer. The polymer may also comprise additional agents, such as a third agent, a fourth agent, a fifth agent, and so on, where the additional agents are released by degradation of the polymer. For example, the additional agent(s) may be incorporated into the backbone of the polymer or attached directly to it, for example through a linker or spacer, or attached to the backbone by direct or indirect chemical linkage to the polymer backbone; or dispersed within the polymer matrix of the polymer or appended to the polymer as described herein, or otherwise annexed to or associated with the polymer such that the additional active agents dissociate from the polymer upon hydrolysis.

Another preferred embodiment comprises a device having at least one surface, the device comprising more than one polymer on all or a part of the surface, such as having first and second polymers that may be the same or different. For example, in one embodiment the polymer is coated on a device such as a stent or graft that experiences expansion, contraction or torsion during the application or its use. In the case of vascular stents, the polymer coating might be used to reduce the incidence of inflammation and resulting hyperproliferation of cells that results in occlusion of the vessel (restenosis). In one embodiment, the linking group is a dicarboxlyic acid hydrocarbon chain with eight carbon atoms. In another embodiment the medical device is a stent. The stent may be any suitable stent, such as those described herein. Suitable stents include, for example, coronary vascular stents, peripheral vascular stents, urethral stents, biliary stents, stents used for supporting the lumen of other anatomical tubes, and stents used for other medical and veterinary treatments. In one embodiment, the medical device comprises a polymer comprising at least one active agent, wherein the active agent or agents are incorporated into the polymer backbone The stent may comprise additional polymers and/or additional active agents, such as, e.g., a second active agent, a third active agent, and so on, where the additional active agents are, e.g., incorporated, attached, appended or dispersed within the polymer, as described herein, or otherwise annexed to or associated with the polymer such that the additional active agents dissociate from the polymer upon hydrolysis. The stent may comprise active agents that combine in vivo to form a new active agent or agents.

In one embodiment, an implantable stent is coated with the therapeutic polymer(s). The implantable stent may be made of many materials well known to those in the art, including but not limited to, electropolished 316L stainless steel and other metallic alloys as well as polymeric materials. In one embodiment, the polymer coating exhibits: 1) adequate wettability and adhesiveness to the surface of the stent to be coated, 2) adequate flexibility when crimped onto a balloon catheter, maneuvered into position, and then expanded in position in the body, 3) adequate hardness to avoid premature removal of the coating or portions thereof or pitting or other damage to the coating during implantation of the stent and thereafter (e.g., from handling, flow of blood or other body fluids, or movement of organs or the recipient's body), and 4) appropriate rates of degradation, enabling therapeutic drug levels to be maintained for predictable lengths of time without causing toxicity locally or systemically. For such a device used as a coronary, renal, or biliary stent, the preferred coating, or set of coatings, applied to the stent preferably has a thickness from about 100 nm to about 100 μm, and most preferably has a thickness of about 1, about 2, about 3.5, about 5, about 7.5, about 10 μm to about 12.5, about 15, about 20, about 24, about 26, about 28.5, about 30 μm. For stents used in other medical or veterinary applications, coatings or sets of coatings preferably have a thickness less than about 100 μm. In another embodiment, the therapeutic polymer is used as a coating(s) for an implantable orthopedic device, including hip, knee, shoulder, or elbow replacements, fixation devices, or devices for other orthopedic application.

In the case of orthopedic and dental implants such a coating could be used to maintain bone strength or induce bone penetration of the device to stabilize it and/or to reduce pain and inflammation and/or to reduce infections. In one embodiment, the linking group is preferably a dicarboxylic acid hydrocarbon chain with four six, eight or ten carbon atoms. In one embodiment, the medical devices are orthopedic implants, including hip, knee, and shoulder implants, and internal and external fixation devices and spinal implants. These orthopedic devices may be made of many kinds of materials well known to those in the art, including but not limited to, electropolished 316L stainless steel and other metallic alloys, inorganic ceramics including calcium phosphate and hydroxyapatite, cadaveric bone from humans and other animals, naturally-occurring and synthetic analogs of bone, biodegradable and non-degradable polymers (such as polymers of glycolic acid, lactic acid, and caprolactone, and copolymers thereof), and blends of the above materials.

In one embodiment, the orthopedic implants are coated with a therapeutic polymer of the invention such that the polymer coating that exhibits: 1) adequate wettability and adhesiveness to the surfaces of the implant to be coated, such that the coating wets and penetrates into porous spaces percolating to the exposed surfaces of the device, 2) adequate flexibility when handled by the clinician, maneuvered into position, and then interfaced to tissue in the body, 3) adequate hardness to avoid premature removal of the coating or portions thereof or pitting or other damage to the coating during implantation and thereafter e.g. from handling, flow of blood or other body fluids, or movement of organs or the recipient's body, and 4) appropriate rates of degradation, enabling therapeutic drug levels to be maintained for predictable lengths of time without causing toxicity locally or systemically. Compositions comprising a polymer may be used to coat orthopedic devices for fixation of bone fractures such as pins or screws, thereby decreasing the local inflammation and bone resorption associated with these devices.

Films comprising an aromatic polyanhydride are also believed to be useful as orthopedic devices to enhance the healing process of bone fractures. A polymer may be coated or applied onto or formed into sutures, wound closures, stitches, staples and other related devices. In the case of sutures, staples and other devices such a coating could be used to reduce infections, pain and/or inflammation in the vicinity of the suture or staple. Fibers made of the present polymer(s) are useful as suture materials, and may be used in oral surgery to suture cleft palates. Use of a polymer that degrades to an active agent, such as a therapeutic salicylate, would enhance the regeneration of the tissue via the sutures while decreasing the pain and inflammation associated with the surgery via the degradation products. Films, membranes, pastes, gels, chips, and microspheres comprising the polymer may also be used to decrease dental pain and promote healing within a tooth, in the pulp chamber and root canal. Films or membranes comprising a polymer may also be used in guided bone or tissue regeneration.

In one embodiment, the polymers, compounds and/or compositions of the invention may be formed into micronized particles or microparticles, or nanoparticles e.g. microspheres, nanospheres, nanocapsules and/or microcapsules. Microparticles of a polymer, compound and/or composition of the invention may be prepared by any means known in the art and may include one or more of the same or different polymer, compound and/or composition of the invention. For example, the microparticles may be prepared using an oil-in-water emulsion method whereby a polymer of the invention is dissolved in an organic solvent. The polymer solution may be then added to a stirring solution of water and polyvinyl alcohol (PVA) as a stabilizer to obtain the precipitation of the desired microparticles. Optionally, a homogenizer may be used. The solution may be then allowed to settle, the solvent decanted off the solution, and the microparticles dried. The microparticles, such as, e.g., microspheres may be applied to the surface of a medical device before placement in the body. A sterile liquid may be used to coat the device to adhere such microspheres for minutes to weeks to enable uncoated medical devices to benefit from the same or similar therapeutic benefits as coated devices. In one embodiment, the nanoparticles or microparticles are typically but not necessarily less than about 10 nm or microns in diameter. In another oil-in-water emulsion method, the polymer solution is added to a solution of water and a surfactant such as PVA, which is stirred rapidly at high shear rates with, for example, a homogenizer or dispersator. After the addition of the polymer solution, the solvent is allowed to evaporate while stirring is continued. The resulting microparticles are recovered by decantation, filtration or centrifugation and dried.

Microparticles of the invention may also be prepared by known microencapsulation processes, e.g. the process described by U.S. Pat. No. 5,407,609, the relevant text of which is incorporated herein by reference. The patent describes a continuous microencapsulation process whereby a polymer, protein, peptide, small molecule, water-soluble, hydrophobic drug, and drugs within a polymer may be added to a mechanically agitated water/surfactant mixture to form a microdroplet emulsion. Water is then employed to extract or remove the solvent, and form hardened microcapsules or microspheres that are collected by centrifugation, filtration or the like. In accordance with this continuous microencapsulation process molecules such as nucleic acids, saccharides, lipids, proteins, peptides, small molecules, water-soluble drugs, hydrophobic drugs, and drugs may be encapsulated in lactide/glycolide polymers to sizes of about 1, 2, 5, 10, 15 to up to about 10, 50, 75, 100, 150, 200, 250 μm, with minimal exposure to polymer solvent and with high encapsulation efficiency and good yields.

Having now generally described this invention, the same will be better understood by reference to certain specific examples, which are included herein for purposes of illustration only and are not intended to be limiting of the invention or any embodiment thereof, unless so specified. While the present invention may be embodied in many different forms, several specific embodiments are discussed herein with the understanding that the present disclosure is to be considered only as an exemplification of the principles of the invention, and it is not intended to limit the invention to the embodiments illustrated.

EXAMPLES

The following abbreviations are employed throughout the examples: BPC (bupivacaine), D (drug), L (linker), DCM (dichloromethane), DF (diflunisal), MPA (mycophenolic acid), MTX (methotrexate), PAC (paclitaxel), SA (salicylic acid), TEA (triethylamine), TFA (trifluoroacetic acid), THF (tetrahydrofuran), TP (triphosgene).

All solvents and reagents employed in the following examples were purchased and used as received. Proton nuclear magnetic resonance ($^1$H NMR) spectra were recorded on a Varian 300 MHz Mercury VX-300 spectrometer using an appropriate deuterated solvent. Chemical shifts (δ) are reported in parts per million (ppm) downfield from tetramethylsilane (TMS) and coupling constants (J values) are given in hertz (Hz). Molecular weights ($M_w$) and polydispersity indices (PDI) were determined by gel permeation chromatography (GPC) on a Viscotek TDA 301 system consisting of a refractive index detector and a Viscotek VE1122 pump using Omnisec software for data collection and processing. Molecular weights were calibrated relative to a narrow molecular weight polystyrene standard (Viscotek, Houston, Tex.). The HPLC impurity profile is performed on an Agilent Rapid Phase C18 column 4.6×70 mm column with a flow rate of 1.8 ml/min and a gradient of 6%/min of mobile phase B (0.1% (v/v) TFA in acetonitrile) in mobile phase A (0.1% (v/v) TFA in water). The gradient runs on an ambient column with a VWD at 225 nm.

Example 1

General Procedure for Preparation of Linker-Diacid Chloride (12)

0.48 mol oxalyl chloride was added to a mixture of 0.16 mol diacid (Compound 11) in 320 ml anhydrous chloroform, and the mixture stirred overnight at room temperature, gently refluxed for 1 hour, and cooled to room temperature. The solvent was then removed in vacuo, and the residue dried in vacuo at 45° C. to obtain the product.

Example 2

Preparation of C14 Diacid Chloride (Compound 12a)

1,12-Dodecanedicarboxylic acid (Compound 11a) was subjected to the conditions described in Example 1.

Results:
Yield C14 Diacid Chloride: 99%
The structure of the product was confirmed by $^1$H NMR.

Example 3

Preparation of C16 Diacid Chloride (Compound 12b)

1,16-Hexadecanedioic acid (Compound 11b) was subjected to the conditions shown in Example 1.
Results:
Yield C16 Diacid Chloride: 99%.
The structure of the product was confirmed by $^1$H NMR.

Example 4

General Procedure for Preparation of D-L-D Aromatic Diacids (Compound 14)

1.0 mol pyridine was added to a solution of 0.325 mol of compound 13 in 800 ml anhydrous THF, and then 125 ml solution of 0.16 mol linker diacid chloride in anhydrous THF was added dropwise. The reaction mixture was stirred for 45 minutes, and poured into an 80 ml solution of HCl (conc.) maintained in 2.4 ice-cold water. The mixture was stirred for 1 hr, and the solid produced was isolated by decanting then supernate, and washing the solid with 1 cold water. The crude solid product was washed with cold water, filtered, and dried in a vacuum oven at 45° C. overnight, and the dried solid was purified twice from 3:1 (v:v) hexane-ethyl acetate.

Example 5

Preparation of Salicylic Acid-C8-Salicylic Acid (SA-C8-SA; Compound 14a)

The diacid was prepared from SA and suberoyl chloride using the general procedure given in Example 4. The structure of the product was confirmed by $^1$H NMR.

Example 6

Preparation of Salicylic Acid-C10-Salicylic Acid (SA-C10-SA; Compound 14b)

The diacid was prepared from SA and sebacoyl chloride employing the procedure described in example 4 above.
Results:
Yield SA-C10-SA: 97%.
The structure of the product was confirmed by $^1$H NMR.

Example 7

Preparation of Diflunisal-C12-Diflunisal (DF-C12-DF; Compound 14c)

The diacid was prepared from DF and 1,10-decane dicarboxylic acid chloride using the general procedure provided in Example 4 above. The structure of the product was confirmed by $^1$H NMR.

Example 8

Preparation of Diflunisal-C14-Diflunisal Diacid (DF-C14-DF; Compound 14d)

The diacid was prepared from diflunisal (DF) and 1,12-dodecane dicarboxylic acid dichloride (Compound 12a) at 99% yield using the general procedure given in Example 4.

Results:
Yield DF-C14-DF: 99%.
The structure of the product was confirmed by $^1$H NMR.

Example 9

Preparation of Diflunisal-C16-Diflunisal Diacid (DF-C16-DF; Compound 14e)

The diacid was prepared from DF and 1,16-hexadecanedioic acid dichloride (Compound 12b) using the general procedure given in Example 4. The structure of the product was confirmed by $^1$H NMR.

Example 10

General Procedure for Preparation of D-L-D Diacid Chloride (Compound 15)

106.6 mol oxalyl chloride were added to a solution of 34.59 mol D-L-D diacid in 200 ml anhydrous chloroform, and the reaction mixture was refluxed gently for three hours. The clear reaction solution was concentrated in vacuo, and the residue recrystallized in 1:1 (v:v) anhydrous DCM-heptane to obtain a white solid. The solid was filtered and washed with heptane to obtain the product.

Example 11

Preparation of Salicylic Acid-C8-Salicylic Acid Diacid Chloride (SA-C8-SA Diacid Chloride; Compound 15a)

The diacid chloride was prepared from SA-C8-SA diacid using the general procedure shown in Example 10 above.
The structure of the product was confirmed by $^1$H NMR.

Example 12

Preparation of Salicylic Acid-C10-Salicylic Acid Diacid Chloride (SA-C10-SA Diacid Chloride; Compound 15b)

The diacid chloride was prepared from SA-C10-SA diacid using the general procedure given in Example 10 above.
The structure of the product was confirmed by $^1$H NMR.

Example 13

Preparation of Diflunisal-C12-Diflunisal Diacid Chloride (DF-C12-DF Diacid Chloride; Compound 15c)

The diacid chloride was prepared from DF-C12-DF diacid employing the procedure provided in Example 10 above.
The structure of the product was confirmed by $^1$H NMR.

Example 14

Preparation of Diflunisal-C14-Diflunisal Diacid Chloride (DF-C14-DF Diacid Chloride; Compound 15d)

The diacid chloride was prepared from DF-C14-DF diacid in 99% yield using the general procedure given in Example 10.
The structure of the product was confirmed by $^1$H NMR.

Example 15

General Procedure for Preparation of D-D-L-D-D Diacid (Compound 16)

0.189 mol anhydrous pyridine was added to a solution of 0.077 mol Compound 13 in 150 ml anhydrous THF, the mixture was stirred for 5 minutes, and a solution of 0.035 mol D-L-D diacid chloride in 150 ml anhydrous THF was added drop-wise. The reaction mixture was stirred for 30 minutes at room temperature, and was poured into a mixture of 180 ml cold water and 20 ml HCl (conc.). The mixture was extracted three times with 150 ml ethyl acetate, and the combined organic layer was washed twice with 100 ml water and 100 ml brine, and was dried over anhydrous sodium sulfate. The solvent was removed in vacuo, and the residue was purified twice from 1:1 (v:v) ethyl ether-pentane to obtain the product.

Example 16

Preparation of Salicylic Acid-Salicylic Acid-C8-Salicylic Acid-Salicylic Acid Diacid (SA-SA-C8-SA-SA Diacid; Compound 16a)

The diacid was prepared from SA and SA-C8-SA diacid chloride (Compound 15a) employing the general procedure given in Example 15.
Yeild: 85%
The structure of the product was confirmed by $^1$H NMR.

Example 17

Preparation of Diflunisal-Diflunisal-C14-Diflunisal-Diflunisal Diacid (DF-DF-C14-DF-DF Diacid; Compound 16d)

The diacid was prepared from DF and DF-C14-DF diacid chloride (Compound 15d) employing the procedure described in Example 15 above.
Results:
Yield: 95%
The structure of the product was confirmed by $^1$H NMR.

Example 18

Preparation of C6 bis-L-Lactate Diol (Compound 19a)

33.60 g 1,6-dibromo hexane (Compound 18a; 0.15 mol) was added to a solution of 33.62 g sodium L-lactate (Compound 17a; 0.3 mol) in 60 ml anhydrous DMF, and the mixture was heated at 60° C. for 3 days. The reaction mixture was cooled to room temperature and poured into 500 ml cold water, acidified to about pH 4 with 1N HCl, and extracted 4 times with 75 ml ethyl acetate. The organic layers were combined and washed with water, dried over anhydrous sodium sulfate, and the solvent removed in vacuo to obtain a slightly brownish oily product. The product was filtered over silica gel with 1:1 (v:v) ethyl acetate-hexane. Thirty-two g of pure product were obtained.
The structure of the product was confirmed by $^1$H NMR.

Example 19

Preparation of C10-bis-L-Lactate Diol (Compound 19b)

25.0 g 1,10-diiododecane (Compound 18b) was dissolved in 7 ml DCM, and the solution added to 120 g tetrabutylammonium-L-lactate (Compound 17b). The reaction mixture was placed in a 40° C. rotary evaporator bath, and rotated at top speed for 20 hours. The solution was then diluted with 100 ml dichloromethane, and washed with 100 ml water. 750 ml diethyl ether were placed into a 2-liter Erlenmeyer flask and stirred magnetically. The lower organic phase from the separatory funnel was dripped into the diethyl ether with stirring until a precipitate appeared. The precipitated salt (tetrabutylammonium iodide) was vacuum-filtered through a medium porosity frit, and the filtrate was collected in a 1-liter round-bottom flask and washed once with 400 ml 1.25% sodium thiosulfate in water, and twice with 400 ml water. The ether layer was dried over anhydrous magnesium sulfate and the solvent was removed in vacuo to produce 15.5 g of the product.

The structure of the product was confirmed by $^1$H NMR.

Example 20

Preparation of C8 bis-L-Lactate Diol (Compound 19c)

The diol was prepared from 1,8-dibromoocatane (Compound 18c) and Compound 17a, employing the same conditions given in Example 18.

The structure of the product was confirmed by $^1$H NMR.

Example 21

Preparation of C6 bis-D,L-Lactate Diol (Compound 19d)

The diol was prepared from Compound 18a and lithium D,L-lactate (Compound 17c) employing the same conditions given in Example 18.

The structure of the product was confirmed by $^1$H NMR.

Example 22

Preparation of C8-bis-Glycolate Diol (Compound 21a)

4.2 ml triethyl amine (30 mmol) were added to a solution of 2.28 g glycolic acid (Compound 20a; 30 mmol) in 10 ml anhydrous DMF. The mixture was stirred for 5 minutes at 60° C., 4.08 g 1,8-dibromoocatane (Compound 18b; 15 mmol) was added, and the reaction mixture was stirred at 60° C. for 24 hours and then cooled to room temperature, poured into 75 ml cold water, and acidified to about pH 4 with 1N HCl. A white precipate that appeared was filtered and dried to obtain 2.8 g of the product.

The structure of the product was confirmed by $^1$H NMR.

Example 23

Preparation of C8 Salicylic Acid Polymer (Compound 23a) by Non-Aqueous Dispersion Method with Dispersing Agent A 50 ml reaction vessel fitted with a 3-neck flanged lid, carrying a sealed Teflon paddle stirrer, a rubber septum over one side neck, and a short Vigreux distillation column and receiver flask, was cooled in a dry ice bath. Fifty ml light white mineral oil, 8.60 g suberoyl bis-salicylic acid-acetic acid mixed anhydride (Compound 22), and 0.26 g polyvinylpyrrolidone/eicosane co-polymer (ISP Corp., Antaron 220) as dispersing agent were added to the reaction vessel, and the mixture was briskly mixed. A slow stream of Argon gas was passed through the stirred mixture as a sparge, and the mixture was heated to 120° C. in an oil bath and maintained in these conditions under Argon for 30 minutes. The vessel was then slowly placed under vacuum at 120-140° C. with constant vigorous stirring to a final vacuum of 2.0 mTorr, and the oil was refluxed halfway in a Vigreux column. The reaction was allowed to proceed for 6 hours, then allowed to cool to 70° C. under vacuum with stirring while the volatile products, e.g., acetic anhydride, were collected in a chilled receiver flask. The vacuum was then released with Argon, and the vessel cooled to room temperature. The reaction mixture was diluted with anhydrous petroleum ether, and centrifuged for 30 minutes to collect the product. The supernate was removed, and the residual solid was washed 3 times with dry petroleum ether, and dried at 40° C. in a vacuum oven for several hours to obtain 4.38 g of the product.

Results:
Yield: 64%
MW=51,000 Dalton, as determined by GPC as compared with a limiting 14,000 Dalton MW obtained by standard bulk-melt polymerization.

Polymer particles were amorphous, clear, and formed perfectly spherical 5 to 50µ diameter particles as determined in a low power optical microscope.

Example 24

Preparation of C14 Diflunisal Polyanhydrides (Compound 23b) by Non-Aqueous Dispersion Method without Dispersing Agent A 50 ml reaction vessel fitted with a 3-neck flanged lid, in turn carrying a sealed Teflon paddle stirrer, a rubber septum over one side neck and a short Vigreux distillation column and receiver flask, was cooled in a dry ice bath, and was charged with 50 mL of light white mineral oil, 8.54 g of bis(2-carboxy-4-(2,4-difluorophenyl) tetradecane dicarboxylate-acetic acid mixed anhydride (22b). The reactor was evacuated to 40 mTorr, and heated to 110° C. for 1 hour with constant vigorous stirring. The temperature was increased to 160° C. and held for the duration of the reaction. A final vacuum of 30 mTorr was achieved, and the oil was refluxed part of the way up a Vigreux column. The volatile reaction products, e.g. acetic anhydride, were collected in a chilled receiver flask. The reaction was allowed to proceed overnight and was cooled to room temperature under vacuum with stirring. The solution consisted of a polymer mass on the bottom of the reactor, and oil above the solids. The oil was decanted off and the residue was washed with petroleum ether twice. The residue was dissolved in anhydrous DCM, and a white precipitate was obtained by precipitation into anhydrous ethyl ether. The white precipitate was dried at 40° C. under vacuum to give the product as a solid (5.6 g).

Results:
Yield: 75%
$M_w$=405,000
PDI=1.75

Example 25

Preparation of High Molecular Weight Poly(Sebacic Anhydride) (Compound 24a)

27.8 ml anhydrous TEA were added to a solution of 20.226 g sebacic acid in 100 ml anhydrous chloroform, and the mixture was cooled to 0° C. in an ice bath. A solution of 9.892 g triphosgene in 25 ml anhydrous chloroform was added very slowly to the reaction mixture at 0° C. with vigorous stirring. The reaction mixture was then warmed up to room temperature and mildly refluxed for 3 hours. The ice-water bath was removed and replaced with a heating mantle while a flow of Argon gas and stirring was maintained, and the flask contents were heated to boiling point until the contents became homogeneous and viscous. To reduce the viscosity of the thin layer of undissolved polymer that remained at the bottom of the flask, 250 ml anhydrous chloroform were added, and the system was heated to near the solvent's boiling point with stirring under Argon gas until the flask's contents completely dissolved. A sample of the polymer solution was removed from the flask, and a conventional calibration was performed with GPC using narrow polydispersity polystyrene standards.
Results:
MW=626,000
PDI=1.79

Example 26

Preparation of Poly Diflunisal-C14-Diflunisal Ester Anhydride (DF-C14-DF Ester Anhydride; Compound 25a)

7.70 ml anhydrous TEA were added to a solution of 20.000 g DF-C14-DF diacid (Compound 14d) in 80 ml anhydrous chloroform at 0° C., the solution was stirred for 30 minutes, and a solution of 2.750 g triphosgene in 20 ml anhydrous chloroform was added drop-wise. The reaction mixture was stirred at 0° C. for 30 minutes, diluted with 40 ml chloroform, and washed once with 100 ml 1N HCl, and once with 100 ml distilled water. The organic layer was dried over anhydrous magnesium sulfate, and the solvent was removed in vacuo. The residue was dissolved in DCM and poured into diethyl ether in a Teflon beaker with stirring to precipitate the product. The supernate was decanted, and the residue washed with additional ether before drying in a vacuum oven at 45° C. overnight to obtain 10.7 g of the product.
Results:
$M_w$=176,000
PDI=1.85

Example 27

Preparation of Poly Salicylic Acid-C8-Salicylic Acid Ester Anhydride (SA-C8-SA Ester Anhydride (Compound 25b)

This polymer was prepared from SA-C8-SA diacid (14a) using the same conditions given in Example 26 above.
Results:
MW=121,000
PDI=1.73

Example 28

Preparation of Poly Salicylic Acid-C8-Salicylic Acid Ester Anhydride (SA-C8-SA Ester Anhydride; Compound 25c)

The polymer was prepared from SA-C10-SA diacid (14b) using the same conditions given in Example 24 above.
Results:
MW=110,000
PDI=1.61
The structure of the product was confirmed by $^1$H NMR.

Example 29

Preparation of Mixed Random Poly Anhydride of SA-C8-SA and SA-SA-C8-SA-SA (Compound 26a)

8.7 ml anhydrous TEA (61.6 mmol) were added to a solution of 8.7 g SA-C8-SA diacid (Compound 14a; 21 mmol) and 4.58 g SA-SA-C8-SA-SA diacid (Compound 16a) (7 mmol) in 70 ml anhydrous DCM at 0° C., and the solution was stirred for 30 minutes. A solution of 2.8 g triphosgene (9.34 mmol) in 20 ml anhydrous DCM was added drop-wise to the mixture at 0° C., stirred for 1 hour at 0° C., diluted with 25 ml DCM, washed once with 25 ml 1N HCl and twice with 100 ml distilled water, and dried over anhydrous magnesium sulfate. The solution was concentrated in vacuo to about 75 ml, and the was product precipitated by pouring the solution into anhydrous diethyl ether in a Teflon cylinder while stirring. The thus obtained solid was washed with diethyl ether and dried in a vacuum oven at 40° C. overnight to obtain 10.0 g of the product.
Results:
MW=110,000
PDI=1.24

Example 30

Preparation of Mixed Random Poly Anhydride of DF-C14-DF and DF-DF-C14-DF-DF (Compound 26b)

21 mmol DF-C14-DF diacid (Compound 14d) and 7 mmol DF-DF-C14-DF-DF diacid (Compound 16d) were employed as described in Example 27 to obtain 25.2 g of the product.
Results:
MW=163,000
PDI=1.32
The structure of the product was confirmed by $^1$H NMR.

Example 31

Preparation of Mixed Random Poly Anhydride of DF-C16-DF and DF-DF-C14-DF-DF (Compound 26c)

42.5 mmol DF-C16-DF diacid (Compound 14e) and 7.5 mmol DF-DF-C14-DF-DF (DF-DF-C14-DF-DF diacid; compound 16d) were subjected to the conditions described in Example 27 above to obtain 30 g of product.
Results:
MW=168,000
PDI=3.1

Example 32

Preparation of Random Poly Diflunisal-C14-Diflunisal-coDF Anhydride (DF-C14-DF-coDF Anhydride; Compound 27a)

A solution of 6.579 g DF and 7.35 ml TEA in 20.0 ml anhydrous chloroform was slowly added to a solution of 10.000 g compound 15d and 3.895 g compound 12b in 80 ml anhydrous chloroform at 0° C.±4° C. The reaction mixture was stirred for 1 hour at 0±4° C., and washed with 100 ml 1N HCl, and 100 ml distilled water. The organic layer was dried over anhydrous magnesium sulfate, the solvent was removed in vacuo, and then the solid was dried in a vacuum oven at 40° C. overnight. Fifteen g of the dried polymer were redissolved in 70 ml anhydrous chloroform and 0.625 ml TEA was added to the solution at 0° C. The reaction solution was stirred for 1 hour, and a solution of 87.2 mg triphosgene in 2.0 ml anhydrous chloroform at 0° C. was slowly added. The reaction mixture was stirred for 1 hour at 0±4° C. and was washed with 100 ml 1N HCl and 100 ml distilled water. The organic layer was dried over anhydrous sodium sulfate, and the solvent was removed in vacuo at 40° C. The crude polymer was dissolved in 120 ml DCM, and then slowly added to 1.21 anhydrous diethyl ether that was placed in a Teflon cylinder while stirring vigorously. The supernate was decanted, and the residue was washed with anhydrous ethyl ether. The thus obtained gummy polymer was transferred into a Teflon dish and dried in a vacuum oven at 40° C. for 24 hours to obtain 11.4 g of product.
Results:
MW=149,000
PDI=2.36

Example 33

Preparation of Random Poly Salicylic Acid-C8-Salicylic Acid-coSalicylic Acid Anhydride (SA-C8-SA-co-SA Anhydride; Compound 27b)

The polymer was prepared from SA-C8-SA diacid (Compound 14a), suberoyl chloride, and SA using the same conditions shown in Example 30 above.
Results:
MW=79,000
PDI=2.66

Example 34

Preparation of Random Poly(DF-C14-DF-coDF) Anhydride (Compound 27c)

A mixture of 3.971 g DF and 4.64 ml TEA in 18 ml anhydrous DCM was added dropwise to a solution of 10.000 g of DF-C14-DF diacid chloride (Compound 15d) in 30 ml anhydrous DCM at 5° C., and the reaction mixture was stirred for 30 minutes at 5° C. The mixture was then diluted with 40 ml DCM, washed with 100 ml 1N HCl and 100 ml distilled water, and dried over anhydrous magnesium sulfate. The solution was concentrated to about 50 ml in vacuo, and was poured into anhydrous diethyl ether in a Teflon cylinder with stirring to precipitate the product. The supernate was decanted, and the solid was washed with ethyl ether, and dried in a vacuum oven at 40° C. overnight to obtain 9.3 g of the product.
Results:
MW=106,000
PDI=1.88

Example 35

Preparation of Random Poly(DF-C14-DF Co-Mycophenolic Acid) Anhydride (Compound 27d)

Compound 27c was prepared from DF-C14-DF diacid (Compound 15d) and MPA using the conditions shown in Example 32 above.

Example 36

Preparation of Random Poly(DF-C14-DF Co-Methotrexate) Anhydride (Compound 27e)

Compound 27e was prepared from DF-C14-DF diacid and MTX using the same conditions given in Example 32.

Example 37

Preparation of Random Poly(DF-C12-DF Co-Diflunisal) Anhydride (Compound 28a)

A solution of 2.755 g C10-bis-L-lactate diol (Compound 19b) and 3.623 ml anhydrous TEA in 25 ml anhydrous THF was added to 19.00 g of a solution of DF-C12-DF diacid chloride (Compound 15c) in 125 ml anhydrous THF. The reaction mixture was stirred for 12 hours at 30° C., concentrated in vacuo, co-evaporated twice with 200 ml additional chloroform, and dried in a vacuum oven at 30° C. overnight. The dried intermediate (prepolymer) was re-dissolved in 100 ml anhydrous chloroform, and was cooled to 0° C. in an ice bath. A mixture of 3.466 g DF and 4.058 ml anhydrous TEA was made in 100 ml anhydrous chloroform, and was slowly added to the pre-polymer solution at 0° C. The reaction mixture was stirred for 1 hour at 0° C., washed with 200 ml 1N HCl and 200 ml distilled water, dried over anhydrous magnesium sulfate, concentrated in vacuo, and dried in a vacuum oven at 40° C. overnight. 0.317 ml anhydrous TEA were added to a solution of 21.6 g intermediate prepolymer in 140 ml DCM, and a solution of 111 mg triphosgene in 5.0 ml anhydrous chloroform was added dropwise at 0° C. The reaction mixture was stirred at 0° C. for 1 hour, diluted with 40 ml chloroform, washed with 100 ml 1N HCl and twice with 500 ml distilled water, and dried over anhydrous $MgSO_4$. The solution was concentrated in vacuo to about 50 ml, and poured into anhydrous diethyl ether in a Teflon cylinder with stirring to precipitate the product. The supernate was decanted, and the solid was washed with ethyl ether, and dried in a vacuum oven at 40° C. overnight to yield 13.3 g of product.
Results:
MW=120,000
PDI=1.35

Example 38

Preparation of Random Poly(Tetradecanedioic Acid-bis-Diflunisal Phenolate DF-C14-DF-co-C10-bis-Lactate-co-DF) Anhydride (Compound 28b)

A random tetradecanedioic acid-bis-diflunisal phenolate ester-co-decanediol-bis-L-lactate-co-diflunisal anhydride polymer (Compound 28b) was prepared from (DF), DF-C14-DF diacid chloride (Compound 15d), and C10-bis-lactate diol (Compound 19b) employing the conditions given in Example 35 above.
Results:
MW=89,000
PDI=1.29

Example 39

Preparation of Random Poly(DF-C14-DF-co-C8-bis-Lactate-co-DF) Anhydride (Compound 28c)

A random tetradecanedioic acid-bis-diflunisal phenolate ester-co-octanediol-bis-L-lactate-co-diflunisal anhydride polymer (Compound 28c) was prepared from DF-DF-C14-DF diacid chloride (Compound 15d), and C8-dilactate diol (Compound 19c) using the conditions shown in Example 35 above.
Results:
  MW=63,000
  PDI=1.46

Example 40

Preparation of 1,3-Propanediyl Bissalicylate (Compound 29a)

13.94 ml TEA (100 mmol) were added to a solution of 13.81 g salicylic acid (SA; 100 mmol) in 40 ml DMF at 60° C., the reaction mixture was stirred for 20 minutes at 60° C., and 12.2 g 1,3-dibromo propane (Compound 18d; 50 mmol) were added. The reaction mixture was stirred at 60° C. for 24 hours, cooled to room temperature, poured into 250 ml cold water, and acidified to about pH 4 with 1N HCl. A white precipitate separated. The precipitate was filtered, washed with water, and dried in a vacuum oven at 40° C. overnight. The thus obtained crude product was recrystallized from n-heptane to obtain a pure product.
Results:
  Yield: 85%

Example 41

Preparation of a Poly(SA-C3-SA) Carbonate (Compound 30a)

2.09 ml TEA (15 mmol) and 0.18 g DMAP were added to a solution of 1.89 g Compound 29a (6 mmol) in 30 ml anhydrous DCM at 0° C. The reaction mixture was stirred for 10 minutes and 20 wt % toluene solution containing 3.18 ml phosgene (6 mmol) in 5 ml anhydrous DCM was added drop-wise. The mixture was warmed to room temperature, stirred for 3 hours, and diluted with 30 ml DCM. The solution was washed with 20 ml 1N HCl, washed three times with 25 ml water, and was dried over anhydrous sodium sulfate, and concentrated in vacuo. The polymer residue was redissolved in 10 ml anhydrous DCM, and was added to 150 ml anhydrous ether with stirring until an insoluble polycarbonate separated. The polymer was washed with ethyl ether and dried in a vacuum oven at 40° C. to obtain 1.3 g of the product.
Results:
  MW=73,643
  PDI=1.85

Example 42

Preparation of a Poly(SA-C6-SA-co-diacid) Ester (Compound 31a)

0.42 ml TEA (3 mmol) and 10 mg DMAP were added to a solution of 0.316 g Compound 29a (1 mmol) in 5 ml anhydrous DCM at 0° C. The reaction mixture was stirred for 10 minutes, and 0.239 g sebacoyl chloride (1 mmol) in 2 ml anhydrous DCM was added thereto. The mixture was then warmed to room temperature, stirred for 3 hours, and diluted with 20 ml DCM. The solution was then washed with 20 ml 1N HCl, three times with 25 ml water, dried over anhydrous sodium sulfate, and concentrated in vacuo to produce 0.4 g of the product.
Results:
  MW=25,293
  PDI=1.6

Example 43

Preparation of a Poly(DF-C8-DF Co-C8-bis-Glycolate) Ester (Compound 32a)

0.7 ml anhydrous TEA (5 mmol) were added to a solution of 0.53 g bis-glycolate diol (Compound 21a; 2 mmol) in 10 ml anhydrous DCM at 0° C. A solution of 2.70 g DF-C8-DF diacid chloride (Compound 15f; 4 mmol) in 15 ml anhydrous DCM was prepared, and added drop-wise to the reaction mixture. The mixture was allowed to warm to room temperature, and maintained at this temperature with stirring for 4 hours. The reaction solution was diluted with 25 ml DCM, washed once with 20 ml 1N HCl, twice with 20 ml distilled water, and was then dried over anhydrous magnesium sulfate, filtered, and concentrated in vacuo to about 5 ml. The polymer solution was poured into 40 ml anhydrous diethyl ether in a 1 liter Teflon cylinder while stirring with a magnetic stir bar to precipitate the product. The supernate was decanted and the remaining was solid rinsed with anhydrous diethyl ether and dried in a vacuum oven at 40° C. overnight to yield 1.8 g of the product.
Results:
  MW=8,349
  PDI=1.33

Example 44

Preparation of a Poly(DF-C10-DF Co-C8-bis-D,L-Lactate Ester) (Compound 32b)

Compound 32b was prepared from Compound 19c and Compound 15e employing the procedures described in Example 43.
Results:
  MW=42,785
  PDI=1.68
  The structure of the product was confirmed by $^1$H NMR.

Example 45

Preparation of a Branched Poly(DF-C14-DF) Anhydride with 1,3,5-Benzene Tricarboxylic Acid (Compound 34a)

3.2 ml anhydrous TEA were added slowly to a mixture of 6.86 g (9.5 mmol) DF-C14-DF diacid (14d) and 0.106 g (0.5 mmol) 1,3,5-benzenetricarboxylic acid (Compound 33) in 40 ml anhydrous DCM at 0° C. A solution of 0.99 g triphosgene in 25.0 ml anhydrous DCM was then added into the reaction flask in a slow drop-wise manner at 0° C., and the reaction was stirred for 1.5 hours at 0±4° C. under Argon. The reaction mixture was diluted with anhydrous 50 ml DCM, and washed once with 50 ml 1N HCl and twice with 50 ml distilled water, dried over anhydrous magnesium sulfate, filtered, and concentrated in vacuo to about 20 ml. The polymer solution was then poured into anhydrous 500 ml diethyl ether contained in a 1 Teflon cylinder while stirring with a magnetic stir bar to precipitate the product. The supernate was decanted, and the solid was rinsed with anhydrous diethyl ether, and dried in a vacuum oven at 40° C. overnight to obtain 4.0 g of the product as a solid.
Results:
  MW=223,000
  PDI=4.2

Example 46

Preparation of a Branched Poly(DF-C14-DF) Anhydride with 1,2,3,4-Butane Tetracarboxylic Acid (Compound 36a)

Compound 36a was prepared from DF-C14-DF diacid (Compound 14d) and 1,2,3,4-butanetetracarboxylic acid (Compound 35) using the conditions described in Example 42 above.

Example 47

Preparation of a Branched Polymer Using Trans-Aconitic Acid (Compound 38a)

Compound 38a was prepared from DF-C14-DF diacid (Compound 14d), and trans-aconitic acid (Compound 37) employing the conditions shown in Example 42 above.

Example 48

Preparation of a Random Block Polyanhydride (Compound 39)

0.256 ml anhydrous TEA was added drop-wise to a solution of 10.83 g Compound 26b ($M_n$=51,000; 0.21 mmol)) and 5.00 g of Compound 25c ($M_n$=22,000; 0.23 mmol) in 70 ml anhydrous DCM at 0° C. The reaction mixture was stirred for 30 minutes, and a solution of 76.4 mg triphosgene (0.26 mmol) in 10 ml DCM was added drop-wise in an ice water bath. The resulting reaction mixture was stirred for 30 minutes at 0° C., and diluted with 70 ml DCM. The solution was washed once with 150 ml 1N HCl, and twice with 50 ml of water, and dried over anhydrous $MgSO_4$. The solution was concentrated in vacuo to about 50 ml, and poured into anhydrous ethyl ether placed in a Teflon cylinder to precipitate the product. The solid was washed with anhydrous ethyl ether and dried in a vacuum oven at 40° C. overnight to obtain 12.2 g of the product.
Results:
  MW=112,000
  PDI=1.53

Example 49

Preparation of Alternating Block Thermoplastic Elastomeric Polyanhydride (Compound 40)

A solution of 0.921 g of Compound 25c ($M_n$=96,000) and 3.2 µl TEA in 19 ml anhydrous chloroform was slowly added to a solution of 7.29 mg Compound 15d in 20 ml anhydrous chloroform. The mixture was stirred for 30 minutes, and then was slowly added to a solution of 1.2 g of Compound 26b and 6.4 µl anhydrous TEA in 20 ml anhydrous chloroform. The reaction mixture was stirred at room temperature for 17 hours, diluted with 20 ml chloroform, washed with 25 ml 1N HCl and then with 25 ml distilled water, and was dried over anhydrous magnesium sulfate. The dried solution was concentrated in vacuo to about 10 ml, and poured into anhydrous ethyl ether in Teflon cylinder to precipitate the polymer. The solid was washed with ethyl ether and dried in the vacuum oven at 40° C. overnight to obtain 1.8 g of the product.
Results:
  MW=167,000
  PDI=1.27

Example 50

Preparation of a Triblock Thermoplastic Elastomeric Polyanhydride (Compound 42)

A solution of 2.849 g Compound 25c ($M_n$=30,000; 0.095 mmol) and 0.0477 ml anhydrous TEA (0.34 mmol) in 30 ml anhydrous chloroform was added drop-wise to a solution of 219.3 mg Compound 15 g (0.31 mmol) in 15 ml anhydrous chloroform. The reaction solution was stirred at 18° C. overnight, and then concentrated in vacuo. The residue was dissolved in 1 ml DCM, and anhydrous ethyl ether was added to precipitate a crude diacid chloride (Compound 41). The supernatant was decanted, the dissolution/precipitation process was repeated three times, and the solid was finally washed with ethyl ether, and dried in a vacuum oven at 40° C. for 5 hours to obtain Compound 41. A solution of the dried solid (Compound 41) in 25 ml anhydrous chloroform was added drop-wise to a solution of 12.008 g Compound 26b ($M_n$=67,000; 0.18 mmol) in 45 ml anhydrous chloroform at 18° C., and the solution was stirred overnight at room temperature. The reaction mixture was then washed once with 75 ml 1N HCl and twice with 50 ml water twice, and was dried over anhydrous sodium sulfate. The solution was concentrated to 30 ml, and dripped into 880 ml anhydrous ethyl ether placed in a Teflon beaker to precipitate the crude product. The crude product was washed with ether and dried in a vacuum oven at 40° C. overnight to produce 12.5 g of the product.
Results:
  Yield: 84%
  MW=129,000
  PDI=1.693
  The structure was confirmed by NMR.

Example 51

Preparation of Polymer Microspheres

One g polymer was dissolved in 5 ml DCM, and 0-500 mg of a drug was added to the solution. The mixture was mixed thoroughly and poured into 1.0-2.5% aqueous solution of PVA while agitating at 3,000-5,000 rpm. The mixture was agitated for 1 hour, magnetically stirred for 2 hours, centrifuged, washed with water several times, and lyophilized to obtain microspheres.

Example 52

Content Uniformity Determination of Drug (Methotrexate) Admixed with Polymer in Microspheres The weight per weight percent (wt/wt %) loading of methotrexate with various polymer polyanhydrides was determined by a liquid-liquid extraction procedure. 5-10 mg polymer were weighed and dissolved with 3 ml ethyl acetate. The methotrexate was then extracted from the ethyl acetate layer into 5 ml of an aqueous phosphate buffer saline (PBS) layer. A 0.3 ml aliquot was removed and was filtered with a 0.45 µm filter into an HPLC vial with a 300 µl insert. The methotrexate response and extraction efficiency were tested by extracting methotrexate-free microspheres and adding between 50 µg and 200 µg of methotrexate into the polymer extract and filtering as above. The HPLC procedure used a Rapid Resolution RP-1, 0.1 v/v % TFA in aqueous as mobile phase A and 0.1 v/v % TFA in acetonitrile as mobile phase B at a 1.0 ml/minute flow rate. The compositions of the microspheres prepared are presented in Table 14 below.

TABLE 14

Microspheric Compositions

| Compound | Polymer No. | Drug | Drug Content (% wt/wt) |
|---|---|---|---|
| 43 | 26b | N/a | n/a |
| 44 | 26b | BPC | 26.5$^\alpha$ |
| 45 | 26b | BPC | 14.8$^\alpha$ |
| 46 | 26b | MTX | 10$^\beta$ |
| 47 | 26b | MTX | 16$^\beta$ |
| 48 | 26a | MTX | 13$^\beta$ |
| 49 | 32a | MTX | 10$^\beta$ |
| 50 | 25a | MTX | 16$^\beta$ |

$^\alpha$Measured by $^1$H NMR
$^\beta$Measured by the method of Example 49

Example 53

Determination of Elution Profile of Methotrexate-Loaded Microspheres

The in vitro release of drug (methotrexate) present in microspheres was determined by kinetic elution. The calculated level of w/w % loading described in Example 51 above was used to calculate the expected % release for about 10 mg methotrexate-loaded microspheres. Aliquots of approximately 10 mg microspheres prepared as in Example 51 above were weighed and placed in 50 ml conical tubes provided with screw cap closures. A 40 ml aliquot of release media, either PBS or serum, was added to each tube with a pipet, and the tubes were capped and placed in a 37° C. incubator chamber for periodic sampling. The test tubes were removed for sampling, centrifuged for 5 minutes and 1 ml samples of either PBS or serum were withdrawn for analysis. The samples were initially withdrawn at 1 hour intervals, then daily until changes were noted in either the presence of polymer microspheres or color of the medium. The samples were removed from the PBS, filtered, and typically injected directly or diluted 10 times (100 µl to 900 µl) with PBS. Any samples removed from serum were extracted with a common solid phase extraction (SPE) procedure, and analyzed by high pressure liquid chromatography (HPLC). The HPLC method was also used for determining content uniformity. The results obtained are shown in Table 15 below.

TABLE 15

MTX-DF Microspheres' Elution Profile

| Elapsed Time (Days) | Cumulative % MTX Compound 48 | Cumulative % MTX Compound 49 | Cumulative % MTX Compound 50 |
|---|---|---|---|
| 0 | 0.00 | 0.00 | 0 |
| 1.00 | 18.80 | 34.40 | 13.09 |
| 2.0 | 48.26 | 52.45 | 37.83 |
| 3.0 | 52.14 | 85.88 | 40.59 |
| 7.0 | 52.68 | 85.81 | 46.77 |
| 10.0 | ND | ND | 45.89 |
| 14.0 | ND | ND | 55.50 |

ND not determined.

Example 54

Biodegradation of Polymer-Coated Coupons

Metal coupons were labeled, cleaned, and air-dried for about 15 minutes. 100 mg polymer were prepared in 400 mg anhydrous DCM and vortexed, and the coupons were coated with 150 µM gap width, air dried for 2 hours, and placed in a vacuum oven at 50° C. for 4 hours. The thickness and mass of the coatings were measured, and the following results were obtained. The results obtained are shown in Table 16 below.

TABLE 16

Coated Polymer Degradation Curve

| Coupon | Total Mass (mg) | Thickness (mg) | Coating µm ± µm | Mass |
|---|---|---|---|---|
| A | 4851.0 | 36.8 | 24.8 ± 17.2 | |
| B | 4932.1 | 23.6 | 18.8 ± 4.2 | |

All coupons were immersed in a phosphate buffered saline medium (pH=7.4) and incubated at 37° C. The release of the drug (diflunisal) was evaluated by periodic sampling of the medium and quantitation by high pressure liquid chromatography (HPLC) as described above. The data are shown in Table 17 below.

TABLE 17

Polymer Elution* Profiles

| Time Elapsed (Days) | Cumulative % SA Compound 26a | Cumulative % DF Compound 26c |
|---|---|---|
| 0 | 0.00 | 0.00 |
| 1.0 | 0.00 | 0.00 |
| 2.0 | 0.94 | 2.02 |
| 3.0 | 2.96 | 5.00 |
| 5.0 | 33.40 | 11.68 |
| 8.0 | 56.74 | 44.07 |
| 13.0 | 99.31 | 68.60 |
| 15.0 | 99.73 | 73.50 |
| 21.0 | 100.15 | 74.30 |
| 27.0 | 101.69 | 76.94 |
| 31.0 | 101.69 | 79.31 |
| 36.0 | 100.51 | 81.75 |

*Eluted from Unsterilized Coupons of Polymers 26a and 26c in PBS at 37° C.

Example 55

Effect of Sterilization Method and Measurement of Polymer Degradation

The degradation of polymers from coupons, with and without E-beam sterilization, with a 3 µm thick coating was measured in PBS (pH=7.4) at 37° C. The results are shown in Table 18 below.

TABLE 18

Polymer Elution Profile with/without E-Beam Sterilization

| Time | Compound 26a (1.7 mg) | | Compound 26c (3.4 mg) | | Compound 28a (3.6 mg) | |
|---|---|---|---|---|---|---|
| Elapsed (days) | Cum. % SA No E-Beam | Cum. % SA E-Beam | Cum. % DF No E-Beam | Cum. % DF E-Beam | Cum. % DF No E-Beam | Cum. % DF E-Beam |
| 0 | 0.00 | 0.00 | 0.00 | 0.00 | 0.00 | 0.00 |
| 1.0 | 0.00 | 0.00 | 0.00 | 0.00 | 0.21 | 0.00 |
| 2.0 | 0.85 | 3.88 | 2.19 | 2.94 | 0.21 | 0.00 |
| 3.0 | 4.61 | 12.60 | 13.59 | 15.46 | 0.31 | 0.45 |
| 4.0 | 17.10 | 23.74 | 21.85 | 25.19 | 1.08 | 2.93 |
| 5.0 | 27.39 | 32.27 | 32.29 | 35.83 | 3.41 | 8.10 |
| 6.0 | 45.73 | 46.10 | 54.72 | 53.92 | 9.39 | 18.28 |
| 9.0 | 65.51 | 64.90 | 79.20 | 81.37 | 67.26 | 87.98 |
| 18.0 | 69.88 | 65.59 | 88.99 | 92.72 | 97.49 | 87.98 |
| 21.0 | 74.38 | 72.09 | 92.84 | 98.20 | 98.16 | 76.60 |
| 30.0 | ND | ND | 97.13 | 98.20 | 99.95 | 77.27 |
| 44.0 | ND | ND | 98.49 | 98.41 | 102.33 | 75.76 |

ND not determined.

As shown in Table 18 above, E-Beam sterilization (3.5 mRad) had substantially no effect on b the pattern of diflunisal released from the polymer-(polyDF- or poly SA) coated stainless steel samples incubated in serum at 37° C. Notwithstanding the lack of effect on polymer degradation, sterilization may produce some changes in the molecular weight and mechanical properties of a polymer. For example, the tensile modulus of a melt-polymerized salicylic acid polymer (polySA) decreased by about ⅓ after gamma sterilization (25-35 Kgys) at room temperature although no change occurred when irradiated at 37° C. Gamma radiation had no effect on the molecular weight, flexibility, or adhesiveness of polySA, and only a very minor effect on its hardness. The effects of gamma radiation and E-beam sterilization on polyDF were similar to those observed with polySA.

Example 56

Biodegradation of Polymers Containing Admixed Drug (Paclitaxel)

Paclitaxel (PAC) was admixed in a solution of polymer at a concentration of 0 to about 40 wt %, i.e., 1 mg of polymer-drug admixture contained 0.8 mg polymer and 0.2 mg drug. Paclitaxel was released at the same rate at which the polymer biodegraded to generate diflunisal (the relatively small amount of paclitaxel released reflects the inability of serum to hold this relatively insoluble drug). Tables 20a, 20b, 20c and 20d below show the concurrent release of paclitaxel from a polydiflunisal (polyDF)-paclitaxel admixture coated onto electro-polished stainless steel samples and incubated in serum or PBS at 37° C.

TABLE 19

Elution of PAC admixed into Diflunisal (DF) Polymer

| Time Elapsed (days) | 0% PAC Cumulative % DF Generated | 5% PAC Cumulative % DF Generated | 40% PAC Cumulative % DF Generated |
|---|---|---|---|
| 0 | 0.0 | 0.0 | 0.0 |
| 1.0 | 13.1 | 8.7 | 11.6 |
| 2.0 | 38.3 | 42.1 | 38.3 |
| 3.0 | 40.5 | 50.1 | 47.3 |
| 4.0 | 44.4 | 53.6 | 57.7 |
| 5.0 | 48.4 | 58.0 | 61.7 |
| 6.0 | 50.4 | 61.0 | 69.0 |
| 7.0 | 52.8 | 64.0 | 74.0 |
| 10.0 | 57.4 | 69.4 | 80.8 |
| 12.0 | 60.6 | 78.8 | 95.1 |
| 14.0 | 67.8 | 82.2 | 99.6 |
| 17.0 | 76.6 | 93.4 | 110.1 |
| 19.0 | 79.5 | 96.9 | 112.2 |
| 21.0 | 82.0 | 100.6 | 115.0 |
| 28.0 | 88.9 | 110.0 | 122.0 |

*Elution of <5 μm Coating of Compound 27a on 1 cm$^2$ Coupons in Serum with 0%, 5% and 40% PAC loading.

TABLE 20a

Elution* of PAC admixed into Polymer

| Time Elapsed (days) | Compound 26b with 10% PAC PAC Released (Cumulative μg) | Compound 27a with 5% PAC PAC Released (Cumulative μg) |
|---|---|---|
| 0 | 0.0 | 0.0 |
| 1.0 | 13.8 | 6.3 |
| 2.0 | 9.7 | 8.2 |
| 3.0 | 13.6 | 8.2 |
| 4.0 | 11.2 | 9.1 |
| 5.0 | 12.8 | 9.7 |
| 6.0 | 14.2 | 13.1 |
| 7.0 | 20.5 | 17.3 |
| 10.0 | 21.2 | 21.7 |
| 12.0 | 31.5 | 21.9 |
| 14.0 | 33.4 | 25.2 |
| 17.0 | 41.7 | 27.4 |
| 19.0 | 41.6 | 27.4 |
| 21.0 | 50.9 | 34.4 |
| 28.0 | 42.0 | 40.4 |

*Elution of Paclitaxel from <5 μm Coating of Compound 26b and Compound 27a on 1 cm$^2$ Coupons in Serum

TABLE 20b

Elution of Paclitaxel

| | PAC Released (Cumulative %) | |
|---|---|---|
| Time Elapsed (days) | Compound 27a with 0% PAC | Compound 27a with 40% PAC |
| 0 | 0.00 | 0.00 |
| 1.0 | 5.79 | 12.16 |
| 2.0 | 7.56 | 11.22 |
| 3.0 | 7.56 | 10.56 |
| 4.0 | 8.38 | 9.67 |
| 5.0 | 8.96 | 17.02 |
| 6.0 | 12.11 | 17.24 |
| 7.0 | 16.05 | 19.19 |
| 10.0 | 20.05 | 19.69 |
| 12.0 | 20.23 | 22.59 |
| 14.0 | 23.34 | 23.05 |
| 17.0 | 25.37 | 27.84 |
| 19.0 | 25.37 | 28.19 |

*Elution of Paclitaxel from <5 μm Compound 27a Coating on 1 $cm^2$ Coupons in Serum

TABLE 20c

Elution of PAC Admixed into Polymer*

| | PAC Released (Cumulative μg) | |
|---|---|---|
| Time Elapsed (days) | Compound 26b With 0% PAC | Compound 26b with 10% PAC |
| 0 | 0 | 0 |
| 1.0 | 59.75 | 38.5 |
| 2.0 | 140.39 | 76.42 |
| 3.0 | 199.18 | 136.22 |
| 4.0 | 307.39 | 174.94 |
| 5.0 | 268.49 | 282.67 |
| 6.0 | 410.89 | 333.27 |
| 7.0 | 485.14 | 407.52 |
| 10.0 | 617.14 | 539.52 |
| 12.0 | 661.33 | 752.02 |
| 14.0 | 671.89 | 779.52 |
| 17.0 | 785.64 | 955.77 |
| 19.0 | 807.97 | 965.04 |
| 21.0 | 842.47 | 1001.29 |
| 28.0 | 837.73 | 985.2 |

*Elution from <5 μm Coating of Compound 26b with 0% and 10% PAC Loadings on 1 $cm^2$ Coupons in PBS

Example 57

Determination of Polymer Glass Transition Temperature ($T_g$) in a Differential Scanning Calorimeter Approximately 10 mg polymer were accurately weighed, and the mass was recorded in a pre-tared aluminum pan (no-hermetic seal). The pan was crimped to complete a seal and to facilitate good heat transfer. The pan was placed in the calorimeter opposite an empty reference pan of mass similar to the sample pan. The calorimeter was closed and sealed in a nitrogen sweep gas atmosphere. The sample temperature was controlled at a program rate of 10° C./min from room temperature to −20° C., followed by heating to 110° C. The sample was then cooled to −20° C., and was heated at the same rate a second time to 110° C. The $T_g$ was observed as the mid-point in the heat capacity inflection. The measurements were made using Thermal Analytical Instruments Q-100 with a circulation bath chiller. The data obtained from each of ten polymers are shown below in Table 21.

TABLE 21

Glass Transition Temperatures

| Compound | $T_g$ (° C.) |
|---|---|
| 23b | 40 |
| 25a | 35.7 |
| 25b | 31.1 |
| 25c | 17.5 |
| 26a | 41.0 |
| 26b | 49.0 |
| 26c | 42.3 |
| 27a | 38.4 |
| 27b | 33.9 |
| 28a | 45.1 |

Example 58

NMR Analyses of Different Bond Types

The polymerization of a Diflunisal-Linker-Diflunisal was conducted to demonstrate the ability of the process of the invention to control bond types and bond type distribution. The bond type was determined by NMR. Melt polymerization produced a distribution labeled as "Dispersion" in the polymer type axes. This polymer released 70% of the contained Diflunisal in approximately 28 days with a more gradual release for another 14+ days. By applying the synthetic methods presented here, a polymer was created with the same % of ingredients but with only one bond type ("Controlled Sequence"). By creating a strictly alternating repeat structure, only one bond type predominates. This polymer will release more rapidly, and will form crystals in the later stage of elution. By altering the rate of addition of phosgene or by changing the pre-polymer, other precise distributions and sequences can be created which result in changes in crystallinity, release kinetics (hours to months from a 5 micron thick coating) and other physical attributes such as compatibility & solubility. "Random" represents a polymer in which the polymerization reaction is allowed to take place in once step. By slowing down the addition rate of phosgene, additional distributions of bond types were achieved ("Random—1 hour Addition" and "Random—6 hour Addition"). As the % of weaker bonds was altered, the breakdown rate, stability, sterilization breakdown, etc. was altered as well but in a controlled manner. Thus, the design capabilities of these polymers are far beyond those of typical melt polymerization or solution polymerization prior to this art. (FIG. 1).

Example 59

Class Transition Temperature

A polymer's glass transition temperature ($T_g$) is a key parameter that significantly influences its mechanical, physical chemical and handling properties. The molecular weight and chemical composition of the linking group may affect the polymer's glass transition temperature ($T_g$), and accordingly, the mechanical properties of the therapeutic polymers and coatings of the therapeutic polymers at body temperatures. The higher the molecular weight, the greater the toughness of the material in terms of elasticity and tear strength. A polymer's tensile modulus may be taken as an index of the polymer's rigidity. The glass transition temperatures and tensile moduli for several polymers are listed in Table 22 below.

TABLE 22

Aliphatic Linker - Effect of Chain Length and Tensile Modulus

| | | Number of Carbons (Linker) | | | |
|---|---|---|---|---|---|
| | Temp. | 6 | 6:8 | 8 | 10 |
| Glass Transition Temp. (Tg) | (° C.) | 44 | 38 | 29 | 16 |
| Tensile Modulus (kPa) | 25° C. | 3300 | 2100 | 140 | 7 |
| | 37° C. | 480 | 45 | 4 | NO |

NO Not observed

Polymer prepared by Solution Process

Table 22 shows a salicylic acid polymer with a $C_6$ linker molecule as having a $T_g=44°$ C., and that the polymer is relatively hard at room temperature. Increasing the carbon-chain length will generally lower the glass transition temperature ($T_g$) of the resulting polymer in a somewhat linear manner, so that a polymer of salicylic acid (polySA) produced with a $C_{12}$ linker molecule has a $T_g=8°$ C. and is a rubbery, elastic material at room temperature. A similar profile is seen with polymers of diflunisal (polyDF), a potent derivative of salicylic acid. For a specific linker chain length, a polydiflunisal will generally exhibit a much higher $T_g$ when compared to the same linker in the corresponding polysalicylic acid. Thus, the data provided in Table 22 show a that in one embodiment of the invention, the tensile modulus (polymer rigidity) and glass transition temperature are inversely proportional to linker chain length. In addition, for each specific linker, the polymer's rigidity decreased with increased temperature from 25° C. to body temperature (37° C.). Table 23 below shows data for another embodiment of the invention.

TABLE 23

Aliphatic Linker in PolySalicylic Acid (Anhydride Ester)

| | | | Linkers | | |
|---|---|---|---|---|---|
| Polymers* | MW | PDI | $T_g$ (° C.) | $T_m$ (° C.) | $T_d$ (° C.) |
| Glutaric acid | 3,206 | 1.1 | 58 | 175 | 424 |
| Adipic acid | 2,221 | 1.7 | 76 | N.C. | 391 |
| Dodecanedioic acid | 18,427 | 1.8 | 53 | 178 | 434 |
| Di-glycolic acid | 3,051 | 1.0 | 68 | N.C. | 408 |

N.C. Not observed

*Synthesized at 180° C. for 2.5 hr under vacuum

In this embodiment, the polymer's $T_g$ increases with increasing chain carbon number, e.g., glutaric acid vs. adipic acid. A linker of a very short carbon chain, for instance, less than about $C_5$, provides a lesser chance for cross-linking by generally known synthetic methods, e.g., melt polymerization variations, probably due to steric hindrance, and the polymer products may have a lower $T_g$, e.g., about 58° C., than with a longer chain linker that may favor more extensive cross-linking and, therefore, higher $T_g$, e.g. about 76° C. This potential cross-linking reactivity generally decreases as the molecular weight of the polymer increases and as the linker chain length increases sufficiently. Dodecanedioic acid, for example, has a $T_g$ of about 53° C. In another embodiment of this invention, the linkers are aromatic molecules that have different structural rigidity (Table 24).

TABLE 24

Aromatic Linker in Salicylic Acid (Anhydride Ester) Polymer

| | | | Linkers | | |
|---|---|---|---|---|---|
| Polymers | MW | PDI | $T_g$ (° C.) | $T_m$ (° C.) | $T_d$ (° C.) |
| Terephthalic | 2,101 | 1.3 | 111 | N.O. | 436 |
| 1-4'-Phenyldiacetic | 1,584 | 1.0 | 89 | N.O. | 386 |
| 4-4'-Biphelyldicarboxylic | 5,531 | 1.1 | 150 | N.O. | 463 |
| 4-4'-Oxybisphenyldicarboxylic | 9,064 | 1.1 | 103 | N.O. | 387 |
| 4-4'-(Hexafluoroisoporpylidene) dicarboxylic | 9,436 | 1.2 | 149 | 315 | 464 |

N.O. Not observed

Synthesized at 180° C. for 2.5 hr under Vacuum

Table 24 provides information that corresponds to a salicylic acid polymer having an aromatic linker, where the introduction in the polymer chain of aromatic linkers of different characteristics, such as structural rigidity, results in different $T_g$ values. The data provided in the previous tables show that the transition temperature $T_g$ may vary with the number of carbons of a straight aliphatic chain linker as well as with other parameters of the linker molecule such as, but not limited to, hydrophobicity, structural rigidity, presence of heteroatoms, etc. The polymers of the invention evidence an extraordinary range of properties that may be varied as required by any one specific application, as exemplified in Tables 4a, 4b and 4c. These data also show that a great variety of polymers, e.g. poly-NSAIDs as well as polymers of other types of molecules, may be created from combinations of a monomer(s) and different linkers that may have varied chain lengths and chemical structures, to attain a polymer of predetermined physical properties, e.g. in-between those of the respective homologous polymers. In addition, the process of the invention also allows the formation of polymers of desired characteristics by combination of molecules with certain linkers in pre-selected proportions to obtain desired values for the polymer characteristics. For example, a co-polymer made from equal amounts of a monomer attached to $C_6$ and $C_8$ linkers should have an intermediate $T_g$ and tensile modulus with respect to those of the $C_6$ and $C_8$ polymers. In addition, different molecules may be introduced into the polymer to obtain a compound of combined activities. For example, NSAIDs of the type of salicylic acid, diflunisal, salsalate (a di-salicylic acid), analgesics, hemostatics, antibiotics, etc., and in general any polymerizable molecule may be employed, examples of which are given herein. This flexibility in the design of a polymer extends to the synthesis of all polymers of the invention, e.g. polymers of salicylic acid, diflunisal, salsalate, etc., and thereby allows the control of polymer properties by varying monomer ratio, e.g. 20:80, 50:50, 80:20, linker combinations, linker structure, molecules in the form of monomers, dimers, trimers, tetramers, etc. combinations of molecules, and others.

Varying the linker chain length may have an inverse influence on the polymer's hardness. When measured by ASTM methods, the relative hardness of the polymer of the invention, e.g., with polyNSAIDs such as poly-salicylic acid and poly-diflunisal, was seen to decrease with increasing linker chain length. That is, shorter linkers produced harder polymers compared to longer linkers. As the carbon number in the linker chain was increased, the polymers also became slightly softer when hydrated. When the data are normalized to the intended use temperature ($T-T_g$), a roughly linear relationship for all polymers is observed, thereby providing a powerful tool for designing polymers of pre-selected characterisitics.

Example 60

Effect of Linker Chain Length on Glass Transition Temperature & Mechanical Properties Glass transition temperature ($T_g$) is a key parameter of polymers that significantly influences their mechanical, physical chemical and handling properties. Polymers of salicylic acid carrying different linkers were tested for their $T_g$s, which are shown in Table 25 below.

TABLE 25

Tg Versus Linker of polySA and polyDF

| Number of Carbon Atoms in Linker | Tg (° C.) PolyAspirin I | Tg (° C.) PolyAspirin II |
|---|---|---|
| 6 | 46 | 76 |
| 8 | 30 | — |
| 10 | 19 | 54 |
| 12 | 6 | 48 |
| 14 | — | 38 |
| 16 | — | 12 |

As shown in Table 25 above, a polySA polymer with a six-carbon linker molecule has a $T_g=44°$ C., and is relatively hard at room temperature. Increasing the carbon-chain length lowers $T_g$ in a linear manner, so that polySA produced with a 12-carbon linker molecule has a $T_g=8°$ C., which results in a rubbery, elastic material at room temperature. A similar profile is seen with polyDF polymers, noting that for a specific linker chain length, a much higher $T_g$ is measured relative to the same linker in the polySA polymers. As summarized in Table 22 shown above, tensile modulus (another index of rigidity) also increased with decreasing linker chain length, while for a specific linker, rigidity decreased as temperature was increased from 25° C. to body temperature (37° C.). As shown above, in one of the embodiments of the invention, the $T_g$ of the polymer was seen to increase with increased length of the carbon chain. In another embodiment shown in Table 25 above, the $T_g$ may increase until certain number of carbons in the chain is obtained, e.g., glutaric acid vs. adipic acid. A linker of a very short carbon chain, e.g., C of about <5, provides less of a chance for cross-linking in any of the generally known synthetic methods, e.g., melt polymerization variations, probably due to steric hindrance, and the polymer produced may have a lower $T_g$, e.g., about 58° C., than when the linker has a longer chain that lends itself to more extensive cross-linking. The latter produced a polymer with higher $T_g$, e.g., about 76° C. This cross-linking reactivity generally decreases as the molecular weight of the polymer increases and as the linker chain length increases sufficiently, e.g., dodecanedioic acid has a $T_g$ of about 53° C. Similar data are provided in Table 25 above, which shows that different aromatic linkers of different structural rigidity resulted in different $T_g$ values. All these data show that the transition temperature $T_g$ not only varies with the number of carbons of a straight aliphatic chain linker but also might vary based on other properties of the linker molecule such as, but not limited to, hydrophobicity, structural rigidity, heteroatoms present, etc. It is evidenced by the results shown in Tables 4a, 4b, and 4c that the polymers of the invention evidence an extraordinary range of properties that may be varied as required by any one specific application. These data also show that poly-NSAIDs may be created from combinations of monomers containing different linker chain lengths, with physical properties in between those of the respective homologous polymers. For example, a co-polymer made from equal amounts of monomers prepared with 6 and 8 carbon atoms had intermediate $T_g$ and tensile modulus values. This flexibility applies to both polySA and polyDF, allowing control of polymer properties by varying the monomer ratio, e.g. 20:80, 50:50, 80:20, etc.

Varying the linker chain length influences polymer hardness as well. In this case, the relative hardness of polymers of the invention, e.g. polySA and polyDF, when measured by ASTM methods, decreased as the linker chain length increased, and the polymers became slightly softer when hydrated. Normalizing the data to the intended use temperature (T-$T_g$) showed a roughly linear relationship for all polymers, thereby creating a convenient application design tool. Essentially across this range, polyNSAIDs were highly flexible at room temperature and body temperature, as flexible as could be measured by standard ASTM methods. Soaking the polymers for an hour in 37° C. PBS caused no observable change in flexibility. This is shown in Table 26 below.

TABLE 26

Adhesion* between Salicylic Acid Coatings

| | Polymer | | | | |
|---|---|---|---|---|---|
| | 510PL | 261PL | 749PL | 125PL | 510PL + 14% Paclitaxel |
| Adhesion Class | 5B | 5B | 5B | 4B | 5B |

*Adhesion as measured in the ASTM test for adhesion under ambient conditions Class Rating 5B = 0% of coating removed from substrate 4B = <5% of coating removed from substrate Essentially across this range, the polymers of the invention, e.g., poly-NSAIDs, are highly flexible at room and body temperature. Soaking the polymers for an hour in PBS at about 37° C. caused no observable change in flexibility All patents, publications and patent applications listed herein are incorporated by reference in their entirety, as though individually incorporated by reference. The invention has been described with reference to various embodiments and techniques. However, it should be understood that many variations and modifications may be made while remaining within the spirit and scope of the invention.

REFERENCES

Erdmann, L., and Uhrich, K. E., Biomaterials, 21, 1941-1946, 2000.

"Polymer Painkiller," Science, 278, 32-33, 1999.

Erdmann, L., Macedo, B., and Uhrich, K. E., Biomaterials, 21, 2507-2512, 2000.

Morrow, J. D. and Roberts, L. J. "Lipid-Derived Autacoids: Eicosanoids and Platelet-Activating Factor" in *Goodman and Gilman's The Pharmacological Basis of Therapeutics*, 10th Edition, J. G. Hardman, L. E. Limbird and A. G. Goodman, eds., McGraw-Hill, New York, N.Y., 2001 pp 669-686.

Herman, J. H., Sowder, W. G., and Hess, E. V., J. Rheumatol. 21: 338-343, 1994.

Soekanto, A., Ohya, K., and Ogura, H., Calcified Tissue Internat., 54(4), 290-295, 1994.

Soekanto, A., Jap. J. Pharmacol., 65(1), 27-324, 1994.

Roberts, L. J., and Morrow, J. D., "Analgesic-Antipyretic and Antiinflammatory Agents and Drugs Employed in the Treatment of Gout" in *Goodman and Gilman's The Pharmacological Basis of Therapeutics*, 10th Edition, J. G.

Hardman, L. E. Limbird, and A. G. Goodman, eds., McGraw-Hill, New York, N.Y., pp 687-732 (2001).

*The Merck Index, 10th Edition*, M. Windholz, ed., Merck & Co., Inc., Rahway, N.J., 1983, pp 123, 456, and 1200.

*The Merck Index, 10th Edition*, M. Windholz, ed., Merck & Co., Inc., Rahway, N.J., 1983, p 1200.

*The United States Pharmacopeia (USP XXI)/The National Formular (NF XVI)*, United States Pharmacopeial Convention, Inc., Rockville, Md., 1985, p 1195.

*Remington's Pharmaceutical Sciences, 17th Edition*, A. R. Gennaro, Ed., Mack Publishing Co., Easton, Pa., p 785 (1985).

*Stedman's Medical Dictionary, 27th Edition*, M. B. Pugh, Ed., Lippincott Williams & Wilkins, Philadelphia, Pa., 2000, p 103.

Chambers, H. F. "Antimicrobial Agents: General Considerations" in Goodman and Gillman's *The Pharmacological Basis of Therapeutics, 10th Edition*, J. G. Hardman, L. E. Limbird, A. G. Goodman, Eds., McGraw-Hill, New York, N.Y., pp 1143-1170638-681 (2001).

*The United States Pharmacopeia (USP XXV)/The National Formulary (NF XX)*, United States Pharmacopeial Convention, Inc., Rockville, Md., 2003, Procedure GM201PMC.01.

Van de Belt, H., Neut, D., Schenk, W. et al., Acta Orethop. Scand. 72(6): 557-571 (2001).

Category IV Monograph: Antiseptic Skin Cleansers. Drugs Directorate, Health Canada, 11 Sep. (1995).

Domb, A. J., and Langer, R., Solid-state and solution stability of poly(anhydrides) and poly(esters). Macromolecules, 22, 2117-2122, 1989.

Schierholz, J. M., and Beuth, J., Med. Dev. Tech., 11(2), 12-17, 2000.

D'Emanuele, A., Hill, J., Tamada, J., et al., Pharm. Res. 9: 1279-1283 (1992).

Dang, W., Daviau, T., Ying, P. et al., J. Controlled Release 42: 83-92 (1996).

Figure from Edelmann, E. R., and Rogers, C., A. J. Cardiol., 81(7A), 4E-6E, 1998. Se also Ref 5.

Van der Giessen, W. J., Lincoff, A. M., Schwartz, R. S. et al., Circulation 94: 1690-1697 (1996).

U.S. Pat. No. 6,153,252, "Process for Coating Stents," issued to Ethicon, Inc.

U.S. Pat. No. 6,358,556 B1, "Drug Release Stent Coating," issued to Boston Scientific Corp.

Holick, M. F., and Krane, S. M., "Introduction to Bone and Mineral Metabolism: Bone Structure and Metabolism," in Harrison's Principles of Internal Medicine, $15^{th}$ Edition, Braunwald, E., Fauci, A. S., Kasper, D. L. et al, Eds. McGraw-Hill Medical Publishing Division, New York, N.Y., 2001, pp 2192-2205.

Keila, S., Kelner, A., and Weinreb, M., J. Endocrinol., 168(1), 131-139, 2001.

Simon, A. M., Manigrasso, M. B., and O'Connor, J. P. J. Bone Min. Res. 17: 963-975 (2002).

Dziak, R., J. Periodont. 64: 407-415 (1993).

Alexander, M., and Damoulis, P. The role of cytokines in the pathogenesis of periodontal disease. Current Opinions in Periodont., 1, 39-53, 1994.

Weibe, S., Hafezi, M., Sandhu, H., et al., Oral Disease 2: 167-180 (1996).

Harten, R. and Uhrich, K. E., Manuscript in preparation, 2003.

Einhorn, T. A., Arthritis Res. Ther. 5: 5-7 (2003).

Persson, U., Persson, M., and Malchau, H. The economics of preventing revisions in total hip replacement. Acta Orthop. Scand., 70, 163-169, 1999. See also Ref. 24.

Lipsky, P. E. "Rheumatoid Arthritis," in Harrison's Principles of Internal Medicine, $15^{th}$ Edition, Baunwald, E., Fauci, A. S., Kasper, D. L. et al., eds. McGraw-Hill Medical Publishing Division, New York, N.Y., 2001, pp 1928-1937.

Goronzy, J. J., and Weyand, C. M., in Primer on the Rheumatic Diseases, $12^{th}$ Ed., Klippel, J. H., Crofford, L. J., Stone, J. H. and Weyand, C. M., Eds., Arthritis Foundation, Atlanta, Ga. 2001, pp 209-217.

Lewis, C. Arthritis: "Timely Treatments for an Ageless Disease," *FDA Consumer Magazine*, U.S. Food and Drug Administration, May-June 2000.

Matteson, E. L. "Rheumatoid Arthritis C. Treatment," in *Primer on the Rheumatic Diseases*, $12^{th}$ Ed., Klippel, J. H., Crofford, L. J., Stone, J. H. and Weyand, C. M., Eds., Arthritis Foundation, Atlanta, Ga., 2001, pp 225-232.

Ishikawa, K., Ohira, T., and Sakata, H. Effects of intraarticular injection of halopredone diacetate on the articular cartilage of rabbit knees: a comparison with methylprednisolone acetate. Toxicol. Appl. Pharmacol., 75, 423-436, 1894.

Stefanich, R. J. Intraarticular corticosteroids in treatment of osteoarthritis. Orthop. Rev., 32, 65-71, 1986.

Kongtawelert, P., Brooks, P., and Ghosh, P., J. Rheumatol. 16: 1454-1459 (1989).

Hochberg, M. C., Altman, R. D., Bradt, K. D., et al., Arthritis Rheum. 38: 1541-1546 (1995).

Horisawa, E., Hirota, T., Kawashima, Y. et al., Pharm. Res. 19: 403-410 (2002).

"Joint Injection/Aspiration", Amer. College of Rheumatol. Fact Sheet @ www.rheumatology.org.

"Joint Injections" @ www.mayoclinic.com.

"Arthritis," American Academy of Orthopedic Surgeons @ www.orthoinfo.aaos.org

Gutstein, H. B. and Akil, H., "Opioid Analgesics," in *Goodman and Gilman's The Pharmacological Basis of Therapeutics*, $10^{th}$ Edition, J. G. Hardman, L. E. Limbird, and A. G. Goodman, eds., McGraw-Hill, New York, N.Y., 2001, pp 569-620.

Stein, C. and Yassouridis A, Pain 71: 119-121 1999.

Dionne, R. A., Lepinski, A. M., Gordon, S. M. et al., Clin. Pharmacol. Ther. 70: 66-73 (2001).

Likar, R., Koppert, W., Blatnig, H. et al., J. Pain Symptom Manage 21: 330-337 (2001).

Stein, A., Yassouridis, A., Szopko, C. et al., Pain 83: 525-532 (1999).

Chaubal, M., Drug Delivery Technology 2: 34-36 (2002).

NUTROPIN®, NUTROPIN AQ®, NUTROPIN DEPOT® product labeling, Genetech, Inc. Physician's Desk Reference, $57^{th}$ Edition.

We claim:

1. A polymerization process, comprising a) forming a mixed di-anhydride pre-polymer from a low molecular weight acid and an HOOC-Agent(s)-Linker(s)-Agent(s)-COOH; and b) heating the mixed di-anhydride pre-polymer at or above its melting point in a non-aqueous dispersion in the presence of a non-aqueous solvent to provide a polymer.

2. The process of claim 1, wherein polymer particles form that are dispersed in the solvent.

3. The process of claim 2, wherein the polymer particles are about 0.5 to about 100 micron in size.

4. The process of claim 2, further comprising separating the polymer particles formed from the dispersion.

5. The process of claim 4, further comprising washing the polymer particles without dissolving them.

6. The process of claim 5, wherein the washing step comprises a continuous washing step conducted at a temperature at or below about the glass transition temperature of the polymer.

7. The process of claim 1, wherein the low molecular weight acid comprises a (C2-C24) carboxylic acid; and the polymerization step is conducted at about 20 to about 200° C. temperature.

8. The process of claim 7, where the temperature of the polymerization step is at or above about the glass transition temperature of the polymer.

9. The process of claim 1, wherein the polymerization process is allowed to proceed for a period and under conditions effective to enable the polymer to attain a molecular weight of up to about 1,500,000 Dalton.

10. The process of claim 1, wherein the polymerization process is allowed to proceed for a period and under conditions effective to enable the polymer to attain a molecular weight of up to about 1,000,000 Dalton.

11. The process of claim 1, wherein the polymerization process is allowed to proceed for a period and under conditions effective to enable the polymer to attain a molecular weight of up to about 500,000 Dalton.

12. The process of claim 1, wherein the polymerization process is allowed to proceed for a period and under conditions effective to enable the polymer to attain a molecular weight of up to about 250,000 Dalton.

13. The process of claim 1, wherein the polymerization process is allowed to proceed for a period and under conditions effective to enable the polymer to attain a molecular weight of up to about 100,000 Dalton.

14. The polymerization process of claim 1 further comprising extending the polymer by coupling or linking, or end-capping.

15. The polymerization process of claim 14, wherein the polymer is extended by coupling with an oligomer or second mixed anhydride under conditions effective to attain linking of the polymer and the oligomer(s) or second polymer(s) in the presence of the corresponding di-acid or di-acid ammonium salt thereof.

16. The polymerization process of claim 14, wherein the polymer is end-capped by reaction with a di-acid ammonium salt or the oligomer(s) or second polymer(s) in the presence of an acylating or dehydrating agent and a non-aqueous solvent.

17. The polymerization process of claim 16, wherein two or more diacid or salts thereof are employed resulting in a random compound.

18. The polymerization process of claim 16, wherein the polymer is end-capped with the aid of cross-linked ammonium salt beads.

* * * * *